United States Patent
Cueva-Garcia et al.

(10) Patent No.: US 12,421,193 B2
(45) Date of Patent: Sep. 23, 2025

(54) GPR52 MODULATORS AND METHODS OF USE

(71) Applicant: Neurocrine Biosciences, Inc., San Diego, CA (US)

(72) Inventors: Juan Pablo Cueva-Garcia, San Diego, CA (US); Neil J. Ashweek, San Diego, CA (US); Collin Regan, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 516 days.

(21) Appl. No.: 17/919,483

(22) PCT Filed: Apr. 21, 2021

(86) PCT No.: PCT/US2021/028394
§ 371 (c)(1),
(2) Date: Oct. 17, 2022

(87) PCT Pub. No.: WO2021/216705
PCT Pub. Date: Oct. 28, 2021

(65) Prior Publication Data
US 2023/0234925 A1 Jul. 27, 2023

Related U.S. Application Data

(60) Provisional application No. 63/013,862, filed on Apr. 22, 2020.

(51) Int. Cl.
| | | |
|---|---|---|
| C07D 213/56 | (2006.01) |
| C07D 213/68 | (2006.01) |
| C07D 213/69 | (2006.01) |
| C07D 213/84 | (2006.01) |
| C07D 239/26 | (2006.01) |
| C07D 401/12 | (2006.01) |
| C07D 405/12 | (2006.01) |

(52) U.S. Cl.
CPC ......... *C07D 213/56* (2013.01); *C07D 213/68* (2013.01); *C07D 213/69* (2013.01); *C07D 213/84* (2013.01); *C07D 239/26* (2013.01); *C07D 401/12* (2013.01); *C07D 405/12* (2013.01)

(58) Field of Classification Search
CPC .. C07D 213/56; C07D 213/68; C07D 213/69; C07D 213/84; C07D 239/26; C07D 401/12; C07D 405/12
See application file for complete search history.

(56) References Cited

U.S. PATENT DOCUMENTS

| | | |
|---|---|---|
| 7,919,260 B2 | 4/2011 | Komatsu et al. |
| 9,676,758 B2 | 6/2017 | Xiong et al. |
| 2011/0009421 A1 | 1/2011 | Setoh et al. |
| 2011/0130384 A1 | 6/2011 | Setoh et al. |
| 2022/0112164 A1 | 4/2022 | Zhou et al. |

FOREIGN PATENT DOCUMENTS

| | | |
|---|---|---|
| EP | 2253618 | 11/2010 |
| EP | 2530078 | 10/2012 |
| EP | 2518054 | 12/2012 |
| WO | WO 1987/005297 | 9/1987 |
| WO | WO 2005/095990 | 10/2005 |
| WO | WO 2009/107391 | 9/2009 |
| WO | WO 2009/157196 | 12/2009 |
| WO | WO 2010/018874 | 2/2010 |
| WO | WO 2011/078360 | 6/2011 |
| WO | WO 2011/093352 | 8/2011 |
| WO | WO 2011/145735 | 11/2011 |
| WO | WO 2012/020738 | 2/2012 |
| WO | WO 2016/176571 | 11/2016 |
| WO | WO 2019/053090 | 3/2019 |
| WO | WO 2021/090030 | 5/2021 |
| WO | WO 2021/181122 | 9/2021 |
| WO | WO 2021/198149 | 10/2021 |
| WO | WO 2021/216705 | 10/2021 |
| WO | WO 2022/043714 | 3/2022 |

(Continued)

OTHER PUBLICATIONS

Chemical Abstracts Registry No. 685109-38-0, indexed in the Registry file on STN CAS Online on May 24, 2004. (Year: 2004).*
PubChem CID 1481731, National Center for Biotechnology Information. PubChem Compound Summary for CID 1481731, [4-(1,3-Benzodioxol-5-yl)-2-pyrimidinyl]methyl 4-fluorophenyl ether. https://pubchem.ncbi.nlm.nih.gov/compound/1481731. Accessed May 6, 2025, create date Jul. 11, 2005. (Year: 2005).*
Berge et al., "Pharmaceutical Salts," Journal of Pharmaceutical Sciences, Jan. 1977, 66(1):1-19.
Collier et al., "Radiosynthesis and in vivo evaluation of the pseudopeptide delta-opioid antagonist [(125)I]ITIPP(psi)," J. Labelled Compd. Radiopharm., 1999, 42:S264-S266.

(Continued)

*Primary Examiner* — Laura L Stockton
(74) *Attorney, Agent, or Firm* — Fish & Richardson P.C.

(57) ABSTRACT

The present disclosure relates to compounds of Formula (I) that modulate the activity of G-protein coupled receptor 52 (GPR52), pharmaceutically acceptable salts of compounds of Formula (I), and pharmaceutical compositions thereof. Compounds, pharmaceutical salts of compounds, and pharmaceutical compositions of the present disclosure are directed to methods useful in the treatment or prophylaxis of a neurological disease or disorder and conditions related thereto.

(I)

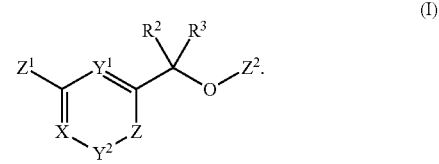

21 Claims, No Drawings

(56) References Cited

FOREIGN PATENT DOCUMENTS

| | | |
|---|---|---|
| WO | WO 2022/232017 | 11/2022 |
| WO | WO 2023/041432 | 3/2023 |
| WO | WO 2023/041909 | 5/2024 |
| WO | WO 2024/091538 | 5/2024 |
| WO | WO 2024/091541 | 5/2024 |
| WO | WO 2024/091542 | 5/2024 |

OTHER PUBLICATIONS

Desai et al., "Pharmacokinetics of ASP4345 from Single Ascending-Dose and Multiple Ascending-Dose Phase I Studies," Clinical Pharmacokinetics, Jun. 2020, 60:79-88.

Hatzipantelis et al., "A B-Arrestin-2-Dependent Mechanism of GPR52 Signaling in Frontal Cortical Neurons," Manuscript, ACS Chemical Neuroscience, Jun. 2020, 11(14):2077-2084.

Hatzipantelis et al., "Translation-Focused Approaches to GPCR Drug Discovery for Cognitive Impairments Associated with Schizophrenia," ACS Pharmacology & Translational Science, Oct. 2020, 3(6):1042-1062.

Komatsu et al., "Anatomical Transcriptome of G Protein-Coupled Receptors Leads to the Identification of a Novel Therapeutic Candidate GPR52 for Psychiatric Disorders," PLOS One, Feb. 2014, 9(2):e90134.

Komatsu, "Discovery of the First Druggable GPR52 Antagonist to Treat Huntington's Disease," Journal of Medicinal Chemistry, 2021, 64(2):938-940.

Le Bas et al., "Radioiodinated analogs of EP 00652218 for the exploration of the tachykinin NK1 receptor by spect," J. Labelled Compd. Radiopharm., 2001, 44:S280-S282.

Lin et al., "Structural basis of ligand recognition and self-activation of orphan GPR52," Nature, Feb. 2020, 579(7797):152-157.

Nishiyama et al., "FTBMT, a Novel and Selective GPR52 Agonist, Demonstrates Antipsychotic-Like and Procognitive Effects in Rodents, Revealing a Potential Therapeutic Agent for Schizophrenia," Journal of Pharmacology and Experimental Therapeutics, Nov. 2017, 363(2):253-264.

Nishiyama et al., "Genetic deletion of GPR52 enhances the locomotor-stimulating effect of an adenosine A2A receptor antagonist in mice: A potential role of GPR52 in the function of striatopallidal neurons," Brain Research, Sep. 2017, 1670:24-31.

Russell et al., "GPR52 agonists attenuate ropinirole-induced preference for uncertain outcomes," Behavioral Neuroscience, 2020, 135(1):8-23.

Sawzdargo et al., "Identification and cloning of three novel human G protein-coupled receptor genes GPR52, ΨGPR53 and GPR55: GPR55 is extensively expressed in human brain," Molecular Brain Research, Feb. 1999, 64(2):193-198.

Setoh et al., "Discovery of the First Potent and Orally Available Agonist of the Orphan G-Protein- Coupled Receptor 52," Journal of Medicinal Chemistry, Jun. 2014, 57(12):5226-5237.

Spark et al., "In the Loop: Extra-striatal Regulation of Spiny Projection Neurons by GPR52," Manuscript, ACS Chemical Neuroscience, Jun. 2020, 11(14):2066-2076.

Tokumaru et al., "Design, synthesis, and pharmacological evaluation of 4-azolyl-benzamide derivatives as novel GPR52 agonists," Bioorganic & Medicinal Chemistry, Jun. 2017, 25(12):3098-3115.

Zhu et al., "Synthesis and Mode of Action of 125I- and 3H-Labeled Thieno[2,3-c]pyridine Antagonists of Cell Adhesion Molecule Expression," The Journal of Organic Chemistry, 2002, 67(3):943-948.

Abdul-Monim et al., "Sub-chronic psychotomimetic phencyclidine induces deficits in reversal learning and alterations in parvalbumin-immunoreactive expression in the rat," Journal of Psychopharmacology, Mar. 2007, 21(2):198-205.

Abdul-Monim, et al., "The effect of atypical and classical antipsychotics on sub-chronic PCP-induced cognitive deficits in a reversal-learning paradigm," Behavioral Brain Research, May 2006, 169(2):263-273.

Aparicio-Legarza et al., "Deficits of [3H]D-aspartate binding to glutamate uptake sites in striatal and accumbens tissue in patients with schizophrenia," Neuroscience Letters, Aug. 1997, 232(1)13-16.

Brown et al., "Drug-induced long QT syndrome: is HERG the root of all evil," Pharmaceutical News, 7(4):15-20, 2000.

Ennaceur et al., "A new one-trial test for neurobiological studies of memory in rats: I. Behavioral data," Behavioral Brain Research, Nov. 1988, 31(1):47-59.

Geyer et al., "Startle response models of sensorimotor gating and habituation deficits in schizophrenia", Brain Research Bulletin, Sep. 1990, 25(3):485-498.

Grayson et al., "Atypical antipsychotics attenuate a sub-chronic PCP-induced cognitive deficit in the novel object recognition task in the rat," Behavioral Brain Research, Nov. 2007, 184(1):31-38.

Idris et al., "Sertindole improves sub-chronic PCP-induced reversal learning and episodic memory deficits in rodents: involvement of 5-HT6 and 5-HT2A receptor mechanisms," Psychopharmacology, Jan. 2010, 208:23-36.

Jentsch et al., "The neuropsychopharmacology of phencyclidine: from NMDA receptor hypofunction to the dopamine hypothesis of schizophrenia," Neuropsychopharmacology, Mar. 1999, 20(3):201-225.

Mclean et al., "D1-like receptor activation improves PCP-induced cognitive deficits in animal models: Implications for mechanisms of improved cognitive function in schizophrenia," European Neuropsychopharmacology, Jun. 2009, 19(6):440-450.

Obach et al., The prediction of human pharmacokinetic parameters from preclinical and in vitro metabolism data, Journal of Pharmacology and Experimental Therapeutics, Oct. 1997, 283(1):46-58.

Redfern et al., "Relationships between preclinical cardiac electrophysiology, clinical QT interval prolongation and torsade de pointes for a broad range of drugs: evidence for a provisional safety margin in drug development," Cardiovascular Research, Apr. 2003, 58(1):32-45.

Snigdha et al., "Attenuation of Phencyclidine-Induced Object Recognition Deficits by the Combination of Atypical Antipsychotic Drugs and Pimavanserin (ACP 103), a 5-Hydroxytryptamine2A Receptor Inverse Agonist," Journal of Pharmacology and Experimental Therapeutics, Feb. 2010, 332(2):622-631.

Snigdha et al., "Improvement of phencyclidine-induced social behavior deficits in rats: Involvement of 5-HT1A receptors," Behavioral Brain Research, Aug. 2008, 191(1)26-31.

Snigdha et al., "Phencyclidine (PCP)-Induced Disruption in Cognitive Performance is Gender-Specific and Associated with A Reduction in Brain-Derived Neurotrophic Factor (BDNF) in Specific Regions of the Female rat Brain," Journal of Molecular Neuroscience, Mar. 2011, 43:337-345.

Song et al., "Targeting Gpr52 lowers mutant HTT levels and rescues Huntington's disease-associated phenotypes," Brain, Jun. 2018, 141(6):1782-98.

Sutcliffe et al., "Influence of gender on working and spatial memory in the novel object recognition task in the rat," Behavioral Brain Research, Feb. 2007, 177(1):117-25.

Wang et al., "Discovery of potent and brain-penetrant GPR52 agonist that suppresses psychostimulant behavior," J. Med. Chem., 2020, 63(22):13951-13972.

Weirich et al., "Rate-dependence of antiarrhythmic and proarrhythmic properties of class I and class III antiarrhythmic drugs," Basic Research in Cardiology, Oct. 1998, 93(Suppl 1):125-132.

Yap et al., "Arrhythmogenic mechanisms of non-sedating antihistamines," Clinical and Experimental Allergy, Jul. 1999, 29(Suppl 3):174-181.

* cited by examiner

GPR52 MODULATORS AND METHODS OF USE

This application is a National Stage Application under 35 U.S.C. § 371 and claims the benefit of International Application No. PCT/US2021/028394, filed Apr. 21, 2021, which claims priority to U.S. Application No. 63/013,862, filed Apr. 22, 2020.

BACKGROUND

Technical Field

The present disclosure generally relates to compounds of Formula (I), or a pharmaceutically acceptable salts thereof, and compositions comprising compounds of Formula (I), or a pharmaceutically acceptable salts thereof, that are useful in treating various neurological conditions.

Description of the Related Technology

G-protein coupled receptors (GPCRs) possess seven conserved membrane-spanning domains connecting at least eight cytoplasmic loops. The transmembrane regions are designated as TM1, TM2, TM3, TM4, TM5, TM6, and TM7. Most GPCRs contain potential phosphorylation sites within the third cytoplasmic loop and/or the carboxy terminus. GPCRs are critical components of many cell-signaling pathways. GPCRs are coupled to various enzymes, ion channels, and transporters. Different G-protein subunits may stimulate particular effectors to modulate various downstream functions in a cell.

Ligand binding causes a conformational change in a GPCR, allowing the GPCR to function as a guanine nucleotide exchange factor (GEF). The GPCR can then activate an associated G protein by exchanging the GDP bound to the G protein for GTP. This GTP, together with the α subunit of the G protein, then dissociate from the β and γ subunits to further modulate intracellular signaling pathways. GPR52 is an orphan GPCR that is highly expressed in the brain and also highly conserved in vertebrates. See Mol. Brain Res., Vol. 64, pp. 193-198 (1999). While GPR52 has been characterized, it remains an orphan receptor, that is, it has no known endogenous ligand. GPR52 is often co-localized with dopamine receptors (D1 and D2). See PLOS One, Vol. 9, No. 2, e90134. GPR52 modulators are proposed to improve the symptoms of various neurological conditions, diseases, and disorders (see e.g., U.S. Pat. Nos. 7,919,260 B2 and 9,676,758 B2). As such, GPR52 represents a potential target for treating various neurological diseases.

Despite the advances that have been made in this field, a need remains in the art for improved GPR52 modulator compounds, including compounds, compositions, and methods related thereto. The present disclosure fulfills these and other needs, as evident in reference to the following disclosure.

SUMMARY

Some embodiments provide a compound of Formula (I):

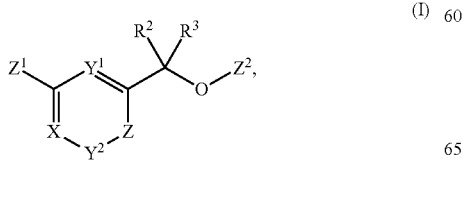

or a pharmaceutically acceptable salt thereof, wherein:
X, $Y^1$ and $Y^2$ are independently N (nitrogen) or CH;
Z is N or $CR^1$, where at least one of Z, X, $Y^1$ and $Y^2$ is N (nitrogen);
$Z^1$ is

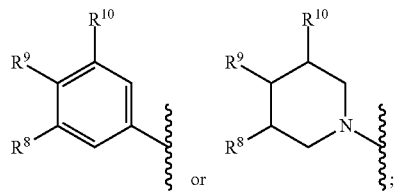

$Z^2$ is

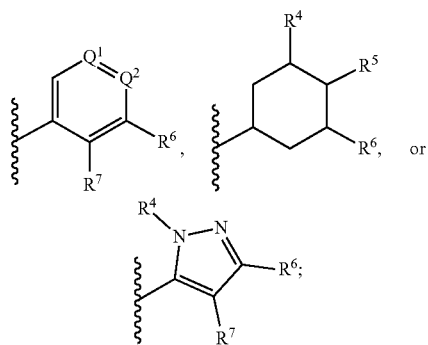

$Q^1$ is N (nitrogen) or $CR^4$;
$Q^2$ is N (nitrogen) or $CR^5$;
$R^1$ is hydrogen, halogen, $C_1$-$C_6$alkyl or halo$C_1$-$C_6$alkyl;
$R^2$ is hydrogen, halogen, $C_1$-$C_6$alkyl, halo$C_1$-$C_6$alkyl, or —$OR^A$;
$R^3$ is hydrogen, halogen, $C_1$-$C_6$alkyl, or halo$C_1$-$C_6$alkyl;
  i) $R^4$, $R^5$, $R^6$, and $R^7$, are independently hydrogen, halogen, —$(CH_2)_n$—CN, nitro, halo$C_1$-$C_6$alkyl, $C_3$-$C_8$cycloalkyl, —NHC(=O)$R^B$, —$OR^B$, —S(O)$_m R^B$, —$(CH_2)_m C(=O)R^B$, —S(O)$_p$N($R^B R^C$) or $C_1$-$C_6$alkyl optionally substituted with hydroxyl, or
  ii) $R^4$ and $R^5$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^6$, and $R^7$, are independently hydrogen, halogen, —$(CH_2)_n$—CN, nitro, $C_1$-$C_6$alkyl optionally substituted with hydroxyl, halo$C_1$-$C_6$alkyl, $C_3$-$C_8$cycloalkyl, —NHC(=O)$R^B$, —$OR^B$, —S(O)$_m R^B$, —$(CH_2)_m C(=O)R^B$ or —S(O)$_p$N($R^B R^C$), or
  iii) $R^5$ and $R^6$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^4$, and $R^7$, are independently hydrogen, halogen, —$(CH_2)_n$—CN, nitro, $C_1$-$C_6$alkyl optionally substituted with hydroxyl, halo$C_1$-$C_6$alkyl, $C_3$-$C_8$cycloalkyl, —NHC(=O)$R^B$, —$OR^B$, —S(O)$_m R^B$, —$(CH_2)_m C(=O)R^B$ or —S(O)$_p$N($R^B R^C$), or iv) $R^6$ and $R^7$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^4$, and $R^5$, are independently hydrogen, halogen, —$(CH_2)_n$—CN, nitro, $C_1$-$C_6$alkyl optionally substituted with hydroxyl, halo$C_1$-$C_6$alkyl, $C_3$-$C_8$cycloalkyl, —NHC(=O)$R^B$, —O$R^B$, —S(O)$_m R^B$, —$(CH_2)_m$C(=O)$R^B$ or —S(O)$_p$N($R^B R^C$);

one of $R^1$ and $R^9$ is —$(CH_2)_n$C(=O)N($R^E R^F$) and the other of $R^8$ and $R^9$ is hydrogen, halogen, $C_1$-$C_6$alkyl, halo$C_1$-$C_6$alkyl, —C(=O)$R^D$, or —O$R^E$, or $R^8$ and $R^9$ together with the carbon atom to which they are attached, form a 5-6 membered heterocyclyl group, said 5-6 membered heterocyclyl group optionally substituted with =O;

$R^{10}$ is hydrogen, halogen, $C_1$-$C_6$alkyl, halo$C_1$-$C_6$alkyl, —C(=O)$R^D$, or —O$R^E$.

each $R^A$, $R^B$, $R^C$, is independently hydrogen, $C_1$-$C_6$alkyl, or halo$C_1$-$C_6$alkyl;

each $R^D$ is independently $C_1$-$C_6$alkyl, halo$C_1$-$C_6$alkyl, —$NH_2$, or —NH($CH_2$)$_q$OH;

each $R^E$, and $R^F$, is independently hydrogen, $C_1$-$C_6$alkyl, or halo$C_1$-$C_6$alkyl, or $R^E$ and $R^F$, together with the nitrogen atom to which they are attached, form a 5-6 membered heterocyclyl group;

each m is independently 0, 1, 2 or 3;
each n is independently 0, 1, 2 or 3;
each p is independently 1 or 2; and
each q is independently 2, 3 or 4.

In some embodiments, the compound of Formula (I), or a pharmaceutically acceptable salt thereof, is a compound described in Table 2, or a pharmaceutically acceptable salt thereof. In some embodiments, the compound of Formula (I), or a pharmaceutically acceptable salt thereof, is a compound of Formula (Ia), Formula (Ib), Formula (Ic), or Formula (Id), or a pharmaceutically acceptable salt of any of the foregoing.

Some embodiments provide a pharmaceutical product selected from: a pharmaceutical composition, a formulation, a unit dosage form, and a kit; each comprising a compound of Formula (I), or a pharmaceutically acceptable salt thereof.

Some embodiments provide a pharmaceutical composition comprising a compound of Formula (I), or a pharmaceutically acceptable salt thereof, and at least one pharmaceutically acceptable excipient.

Some embodiments provide a method of modulating an activity of a G protein-coupled receptor (e.g., GPR52) comprising contacting the receptor with a compound of Formula (I), or a pharmaceutically acceptable salt thereof.

Some embodiments provide a method of treating a disease or disorder associated with abnormal expression and/or activity of a G protein-coupled receptor (e.g., GPR52) in a patient, comprising administering to the patient a therapeutically effective amount of a compound of Formula (I), or a pharmaceutically acceptable salt thereof.

Some embodiments provide a method of treating a neurological disorder, comprising administering to a subject in need thereof an effective amount of a compound of Formula (I), or a pharmaceutically acceptable salt thereof; wherein the neurological disorder is selected from the group consisting of: schizophrenia, cognitive impairment, a panic disorder, a phobic disorder, drug-induced psychotic disorder, delusional psychosis, neuroleptic-induced dyskinesia, Parkinson's disease, drug-induced Parkinson's syndrome, extrapyramidal syndrome, Alzheimer's Disease, Lewy Body Dementia, bipolar disorder, ADHD, Tourette's syndrome, an extrapyramidal or movement disorder, a motor disorder, a hyperkinetic movement disorder, a psychotic disorder, catatonia, a mood disorder, a depressive disorder, an anxiety disorder, obsessive-compulsive disorder (OCD), an autism spectrum disorder, a prolactin-related disorder (e.g., hyperprolactinemia), a neurocognitive disorder, a trauma- or stressor-related disorder (e.g., PTSD); a disruptive, impulse-control, or conduct disorder, a sleep-wake disorder, a substance-related disorder, an addictive disorder, a behavioral disorder, hypofrontality, an abnormality in the tuberoinfundibular, mesolimbic, mesocortical, or nigrostriatal pathway, decreased activity in the striatum, cortical dysfunction, neurocognitive dysfunction and the cognitive deficits associated with schizophrenia; Parkinson's Disease, drug induced Parkinsonism, dyskinesias, dystonia, chorea, levodopa induced dyskinesia, cerebral palsy and progressive supranuclear palsy, and Huntington's disease, including chorea associated with Huntington's disease.

Some embodiments provide a method of ameliorating one or more symptoms of a neurological disorder, comprising administering to a subject in need thereof an effective amount of a compound of Formula (I), or a pharmaceutically acceptable salt thereof; wherein the neurological disorder is selected from the group consisting of: schizophrenia, cognitive impairment, a panic disorder, a phobic disorder, drug-induced psychotic disorder, delusional psychosis, neuroleptic-induced dyskinesia, Parkinson's disease, drug-induced Parkinson's syndrome, extrapyramidal syndrome, Alzheimer's Disease, Lewy Body Dementia, bipolar disorder, ADHD, Tourette's syndrome, an extrapyramidal or movement disorder, a motor disorder, a hyperkinetic movement disorder, a psychotic disorder, catatonia, a mood disorder, a depressive disorder, an anxiety disorder, obsessive-compulsive disorder (OCD), an autism spectrum disorder, a prolactin-related disorder (e.g., hyperprolactinemia), a neurocognitive disorder, a trauma- or stressor-related disorder (e.g., PTSD); a disruptive, impulse-control, or conduct disorder, a sleep-wake disorder, a substance-related disorder, an addictive disorder, a behavioral disorder, hypofrontality, an abnormality in the tuberoinfundibular, mesolimbic, mesocortical, or nigrostriatal pathway, decreased activity in the striatum, cortical dysfunction, neurocognitive dysfunction and the cognitive deficits associated with schizophrenia; Parkinson's Disease, drug induced Parkinsonism, dyskinesias, dystonia, chorea, levodopa induced dyskinesia, cerebral palsy and progressive supranuclear palsy, and Huntington's disease, including chorea associated with Huntington's disease.

DETAILED DESCRIPTION

Definitions

For clarity and consistency, the following definitions will be used throughout this patent document.

As used herein, "about" means ±20% of the stated value, and includes more specifically values of ±10%, ±5%, ±2% and ±1% of the stated value.

As used herein, "administering" refers to providing a compound described herein or other therapy to a subject in a form that can be introduced into that subject's body in a therapeutically useful form and therapeutically useful amount, including, but not limited to: oral dosage forms, such as, tablets, capsules, syrups, suspensions, and the like;

injectable dosage forms, such as, IV, IM, IP, and the like; transdermal dosage forms, including creams, jellies, powders, and patches; buccal dosage forms; inhalation powders, sprays, suspensions, and the like; and rectal suppositories.

A health care practitioner can directly provide a compound described herein to a subject in the form of a sample or can indirectly provide a compound to a subject by providing an oral or written prescription for the compound. Also, for example, a subject can obtain a compound by themselves without the involvement of a health care practitioner. When the compound is administered to the subject, the body is transformed by the compound in some way. When a compound described herein is provided in combination with one or more other agents, "administration" is understood to include the compound and other agents are administered at the same time or at different times. When the agents of a combination are administered at the same time, they can be administered together in a single composition or they can be administered separately. The preferred method of administration can vary depending on various factors, e.g., the components of the pharmaceutical formulation, the site of the disease, and the severity of the disease.

The term "composition" refers to a compound or crystalline form thereof, including but not limited to, salts, solvates, and hydrates of a compound described herein, in combination with at least one additional component, such as, a composition obtained/prepared during synthesis, preformulation, in-process testing (e.g., TLC, HPLC, NMR samples), and the like.

The term, "compound," as used herein is meant to include all stereoisomers, geometric isomers, tautomers and isotopes of the structures depicted. The term is also meant to refer to compounds described herein, regardless of how they are prepared, e.g., synthetically, through biological process (e.g., metabolism or enzyme conversion), or a combination thereof. All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds can be in any solid state form, such as a polymorph or solvate, so unless clearly indicated otherwise, reference in the specification to compounds and salts thereof should be understood as encompassing any solid state form of the compound. In some embodiments, the compounds described herein, or salts thereof, are substantially isolated. By "substantially isolated" is meant that the compound is at least partially or substantially separated from the environment in which it was formed or detected. Partial separation can include, e.g., a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salts thereof.

The term "hydrate" as used herein refers to a compound described herein or a salt thereof that further includes a stoichiometric or non-stoichiometric amount of water bound by non-covalent intermolecular forces.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that a subject or animal requires or will benefit from treatment. This judgment is made based on a variety of factors that are in the realm of a caregiver's expertise, but that includes the knowledge that the subject or animal is ill, or will become ill, as the result of a disease, condition or disorder that is treatable by the compound described herein. Accordingly, the compound described herein can be used in a protective or preventive manner; or compound described herein can be used to alleviate, inhibit, or ameliorate the disease, condition, or disorder.

The term "subject" refers to any animal, including mammals, such as, mice, rats, other rodents, rabbits, dogs, cats, swine, cattle, sheep, horses, primates, and humans. In the context of a clinical trial or screening or activity experiment the subject can be a healthy volunteer or healthy participant without an underlying GPR52 mediated disorder or condition or a volunteer or participant that has received a diagnosis for a disorder or condition in need of medical treatment as determined by a health care professional. In the context outside of a clinical trial a subject under the care of a health care professional who has received a diagnosis for a disorder or condition is typically described as a subject.

The term "pediatric subject" refers to a subject under the age of 21 years at the time of diagnosis or treatment. The term "pediatric" can be further divided into various sub-populations including: neonates (from birth through the first month of life); infants (1 month up to two years of age); children (two years of age up to 12 years of age); and adolescents (12 years of age through 21 years of age (up to, but not including, the twenty-second birthday)) see e.g., Berhman et al., *Textbook of Pediatrics,* 15th Ed. Philadelphia: W.B. Saunders Company, 1996; Rudolph et al., *Rudolph's Pediatrics,* 21st Ed. New York: McGraw-Hill, 2002; and Avery et al., *Pediatric Medicine,* 2nd Ed. Baltimore: Williams & Wilkins; 1994.

The phrase "pharmaceutically acceptable" refers to compounds (and salts thereof), compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutical composition" refers to a specific composition comprising at least one active ingredient; including but not limited to, salts, solvates, and hydrates of compounds described herein, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The terms "prevent", "preventing", and "prevention" refer to the elimination or reduction of the occurrence or onset of one or more symptoms associated with a particular disorder. For example, the terms "prevent", "preventing", and "prevention" can refer to the administration of therapy on a prophylactic or preventative basis to a subject who may ultimately manifest at least one symptom of a disorder but who has not yet done so. Such subjects can be identified on the basis of risk factors that are known to correlate with the subsequent occurrence of the disease, such as the presence of a biomarker. Alternatively, prevention therapy can be administered as a prophylactic measure without prior identification of a risk factor. Delaying the onset of the at least one episode and/or symptom of a disorder can also be considered prevention or prophylaxis.

The term "solvate" as used herein refers to a solid-state form of a compound described herein, or a pharmaceutically acceptable salt thereof which includes a stoichiometric or non-stoichiometric amount of a solvent bound by non-covalent intermolecular forces. When the solvent is water, the solvate is a hydrate.

The terms "treat", "treating", and "treatment" refer to medical management of a disease, disorder, or condition of a subject (e.g., subject) (see, e.g., Stedman's Medical Dictionary). In general, an appropriate dose and treatment regimen provide the GPR52 agonist in an amount sufficient to provide therapeutic benefit. Therapeutic benefit for subjects to whom the GPR52 agonist compound(s) described herein are administered, includes, for example, an improved clinical outcome, wherein the object is to prevent or slow or retard (lessen) an undesired physiological change associated with the disease, or to prevent or slow or retard (lessen) the expansion or severity of such disease. The effectiveness of one or more GPR52 agonists may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival.

The term "therapeutically effective amount" refers to the amount of the compound described herein, or a pharmaceutically acceptable salt thereof, or an amount of a pharmaceutical composition comprising the compound described herein or a pharmaceutically acceptable salt thereof, that elicits the biological or medicinal response in a tissue, system, animal, or human that is being sought by a subject, researcher, veterinarian, medical doctor, or other clinician or caregiver, which can include one or more of the following:

(1) preventing the disorder, for example, preventing a disease, condition, or disorder in a subject who can be predisposed to the disease, condition, or disorder but does not yet experience or display the relevant pathology or symptomatology;

(2) inhibiting the disorder, for example, inhibiting a disease, condition, or disorder in a subject who is experiencing or displaying the relevant pathology or symptomatology (i.e., arresting further development of the pathology and/or symptomatology); and (3) ameliorating the disorder, for example, ameliorating a disease, condition, or disorder in a subject who is experiencing or displaying the relevant pathology or symptomatology (i.e., reversing the pathology and/or symptomatology).

As used herein, the term "contacting" refers to the bringing together of indicated moieties in an in vitro system or an in vivo system. For example, "contacting" GPR52 with a compound provided herein includes the administration of a compound provided herein (or a pharmaceutically acceptable salt thereof) to a subject, such as a human, having a GPR52 protein, as well as, for example, introducing a compound provided herein into a sample containing a cellular or purified preparation containing the GPR52 protein.

Chemical Groups

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

The term "n-membered" where n is an integer typically describes the number of ring-forming atoms in a moiety where the number of ring-forming atoms is n. For example, piperidinyl is an example of a 6-membered heterocyclyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of Formula (I), and pharmaceutically acceptable salts thereof, in which a variable appears more than once, each variable can be a different moiety independently selected from the group defining the variable. For example, where a structure is described having two R groups that are simultaneously present on the same compound, the two R groups can represent different moieties independently selected from the group defined for R.

Whenever a group is described as being "optionally substituted" that group can be unsubstituted, or can be substituted with one or more of the indicated substituents. Likewise, when a group is described as being "unsubstituted or substituted" if substituted, the substituent(s) can be selected from one or more of the indicated substituents. It is to be understood that substitution at a given atom is limited by valency.

As used herein, "$C_a$-$C_b$" in which "a" and "b" are integers refer to the number of carbon atoms in an alkyl, alkenyl, or alkynyl group, or the number of carbon atoms in the ring of a cycloalkyl, cycloalkenyl, or aryl group. That is, these groups can contain from "a" to "b", inclusive, carbon atoms. Thus, for example, a "$C_1$-$C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$, $CH_3CH_2CH(CH_3)$ and $(CH_3)_3C$—. If no "a" and "b" are designated with regard to an alkyl, alkenyl, alkynyl, cycloalkyl, cycloalkenyl, or aryl group, the broadest range described in these definitions is to be assumed.

In addition to the foregoing, as used in the specification and appended claims, unless specified to the contrary, the following terms have the meaning indicated:

The term "amino" refers to the group —$NH_2$.

The term "alkylamino" refers to a group of formula —NH(alkyl), where alkyl is as defined herein. Example alkylamino groups include methylamino, ethylamino, propylamino (e.g., n-propylamino and iso-propylamino), and the like.

The term "dialkylamino" refers to a group of formula —N(alkyl)$_2$, where alkyl is as defined herein. Example dialkylamino groups include dimethylamino, diethylamino, di-n-propylamino, di-iso-propylamino), and the like.

The term "alkenyl" refers to an alkyl group that contains in the straight or branched hydrocarbon chain one or more double bonds. Examples of alkenyl groups include allenyl, vinylmethyl, and ethenyl. In some embodiments, an alkenyl group can be unsubstituted or substituted. In some embodiments, the alkenyl group can have 2 to 6 carbon atoms. The alkenyl group of the compounds can be designated as "$C_2$-$C_6$ alkenyl" or similar designations.

The term "alkynyl" refers to an alkyl group that contains in the straight or branched hydrocarbon chain one or more triple bonds. Examples of alkynyls include ethynyl and propynyl. An alkynyl group can be unsubstituted or substituted. In some embodiments, an alkynyl group can be unsubstituted or substituted. In some embodiments, the alkynyl group can have 2 to 6 carbon atoms. The alkenyl group of the compounds can be designated as "$C_2$-$C_6$ alkynyl" or similar designations.

The term "aryl" refers to an aromatic ring system containing 6, 10 or 14 carbon atoms that can contain a single ring, two fused rings or three fused rings, such as phenyl, naphthalenyl and phenanthrenyl. In some embodiments, the aryl group can have 6 or 10 carbon atoms (i.e., $C_6$ or $C_{10}$ aryl). When one or more substituents are present on the "aryl" ring, the substituent(s) can be bonded at any available ring carbon. In some embodiments, an aryl group can be substituted or unsubstituted.

The term "alkyl" refers to a fully saturated straight or branched hydrocarbon radical. The alkyl group can have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms. In some embodiments, the alkyl group can have 1 to 6 carbons (i.e., "$C_1$-$C_6$ alkyl"). Some embodiments are 1 to 5 carbons (i.e., $C_1$-$C_5$ alkyl), some embodiments are 1 to 4 carbons (i.e., $C_1$-$C_4$ alkyl), some embodiments are 1 to 3 carbons (i.e., $C_1$-$C_3$ alkyl), and some embodiments are 1 or 2 carbons. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Examples of an alkyl group include: methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH($CH_3$)$CH_2CH_2CH_3$], 2-methylbutyl [i.e., —$CH_2CH(CH_3$)$CH_2CH_3$], n-hexyl and the like. When one or more substituents are present on the alkyl group, the substituent(s) can be bonded at any available carbon atom. In some embodiments, an alkyl group can be substituted or unsubstituted.

The term "haloalkyl" refers to an alkyl group, as defined herein, wherein one or more hydrogen atoms of the alkyl group have been replaced by a halogen atom (e.g., mono-haloalkyl, di-haloalkyl, and tri-haloalkyl). In some embodiments, the haloalkyl group can have 1 to 6 carbons (i.e., "halo$C_1$-$C_6$ alkyl"). The halo$C_1$-$C_6$ alkyl can be fully substituted in which case it can be represented by the formula $C_nL_{2n+1}$, wherein L is a halogen and "n" is 1, 2, 3, 4, 5, or 6. When more than one halogen is present then they can be the same or different and selected from: fluorine, chlorine, bromine, and iodine. In some embodiments, haloalkyl contains 1 to 5 carbons (i.e., halo$C_1$-$C_5$ alkyl). In some embodiments, haloalkyl contains 1 to 4 carbons (i.e., halo$C_1$-$C_4$ alkyl). In some embodiments, haloalkyl contains 1 to 3 carbons (i.e., halo$C_1$-$C_3$ alkyl). In some embodiments, haloalkyl contains 1 or 2 carbons. Examples of haloalkyl groups include fluoromethyl, difluoromethyl, trifluoromethyl, chlorodifluoromethyl, 1-fluoroethyl, 2,2,2-trifluoroethyl, pentafluoroethyl, 4,4,4-trifluorobutyl, and the like.

The term "carbonyl" refers to the group —C(=O)—.

The term "oxo" refers to the =O substituent.

The term "cycloalkyl" refers to a fully saturated all carbon mono- or multi-cyclic ring system. In some embodiments, the cycloalkyl is a monocyclic ring containing 3 to 7 carbon atoms (i.e., "$C_3$-$C_7$ cycloalkyl"). Some embodiments contain 3 to 6 carbons. Some embodiments contain 3 to 5 carbons. Some embodiments contain 5 to 7 carbons. Some embodiments contain 3 to 4 carbons. Examples include cyclopropyl, cyclobutyl, cyclopentyl, and cyclohexyl. When one or more substituents are present on the alkyl group, the substituent(s) can be bonded at any available carbon atom. In some embodiments, a cycloalkyl group can be substituted or unsubstituted.

The term "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (i.e., an aromatic system), otherwise the group would be "aryl," as defined herein. When composed of two or more rings, the rings can be connected together in a fused, bridged, or spiro fashion. A cycloalkenyl can contain 3 to 12 atoms in the ring(s) or 3 to 8 atoms in the ring(s). In some embodiments, a cycloalkenyl group can be unsubstituted or substituted. In some embodiments, the cycloalkenyl group may have 4 to 8 carbon atoms (i.e., "$C_4$-$C_8$ cycloalkenyl"). An example is cyclohexenyl.

The term "heteroaryl" refers to an monocyclic or fused multicyclic aromatic ring system and having at least one heteroatom in the ring system, that is, an element other than carbon, including but not limited to, nitrogen, oxygen and sulfur. Some embodiments are "5-6 membered heteroaryl" and refers to an aromatic ring containing 5 to 6 ring atoms in a single ring and having at least one heteroatom in the ring system. Examples of heteroaryl rings include, but are not limited to, pyridyl, pyrimidinyl, pyrazinyl, pyridazinyl, triazinyl, furyl, quinolyl, isoquinolyl, thienyl, imidazolyl, thiazolyl, indolyl, isoindolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, dibenzo[b,d]furan, dibenzo[b,d]thiophene, phenanthridinyl, benzimidazolyl, pyrrolyl, quinolinyl, isoquinolinyl, benzisoxazolyl, imidazo[1,2-b]thiazolyl, and the like. A heteroaryl group can be substituted or unsubstituted. In some embodiments, the heteroaryl group has 5 to 10 ring members or 5 to 7 ring members. The heteroaryl group can be designated as "5-7 membered heteroaryl," "5-10 membered heteroaryl," or similar designations. In some embodiments, the heteroaryl can be a substituted or unsubstituted $C_1$-$C_{13}$ five-, six-, seven-, eight-, nine-, ten-, up to 14-membered monocyclic, bicyclic, or tricyclic ring system including 1 to 5 heteroatoms selected from nitrogen, oxygen and sulfur. In some embodiments, the heteroaryl can be a substituted or unsubstituted $C_1$-$C_5$ five- or six-membered monocyclic ring including 1 to 5 heteroatoms selected from nitrogen, oxygen and sulfur. In some embodiments, the heteroaryl can be a substituted or unsubstituted $C_5$-$C_9$ eight-, nine- or ten-membered bicyclic ring system including 1 to 5 heteroatoms selected from nitrogen, oxygen and sulfur. In some embodiments, the heteroaryl is a substituted or unsubstituted $C_5$-$C_9$ eight-, nine- or ten-membered heteroaryl. In some embodiments, the $C_5$-$C_9$ eight-, nine- or ten-membered bicyclic heteroaryl is imidazo[2,1-b]thiazolyl, 1H-indolyl, isoindolyl, benzofuranyl, benzothienyl, benzimidazolyl, benzisoxazolyl, indazolyl, purinyl, quinolinyl, isoquinolinyl, quinoxalinyl, pyrido[3,4-b]pyrazinyl or pyrido[4,3-d]pyrimidinyl. In some embodiments, the heteroaryl is a substituted or unsubstituted $C_8$-$C_{13}$ 13- or 14-membered tricyclic ring system including 1 to 5 heteroatoms selected from nitrogen, oxygen and sulfur. In some embodiments, the heteroaryl can be an azolyl such as imidazolyl, pyrazolyl, 1,2,3-triazolyl, 1,2,4-triazolyl, tetrazolyl, 1,2,4-thiadiazolyl, thiazolyl, isothiazolyl, oxazolyl, or isoxazolyl, each of which can be substituted or unsubstituted. In some embodiments, the heteroaryl is a $C_1$-$C_{13}$ 5-membered heteroaryl. In some embodiments, the $C_1$-$C_4$ 5-membered heteroaryl is furanyl, thienyl, 1,2,4-thiadiazolyl, 1,2,3-thiadiazolyl, isothiazolyl, thiazolyl, imidazolyl, pyrazolyl, isoxazolyl, oxazolyl, pyrrolyl, triazolyl, tetrazolyl. In some embodiments, the heteroaryl is a $C_3$-$C_5$ 6-membered heteroaryl. In some embodiments, the $C_3$-$C_5$ 6-membered heteroaryl is pyridinyl, pyrimidinyl, pyrazinyl, pyridazinyl, or triazinyl. In some embodiments, "5-10 membered heteroaryl" refers to: furanyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, quinoxalinyl, triazinyl, benzofuranyl, 1H-indolyl, benzo[b]thiophenyl, and the like. In some embodiments, "5-10 membered heteroaryl" refers to: pyrazinyl, pyridazinyl, pyridinyl, pyrimidinyl, 1H-indolyl, quinoxalinyl, thiadiazolyl, and the like. In some embodiments, a heteroaryl group can be substituted or unsubstituted.

The term "heterocyclyl" refers to a three-, four-, five-, six-, seven-, eight-, nine-, ten-, up to 18-membered monocyclic, bicyclic, and tricyclic ring system wherein carbon atoms together with from 1 to 5 heteroatoms constitute said ring system and optionally containing one or more unsaturated bonds situated in such a way, however, that a fully delocalized pi-electron system (aromatic system) does not occur in the monocyclic ring or in at least one ring of the bicyclic or tricyclic ring system. The heteroatom(s) is an element other than carbon including, but not limited to, oxygen, sulfur, and nitrogen. When composed of two or more rings, the rings can be joined together in a fused, bridged, or spiro fashion where the heteroatom(s) can be present in either a non-aromatic or aromatic ring in the ring system. In some embodiments, the heterocyclyl can be a 3-7 membered saturated non-aromatic ring system containing 3 to 7 ring atoms, where at least one ring atom is a heteroatom. In some embodiments, "3-6 membered heterocyclyl" refers to a saturated non-aromatic ring radical containing 3 to 6 ring atoms, where at least one ring atom is a heteroatom. In some embodiments, "4-6 membered heterocyclyl" refers to a saturated non-aromatic ring radical containing 4 to 6 ring atoms, where at least one ring atom is a heteroatom. In some embodiments, the one or two heteroatoms in the ring system are selected independently from: O (oxygen) and N (nitrogen). In some embodiments, a heterocyclyl can include a carbonyl (C=O) group adjacent to a hetero atom, that is, be substituted with an oxo on a carbon adjacent to a hetero atom, where the substituted ring system is a lactam, lactone, cyclic imide, cyclic thioimide or cyclic carbamate. Examples of unsubstituted or oxo substituted "heterocyclyl" groups include but are not limited to, aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,4-dioxolanyl, 1,3-oxathianyl, 1,4-oxathiinyl, 1,3-oxathiolanyl, 1,3-dithiolyl, 1,3-dithiolanyl, 1,4-oxathianyl, tetrahydro-1,4-thiazinyl, 2H-1,2-oxazinyl, maleimidyl, succinimidyl, dioxopiperazinyl, hydantoinyl, imidazolinyl, imidazolidinyl, isoxazolinyl, isoxazolidinyl, isoindolinyl, indolinyl, oxazolinyl, oxazolidinyl, oxazolidinonyl, thiazolinyl, thiazolidinyl, morpholinyl, oxiranyl, piperidinyl N-oxide, piperidinyl, piperazinyl, pyrrolidinyl, pyrrolidonyl, pyrrolidionyl, 4-piperidonyl, pyrazolinyl, pyrazolidinyl, 2-oxopyrrolidinyl, tetrahydropyranyl, 4H-pyranyl, tetrahydrothiopyranyl, 1,4-diazabicyclo[2.2.2]octane, 1,4-diazabicyclo[3.1.1]heptane, 2-azaspiro[3,3]heptane, 2,6-diazaspiro[3,3]heptane, 2-oxa-6-azaspiro[3,3]heptane, and their benzo-fused analogs (e.g., benzimidazolidinonyl, tetrahydroquinolinyl, and 3,4-methylenedioxyphenyl). The heterocyclyl group can be designated as "3-10 membered heterocyclyl" or similar designations. In some embodiments, the heterocyclyl can be a $C_2$-$C_{12}$ three-, four-, five-, six-, seven-, eight-, nine-, ten-, up to 13-membered monocyclic, bicyclic, or tricyclic ring system including 1 to 5 heteroatoms selected from nitrogen, oxygen and sulfur. In some embodiments, the heterocyclyl can be a substituted or unsubstituted $C_2$-$C_6$ three-, four-, five-, six-, or seven-membered monocyclic ring including 1 to 5 heteroatoms selected from nitrogen, oxygen and sulfur. In some embodiments, the heterocyclyl can be a substituted or unsubstituted $C_2$-$C_{10}$ four-, five-, six-, seven-, eight-, nine-, ten- or eleven-membered bicyclic ring system including 1 to 5 heteroatoms selected from nitrogen, oxygen and sulfur. In some embodiments, the heterocyclyl can be a substituted or unsubstituted $C_7$-$C_{12}$ 12- or 13-membered tricyclic ring system including 1 to 5 heteroatoms selected from nitrogen, oxygen and sulfur. In some embodiments, the heteroatom(s) of six membered monocyclic heterocyclyls are selected from one up to three of O (oxygen), N (nitrogen) or S (sulfur), and the heteroatom(s) of five membered monocyclic heterocyclyls are selected from one or two heteroatoms selected from O (oxygen), N (nitrogen) or S (sulfur). In some embodiments, the heterocyclyl can be aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,3-oxathianyl, 1,4-oxathianyl, 1,3-oxathiolanyl, 1,3-dithiolyl, 1,3-dithiolanyl, 1,4-oxathianyl, tetrahydro-1,4-thiazinyl, imidazolinyl, imidazolidinyl, isoxazolinyl, isoxazolidinyl, isoindolinyl, indolinyl, oxazolinyl, oxazolidinyl, thiazolinyl, thiazolidinyl, morpholinyl, oxiranyl, piperidinyl, piperazinyl, pyrrolidinyl, pyrazolinyl, pyrazolidinyl, tetrahydropyranyl, tetrahydrothiopyranyl, 1,4-diazabicyclo[2.2.2]octane, 1,4-diazabicyclo[3.1.1]heptane, 2-azaspiro[3,3]heptane, 2,6-diazaspiro[3,3]heptane, tetrahydroquinolinyl, 1,2,3,4-tetrahydroisoquinolinyl, 1,2,3,4-tetrahydro-2,6-naphthyridinyl, 1,2,3,4-tetrahydro-2,7-naphthyridinyl, 1,2,3,4-tetrahydro-1,7-naphthyridinyl, 1,2,3,4-tetrahydro-1,6-naphthyridinyl, 5,6,7,8-tetrahydropyrido[2,3-d]pyrimidinyl, 5,6,7,8-tetrahydropyrido[3,4-d]pyrimidinyl, [1,3]dioxolo[4,5-c]pyridinyl, [1,3]dioxolo[4,5-b]pyridinyl, [1,3]dioxolo[4,5-d]pyrimidinyl or 3,4-methylenedioxyphenyl. In some embodiments, the unsubstituted or substituted heterocyclyl can be selected from aziridinyl, azetidinyl, piperidinyl, morpholinyl, oxetanyl, piperazinyl, pyrrolidinyl, thiomorpholinyl, 2-piperidone, 1,1-dioxidothiomorpholinyl, oxolanyl (tetrahydrofuranyl), and oxanyl (tetrahydropyranyl). When one or more substituents are present on the heterocyclyl group, the substituent(s) can be bonded at any available carbon atom and/or heteroatom. In some embodiments, a heterocyclyl group can be substituted or unsubstituted.

The term "alkoxy" refers to the formula —OR wherein R is an alkyl defined herein. A non-limiting list of alkoxys are methoxy, ethoxy, n-propoxy, 1-methylethoxy (iso-propoxy), n-butoxy, iso-butoxy, sec-butoxy, and tert-butoxy. The alkoxy group of the compounds can be designated as "$C_1$-$C_6$ alkoxy" or similar designations. In some embodiments, an alkoxy can be substituted or unsubstituted.

The term "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. In some embodiments, the haloalkoxy group may have 1 to 6 carbon atoms. The haloalkoxy group of the compounds can be designated as "halo$C_1$-$C_6$ alkoxy" or similar designations.

The term "cyano" refers to the group —CN.

The term "halogen" or "halo" refers to fluoro, chloro, bromo, or iodo group. In some embodiments, halogen or halo is fluoro, chloro, or bromo. In some embodiments, halogen or halo is fluoro or chloro. In some embodiments, halogen or halo is fluoro.

A "C-amido" group refers to a "C(=O)N($R^A R^B$)" group that is connected to the rest of the molecule via a carbon atom, and in which $R^A$ and $R^B$ can be independently hydrogen, $C_1$-$C_6$ alkyl, $C_2$-$C_6$ alkenyl, $C_2$-$C_6$ alkynyl, $C_3$-$C_7$ cycloalkyl, $C_5$-$C_8$ cycloalkenyl, $C_6$ or $C_{10}$ aryl, heteroaryl, or heterocyclyl.

An "N-amido" group refers to a "RC(=O)N($R^A$)—" group that is connected to the rest of the molecule via a nitrogen atom, and in which R and $R^A$ can be independently hydrogen, $C_1$-$C_6$ alkyl, $C_2$-$C_6$ alkenyl, $C_2$-$C_6$ alkynyl, $C_3$-$C_7$ cycloalkyl, $C_5$-$C_8$ cycloalkenyl, $C_6$ or $C_{10}$ aryl, heteroaryl, or heterocyclyl.

The term "hydroxyalkyl" refers to an alkyl group in which one or more of the hydrogen atoms are replaced by a hydroxy group. In some embodiments, the hydroxyalkyl group may have 1 to 6 carbon atoms (i.e., "hydroxy$C_1$-$C_6$ alkyl"). Exemplary hydroxyalkyl groups include, but are not limited to, 2-hydroxyethyl, 3-hydroxypropyl, 2-hydroxypropyl, and 2,2-dihydroxyethyl.

The term "hydroxy" refers to a —OH group.

The term "nitro" refers to a —$NO_2$ group.

As used herein, an "excipient" refers to a substance that is added to a composition to provide, without limitation, bulk, consistency, stability, binding ability, lubrication, disintegrating ability, etc., to the composition. A "diluent" is a type of excipient and refers to an ingredient in a pharmaceutical composition that lacks pharmacological activity but can be pharmaceutically necessary or desirable. For example, a diluent can be used to increase the bulk of a potent drug whose mass is too small for manufacture and/or administration. It may also be a liquid for the dissolution of a drug to be administered by injection, ingestion, or inhalation. A pharmaceutically acceptable excipient is a physiologically and pharmaceutically suitable non-toxic and inactive material or ingredient that does not interfere with the activity of the drug substance. Pharmaceutically acceptable excipients are well known in the pharmaceutical art and described, for example, in Rowe et al., *Handbook of Pharmaceutical Excipients: A Comprehensive Guide to Uses, Properties, and Safety*, 5th Ed., 2006, and in *Remington: The Science and Practice of Pharmacy* (Gennaro, 21st Ed. Mack Pub. Co., Easton, PA (2005)). Preservatives, stabilizers, dyes, buffers, and the like can be provided in the pharmaceutical composition. In addition, antioxidants and suspending agents may also be used. For compositions formulated as liquid solutions, acceptable carriers and/or diluents include saline and sterile water, and may optionally include antioxidants, buffers, bacteriostats and other common additives. In some embodiments, the diluents can be a buffered aqueous solution such as, without limitation, phosphate buffered saline. The compositions can also be formulated as capsules, granules, or tablets which contain, in addition to a compound as disclosed and described herein, diluents, dispersing and surface-active agents, binders, and lubricants. One skilled in this art may further formulate a compound as disclosed and described herein in an appropriate manner, and in accordance with accepted practices, such as those disclosed in Remington, supra.

As used herein, a "dose" or "dosage" refers to the measured quantity of drug substance to be taken at one time by a subject. In certain embodiments, wherein the drug substance is not a free base or free acid, the quantity is the molar equivalent to the corresponding amount of free base or free acid.

As used herein, a "pharmaceutically acceptable salt" refers to salts of a compound having an acidic or basic moiety which are not biologically or otherwise undesirable for use in a pharmaceutical. In many cases, the compounds disclosed herein are capable of forming acid and/or base salts by virtue of the presence of an acidic or basic moiety (e.g. amino and/or carboxyl groups or groups similar thereto). Pharmaceutically acceptable acid addition salts can be formed by combining a compound having a basic moiety with inorganic acids and organic acids. Inorganic acids which can be used to prepare salts include, for example, hydrochloric acid, hydrobromic acid, sulfuric acid, nitric acid, phosphoric acid, and the like. Organic acids which can be used to prepare salts include, for example, methanesulfonic acid, ethanesulfonic acid, p-toluenesulfonic acid, and the like. Pharmaceutically acceptable base addition salts can be formed by combining a compound having an acidic moiety with inorganic and organic bases. Inorganic bases which can be used to prepare salts include, for example, sodium, potassium, lithium, ammonium, calcium, magnesium, iron, zinc, manganese, aluminum hydroxides, carbonates, bicarbonates, phosphates, and the like.

In some embodiments, the inorganic base salt is ammonium, potassium, sodium, calcium, and magnesium hydroxides, carbonates, bicarbonates, or phosphates. Organic bases from which can be used to prepare salts include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Generally, such salts can be prepared by reacting the free acid or base forms of these compounds with at least a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN). Lists of suitable salts are found in WO 87/05297; Johnston et al., published Sep. 11, 1987; Remington's Pharmaceutical Sciences, 17th ed., Mack Publishing Company, Easton, Pa., 1985, p. 1418; and *J. Pharm. Sci.,* 66, 2 (1977); each of which is incorporated herein by reference in its entirety. A reference for the preparation and selection of pharmaceutical salts of the present disclosure is P. H. Stahl & C. G. Wermuth, *Handbook of Pharmaceutical Salts*, Verlag Helvetica Chimica Acta, Zurich, 2002 which is incorporated herein by reference in its entirety.

The compounds described herein can be asymmetric (e.g., having one or more stereocenters). All stereoisomers, such as enantiomers and diastereomers, are intended unless otherwise indicated. It is understood that, in any compound described herein having one or more chiral centers, if an absolute stereochemistry is not expressly indicated, then each center may independently be the (R)-configuration, or the (S)-configuration, or a mixture thereof. Thus, the compounds provided herein can be enantiomerically pure, enantiomerically enriched, a racemic mixture, diastereomerically pure, diastereomerically enriched, or a stereoisomeric mixture.

Preparation of enantiomerically pure or enantiomerically enriched forms can be accomplished by resolution of racemic mixtures or by using enantiomerically pure or enriched starting materials or by stereoselective or stereospecific synthesis. Stereochemical definitions are available in E. L. Eliel, S. H. Wilen & L. N. Mander, *Stereochemistry of Organic Compounds*, John Wiley & Sons, Inc., New York, NY, 1994 which is incorporated herein by reference in its entirety. In some embodiments, where the compound described herein is chiral or otherwise includes one or more stereocenters, the compound can be prepared with an enantiomeric excess or diastereomeric excess of greater than about 75%, greater than about 80%, greater than about 85%, greater than about 90%, greater than about 95%, or greater than about 99%.

Resolution of racemic mixtures of compounds can be carried out by any of numerous methods known in the art. An example method includes fractional recrystallization using a chiral resolving organic acid with a racemic compound containing a basic group. Suitable resolving agents for fractional recrystallization methods are, for example, optically active acids, such as the D and L forms of tartaric acid, diacetyltartaric acid, dibenzoyltartaric acid, di-(p-toluoyl)-tartaric acid, mandelic acid, malic acid, lactic acid or the various optically active camphorsulfonic acids. Other chiral resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Similarly, fractional recrystallization using a chiral resolving base can be utilized with a racemic compound containing a basic group.

Resolution of racemic mixtures can also be carried out by elution on a column packed with an optically active resolving agent (e.g., dinitrobenzoylphenylglycine). A suitable elution solvent composition can be determined by one skilled in the art.

In some embodiments, a compound described herein can be prepared having at least about 5%, at least about 10%, at least about 20%, at least about 30%, at least about 40%, at least about 50%, at least about 60%, at least about 70%, at least about 80%, at least about 90%, at least about 95%, at least about 99%, or at least about 99.9% enantiomeric excess, or an enantiomeric excess within a range defined by any of the preceding numbers.

In addition, it is understood that, when a compound described herein contain one or more double bond(s) (e.g., C=C, C=N, and the like) or other centers of geometric asymmetry, and unless specified otherwise, it is understood that the compound includes both E and Z geometric isomers (e.g., cis or trans). Cis and trans geometric isomers of the compounds described herein can be isolated as a mixture of isomers or as separated isomeric form.

The compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein and their pharmaceutically acceptable salts can be found together with other substances such as water and solvents, for example, in the form of hydrates or solvates. When in the solid-state, the compounds described herein and salts thereof may occur in various forms and may, e.g., take the form of solvates, including hydrates. The compounds can be in any solid-state form, such as a crystalline form, amorphous form, solvated form, etc. and unless clearly indicated otherwise, reference in the specification to compounds and salts thereof should be understood as reading on any solid-state form of the compound.

The compounds described herein can be used in a neutral form, such as, a free acid or free base form. Alternatively, the compounds can be used in the form of pharmaceutically acceptable salts, such as pharmaceutically acceptable addition salts of acids or bases.

In some embodiments, the compounds described herein, or salts thereof, are substantially isolated. The phrase "substantially isolated" refers to the compound that is at least partially or substantially separated from the environment in which it was formed or detected. Partial separation can include, for example, a composition enriched in the compound described herein. Substantial separation can include compositions containing at least about 50%, at least about 60%, at least about 65%, at least about 70%, at least about 75%, at least about 80%, at least about 85%, at least about 90%, at least about 95%, at least about 97%, or at least about 99% by weight of the compound described herein, or salt thereof.

Isotopes

The compounds disclosed and described herein allow atoms at each position of the compound independently to have: 1) an isotopic distribution for a chemical element in proportional amounts to those usually found in nature or 2) an isotopic distribution in proportional amounts different to those usually found in nature unless the context clearly dictates otherwise. A particular chemical element has an atomic number defined by the number of protons within the atom's nucleus. Each atomic number identifies a specific element, but not the isotope; an atom of a given element may have a wide range in its number of neutrons. The number of both protons and neutrons in the nucleus is the atom's mass number, and each isotope of a given element has a different mass number. A compound wherein one or more atoms have an isotopic distribution for a chemical element in proportional amounts different to those usually found in nature is commonly referred to as being an isotopically-labeled compound. Each chemical element as represented in a compound structure may include any isotopic distribution of said element. For example, in a compound structure a hydrogen atom can be explicitly disclosed or understood to be present in the compound. At any position of the compound that a hydrogen atom can be present, the hydrogen atom can be an isotopic distribution of hydrogen, including but not limited to protium ($^1H$) and deuterium ($^2H$) in proportional amounts to those usually found in nature and in proportional amounts different to those usually found in nature. Thus, reference herein to a compound encompasses all potential isotopic distributions for each atom unless the context clearly dictates otherwise. Examples of isotopes include isotopes of hydrogen, carbon, nitrogen, oxygen, phosphorous, sulfur, fluorine, chlorine, bromine, and iodine. As one of skill in the art would appreciate, any of the compounds as disclosed and described herein may include radioactive isotopes. Accordingly, also contemplated is use of compounds as disclosed and described herein, wherein one or more atoms have an isotopic distribution different to those usually found in nature, such as having $^2H$ or $^3H$ in greater proportion, or $^{11}C$, $^{13}C$, or $^{14}C$ in greater proportion than found in nature. By way of general example, and without limitation, isotopes of hydrogen include protium ($^1H$), deuterium ($^2H$), and tritium ($^3H$). Isotopes of carbon include carbon-11 ($^{11}C$), carbon-12 ($^{12}C$), carbon-13 ($^{13}C$), and carbon-14 ($^{14}C$). Isotopes of nitrogen include nitrogen-13 ($^{13}$N), nitrogen-14 ($^{14}$N) and nitrogen-15 ($^{15}$N). Isotopes of oxygen include oxygen-14 ($^{14}$O), oxygen-15 ($^{15}$O), oxygen-16 ($^{16}$O), oxygen-17 ($^{17}$O), and oxygen-18 ($^{18}$O). Isotope of fluorine include fluorine-17 ($^{17}$F), fluorine-18 ($^{18}$F) and fluorine-19 ($^{19}$F). Isotopes of phosphorous include phosphorus-31 ($^{31}$P), phosphorus-32 ($^{32}$P), phosphorus-33 ($^{33}$P), phosphorus-34 ($^{34}$P), phosphorus-35 ($^{35}$P) and phosphorus-36 ($^{36}$P). Isotopes of sulfur include sulfur-32 ($^{32}$S), sulfur-33 ($^{33}$S), sulfur-34 ($^{34}$S), sulfur-35 ($^{35}$S), sulfur-36 ($^{36}$S) and sulfur-38 ($^{38}$S). Isotopes of chlorine include chlorine-35 ($^{35}$Cl), chlorine-36 ($^{36}$Cl) and chlorine-37 ($^{37}$Cl). Isotopes of bromine include bromine-75 ($^{75}$Br), bromine-76 ($^{76}$Br), bromine-77 ($^{77}$Br), bromine-79 ($^{79}$Br), bromine-81 ($^{81}$Br) and bromine-82 ($^{82}$Br). Isotopes of iodine include iodine-123 ($^{123}$I), iodine-124 ($^{124}$I), iodine-125 ($^{125}$I), iodine-131 ($^{131}$I) and iodine-135 ($^{135}$I). In some embodiments, atoms at every position of the compound have an isotopic distribution for each chemical element in proportional amounts to those usually found in nature. In some embodiments, an atom in one position of the compound has an isotopic distribution for a chemical element in proportional amounts different to those usually found in nature (remainder atoms having an isotopic distribution for a chemical element in proportional amounts to those usually found in nature). In some embodiments, atoms in at least two positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least three positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least four positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least five positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least six positions of the compound independently have an isotopic distribution for a chemical element in proportional amounts different to those usually found in nature (remainder atoms having an isotopic distribution for a chemical element in proportional amounts to those usually found in nature).

Certain compounds, for example those having incorporated radioactive isotopes such as $^3$H and $^{14}$C, are also useful in drug or substrate tissue distribution assays. Tritium ($^3$H) and carbon-14 ($^{14}$C) isotopes are particularly preferred for their ease of preparation and detectability. Compounds with isotopes such as deuterium ($^2$H) in proportional amounts greater than usually found in nature may afford certain therapeutic advantages resulting from greater metabolic stability, such as, for example, increased in vivo half-life or reduced dosage requirements. Isotopically-labeled compounds can generally be prepared by performing procedures routinely practiced in the chemical art. Methods are readily available to measure such isotope perturbations or enrichments, such as, mass spectrometry, and for isotopes that are radio-isotopes additional methods are available, such as, radio-detectors used in connection with HPLC or GC.

As used herein, "isotopic variant" means a compound that contains an unnatural proportion of an isotope at one or more of the atoms that constitute such a compound. In certain embodiments, an "isotopic variant" of a compound contains unnatural proportions of one or more isotopes, including, but not limited to, protium (H), deuterium (2H), tritium ($^3$H), carbon-11 ($^{11}$C), carbon-12 ($^{12}$C), carbon-13 ($^{13}$C), carbon-14 (14C), nitrogen-13 ($^{13}$N), nitrogen-14 (14N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I) iodine-125 ($^{125}$I), iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), and oxygen-18 ($^{18}$O). In certain embodiments, an "isotopic variant" of a compound is in an unstable form, that is, radioactive. In certain embodiments, an "isotopic variant" of a compound described herein contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), and oxygen-15 ($^{15}$O). It will be understood that, in a compound as provided herein, any hydrogen can include $^2$H as the major isotopic form, as example, or any carbon include be $^{13}$C as the major isotopic form, as example, or any nitrogen can include $^{15}$N as the major isotopic form, as example, and any oxygen can include $^{18}$O as the major isotopic form, as example. In certain embodiments, an "isotopic variant" of a compound contains an unnatural proportion of deuterium ($^2$H).

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 ($^{99}$% deuterium incorporation), or at least 6633.3 ($^{99}$0.5% deuterium incorporation) at each designated deuterium position.

Synthetic methods for incorporating radio-isotopes into organic compounds are applicable to compound described herein and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A representative procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two-step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.*, 2001, 44, S280-S282.

A radiolabeled form of a compound described herein can be used in a screening assay to identify/evaluate compounds. In general terms, a newly synthesized or identified compound (i.e., test compound) can be evaluated for its ability to reduce binding of a radiolabeled form of a compound disclosed herein to GPR52. The ability of a test compound to compete with a radiolabeled form of a compound described herein for the binding to GPR52 correlates to its binding affinity.

Compounds

Some embodiments provide a compound of Formula (I):

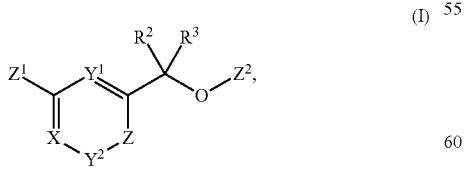

(I)

or a pharmaceutically acceptable salt thereof, wherein:

X, Y$^1$ and Y$^2$ are independently N (nitrogen) or CH;

Z is N or CR$^1$, where at least one of Z, X, Y$^1$ and Y$^2$ is N (nitrogen);

Z$^1$ is

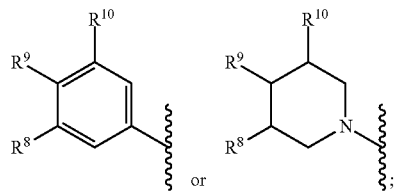

Z$^2$ is

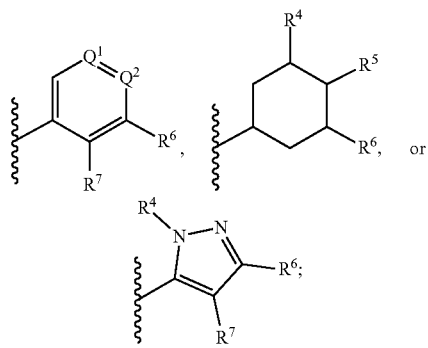

Q$^1$ is N (nitrogen) or CR$^4$;
Q$^2$ is N (nitrogen) or CR$^5$;
R$^1$ is hydrogen, halogen, C$_1$-C$_6$alkyl or haloC$_1$-C$_6$alkyl;
R$^2$ is hydrogen, halogen, C$_1$-C$_6$alkyl, haloC$_1$-C$_6$alkyl, or —OR$^A$;
R$^3$ is hydrogen, halogen, C$_1$-C$_6$alkyl, or haloC$_1$-C$_6$alkyl;
v) R$^4$, R$^5$, R$^6$, and R$^7$, are independently hydrogen, halogen, —(CH$_2$)$_n$—CN, nitro, haloC$_1$-C$_6$alkyl, C$_3$-C$_8$cycloalkyl, —NHC(=O)R$^B$, —OR$^B$, —S(O)$_m$R$^B$, —(CH$_2$)$_m$C(=O)R$^B$, —S(O)$_p$N(R$^B$R$^C$) or C$_1$-C$_6$alkyl optionally substituted with hydroxyl, or vi) R$^4$ and R$^5$, together with the carbon atoms to which they are attached, form a 6 membered aryl group, a 5-6 membered heteroaryl group optionally substituted with C$_1$-C$_6$alkyl, a 5-6 membered cycloalkyl group optionally substituted with =O, or a 5-6 membered heterocyclyl group, and R$^6$, and R$^7$, are independently hydrogen, halogen, —(CH$_2$)$_n$—CN, nitro, C$_1$-C$_6$alkyl optionally substituted with hydroxyl, haloC$_1$-C$_6$alkyl, C$_3$-C$_8$cycloalkyl, —NHC(=O)R$^B$, —OR$^B$, —S(O)$_m$R$^B$, —(CH$_2$)$_m$C(=O)R$^B$ or —S(O)$_p$N(R$^B$R$^C$), or vii) R$^5$ and R$^6$, together with the carbon atoms to which they are attached, form a 6 membered aryl group, a 5-6 membered heteroaryl group optionally substituted with C$_1$-C$_6$alkyl, a 5-6 membered cycloalkyl group optionally substituted with =O, or a 5-6 membered heterocyclyl group, and R$^4$, and R$^7$, are independently hydrogen, halogen, —(CH$_2$)$_n$—CN, nitro, C$_1$-C$_6$alkyl optionally substituted with hydroxyl, haloC$_1$-C$_6$alkyl, C$_3$-C$_8$cycloalkyl, —NHC(=O)R$^B$, —OR$^B$, —S(O)$_m$R$^B$, —(CH$_2$)$_m$C(=O)R$^B$ or —S(O)$_p$N(R$^B$R$^C$), or viii) R$^6$ and R$^7$, together with the carbon atoms to which they are attached, form a 6 membered aryl group, a 5-6 membered heteroaryl group optionally substituted with C$_1$-C$_6$alkyl, a 5-6 membered cycloalkyl group optionally substituted with =O, or a 5-6 membered heterocyclyl group, and $R^4$, and $R^5$, are independently hydrogen, halogen, —$(CH_2)_n$—CN, nitro, $C_1$-$C_6$alkyl optionally substituted with hydroxyl, halo$C_1$-$C_6$alkyl, $C_3$-$C_8$cycloalkyl, —NHC(=O)$R^B$, —O$R^B$, —S(O)$_m R^B$, —$(CH_2)_m$C(=O)$R^B$ or —S(O)$_p$N($R^B R^C$);

one of $R^1$ and $R^9$ is —$(CH_2)_n$C(=O)N($R^E R^F$) and the other of $R^1$ and $R^9$ is hydrogen, halogen, $C_1$-$C_6$alkyl, halo$C_1$-$C_6$alkyl, —C(=O)$R^D$, or —O$R^E$, or $R^8$ and $R^9$ together with the carbon atom to which they are attached, form a 5-6 membered heterocyclyl group, said 5-6 membered heterocyclyl group optionally substituted with =O;

$R^{10}$ is hydrogen, halogen, $C_1$-$C_6$alkyl, halo$C_1$-$C_6$alkyl, —C(=O)$R^D$, or —O$R^E$.

each $R^A$, $R^B$, $R^C$, is independently hydrogen, $C_1$-$C_6$alkyl, or halo$C_1$-$C_6$alkyl;

each $R^D$ is independently hydrogen, $C_1$-$C_6$alkyl, halo$C_1$-$C_6$alkyl, —$NH_2$, or —NH$(CH_2)_q$OH;

each $R^E$, and $R^F$, is independently hydrogen, $C_1$-$C_6$alkyl, or halo$C_1$-$C_6$alkyl, or $R^E$ and $R^F$, together with the nitrogen atom to which they are attached, form a 5-6 membered heterocyclyl group;

each m is independently 0, 1, 2 or 3;
each n is independently 0, 1, 2 or 3;
each p is independently 1 or 2; and
each q is independently 2, 3 or 4.

In some embodiments, X and $Y^1$ are independently N (nitrogen) or CH. In some embodiments, one of X and $Y^1$ is CH, and the other of X and $Y^1$ is N (nitrogen). In some embodiments, X and $Y^1$ are each N (nitrogen). In some embodiments, X and $Y^1$ are each CH. In some embodiments, X, $Y^1$ and $Y^2$ are CH and Z is N (nitrogen). In some embodiments, Z, $Y^1$ and $Y^2$ are CH and X is N (nitrogen). In some embodiments, X, $Y^2$ and Z are CH and $Y^1$ is N (nitrogen). In some embodiments, X, $Y^1$ and Z are CH and $Y^2$ is N (nitrogen).

In some embodiments, $R^1$ is hydrogen, halogen, $C_1$-$C_6$alkyl or halo$C_1$-$C_6$alkyl. In some embodiments, $R^1$ is halogen. In some embodiments, $R^1$ is fluoro or chloro. In some embodiments, $R^1$ is $C_1$-$C_6$alkyl. In some embodiments, $R^1$ is methyl. In some embodiments, $R^1$ is halo$C_1$-$C_6$alkyl. In some embodiments, $R^1$ is trifluoromethyl. In some embodiments, $R^1$ is hydrogen.

In some embodiments, $R^2$ is hydrogen, halogen, $C_1$-$C_3$alkyl, halo$C_1$-$C_3$alkyl, or —O$R^A$. In some embodiments, $R^2$ is halogen. In some embodiments, $R^2$ is fluoro or chloro. In some embodiments, $R^2$ is $C_1$-$C_3$alkyl. In some embodiments, $R^2$ is methyl. In some embodiments, $R^2$ is halo$C_1$-$C_3$alkyl. In some embodiments, $R^2$ is trifluoromethyl. In some embodiments, $R^2$ is hydrogen. In some embodiments, $R^2$ is —O$R^A$.

In some embodiments, $R^A$ is hydrogen, $C_1$-$C_6$alkyl, or halo$C_1$-$C_6$alkyl. In some embodiments, $R^A$ is $C_1$-$C_6$alkyl. In some embodiments, $R^A$ is methyl. In some embodiments, $R^A$ is halo$C_1$-$C_6$alkyl. In some embodiments, $R^A$ is trifluoromethyl. In some embodiments, $R^A$ is hydrogen.

In some embodiments, $R^3$ is hydrogen, halogen, $C_1$-$C_3$alkyl or halo$C_1$-$C_3$alkyl. In some embodiments, $R^3$ is halogen. In some embodiments, $R^3$ is fluoro or chloro. In some embodiments, $R^3$ is $C_1$-$C_3$alkyl. In some embodiments, $R^3$ is methyl. In some embodiments, $R^3$ is halo$C_1$-$C_3$alkyl. In some embodiments, $R^3$ is trifluoromethyl. In some embodiments, $R^3$ is hydrogen.

In some embodiments, $Z^2$ is

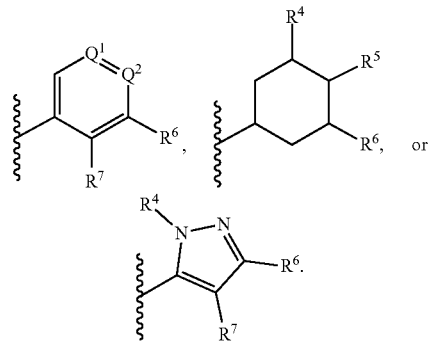

In some embodiments, $Z^2$ is

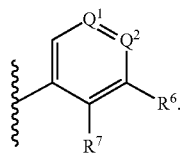

In some embodiments, $Z^2$ is

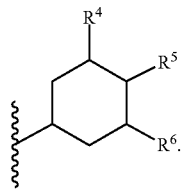

In some embodiments, $Z^2$ is

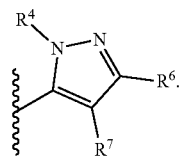

In some embodiments, $Q^1$ is N (nitrogen) or $CR^4$. In some embodiments, $Q^1$ is N (nitrogen). In some embodiments, $Q^1$ is $CR^4$.

In some embodiments, $Q^2$ is N (nitrogen) or CR. In some embodiments, $Q^2$ is N (nitrogen). In some embodiments, $Q^2$ is $CR^5$.

In some embodiments, $R^4$ is hydrogen, halogen, —$(CH_2)_n$—CN, nitro, $C_1$-$C_6$alkyl optionally substituted with hydroxyl, $C_3$-$C_8$cycloalkyl, halo$C_1$-$C_6$alkyl, —O$R^B$, —NHC(=O)$R^B$, —$(CH_2)_m$C(=O)$R^B$, —S(O)$_m R^B$, or —S(O)$_p$N($R^B R^C$). In some embodiments, $R^4$ is hydrogen. In some embodiments, $R^4$ is halogen. In some embodiments, $R^4$ is fluoro or chloro. In some embodiments, $R^4$ is unsubstituted $C_1$-$C_6$. In some embodiments, $R^4$ is $C_1$-$C_6$alkyl substituted with hydroxyl. In some embodiments, $R^4$ is methyl. In some embodiments, $R^4$ is halo$C_1$-$C_6$alkyl. In some embodiments, $R^4$ is trifluoromethyl. In some embodiments, $R^4$ is —$(CH_2)_n$—CN. In some embodiments, $R^4$ is cyano. In some embodiments, $R^4$ is nitro. In some embodiments, $R^4$ is $—S(O)_mR^B$. In some embodiments, $R^4$ is $—S(O)_pN(R^BR^C)$. In some embodiments, $R^4$ is $—NHC(=O)R^B$. In some embodiments, $R^4$ is $—OR^B$. In some embodiments, $R^4$ is $—(CH_2)_mC(=O)R^B$.

In some embodiments, $R^5$ is hydrogen, halogen, $—(CH_2)_n—CN$, nitro, $C_1$-$C_6$alkyl optionally substituted with hydroxyl, $C_3$-$C_8$cycloalkyl, halo$C_1$-$C_6$alkyl, $—OR^B$, $—NHC(=O)R^B$, $—(CH_2)_mC(=O)R^B$, $—S(O)_mR^B$, or $—S(O)_pN(R^BR^C)$. In some embodiments, $R^5$ is hydrogen. In some embodiments, $R^5$ is halogen. In some embodiments, $R^5$ is fluoro or chloro. In some embodiments, $R^5$ is unsubstituted $C_1$-$C_6$alkyl. In some embodiments, $R^5$ is methyl. In some embodiments, $R^5$ is $C_1$-$C_6$alkyl substituted by hydroxyl. In some embodiments, $R^5$ is halo$C_1$-$C_6$alkyl. In some embodiments, $R^5$ is trifluoromethyl. In some embodiments, $R^5$ is hydrogen. In some embodiments, $R^5$ is $—(CH_2)_n—CN$. In some embodiments, $R^5$ is cyano. In some embodiments, $R^5$ is nitro. In some embodiments, $R^5$ is $—OR^B$. In some embodiments, $R^5$ is $—S(O)_mR^B$. In some embodiments, $R^5$ is $—S(O)_pN(R^BR^C)$. In some embodiments, $R^5$ is methoxy, methylsulfanyl trifluoromethanesulfonyl, methyl or trifluoromethyl. In some embodiments, $R^5$ is $—NHC(=O)R^B$. In some embodiments, $R^5$ is $—OR^B$. In some embodiments, $R^5$ is $—(CH_2)_mC(=O)R^B$.

In some embodiments, $R^6$ is hydrogen, halogen, $—(CH_2)_n—CN$, nitro, $C_1$-$C_6$alkyl optionally substituted with hydroxyl, $C_3$-$C_8$cycloalkyl, halo$C_1$-$C_6$alkyl, $—OR^B$, $—NHC(=O)R^B$, $—(CH_2)_mC(=O)R^B$, $—S(O)_mR^B$, or $—S(O)_pN(R^BR^C)$. In some embodiments, $R^6$ is halogen. In some embodiments, $R^6$ is fluoro or chloro. In some embodiments, $R^6$ is unsubstituted $C_1$-$C_6$alkyl. In some embodiments, $R^6$ is methyl. In some embodiments, $R^6$ is $C_1$-$C_6$alkyl substituted by hydroxyl. In some embodiments, $R^6$ is halo$C_1$-$C_6$alkyl. In some embodiments, $R^6$ is trifluoromethyl. In some embodiments, $R^6$ is hydrogen. In some embodiments, $R^6$ is $—(CH_2)_n—CN$. In some embodiments, $R^6$ is cyano. In some embodiments, $R^6$ is nitro. In some embodiments, $R^6$ is $—OR^B$. In some embodiments, $R^6$ is $—S(O)_mR^B$. In some embodiments, $R^6$ is $—S(O)_pN(R^BR^C)$. In some embodiments, $R^6$ is $—NHC(=O)R^B$. In some embodiments, $R^6$ is $—OR^B$. In some embodiments, $R^6$ is $—(CH_2)_mC(=O)R^B$.

In some embodiments, Q is N or $CR^7$. In some embodiments, Q is N. In some embodiments, Q is $CR^7$.

In some embodiments, $R^7$ is hydrogen, halogen, $—(CH_2)_n—CN$, nitro, $C_1$-$C_6$alkyl optionally substituted with hydroxyl, $C_3$-$C_8$cycloalkyl, halo$C_1$-$C_6$alkyl, $—OR^B$, $—NHC(=O)R^B$, $—(CH_2)_mC(=O)R^B$, $—S(O)_mR^B$, or $—S(O)_pN(R^BR^C)$. In some embodiments, $R^7$ is halogen. In some embodiments, $R^7$ is fluoro or chloro. In some embodiments, $R^7$ is unsubstituted $C_1$-$C_6$alkyl. In some embodiments, $R^7$ is methyl. In some embodiments, $R^7$ is nitro. In some embodiments, $R^7$ is halo$C_1$-$C_6$alkyl. In some embodiments, $R^7$ is trifluoromethyl. In some embodiments, $R^7$ is hydrogen. In some embodiments, $R^7$ is cyano. In some embodiments, $R^7$ is $—OR^B$. In some embodiments, $R^7$ is $—S(O)_mR^B$. In some embodiments, $R^7$ is $—S(O)_pN(R^BR^C)$. In some embodiments, $R^7$ is $—NHC(=O)R^B$. In some embodiments, $R^7$ is $—OR^B$. In some embodiments, $R^7$ is $—(CH_2)_mC(=O)R^B$.

In some embodiments, $R^4$ and $R^5$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^6$ and $R^7$ are independently hydrogen, halogen, $—(CH_2)_n—CN$, nitro, $C_1$-$C_6$alkyl optionally substituted with hydroxyl, halo$C_1$-$C_6$alkyl, $C_3$-$C_8$cycloalkyl, $—NHC(=O)R^B$, $—OR^B$, $—S(O)_mR^B$, $—(CH_2)_mC(=O)R^B$ or $—S(O)_pN(R^BR^C)$. In some embodiments, $R^4$ and $R^5$, together with the carbon atoms to which they are attached, form a 6 membered aryl group. In some embodiments, $R^4$ and $R^5$, together with the carbon atoms to which they are attached, form a 5-6 membered heteroaryl group optionally substituted with $C_1$-$C_6$alkyl. In some embodiments, $R^4$ and $R^5$, together with the carbon atoms to which they are attached, form a 5-6 membered cycloalkyl group optionally substituted with =O. In some embodiments, $R^4$ and $R^5$, together with the carbon atoms to which they are attached, form a 6 membered heterocyclyl group.

In some embodiments, $R^5$ and $R^6$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^4$ and $R^7$ are independently hydrogen, halogen, $—(CH_2)_n—CN$, nitro, $C_1$-$C_6$alkyl optionally substituted with hydroxyl, halo$C_1$-$C_6$alkyl, $C_3$-$C_8$cycloalkyl, $—NHC(=O)R^B$, $—OR^B$, $—S(O)_mR^B$, $—(CH_2)_mC(=O)R^B$ or $—S(O)_pN(R^BR^C)$. In some embodiments, $R^5$ and $R^6$, together with the carbon atoms to which they are attached, form a 6 membered aryl group. In some embodiments, $R^5$ and $R^6$, together with the carbon atoms to which they are attached, form a 5-6 membered heteroaryl group optionally substituted with $C_1$-$C_6$alkyl. In some embodiments, $R^5$ and $R^6$, together with the carbon atoms to which they are attached, form a 5-6 membered cycloalkyl group optionally substituted with =O. In some embodiments, $R^5$ and $R^6$, together with the carbon atoms to which they are attached, form a 6 membered heterocyclyl group.

In some embodiments, $R^6$ and $R^7$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^4$ and $R^5$ are independently hydrogen, halogen, $—(CH_2)_n—CN$, nitro, $C_1$-$C_6$alkyl optionally substituted with hydroxyl, halo$C_1$-$C_6$alkyl, $C_3$-$C_8$cycloalkyl, $—NHC(=O)R^B$, $—OR^B$, $—S(O)_mR^B$, $—(CH_2)_mC(=O)R^B$ or $—S(O)_pN(R^BR^C)$. In some embodiments, $R^6$ and $R^7$, together with the carbon atoms to which they are attached, form a 6 membered aryl group. In some embodiments, $R^6$ and $R^7$, together with the carbon atoms to which they are attached, form a 5-6 membered heteroaryl group optionally substituted with $C_1$-$C_6$alkyl. In some embodiments, $R^6$ and $R^7$, together with the carbon atoms to which they are attached, form a 5-6 membered cycloalkyl group optionally substituted with =O. In some embodiments, $R^6$ and $R^7$, together with the carbon atoms to which they are attached, form a 6 membered heterocyclyl group.

In some embodiments, each m is independently 0, 1, 2, or 3. In some embodiments, m is 0. In some embodiments, m is 1. In some embodiments, m is 2. In some embodiments, m is 3.

In some embodiments, each p is independently 1 or 2. In some embodiments, p is 1. In some embodiments, p is 2.

In some embodiments, each n is independently 0, 1, 2, or 3. In some embodiments, n is 0. In some embodiments, n is 1. In some embodiments, n is 2. In some embodiments, n is 3.

In some embodiments, $R^B$ is hydrogen, $C_1$-$C_6$alkyl, or halo$C_1$-$C_6$alkyl. In some embodiments, $R^B$ is $C_1$-$C_6$alkyl. In some embodiments, $R^B$ is methyl. In some embodiments, $R^B$ is haloC$_1$-C$_6$alkyl. In some embodiments, R$^B$ is trifluoromethyl. In some embodiments, R$^B$ is hydrogen.

In some embodiments, R$^C$ is hydrogen, C$_1$-C$_6$alkyl, or haloC$_1$-C$_6$alkyl. In some embodiments, R$^C$ is C$_1$-C$_6$alkyl. In some embodiments, R$^C$ is methyl. In some embodiments, R$^C$ is haloC$_1$-C$_6$alkyl. In some embodiments, R$^C$ is trifluoromethyl. In some embodiments, R$^C$ is hydrogen.

In some embodiments, not more than one of R$^4$, R$^5$, R$^6$, and R$^7$ is —(CH$_2$)$_n$—CN, nitro, —NHC(=O)R$^B$, —S(O)$_m$R$^B$, —(CH$_2$)$_m$C(=O)R$^B$ or —S(O)$_p$N(R$^B$R$^C$). In some embodiments, when one of R$^4$, R$^5$, R$^6$, and R$^7$ is —(CH$_2$)$_n$—CN, nitro, —NHC(=O)R$^B$, —S(O)$_m$R$^B$, —(CH$_2$)$_m$C(=O)R$^B$ or —S(O)$_p$N(R$^B$R$^C$); the other of R$^4$, R$^5$, R$^6$, and R$^7$ is not —(CH$_2$)$_n$—CN, nitro, —NHC(=O)R$^B$, —S(O)$_m$R$^B$, —(CH$_2$)$_m$C(=O)R$^B$ or —S(O)$_p$N(R$^B$R$^C$). In some embodiments, not more than one of R$^4$, R$^5$, and R$^6$ is —(CH$_2$)$_n$—CN, nitro, —NHC(=O)R$^B$, —S(O)$_m$R$^B$, —(CH$_2$)$_m$C(=O)R$^B$ or —S(O)$_p$N(R$^B$R$^C$). In some embodiments, when one of R$^4$, R$^5$, and R$^6$ is —(CH$_2$)$_n$—CN, nitro, —NHC(=O)R$^B$, —S(O)$_m$R$^B$, —(CH$_2$)$_m$C(=O)R$^B$ or —S(O)$_p$N(R$^B$R$^C$); the other of R$^4$, R$^5$, R$^6$, and R$^7$ is not —(CH$_2$)$_n$—CN, nitro, —NHC(=O)R$^B$, —S(O)$_m$R$^B$, —(CH$_2$)$_m$C(=O)R$^B$ or —S(O)$_p$N(R$^B$R$^C$).

In some embodiments, not more than one of R$^4$, R$^5$, R$^6$, and R$^7$ is —CN, nitro, —S(O)$_m$R$^B$, or —S(O)$_p$N(R$^B$R$^C$). In some embodiments, when one of R$^4$, R$^5$, R$^6$, and R$^7$ is —CN, nitro, —S(O)$_m$R$^B$ or —S(O)$_p$N(R$^B$R$^C$); the other of R$^4$, R$^5$, R$^6$, and R$^7$ is not —CN, nitro, —S(O)$_m$R$^B$, or —S(O)$_p$N(R$^B$R$^C$). In some embodiments, not more than one of R$^4$, R$^5$, and R$^6$ is —CN, nitro, —S(O)$_m$R$^B$, or —S(O)$_p$N(R$^B$R$^C$). In some embodiments, when one of R$^4$, R$^5$, and R$^6$ is —CN, nitro, —S(O)$_m$R$^B$, or —S(O)$_p$N(R$^B$R$^C$); the other of R$^4$, R$^5$, R$^6$, and R$^7$ is not —CN, nitro, —S(O)$_m$R$^B$, or —S(O)$_p$N(R$^B$R$^C$).

In some embodiments, Z$^2$ is:

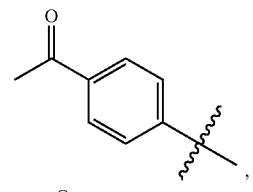,
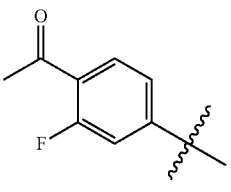,

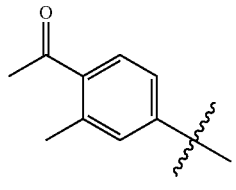,
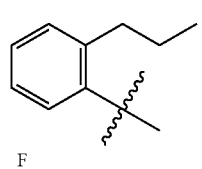,

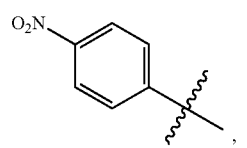,
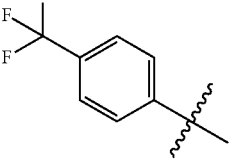,

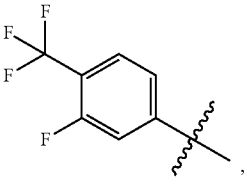,
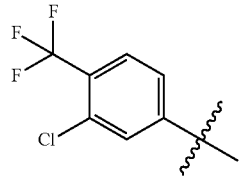,

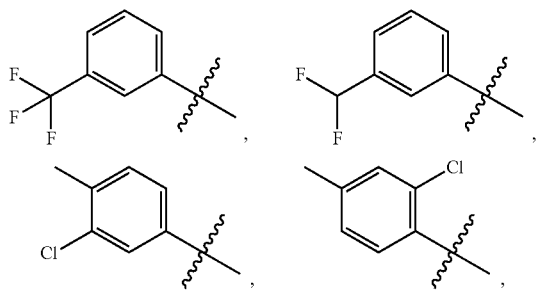

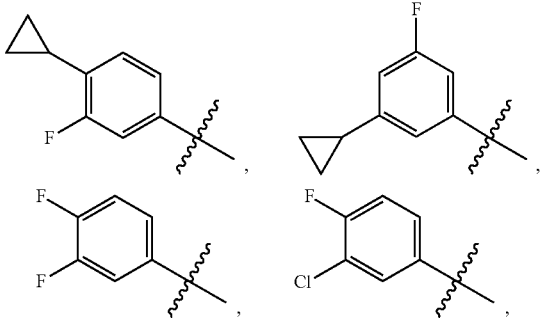

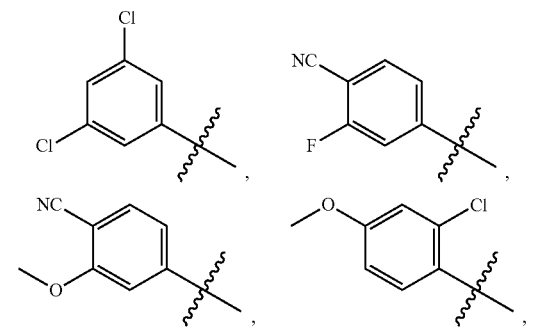

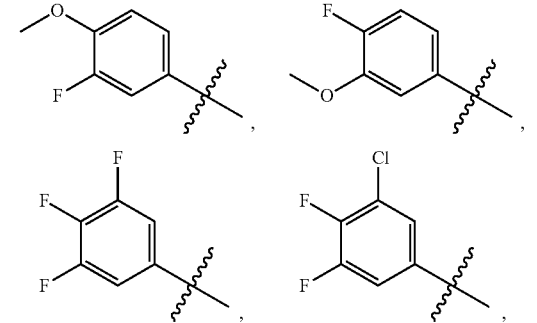

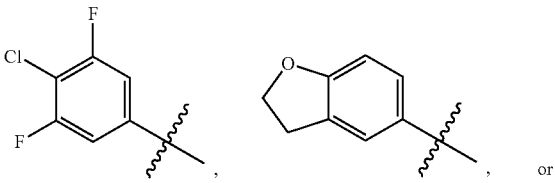

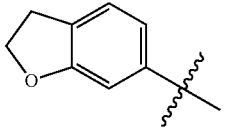.

In some embodiments, $Z^1$ is

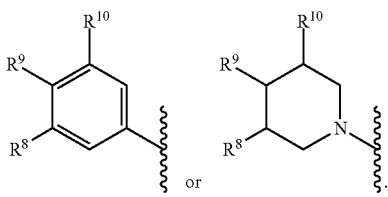

or

In some embodiments, $Z^1$ is

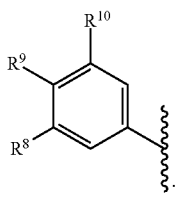

In some embodiments, $Z^1$ is

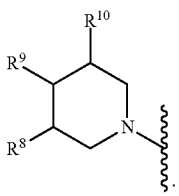

In some embodiments, one of $R^1$ and $R^9$ is —$(CH_2)_nC(=O)N(R^ER^F)$ and the other of $R^1$ and $R^9$ is hydrogen, halogen, $C_1$-$C_6$alkyl, halo$C_1$-$C_6$alkyl, —$C(=O)R^D$, or —$OR^E$. In some embodiments, $R^8$ is —$(CH_2)_nC(=O)N(R^ER^F)$ and $R^9$ is hydrogen. In some embodiments, $R^8$ is —$(CH_2)_nC(=O)N(R^ER^F)$ and $R^9$ is halogen. In some embodiments, $R^8$ is —$(CH_2)_nC(=O)N(R^ER^F)$ and $R^9$ is $C_1$-$C_6$alkyl. In some embodiments, $R^8$ is —$(CH_2)_nC(=O)N(R^ER^F)$ and $R^9$ is halo$C_1$-$C_6$alkyl. In some embodiments, $R^8$ is —$(CH_2)_nC(=O)N(R^ER^F)$ and $R^9$ is —$C(=O)R^D$. In some embodiments, $R^8$ is —$(CH_2)_nC(=O)N(R^ER^F)$ and $R^9$ is —$OR^E$. In some embodiments, $R^9$ is —$(CH_2)_nC(=O)N(R^ER^F)$ and $R^8$ is hydrogen. In some embodiments, $R^9$ is —$(CH_2)_nC(=O)N(R^ER^F)$ and $R^8$ is halogen. In some embodiments, $R^9$ is —$(CH_2)_nC(=O)N(R^ER^F)$ and $R^8$ is $C_1$-$C_6$alkyl. In some embodiments, $R^9$ is —$(CH_2)_nC(=O)N(R^ER^F)$ and $R^8$ is halo$C_1$-$C_6$alkyl. In some embodiments, $R^9$ is —$(CH_2)_nC(=O)N(R^ER^F)$ and $R^8$ is —$C(=O)R^D$. In some embodiments, $R^9$ is —$(CH_2)_nC(=O)N(R^ER^F)$ and $R^8$ —$OR^E$.

In some embodiments, $R^8$ is hydrogen, halogen, $C_1$-$C_6$alkyl, halo$C_1$-$C_6$alkyl, —$C(=O)R^D$, —$OR^E$, or —$(CH_2)_nC(=O)N(R^ER^F)$. In some embodiments, $R^8$ is halogen. In some embodiments, $R^8$ is fluoro or chloro. In some embodiments, $R^8$ is $C_1$-$C_6$alkyl. In some embodiments, $R^8$ is methyl. In some embodiments, $R^8$ is halo$C_1$-$C_6$alkyl. In some embodiments, $R^8$ is trifluoromethyl. In some embodiments, $R^8$ is hydrogen. In some embodiments, $R^8$ is —$OR^E$. In some embodiments, $R^8$ is —$C(=O)R^D$. In some embodiments, $R^8$ is —$(CH_2)_nC(=O)N(R^ER^F)$.

In some embodiments, $R^9$ is hydrogen, halogen, $C_1$-$C_6$alkyl, halo$C_1$-$C_6$alkyl, —$C(=O)R^D$, —$OR^E$, or —$(CH_2)_nC(=O)N(R^ER^F)$. In some embodiments, $R^9$ is halogen. In some embodiments, $R^9$ is fluoro or chloro. In some embodiments, $R^9$ is $C_1$-$C_6$alkyl. In some embodiments, $R^9$ is methyl. In some embodiments, $R^9$ is halo$C_1$-$C_6$alkyl. In some embodiments, $R^9$ is trifluoromethyl. In some embodiments, $R^9$ is hydrogen. In some embodiments, $R^9$ is —$OR^E$. In some embodiments, $R^9$ is —$C(=O)R^D$. In some embodiments, $R^9$ is —$(CH_2)_nC(=O)N(R^ER^F)$.

In some embodiments, $R^{10}$ is hydrogen, halogen, $C_1$-$C_6$alkyl, halo$C_1$-$C_6$alkyl, —$C(=O)R^D$, or —$OR^E$. In some embodiments, $R^{10}$ is halogen. In some embodiments, $R^{10}$ is fluoro or chloro. In some embodiments, $R^{10}$ is $C_1$-$C_6$alkyl. In some embodiments, $R^{10}$ is methyl. In some embodiments, $R^{10}$ is halo$C_1$-$C_6$alkyl. In some embodiments, $R^{10}$ is trifluoromethyl. In some embodiments, $R^{10}$ is hydrogen. In some embodiments, $R^{10}$ is —$OR^E$. In some embodiments, $R^{10}$ is —$C(=O)R^D$.

In some embodiments, $R^8$ and $R^9$, together with the carbon atom to which they are attached, form a 5-6 membered heterocyclyl group, said 5-6 membered heterocyclyl group optionally substituted with =O where the 5-6 membered heterocyclyl includes a C=O group. In some embodiments, $R^8$ and $R^9$, together with the carbon atom to which they are attached, form a pyrrolidine, piperidine, piperidone, piperazine, morpholine, or tetrahydropyran.

In some embodiments, each $R^D$ is independently hydrogen, $C_1$-$C_6$alkyl, halo$C_1$-$C_6$alkyl, —$NH_2$, or —$NH(CH_2)_qOH$. In some embodiments, $R^D$ is hydrogen. In some embodiments, $R^D$ is $C_1$-$C_6$alkyl. In some embodiments, $R^D$ is methyl. In some embodiments, $R^D$ is halo$C_1$-$C_6$alkyl. In some embodiments, $R^D$ is trifluoromethyl. In some embodiments, $R^D$ is —$NH_2$. In some embodiments, $R^D$ is —$NHCH_2CH_2OH$, —$NHCH_2CH_2CH_2OH$ or —$NHCH_2CH_2CH_2CH_2OH$. In some embodiments, $R^D$ is NHCH$_2$CH$_2$OH. In some embodiments, $R^D$ is —$NHCH_2CH_2CH_2OH$. In some embodiments, $R^D$ is —$NHCH_2CH_2CH_2CH_2OH$.

In some embodiments, each q is independently 2, 3, or 4. In some embodiments, q is 2. In some embodiments, q is 3. In some embodiments, q is 4.

In some embodiments, $R^E$ is hydrogen, $C_1$-$C_6$alkyl, or halo$C_1$-$C_6$alkyl. In some embodiments, $R^E$ is $C_1$-$C_6$alkyl. In some embodiments, $R^E$ is methyl. In some embodiments, $R^E$ is halo$C_1$-$C_6$alkyl. In some embodiments, $R^E$ is trifluoromethyl. In some embodiments, $R^E$ is hydrogen.

In some embodiments, $R^F$ is hydrogen, $C_1$-$C_6$alkyl, or halo$C_1$-$C_6$alkyl. In some embodiments, $R^F$ is $C_1$-$C_6$alkyl. In some embodiments, $R^F$ is methyl. In some embodiments, $R^F$ is halo$C_1$-$C_6$alkyl. In some embodiments, $R^F$ is trifluoromethyl. In some embodiments, $R^F$ is hydrogen.

In some embodiments, $R^E$ and $R^F$, together with the nitrogen atom to which they are attached, form a 5-6 membered heterocyclyl group. In some embodiments, $R^E$ and $R^F$, together with the nitrogen atom to which they are attached, form a pyrrolidine, piperidine, piperidone, piperazine, or morpholine.

In some embodiments, $Z^1$ is

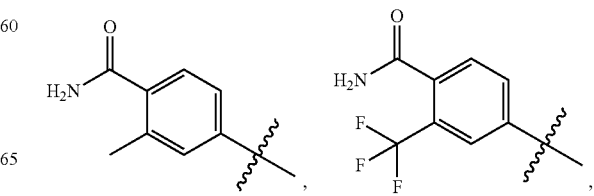

,

-continued
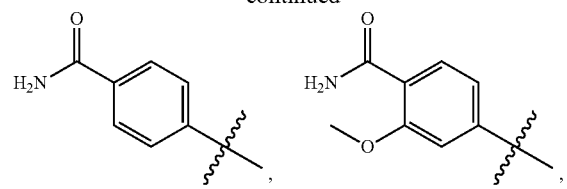
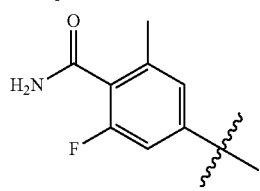
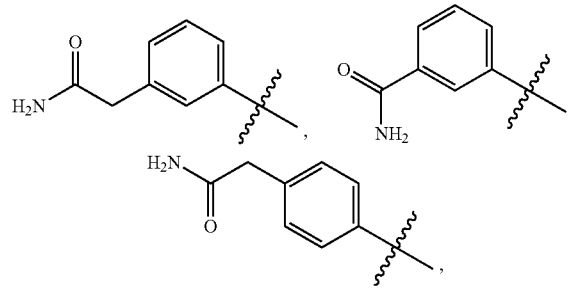
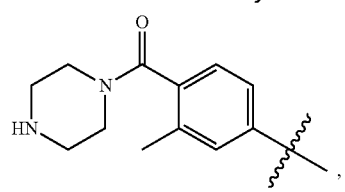
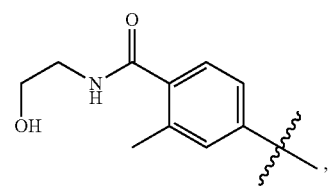
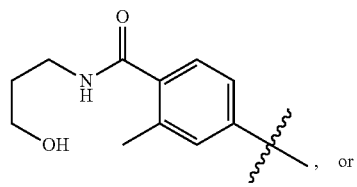, or
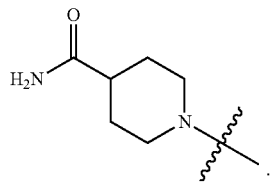.
In some embodiments, $Z^1$ is
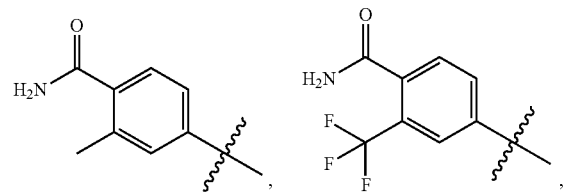
-continued
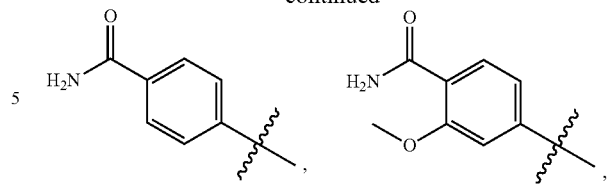
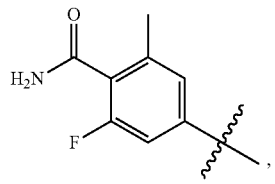
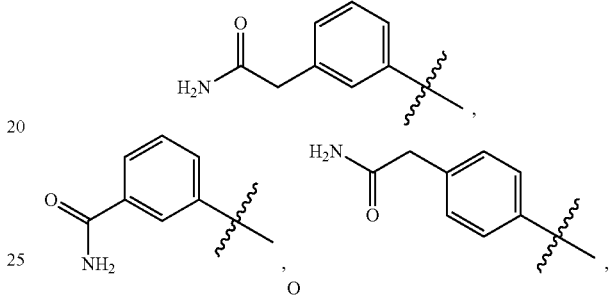
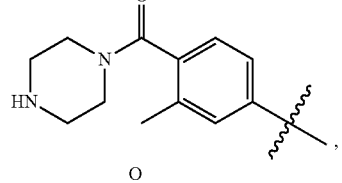
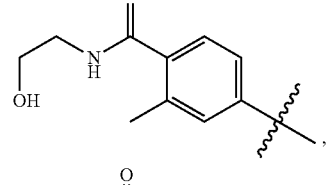
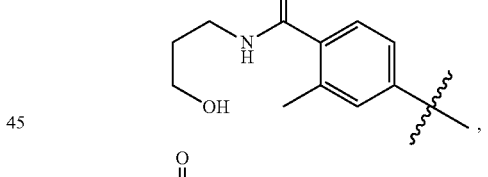; and $Z^2$ is:
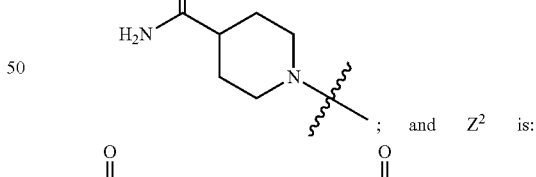
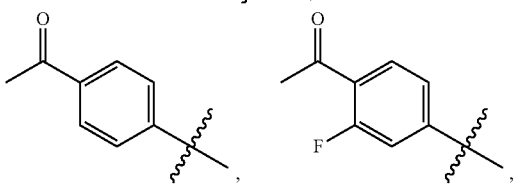
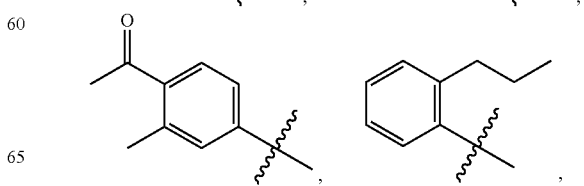

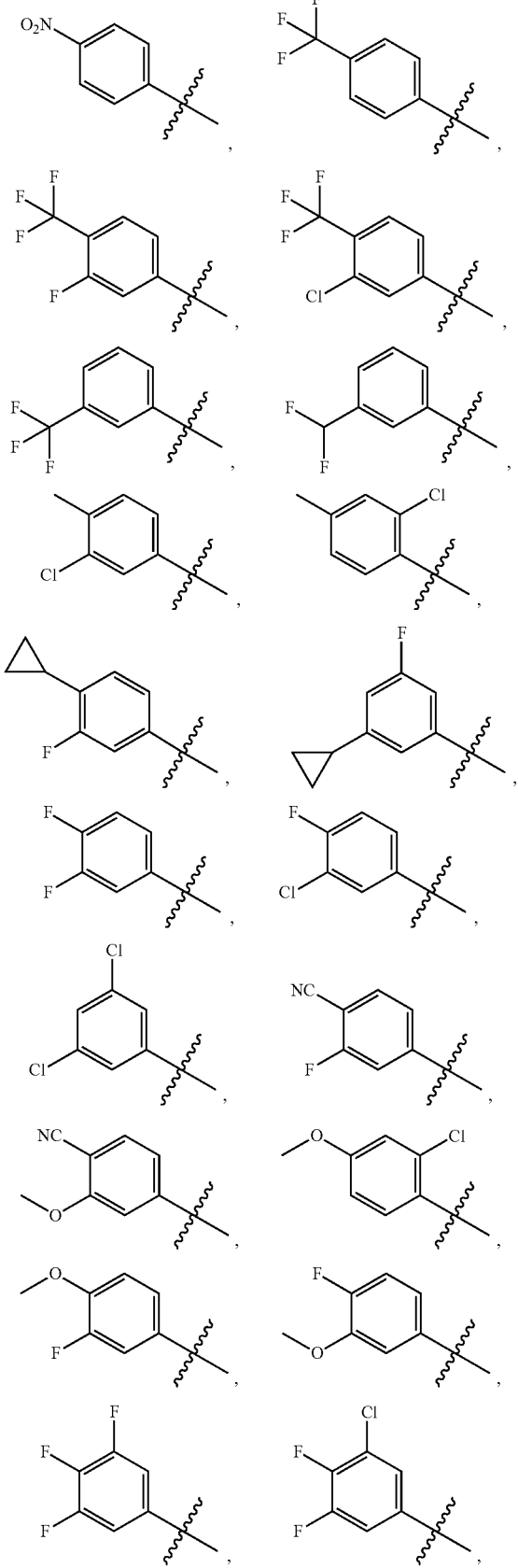

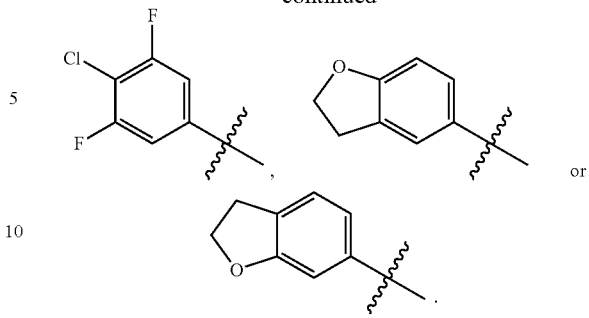

In some embodiments, the compound of Formula (I) is a compound of Formula (Ia):

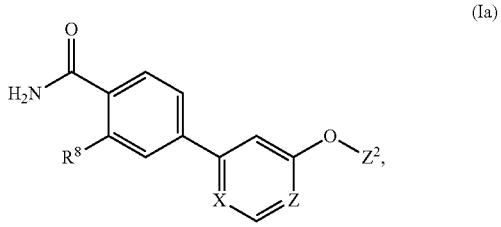
(Ia)

or pharmaceutically acceptable salts thereof.

In some embodiments, the compound of Formula (I) is a compound of Formula (Ib):

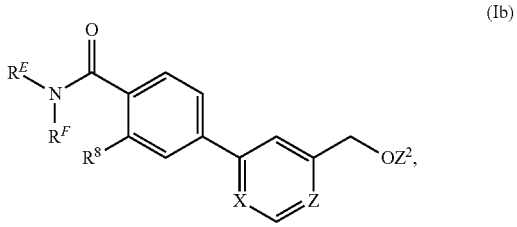
(Ib)

or pharmaceutically acceptable salts thereof.

In some embodiments, the compound of Formula (I) is a compound of Formula (Ic):

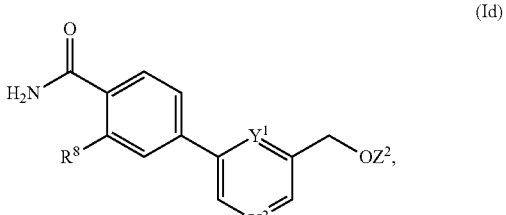
(Id)

or pharmaceutically acceptable salts thereof.

In some embodiments, the compound of Formula (I) is a compound of Formula (Id):

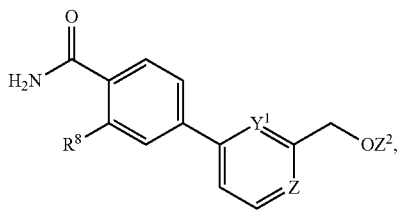

(Id)

or pharmaceutically acceptable salts thereof.

In some embodiments, the compounds of Formula (I) are as listed in Table 2, disclosed herein, or pharmaceutically acceptable salts thereof.

In some embodiments, pharmaceutical compositions are provided that comprise a compound of Formula (I), including one or more of the specific compounds described herein (see, e.g., Table 2), and at least one pharmaceutically acceptable excipient.

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

Pharmaceutical Compositions, Formulation, and Dosage Forms

The present disclosure further provides for pharmaceutical products such as pharmaceutical compositions, formulations, unit dosage forms, and kits; each comprising a compound of Formula (I), or a pharmaceutically acceptable salt thereof.

The present disclosure also provides for pharmaceutical compositions comprising any of the compounds described herein (e.g., a compound of Formula (I), including specific compounds described herein) or pharmaceutically acceptable salts thereof, and an excipient such as a pharmaceutically acceptable excipient. A pharmaceutically acceptable excipient is a physiologically and pharmaceutically suitable non-toxic and inactive material or ingredient that does not interfere with the activity of the drug substance; an excipient also can be called a carrier. The formulation methods and excipients described herein are exemplary and are in no way limiting. Pharmaceutically acceptable excipients are well known in the pharmaceutical art and described, for example, in Rowe et al., *Handbook of Pharmaceutical Excipients: A Comprehensive Guide to Uses, Properties, and Safety*, 5th Ed., 2006, and in *Remington: The Science and Practice of Pharmacy* (Gennaro, 21st Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like can be provided in the pharmaceutical composition. In addition, antioxidants and suspending agents may also be used.

For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GPR52 agonist, diluents, dispersing and surface active agents, binders, and lubricants. One skilled in this art may further formulate the GPR52 agonist in an appropriate manner, and in accordance with accepted practices, such as those disclosed in Remington, supra.

Methods of administration include systemic administration of a GPR52 agonist described herein, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds described herein (or pharmaceutically acceptable salts thereof) can be prepared in aqueous injection solutions which may contain, in addition to the GPR52 agonist, buffers, antioxidants, bacteriostats, and other additives commonly employed in such solutions.

Pharmaceutical preparations for oral administration can be obtained by any suitable method, typically by uniformly mixing the compound(s) with liquids or finely divided solid carriers, or both, in the required proportions and then, if necessary, processing the mixture, after adding suitable auxiliaries, if desired, forming the resulting mixture into a desired shape to obtain tablets or dragee cores.

Conventional excipients, such as binding agents, fillers, adjuvant, carrier, acceptable wetting agents, tableting lubricants and disintegrants can be used in tablets and capsules for oral administration. Liquid preparations for oral administration can be in the form of solutions, emulsions, aqueous or oily suspensions and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives and flavorings and colorants can be added to the liquid preparations. Parenteral dosage forms can be prepared by dissolving the compound described herein in a suitable liquid vehicle and filter sterilizing the solution before lyophilization, or simply filling and sealing an appropriate vial or ampule.

Some embodiments provide methods for preparing a pharmaceutical composition comprising the step of admixing a compound of Formula (I), or a pharmaceutically acceptable salt thereof, and a pharmaceutically acceptable carrier.

In making pharmaceutical compositions comprising a compound of Formula (I), or pharmaceutically acceptable salts thereof, the drug substance is typically mixed (i.e., admixed) with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier, or medium for the drug substance. Thus, the compositions can be in the form of tablets, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

For preparing solid form pharmaceutical compositions such as powders, tablets, capsules, cachets, suppositories and dispersible granules an excipient can be one or more substances which may also act as diluents, flavoring agents, solubilizers, lubricants, suspending agents, binders, preservatives, tablet disintegrating agents, or an encapsulating material. Also included are solid form preparations which are intended to be converted, shortly before use, to liquid form preparations for oral administration. Such liquid forms include solutions, suspensions and emulsions. These preparations may contain, in addition to the drug substance, colorants, flavors, stabilizers, buffers, artificial and natural sweeteners, dispersants, thickeners, solubilizing agents and the like.

For preparing suppositories, a low melting wax, such as an admixture of fatty acid glycerides or cocoa butter, is first melted and the drug substance is dispersed homogeneously therein, as by stirring. The molten homogenous mixture is then poured into convenient sized molds, allowed to cool and thereby to solidify.

Formulations suitable for vaginal administration can be presented as pessaries, tampons, creams, gels, pastes, foams or sprays containing in addition to the drug substance such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions can be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The pharmaceutical compositions may take such forms as suspensions, solutions, or emulsions in oily or aqueous vehicles and may contain formulatory agents such as suspending, stabilizing and/or dispersing agents. Alternatively, the pharmaceutical compositions can be in powder form, obtained by aseptic isolation of sterile solid or by lyophilization from solution, for constitution with a suitable vehicle, e.g., sterile, pyrogen-free water, before use.

The pharmaceutical compositions can be formulated as an aqueous solution, an aqua-alcoholic solution, a solid suspension, an emulsion, a liposomal suspension, or a freeze-dried powder for reconstitution. Such pharmaceutical compositions can be administered directly or as an admixture for further dilution/reconstitution. Route of administration includes intravenous bolus, intravenous infusion, irrigation, and instillation. Suitable solvents include water, alcohols, PEG, propylene glycol, and lipids; pH adjustments using an acid, e.g., HCl or citric acid, can be used to increase solubility and resulting compositions subjected to suitable sterilization procedures know in the art, such as, aseptic filtration. In some embodiments, the pH of the aqueous solution is about 2.0 to about 4.0. In some embodiments, the pH of the aqueous solution is about 2.5 to about 3.5.

Aqueous formulations suitable for oral use can be prepared by dissolving or suspending the drug substance in water and adding suitable colorants, flavors, stabilizing and thickening agents, as desired.

Aqueous suspensions suitable for oral use can be made by dispersing the finely divided drug substance in water with viscous material, such as natural or synthetic gums, resins, methylcellulose, sodium carboxymethylcellulose, or other well-known suspending agents.

For topical administration to the epidermis the compounds described herein, or pharmaceutically acceptable salts thereof can be formulated as gels, ointments, creams or lotions, or as a transdermal patch. Also, formulations suitable for topical administration in the mouth include lozenges comprising drug substance in a flavored base, usually sucrose and acacia or tragacanth; pastilles comprising the drug substance in an inert base such as gelatin and glycerin or sucrose and acacia; and mouthwashes comprising the drug substance in a suitable liquid carrier. Ointments and creams may, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. In some embodiments, topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like.

Solutions or suspensions can be applied directly to the nasal cavity by conventional means, for example with a dropper, pipette or spray. The formulations can be provided in single or multi-dose form. In the latter case of a dropper or pipette, this can be achieved by the subject administering an appropriate, predetermined volume of the solution or suspension. In the case of a spray, this can be achieved for example by means of a metering atomizing spray pump.

Administration to the respiratory tract may also be achieved by means of an aerosol formulation provided in a pressurized pack with a suitable propellant. If the compounds described herein, or pharmaceutically acceptable salts thereof or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds described herein (or pharmaceutically acceptable salts thereof), as an aerosol can be prepared by processes well known to the person skilled in the art. For their preparation, for example, solutions or dispersions of the compounds described herein (or pharmaceutically acceptable salts thereof), in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug can be controlled by provision of a metered valve.

Alternatively, the pharmaceutical composition can be provided in the form of a dry powder, for example, a powder mix of the compound in a suitable, powder base such as lactose, starch, starch derivatives such as hydroxypropylmethyl cellulose and polyvinylpyrrolidone (PVP). Conveniently the powder carrier will form a gel in the nasal cavity. The powder composition can be presented in unit dose form for example in capsules or cartridges of, e.g., gelatin, or blister packs from which the powder can be administered by means of an inhaler.

The compounds of Formula (I), or pharmaceutically acceptable salts thereof may also be administered via a rapid dissolving or a slow release composition, wherein the composition includes a biodegradable rapid dissolving or slow release carrier (such as a polymer carrier and the like). Rapid dissolving or slow release carriers are well known in the art and are used to form complexes that capture therein compounds of Formula (I), or pharmaceutically acceptable salts thereof and either rapidly or slowly degrade/dissolve in a suitable environment (e.g., aqueous, acidic, basic, etc.).

The pharmaceutical preparations are preferably in unit dosage forms. In such form, the preparation is subdivided into unit doses containing appropriate quantities of the drug substance. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form. In some embodiments, the pharmaceutical preparation is a tablet or capsule for oral administration. In some embodiments, the pharmaceutical preparation is a liquid formulated for intravenous administration.

The compositions can be formulated in a unit dosage form, each dosage containing the drug substance or equivalent mass of the drug substance. The term "unit dosage forms" refers to physically discrete units of a formulation suitable as unitary dosages for human subjects and other mammals, each unit containing a predetermined quantity of drug substance calculated to produce the desired therapeutic effect, in association with a suitable excipient, as described herein.

The compositions described herein can be formulated to provide immediate and/or timed release (also called extended release, sustained release, controlled release, or slow release) of the drug substance after administration to a subject by employing procedures known in the art. For example, the tablets including compounds of Formula (I), or pharmaceutically acceptable salts thereof, can be coated or otherwise compounded to provide a dosage form affording the advantage of prolonged action. For example, the tablet can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms including the drug substance can be incorporated for administration orally or by injection include aqueous solutions, suitably flavored syrups, aqueous or oil suspensions, and flavored emulsions with edible oils such as cottonseed oil, sesame oil, coconut oil, or peanut oil, and similar excipients.

The pharmaceutical compositions described herein can be sterilized by conventional sterilization techniques, or can be sterile filtered. Aqueous solutions can be packaged for use as is, or lyophilized, the lyophilized preparation being combined with a sterile aqueous carrier prior to administration. The pH of the compound preparations is typically between 3 and 11, more preferably from 5 to 9 and most preferably from 7 to 8. It will be understood that use of certain of the foregoing excipients may result in the formation of pharmaceutically acceptable salts.

Compositions for inhalation or insufflation include solutions and suspensions in pharmaceutically acceptable, aqueous or organic solvents, or mixtures thereof, and powders. The liquid or solid compositions may contain suitable excipients as described herein. In some embodiments, the compositions are administered by the oral or nasal respiratory route for local or systemic effect. Compositions can be nebulized by use of inert gases. Nebulized solutions can be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions may, if desired, be presented in a pack or dispenser device which may contain one or more-unit dosage forms containing the drug substance. The pack may for example comprise metal or plastic foil, such as a blister pack. The pack or dispenser device can be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

For preparing solid compositions such as tablets, the drug substance can be mixed with an excipient to form a solid preformulation composition containing a homogeneous mixture of components. When referring to these preformulation compositions as homogeneous, the drug substance is typically dispersed evenly throughout the composition so that the composition can be readily subdivided into equally effective unit dosage forms such as tablets and capsules.

Kits with unit doses of one or more of the compounds described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

The compounds described herein, or a pharmaceutically acceptable salt thereof, can be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The amount of compound or composition administered to a subject will also vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptomology and/or pathology of the disease and its complications. Therapeutically effective doses will depend on the disease condition being treated as well as by the judgment of the attending clinician depending upon factors such as the severity of the disease, the age, weight and general condition of the subject, and the like.

The desired dose may conveniently be presented in a single dose or presented as divided doses administered at appropriate intervals, for example, as two, three, four, or more sub-doses per day. The sub-dose itself can be further divided, e.g., into a number of discrete loosely spaced administrations. The daily dose can be divided, especially when relatively large amounts are administered as deemed appropriate, into several, for example two, three, or four-part administrations. If appropriate, depending on individual behavior, it can be necessary to deviate upward or downward from the daily dose indicated.

It will be apparent to those skilled in the art that the dosage forms described herein may comprise a compound described herein or pharmaceutically acceptable salt thereof.

Some embodiments provide use of a least one compound as disclosed and described herein, or a pharmaceutically acceptable salt thereof, or a pharmaceutical composition as disclosed and described herein, in the manufacture of a medicament for treating a neurological disorder, wherein the neurological disorder is selected from the group consisting of schizophrenia, cognitive impairment, a panic disorder, a phobic disorder, drug-induced psychotic disorder, delusional psychosis, neuroleptic-induced dyskinesia, Parkinson's disease, drug-induced Parkinson's syndrome, extrapyramidal syndrome, Alzheimer's Disease, Lewy Body Dementia, bipolar disorder, ADHD, Tourette's syndrome, an extrapyramidal or movement disorder, a motor disorder, a hyperkinetic movement disorder, a psychotic disorder, catatonia, a mood disorder, a depressive disorder, an anxiety disorder, obsessive-compulsive disorder (OCD), an autism spectrum disorder, a prolactin-related disorder (e.g., hyperprolactinemia), a neurocognitive disorder, a trauma- or stressor-related disorder (e.g., PTSD); a disruptive, impulse-control, or conduct disorder, a sleep-wake disorder, a substance-related disorder, an addictive disorder, a behavioral disorder, hypofrontality, an abnormality in the tuberoinfundibular, mesolimbic, mesocortical, or nigrostriatal pathway, decreased activity in the striatum, cortical dysfunction, neurocognitive dysfunction and the cognitive deficits associated with schizophrenia; Parkinson's Disease, drug induced Parkinsonism, dyskinesias, dystonia, chorea, levodopa induced dyskinesia, cerebral palsy and progressive supranuclear palsy, and Huntington's disease, including chorea associated with Huntington's disease.

Some embodiments provide use of a least one compound as disclosed and described herein, or a pharmaceutically acceptable salt thereof, or a pharmaceutical composition as disclosed and described herein, in the manufacture of a medicament for ameliorating one or more symptoms of a neurological disorder, wherein the neurological disorder is selected from the group consisting of schizophrenia, cognitive impairment, a panic disorder, a phobic disorder, drug-induced psychotic disorder, delusional psychosis, neuroleptic-induced dyskinesia, Parkinson's disease, drug-induced Parkinson's syndrome, extrapyramidal syndrome, Alzheimer's Disease, Lewy Body Dementia, bipolar disorder, ADHD, Tourette's syndrome, an extrapyramidal or movement disorder, a motor disorder, a hyperkinetic movement disorder, a psychotic disorder, catatonia, a mood disorder, a depressive disorder, an anxiety disorder, obsessive-compulsive disorder (OCD), an autism spectrum disorder, a prolactin-related disorder (e.g., hyperprolactinemia), a neurocognitive disorder, a trauma- or stressor-related disorder (e.g., PTSD); a disruptive, impulse-control, or conduct disorder, a sleep-wake disorder, a substance-related disorder, an addictive disorder, a behavioral disorder, hypofrontality, an abnormality in the tuberoinfundibular, mesolimbic, mesocortical, or nigrostriatal pathway, decreased activity in the striatum, cortical dysfunction, neurocognitive dysfunction and the cognitive deficits associated with schizophrenia; Parkinson's Disease, drug induced Parkinsonism, dyskinesias, dystonia, chorea, levodopa induced dyskinesia, cerebral palsy and progressive supranuclear palsy, and Huntington's disease, including chorea associated with Huntington's disease.

Methods of Treatment

The present disclosure further provides for methods of treating a neurological disease in a subject in need thereof, comprising administering to the subject a therapeutically effective amount of a compound as disclosed and described herein, or a pharmaceutically acceptable salt thereof (e.g. a compound of Formulae (I), (Ia), (Ib), (Ic) or (Id), or a pharmaceutically acceptable salt thereof, or compound of Table 2, or a pharmaceutically acceptable salt thereof), or a pharmaceutical composition comprising a compound as disclosed and described herein, or a pharmaceutically acceptable salt thereof (e.g. a compound of Formulae (I), (Ia), (Ib), (Ic) or (Id), or a pharmaceutically acceptable salt thereof, or compound of Table 2, or a pharmaceutically acceptable salt thereof), and a pharmaceutically acceptable excipient. The present disclosure also provides use of a compound as disclosed and described herein, or a pharmaceutically acceptable salt thereof (e.g. a compound of Formulae (I), (Ia), (Ib), (Ic) or (Id), or a pharmaceutically acceptable salt thereof, or compound of Table 2, or a pharmaceutically acceptable salt thereof) for treating a neurological disease in a subject in need thereof.

In some embodiments, the subject has been previously diagnosed with a neurological disorder. In some embodiments, the subject is currently suffering from a neurological disorder. In some embodiments, the subject is suspected of having a neurological disorder. In some embodiments, the subject has been previously treated with one or more therapeutic agents approved for the treatment of a neurological disorder.

In some embodiments, the neurological disorder is selected from schizophrenia, cognitive impairment, a panic disorder, a phobic disorder, drug-induced psychotic disorder, delusional psychosis, neuroleptic-induced dyskinesia, Parkinson's disease, drug-induced Parkinson's syndrome, extrapyramidal syndrome, Alzheimer's Disease, Lewy Body Dementia, bipolar disorder, ADHD, Tourette's syndrome, an extrapyramidal or movement disorder, a motor disorder, a hyperkinetic movement disorder, a psychotic disorder, catatonia, a mood disorder, a depressive disorder, an anxiety disorder, obsessive-compulsive disorder (OCD), an autism spectrum disorder, a prolactin-related disorder (e.g., hyperprolactinemia), a neurocognitive disorder, a trauma- or stressor-related disorder (e.g., PTSD); a disruptive, impulse-control, or conduct disorder, a sleep-wake disorder, a substance-related disorder, an addictive disorder, a behavioral disorder, hypofrontality, an abnormality in the tuberoinfundibular, mesolimbic, mesocortical, or nigrostriatal pathway, decreased activity in the striatum, cortical dysfunction, neurocognitive dysfunction and the cognitive deficits associated with schizophrenia; Parkinson's Disease, drug induced Parkinsonism, dyskinesias, dystonia, chorea, levodopa induced dyskinesia, cerebral palsy, progressive supranuclear palsy, Huntington's disease, and chorea associated with Huntington's disease.

In some embodiments, the neurological disorder is selected from schizophrenia, cognitive impairment, drug-induced psychotic disorder, delusional psychosis, neuroleptic-induced dyskinesia, Parkinson's disease, drug-induced Parkinson's syndrome, extrapyramidal syndrome, Alzheimer's Disease, Lewy Body Dementia, bipolar disorder, ADHD, Tourette's syndrome, catatonia, a mood disorder, obsessive-compulsive disorder (OCD), hyperprolactinemia, PTSD, hypofrontality, Parkinson's Disease, drug induced Parkinsonism, dyskinesias, dystonia, chorea, levodopa induced dyskinesia, cerebral palsy, progressive supranuclear palsy, Huntington's disease, and chorea associated with Huntington's disease.

In some embodiments. In some embodiments, the neurological disorder is the neurological disorder is selected from schizophrenia. In some embodiments, the neurological disorder is cognitive impairment. In some embodiments, the neurological disorder is a panic disorder. In some embodiments, the neurological disorder is a phobic disorder. In some embodiments, the neurological disorder is drug-induced psychotic disorder. In some embodiments, the neurological disorder is delusional psychosis. In some embodiments, the neurological disorder is neuroleptic-induced dyskinesia. In some embodiments, the neurological disorder is Parkinson's disease. In some embodiments, the neurological disorder is drug-induced Parkinson's syndrome. In some embodiments, the neurological disorder is extrapyramidal syndrome. In some embodiments, the neurological disorder is Alzheimer's Disease. In some embodiments, the neurological disorder is Lewy Body Dementia. In some embodiments, the neurological disorder is bipolar disorder. In some embodiments, the neurological disorder is ADHD. In some embodiments, the neurological disorder is Tourette's syndrome. In some embodiments, the neurological disorder is an extrapyramidal or movement disorder. In some embodiments, the neurological disorder is a motor disorder. In some embodiments, the neurological disorder is a hyperkinetic movement disorder. In some embodiments, the neurological disorder is a psychotic disorder. In some embodiments, the neurological disorder is catatonia. In some embodiments, the neurological disorder is a mood disorder. In some embodiments, the neurological disorder is a depressive disorder. In some embodiments, the neurological disorder is an anxiety disorder. In some embodiments, the neurological disorder is obsessive-compulsive disorder (OCD). In some embodiments, the neurological disorder is an autism spectrum disorder. In some embodiments, the neurological disorder is a prolactin-related disorder. In some embodiments, the neurological disorder is hyperprolactinemia). In some embodiments, the neurological disorder is a neurocognitive disorder. In some embodiments, the neurological disorder is a trauma- or stressor-related disorder. In some embodiments, the neurological disorder is PTSD. In some embodiments, the neurological disorder is impulse-control. In some embodiments, the neurological disorder is or conduct disorder. In some embodiments, the neurological disorder is a sleep-wake disorder. In some embodiments, the neurological disorder is a substance-related disorder. In some embodiments, the neurological disorder is an addictive disorder. In some embodiments, the neurological disorder is a behavioral disorder. In some embodiments, the neurological disorder is hypofrontality. In some embodiments, the neurological disorder comprises an abnormality in the tuberoinfundibular pathway. In some embodiments, the neurological disorder comprises an abnormality in the mesolimbic pathway. In some embodiments, the neurological disorder comprises decreased activity in the striatum. In some embodiments, the neurological disorder is cortical dysfunction. In some embodiments, the neurological disorder is neurocognitive dysfunction and the cognitive deficits associated with schizophrenia; Parkinson's Disease. In some embodiments, the neurological disorder is drug induced Parkinsonism. In some embodiments, the neurological disorder is dyskinesias. In some embodiments, the neurological disorder is dystonia. In some embodiments, the neurological disorder is chorea. In some embodiments, the neurological disorder is levodopa induced dyskinesia. In some embodiments, the neurological disorder is cerebral palsy. In some embodiments, the neurological disorder is progressive supranuclear palsy. In some embodiments, the neurological disorder is Huntington's disease. In some embodiments, the neurological disorder is and chorea associated with Huntington's disease.

In some embodiments, the panic disorder comprises panic attacks. In some embodiments, the phobic disorder is related to a situation (e.g., social phobia). In some embodiments, the phobic disorder is related to an object (e.g., arachnophobia). In some embodiments, the extrapyramidal syndrome comprises continuous spasms or muscle contractions, motor restlessness, muscle rigidity, slowed muscle response, tremors, or irregular, jerky movements. In some embodiments, the extrapyramidal or movement disorder is tardive dyskinesia, an acute dystonic reaction, akathisia, or pseudo-Parkinsonism. In some embodiments, the motor disorder is developmental coordination disorder, stereotypic movement disorder, or Tourette syndrome. In some embodiments, the hyperkinetic movement disorder comprises athetosis, ballism, chorea, dystonia, myoclonus, restless leg syndrome, stereopathy, tics, or tremors. In some embodiments, the psychotic disorder is schizophrenia, schizophreniform disorder, delusional disorder, or chronic hallucinatory psychosis. In some embodiments, the mood disorder is major depression or bipolar depression. In some embodiments, the depressive disorder is major depression, atypical depression, melancholic depression, catatonic major depression, postpartum depression, seasonal affective disorder, or double depression. In some embodiments, the anxiety disorder is generalized anxiety disorder, post-traumatic stress disorder, obsessive compulsive disorder, a phobic disorder, or a panic disorder. In some embodiments, the autism spectrum disorder is autism or Asperger syndrome. In some embodiments, the neurocognitive disorder is major neurocognitive disorder or mild neurocognitive disorder. In some embodiments, the disruptive, impulse-control, or conduct disorder is attention deficit disorder, attention deficit hyperactivity disorder, oppositional defiant disorder, sexual compulsion, internet addiction, pyromania, intermittent explosive disorder, compulsive shopping, or kleptomania. In some embodiments, the sleep-wake disorder is insomnia, narcolepsy, or night terrors. In some embodiments, the substance-related disorder is alcoholism, opioid addiction, prescription drug addiction, and/or illegal drug addiction. In some embodiments, the addictive disorder comprises substance addition (e.g., alcoholism) or experiential additional (e.g., gambling addiction). In some embodiments, the behavioral disorder is attention deficit disorder, attention deficit hyperactivity disorder, or oppositional defiant disorder.

It is understood in the art that some of the syndromes and symptoms described herein may have overlapping symptoms, and/or some of the particular disorders described herein may fall under multiple categories of disorders described herein. For example, tardive dyskinesia can be categorized at least as an extrapyramidal or movement disorder, a hyperkinetic movement disorder, a motor disorder, or an extrapyramidal syndrome.

Some embodiments provide a method for modulating GPR52 in a cell comprising contacting the cell with a compound of any of Formulae (I), (Ia), (Ib), (Ic) or (Id). In some embodiments, the compound is described in Table 2. Without being bound by any theory, the compound and the receptor can be in contact for a time sufficient and under appropriate conditions to permit interaction between the cell and the compound.

In some embodiments, the contacting is in vitro. In some embodiments, the contacting is in vivo. In some embodiments, the contacting is in vivo, wherein the method comprises administering a therapeutically effective amount of a compound of Formula (I), or a pharmaceutically acceptable salt thereof, to a subject having a cell having GPR52 activity.

In certain embodiments, the cell is in a subject who is in need of treatment with a compound disclosed herein. In certain embodiments, the cell is from a subject who is in need of treatment with a compound disclosed herein. In some embodiments, the subject has a neurological disease, condition, or disorder. In some embodiments, the subject is at risk for developing a neurological disease, condition, or disorder. In some embodiments, the subject has been previously diagnosed with a neurological disease, condition, or disorder. In some embodiments, the subject is currently being treated for a neurological disease, condition, or disorder. In some embodiments, the subject is suffering from a neurological disease, condition, or disorder. In some embodiments, the subject is suspected of having a neurological disease, condition, or disorder. In some embodiments, the neurological disease, condition, or disorder is Alzheimer's Disease, Lewy Body Dementia, bipolar disorder, ADHD, Tourette's syndrome, an extrapyramidal or movement disorder, a motor disorder, a hyperkinetic movement disorder, a psychotic disorder, catatonia, a mood disorder, a depressive disorder, an anxiety disorder, obsessive-compulsive disorder (OCD), an autism spectrum disorder, a prolactin-related disorder (e.g., hyperprolactinemia), a neurocognitive disorder, a trauma- or stressor-related disorder (e.g., PTSD); a disruptive, impulse-control, or conduct disorder, a sleep-wake disorder, a substance-related disorder, an addictive disorder, a behavioral disorder, hypofrontality, an abnormality in the tuberoinfundibular, mesolimbic, mesocortical, or nigrostriatal pathway, decreased activity in the striatum, cortical dysfunction, neurocognitive dysfunction and the cognitive deficits associated with schizophrenia, Parkinson's Disease, drug induced Parkinsonism, dyskinesias, dystonia, chorea, levodopa induced dyskinesia, cerebral palsy and progressive supranuclear palsy, and Huntington's disease, particularly chorea associated with Huntington's disease.

Combinations of Embodiments

It is further appreciated that certain features of the present disclosure, which are, for clarity, described in the context of separate embodiments, can also be provided in combination in a single embodiment. Conversely, various features of the present disclosure which are, for brevity, described in the context of a single embodiment, can also be provided separately or in any suitable subcombination.

EXAMPLES

Detailed compound synthesis methods are described in the Examples provided herein. A person having ordinary skill in the chemical art would be able to make a compound of Formula (Ia) and the formulae related thereto, including specific compounds described herein, by these methods or similar methods or other methods practiced by a person skilled in the art. In general, starting components are commercially available chemicals and can be obtained from commercial sources or can be made according to organic synthesis techniques known to those skilled in this art, starting from commercially available chemicals and/or from compounds described in the chemical literature. The compounds described herein, supra and infra, are named according to MarvinSketch 18.24.0 or ChemDraw Professional 18.2.0.48. In certain instances, when common names are used it is understood that these common names would be recognized by those skilled in the art.

In general, the compounds used in the reactions described herein can be made according to organic synthesis techniques known to those skilled in this art, starting from commercially available chemicals and/or from compounds described in the chemical literature. "Commercially available chemicals" can be obtained from standard commercial sources including Acros Organics (Pittsburgh PA), Aldrich Chemical (Milwaukee WI, including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester PA), Crescent Chemical Co. (Hauppauge NY), Eastman Organic Chemicals, Eastman Kodak Company (Rochester NY), Fisher Scientific Co. (Pittsburgh PA), Fisons Chemicals (Leicestershire UK), Frontier Scientific (Logan UT), ICN Biomedicals, Inc. (Costa Mesa CA), Key Organics (Cornwall U.K.), Lancaster Synthesis (Windham NH), Maybridge Chemical Co. Ltd. (Cornwall U.K.), Parish Chemical Co. (Orem UT), Pfaltz & Bauer, Inc. (Waterbury CN), Polyorganix (Houston TX), Pierce Chemical Co. (Rockford IL), Riedel de Haen AG (Hanover, Germany), Spectrum Quality Product, Inc. (New Brunswick, NJ), TCI America (Portland OR), Trans World Chemicals, Inc. (Rockville MD), and Wako Chemicals USA, Inc. (Richmond VA).

Methods known to one of ordinary skill in the art can be identified through various reference books and databases. Suitable reference books and treatise that detail the synthesis of reactants useful in the preparation of compounds of the present disclosure, or provide references to articles that describe the preparation, include for example, *Synthetic Organic Chemistry*, John Wiley & Sons, Inc., New York; S. R. Sandler et al., *Organic Functional Group Preparations*, 2nd Ed., Academic Press, New York, 1983; H. O. House, *Modern Synthetic Reactions*, 2nd Ed., W. A. Benjamin, Inc. Menlo Park, Calif 1972; T. L. Gilchrist, *Heterocyclic Chemistry, 2nd Ed.*, John Wiley & Sons, New York, 1992; J. March, *Advanced Organic Chemistry: Reactions, Mechanisms and Structure*, 4th Ed., Wiley Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. *Organic Synthesis: Concepts, Methods, Starting Materials*, Second, Revised and Enlarged Edition (1994) John Wiley & Sons ISBN: 3 527-29074-5;

Hoffman, R. V. *Organic Chemistry, An Intermediate Text* (1996) Oxford University Press, ISBN 0-19-509618-5; Larock, R. C. *Comprehensive Organic Transformations: A Guide to Functional Group Preparations*, 2nd Edition (1999) Wiley-VCH, ISBN: 0-471-19031-4; March, J. *Advanced Organic Chemistry: Reactions, Mechanisms, and Structure*, 4th Edition (1992) John Wiley & Sons, ISBN: 0-471-60180-2; Otera, J. (editor) *Modern Carbonyl Chemistry*, (2000) Wiley-VCH, ISBN: 3-527-29871-1; Patai, S., *Patai's* 1992 *Guide to the Chemistry of Functional Groups*, (1992) Interscience ISBN: 0-471-93022-9; Quin, L. D. et al. *A Guide to Organophosphorus Chemistry*, (2000) Wiley-Interscience, ISBN: 0-471-31824-8; Solomons, T. W. G. *Organic Chemistry*, 7th Edition (2000) John Wiley & Sons, ISBN: 0-471-19095-0; Stowell, J. C., *Intermediate Organic Chemistry*, 2nd Edition (1993) Wiley-Interscience, ISBN: 0-471-57456-2; *Industrial Organic Chemicals: Starting Materials and Intermediates: An Ullmann's Encyclopedia*, (1999) John Wiley & Sons, ISBN: 3-527-29645-X, in 8 volumes; *Organic Reactions*, (1942-2019) John Wiley & Sons, in over 95 volumes; and *Chemistry of Functional Groups*, John Wiley & Sons, in hardcover volumes (86) and electronic volumes (26).

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., can be contacted for more details). Chemicals that are known but not commercially available in catalogs can be prepared by custom chemical synthesis houses according to known methods, where many of the standard chemical supply houses (e.g., those listed above) provide custom synthesis services.

The term "reducing agent" refers to a compound that contributes a hydride to an electrophilic position of a reactant compound such as an unsaturated carbon (e.g. carbon of a carbonyl moiety) such as converting a ketone containing reactant compound to an alcohol product compound or converting an ester containing reactant compound to an alcohol product compound. The reducing agent can be a hydride reducing agent. Example hydride reducing agents include, but are not limited to, diborane, borane (e.g. borane tetrahydrofuran complex), 9-borabicyclo[3.3.1]nonane, lithium aluminum hydride, diisobutylaluminum hydride, lithium diisobutyl-tert-butoxyaluminum hydride, lithium tri-tert-butoxyaluminum hydride, lithium tris[(3-ethyl-3-pentyl)oxy]aluminohydride, sodium bis(2-methoxyethoxy)aluminum dihydride, sodium aluminum hydride, calcium borohydride, lithium borohydride, magnesium borohydride, potassium borohydride, tetrabutylammonium borohydride, tetraethylammonium borohydride, tetramethylammonium borohydride, bis(triphenylphosphine)copper(I) borohydride, lithium 9-borabicyclo[3.3.1]nonane hydride, sodium triacetoxyborohydride, potassium tri-sec-butylborohydride, sodium tri-sec-butylborohydride, potassium trisiamylborohydride, lithium triethylborohydride, potassium triethylborohydride, sodium triethylborohydride, potassium triphenylborohydride, lithium dimethylaminoborohydride, lithium pyrrolidinoborohydride, sodium cyanoborohydride, sodium trimethoxyborohydride, sodium borohydride, and the like.

The term "halogenating agent" refers to a compound that contributes a halogen atom to a reactant compound such as converting an alcohol reactant compound to an alkyl halide product compound. Examples of halogenating agents include, but are not limited to, thionyl chloride, oxalyl chloride, phosphorus oxychloride, phosphorus pentachloride, phosphorus trichloride, methanesulfonyl chloride and NaI, p-toluenesulfonyl chloride and NaI, phosphorus tribromide, triphenylphosphine dibromide, phosphorus pentabromide or thionyl bromide, and the like.

The term "amide coupling agent" refers to a compound that facilitates formation of an amide bond where carboxylic acid activation is required to promote coupling with an amine. Examples of amide coupling agents include, but not limited to, thionyl chloride, oxalyl chloride, phosphorus oxychloride, Vilsmeier reagent, propylphosphonic anhydride, ethylmethylphosphinic anhydride (EMPA), Ac$_2$O, pivaloyl chloride, ethyl chloroformate (ECF), isobutyl chloroformate (IBCF), 2-ethoxy-1-ethoxycarbonyl-1,2-dihydroquinoline (EEDQ), methanesulfonyl chloride (MsCl), p-toluenesulfonyl chloride (TsCl), pentafluorophenyl trifluoroacetate, cyanuric chloride, 2-chloro-4,6-dimethoxy-1,3,5-triazine (CDMT), 4-(4,6-dimethoxy-1,3,5-triazin-2-yl)-4-methyl morpholinium chloride (DMTMM), 1-tert-butyl-3-ethylcarbodiimide, 1,1'-carbonyldiimidazole (CDI), N,N'-dicyclohexylcarbodiimide (DCC), N,N'-diisopropylcarbodiimide (DIC), N-(3-dimethylaminopropyl)-N'-ethylcarbodiimide (EDC), 1,3-di-p-tolylcarbodiimide, benzotriazole-1-yl-oxy-tris-(dimethylamino)-phosphonium hexafluorophosphate (BOP), benzotriazole-1-yl-oxy-tris-pyrrolidino-phosphonium hexafluorophosphate (PyBOP), 6-chloro-benzotriazole-1-yloxy-tris-pyrrolidinophosphonium hexafluorophosphate (PyClock), (7-azabenzotriazol-1-yloxy) trispyrrolidinophosphonium hexafluorophosphate (PyAOP), 1-cyano-2-ethoxy-2-oxoethylideneaminooxy-tris-pyrrolidino-phosphonium hexafluorophosphate (PyOxim), 1-[(1-(cyano-2-ethoxy-2-oxoethylideneaminooxy) dimethylaminomorpholino)] uronium hexafluorophosphate (COMU), 3-(diethoxy-phosphoryloxy)-1,2,3-benzo[d]triazin-4(3H)-one (DEPBT), 0-[(ethoxycarbonyl)cyanomethylenamino]-N,N,N',N'-tetramethyluronium tetrafluoroborate (TOTU), 0-(2-Oxo-1(2H)pyridyl)-N,N,N',N'-tetramethyluronium tetrafluoroborate (TPTU), 2-(1H-benzotriazole-1-yl)-1,1,3,3-tetramethylaminium tetrafluoroborate (TBTU), N,N,N',N'-tetramethyl-O—(N-succinimidyl)uronium hexafluorophosphate (HSTU), 2-(1H-benzotriazole-1-yl)-1,1,3,3-tetramethyluronium hexafluorophosphate (HBTU), 2-(6-Chloro-1H-benzotriazole-1-yl)-1,1,3,3-tetramethylaminium hexafluorophosphate (HCTU), and 1-[bis(dimethylamino)methylene]-1H-1,2,3-triazolo[4,5-b]pyridinium 3-oxide hexafluorophosphate (HATU).

The term "base" refers to a compound that is an electron pair donor in an acid-base reaction.

The base can be an inorganic base or an organic base.

The term "organic base" refers to a base including at least one C—H bond (e.g. an amine base). In some embodiments, the amine base can be a primary, secondary, or tertiary amine. Examples of an amine base include, but are not limited to, methylamine, dimethylamine, diethylamine, diphenylamine, trimethylamine, triethylamine, N,N-diisopropylethylamine, diisopropylamine, piperidine, 2,2,6,6-tetramethylpiperidine, pyridine, 2,6-lutidine, 4-methylmorpholine, 4-ethylmorpholine, 1,5-diazabicyclo[4.3.0]non-5-ene, 1,8-diazabicyclo[5.4.0]undec-7-ene, 1,8-diazabicyclo[5.4.0]undec-7-ene, 1,4-diazabicyclo[2.2.2]octane, 1,8-bis(dimethylamino)naphthalene, 4-(dimethylamino)pyridine, and the like. In some embodiments, the amine base can include one alkali metal or alkaline earth metal. Examples of an amine base including one alkali metal include, but are not limited to, sodium bis(trimethylsilyl)amide, potassium bis(trimethylsilyl)amide, lithium bis(trimethylsilyl)amide, lithium dicyclohexylamide, lithium dimethylamide, lithium diethylamide, lithium diisopropylamide, lithium 2,2,6,6-tetramethylpiperidide, and the like. In some embodiments, the organic base can be a metal alkoxide base. Examples of a metal alkoxide base include, but are not limited to, barium tert-butoxide, lithium tert-amoxide, lithium tert-butoxide, lithium ethoxide, lithium isopropoxide, lithium methoxide, magnesium di-tert-butoxide, magnesium ethoxide, magnesium methoxide, potassium tert-butoxide, potassium ethoxide, potassium methoxide, potassium tert-pentoxide, sodium tert-butoxide, sodium ethoxide, sodium methoxide, sodium tert-pentoxide, and the like. In some embodiments, the organic base can be an organometal base (e.g. organolithium base or organomagnesium base). Examples of an organolithium base include, but are not limited to, n-butyllithium, sec-butyllithium, tert-butyllithium, ethyllithium, hexyllithium, isobutyllithium, isopropyllithium, methyllithium, hexyllithium, phenyllithium, and the like. Examples of an organomagnesium base include, but are not limited to, methylmagnesium bromide, methylmagnesium chloride, methylmagnesium iodide, ethylmagnesium bromide, ethylmagnesium chloride, isopropylmagnesium bromide, isopropylmagnesium chloride, n-propylmagnesium chloride, propylmagnesium chloride, isobutylmagnesium bromide, isobutylmagnesium chloride, butylmagnesium chloride, sec-butylmagnesium chloride, tert-butylmagnesium chloride, cyclopentylmagnesium bromide, cyclopentylmagnesium chloride, 2-pentylmagnesium bromide, 3-pentylmagnesium bromide, isopentylmagnesium bromide, pentylmagnesium bromide, phenylmagnesium bromide, phenylmagnesium chloride, cyclohexylmagnesium chloride, pentadecylmagnesium bromide, octadecylmagnesium chloride, and the like.

The term "inorganic base" refers to a base that does not include at least one C—H bond and includes at least one alkali metal or alkaline earth metal. Examples of an inorganic base include, but are not limited to, sodium hydride, potassium hydride, lithium hydride, calcium hydride, barium carbonate, calcium carbonate, cesium carbonate, lithium carbonate, magnesium carbonate, potassium carbonate, sodium carbonate, cesium hydrogen carbonate, potassium hydrogen carbonate, sodium hydrogen carbonate, barium hydroxide, calcium hydroxide, cesium hydroxide, lithium hydroxide, magnesium hydroxide, potassium hydroxide, sodium hydroxide, and the like.

The term "acid" refers to a compound that is an electron pair acceptor in an acid-base reaction.

The acid can be an inorganic acid or organic acid.

The term "inorganic acid" refers to an acid that does not include a carbon bond. Inorganic acids can be a strong acid or a weak acid. Examples of inorganic acids include, but are not limited to, sulfamic acid, hydrochloric acid, hydriodic acid, hydrobromic acid, perchloric acid, sulfuric acid, nitric acid, boric acid, fluorophosphoric acid, phosphoric acid, and the like.

The term "organic acid" refers to an acid including at least one C—H bond, C—F bond, or C—C bond. Examples of organic acid include but not limited to acetic acid, benzenesulfonic acid, benzoic acid, camphorsulfonic acid, citric acid, difluoroacetic acid, ethanesulfonic acid, formic acid, fumaric acid, gallic acid, glycolic acid, lactic acid, maleic acid, malonic acid, methanesulfonic acid, nitrilotriacetic acid, oxalic acid, phthalic acid, propionic acid, salicylic acid, succinic acid, 5-sulfosalicylic acid, L-(+)-tartaric acid, p-toluenesulfonic acid, trifluoroacetic acid, trifluoromethanesulfonic acid, and the like.

| CERTAIN ABBREVIATIONS |
|---|
| The specification includes numerous abbreviations, whose definitions are listed in the following Table: |

| Abbreviation | Definition |
|---|---|
| ACN or CH$_3$CN | Acetonitrile |
| BOC | tert-Butyloxycarbonyl |
| CDI | 1,1'-Carbonyldiimidazole |
| EtOAc | Ethyl acetate |
| DBU | 1,8-Diazabicyclo[5.4.0]undec-7-ene |
| DCC | Dicyclohexylcarbodiimide |
| DCE | Dichloroethane |
| DCM | Dichloromethane or methylene chloride |
| de | Diastereomeric excess |
| DIPEA | N,N-Diisopropylethylamine |
| DMSO | Dimethylsulfoxide |
| DMSO-d$_6$ | Dimethylsulfoxide-d$_6$ |
| ee | Enantiomeric excess |
| HPLC | High-performance liquid chromatography |
| KHMDS | Potassium bis(trimethylsilyl)amide |
| LCMS | Liquid chromatography-mass spectrometry |
| min. | Minute(s) |
| NH$_4$Cl | Ammonium chloride |
| Pd(PPh$_3$)$_4$ | Palladium-tetrakis(triphenylphosphine) |
| TEA | Triethylamine |
| TFA | Trifluoroacetic acid |
| THF | Tetrahydrofuran |

The following examples are included to demonstrate embodiments of the disclosure. However, those of skill in the art should, in light of the present disclosure, appreciate that many changes can be made in the specific embodiments which are disclosed and still obtain a like or similar result without departing from the spirit and scope of the disclosure.

Analytical HPLC analyses were performed on an LC-MS system with a UV Detector (Dionex™ UVD 170u UV/VIS Detector), Corona array detector (Thermo™ Veo™ RS), and mass spectrometer (Dionex MSQ Plus™). Reverse-phase preparative HPLC purifications were performed on an LCMS system C18 Kinetix 5μ 100 A 150×21.2 mm column by Phenomenex using ACN/water gradient containing 0.05% TFA. All final compounds were analyzed by analytical HPLC and peaks were monitored at 210, 254 and 280 nM for purity. $^1$H was recorded in an appropriate NMR solvent, such as, DMSO-d$_6$, on a Bruker 400 MHz spectrometer equipped with a Broad Band NMR probe. The $^1$H chemical signals are given in parts per million (ppm) with the residual solvent signal used as reference. The chemical shifts are expressed in ppm (δ) and coupling constants (J) are reported in hertz (Hz). Reactions were performed under an atmosphere of dry nitrogen unless otherwise stated.

I. General Synthetic Scheme for the Preparation of Compounds of Formula (Ia)

Scheme 1

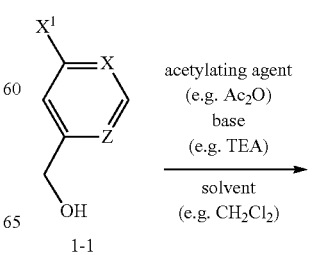

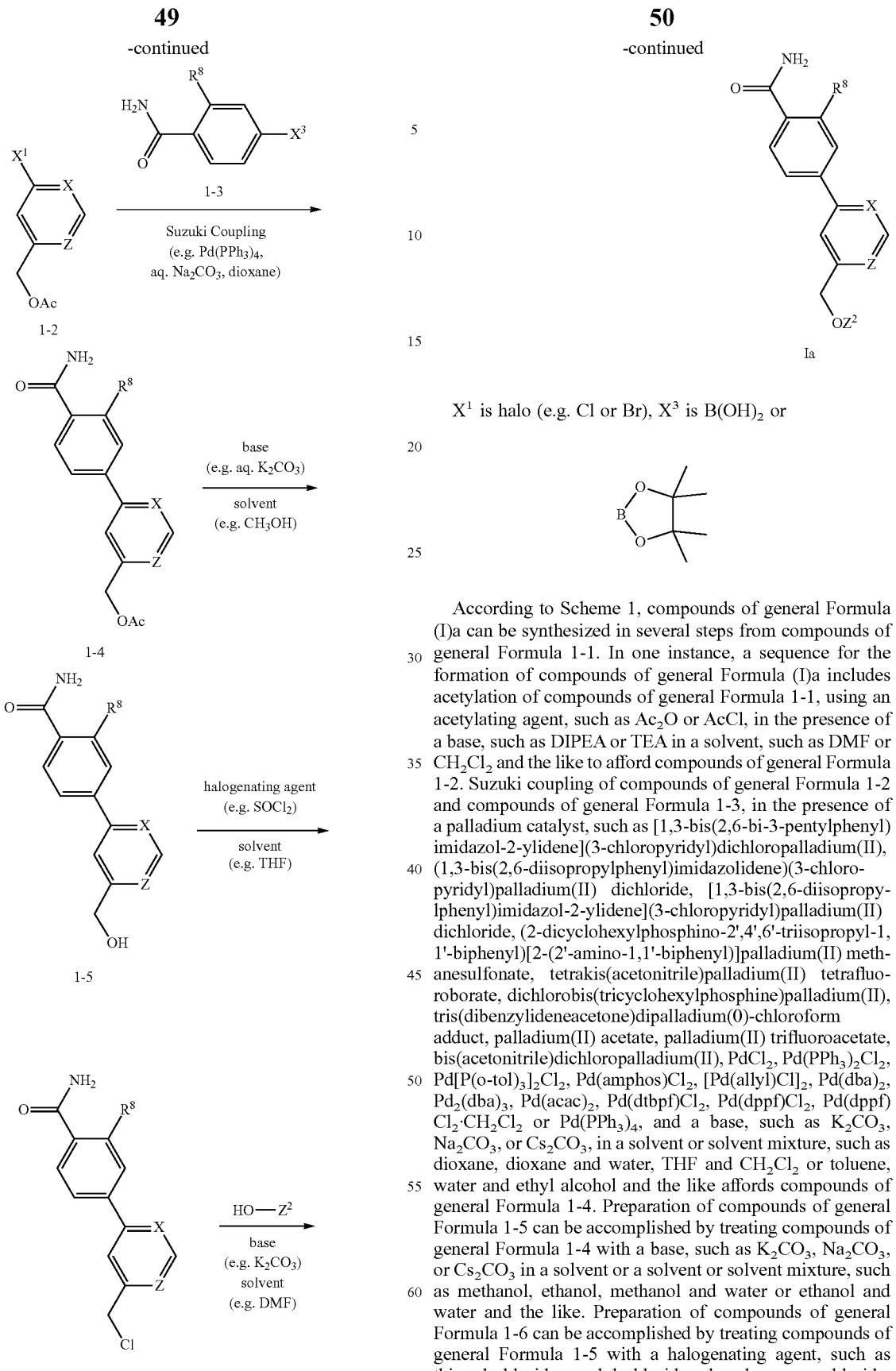

$X^1$ is halo (e.g. Cl or Br), $X^3$ is $B(OH)_2$ or

According to Scheme 1, compounds of general Formula (I)a can be synthesized in several steps from compounds of general Formula 1-1. In one instance, a sequence for the formation of compounds of general Formula (I)a includes acetylation of compounds of general Formula 1-1, using an acetylating agent, such as $Ac_2O$ or AcCl, in the presence of a base, such as DIPEA or TEA in a solvent, such as DMF or $CH_2Cl_2$ and the like to afford compounds of general Formula 1-2. Suzuki coupling of compounds of general Formula 1-2 and compounds of general Formula 1-3, in the presence of a palladium catalyst, such as [1,3-bis(2,6-bi-3-pentylphenyl)imidazol-2-ylidene](3-chloropyridyl)dichloropalladium(II), (1,3-bis(2,6-diisopropylphenyl)imidazolidene)(3-chloropyridyl)palladium(II) dichloride, [1,3-bis(2,6-diisopropylphenyl)imidazol-2-ylidene](3-chloropyridyl)palladium(II) dichloride, (2-dicyclohexylphosphino-2',4',6'-triisopropyl-1,1'-biphenyl)[2-(2'-amino-1,1'-biphenyl)]palladium(II) methanesulfonate, tetrakis(acetonitrile)palladium(II) tetrafluoroborate, dichlorobis(tricyclohexylphosphine)palladium(II), tris(dibenzylideneacetone)dipalladium(0)-chloroform adduct, palladium(II) acetate, palladium(II) trifluoroacetate, bis(acetonitrile)dichloropalladium(II), $PdCl_2$, $Pd(PPh_3)_2Cl_2$, $Pd[P(o-tol)_3]_2Cl_2$, $Pd(amphos)Cl_2$, $[Pd(allyl)Cl]_2$, $Pd(dba)_2$, $Pd_2(dba)_3$, $Pd(acac)_2$, $Pd(dtbpf)Cl_2$, $Pd(dppf)Cl_2$, $Pd(dppf)Cl_2 \cdot CH_2Cl_2$ or $Pd(PPh_3)_4$, and a base, such as $K_2CO_3$, $Na_2CO_3$, or $Cs_2CO_3$, in a solvent or solvent mixture, such as dioxane, dioxane and water, THF and $CH_2Cl_2$ or toluene, water and ethyl alcohol and the like affords compounds of general Formula 1-4. Preparation of compounds of general Formula 1-5 can be accomplished by treating compounds of general Formula 1-4 with a base, such as $K_2CO_3$, $Na_2CO_3$, or $Cs_2CO_3$ in a solvent or a solvent or solvent mixture, such as methanol, ethanol, methanol and water or ethanol and water and the like. Preparation of compounds of general Formula 1-6 can be accomplished by treating compounds of general Formula 1-5 with a halogenating agent, such as thionyl chloride, oxalyl chloride, phosphorus oxychloride, phosphorus pentachloride, phosphorus trichloride, methanesulfonyl chloride and NaI, p-toluenesulfonyl chloride and NaI, phosphorus tribromide, triphenylphosphine dibromide, phosphorus pentabromide or thionyl bromide, in a solvent, such as CH$_2$Cl$_2$, THF, dioxane or acetone and the like. Finally, compounds of general Formula 1-6 can be treated with HO—Z$^1$ in the presence of a base, such as K$_2$CO$_3$, Na$_2$CO$_3$, or Cs$_2$CO$_3$ in a solvent, such as DMF and the like to afford compounds of general Formula (I)a.

II. General Synthetic Methods for the Preparation of Compounds of Formula (Ia)

General Method (GM) 1: Preparation of Compound of General Formula 1-1

A compound of general Formula 1-1 in CH$_2$Cl$_2$ (20 mg/mL) in a round-bottom flask is treated with Et$_3$N (2 eq.) followed by acetic anhydride (1 eq.) to afford a mixture. The mixture is stirred overnight, and then washed twice with water, dried over MgSO$_4$, filtered to remove solid and dried under vacuum to afford compound of general Formula 1-2.

General Method (GM) 2: Preparation of Compound of General Formula 1-4

A mixture of compound of general Formula 1-2 and compound of general Formula 1-3 in an amount of 1,4-dioxane or specified solvent is treated with a specified amount of a 4 M aqueous solution of Na$_2$CO$_3$ in a round-bottom flask. The resulting mixture is sparged with nitrogen gas for 10 min. and then Pd(PPh$_3$)$_4$(5 mol %) is added. A condenser is placed on top of the flask and the mixture is heated under nitrogen with vigorous stirring at a specific temperature, for a specific amount of time. The mixture is then cooled and filtered to remove solid. The filtrate is then rotary evaporated to leave behind a crude mixture that is purified as specified to afford a compound of general Formula 1-4.

General Method (GM) 3: Preparation of Compound of General Formula 1-5

A mixture of compound of general Formula 2-4 and 4 M Na$_2$CO$_3$ in an amount of MeOH (20 mg/mL) is heated overnight at 65° C. The solvent is then rotary-evaporated to afford a remainder that is triturated under water, and collected by filtration to afford compound 1-5.

General Method (GM) 4: Preparation of Compound of General Formula 1-6

A compound of general Formula 1-5 in THF (20 mg/mL) in a round-bottom flask is treated with SOCl$_2$ (10 equiv.). The resulting mixture is then stirred vigorously overnight, and a compound of general Formula 1-6 isolated as specified.

General Method (GM) 5: Preparation of Compound of Formula (Ia)

A compound of general Formula 1-6 was treated with a solution of HO—Z$^1$ in DMF (1 eq, 0.5 M unless otherwise noted). The resulting mixture is treated with K$_2$CO$_3$ (2 equiv.) and then heated to 85° C. overnight. The mixture was then filtered and purified by preparative HPLC or as otherwise noted to afford compound of Formula (Ia). The HCl salt was formed upon addition of 4 eq of HCl as a 1 M solution in Et$_2$O into a solution of the product in MeOH (1 mL/mg) and evaporation under vacuum or purified as specified.

III. Preparation of Compounds of Formula (Ia): R$^8$ is CH$_3$, X is N, Y is CH

Example 1: 4-{4-[4-(trifluoromethyl)phenoxymethyl]pyridin-2-yl}2-methyl-benzamide hydrochloride (1)

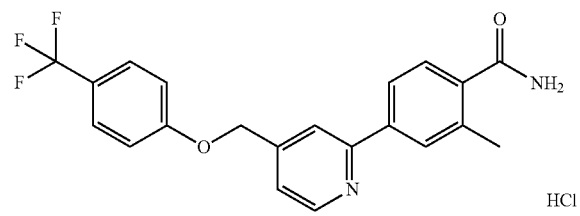 [SMILES: Cc1cc(-c2cc(COc3ccc(C(F)(F)F)cc3)ccn2)ccc1C(N)=O ; Cl]

The title compound was prepared as shown in Scheme 2.

Scheme 2

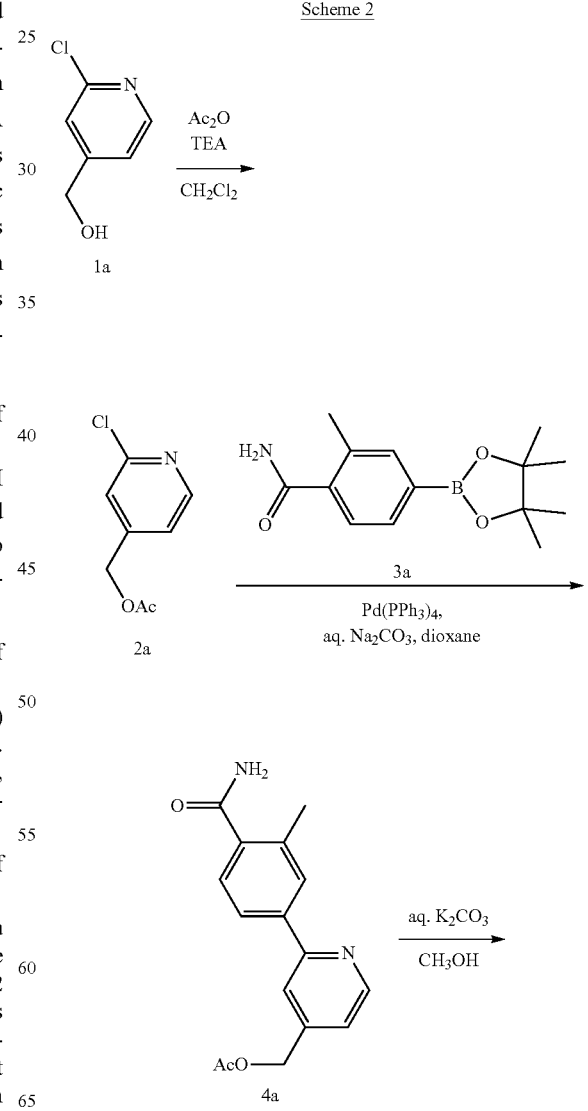

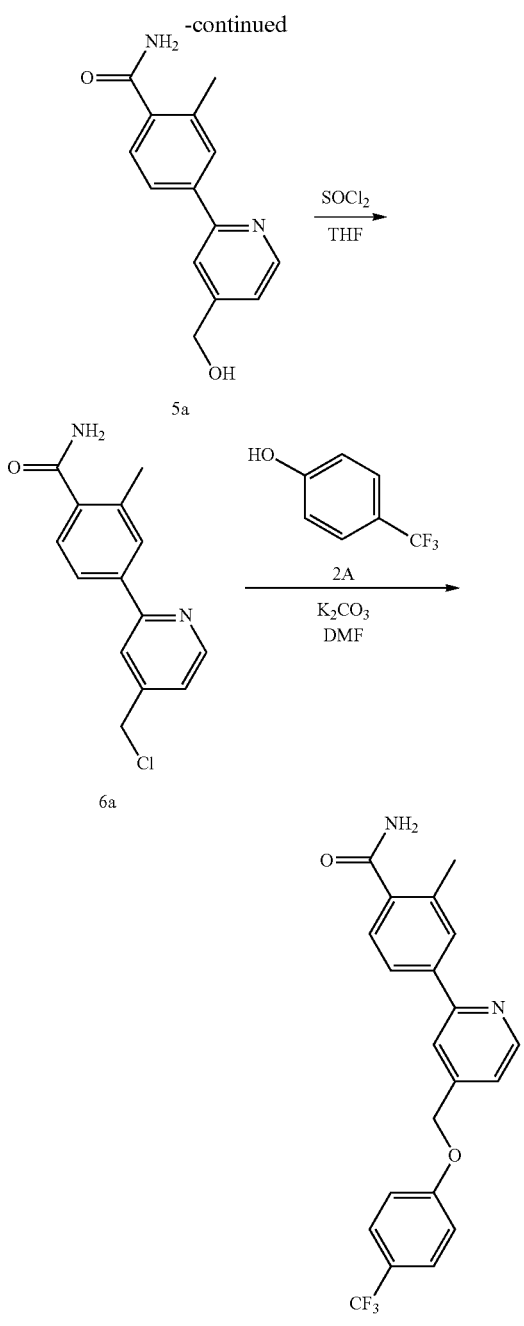

Step 1: Preparation of (2-chloropyridin-4-yl)methyl acetate (2a)

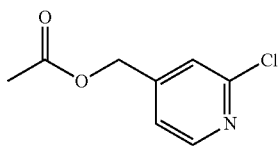

GM 1 was employed using 2-chloro-4-hydroxymethylpyridine (1a, 1.07 g, 7.45 mmol.) as the compound of general Formula 1-1, and affording the title compound (2a, 1.02 g) as the compound of general Formula 1-2 as a yellow oil. ESIMS=186 (M+H⁺, 100).

Step 2: Preparation of [2-(4-carbamoyl-3-methylphenyl)pyridin-4-yl]methyl acetate (4a)

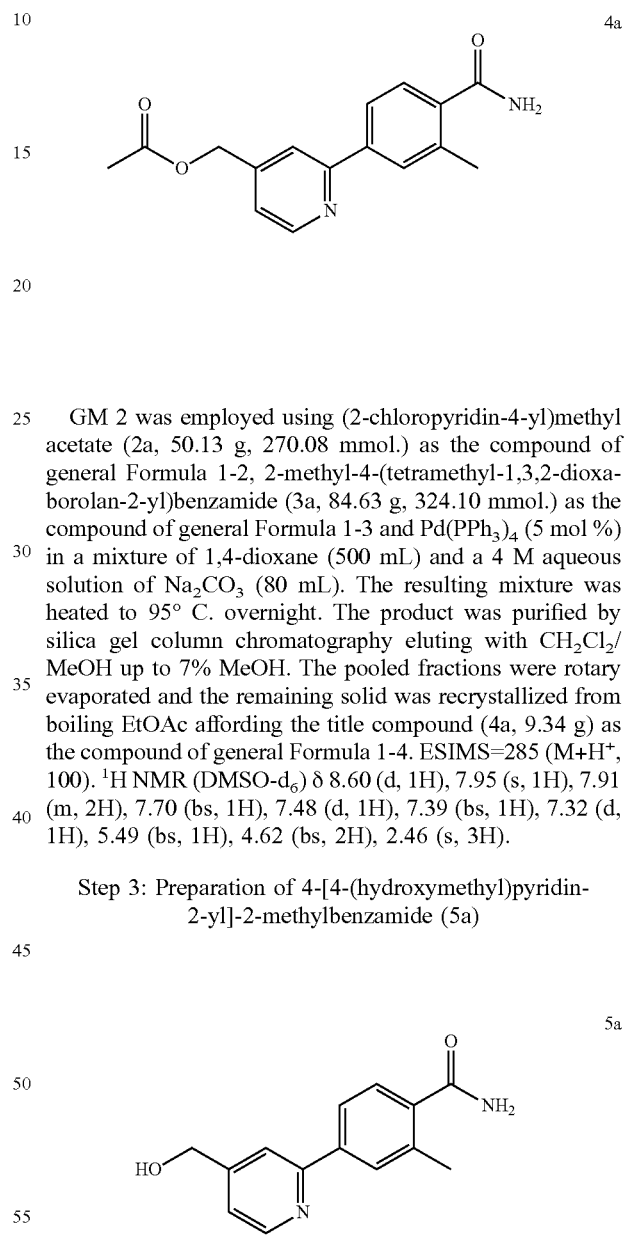

GM 2 was employed using (2-chloropyridin-4-yl)methyl acetate (2a, 50.13 g, 270.08 mmol.) as the compound of general Formula 1-2, 2-methyl-4-(tetramethyl-1,3,2-dioxaborolan-2-yl)benzamide (3a, 84.63 g, 324.10 mmol.) as the compound of general Formula 1-3 and Pd(PPh$_3$)$_4$ (5 mol %) in a mixture of 1,4-dioxane (500 mL) and a 4 M aqueous solution of Na$_2$CO$_3$ (80 mL). The resulting mixture was heated to 95° C. overnight. The product was purified by silica gel column chromatography eluting with CH$_2$Cl$_2$/MeOH up to 7% MeOH. The pooled fractions were rotary evaporated and the remaining solid was recrystallized from boiling EtOAc affording the title compound (4a, 9.34 g) as the compound of general Formula 1-4. ESIMS=285 (M+H⁺, 100). ¹H NMR (DMSO-d$_6$) δ 8.60 (d, 1H), 7.95 (s, 1H), 7.91 (m, 2H), 7.70 (bs, 1H), 7.48 (d, 1H), 7.39 (bs, 1H), 7.32 (d, 1H), 5.49 (bs, 1H), 4.62 (bs, 2H), 2.46 (s, 3H).

Step 3: Preparation of 4-[4-(hydroxymethyl)pyridin-2-yl]-2-methylbenzamide (5a)

GM 3 was employed using [2-(4-carbamoyl-3-methylphenyl)pyridin-4-yl]methyl acetate (4a, 9.34 g) as the compound of general Formula 1-4 and aqueous Na$_2$CO$_3$ (4 M, 20 mL) in MeOH (100 mL) and water (20 mL). This mixture was heated overnight at 65° C. and purified as described in GM 3 affording the title compound (5a, 8.10 g) as a white solid. ESIMS=243 (M+H⁺, 100). (DMSO-d$_6$) δ 8.69 (d, 1H), 8.06 (s, 1H), 7.98 (s, 1H), 7.93 (d, 1H), 7.78 (bs, 1H), 7.49 (d, 1H), 7.45 (d, 1H), 7.41 (s, 1H) 4.86 (s, 2H), 2.47 (s, 3H).

4-[4-(chloromethyl)pyridin-2-yl]-2-methylbenzamide HCl (6a)

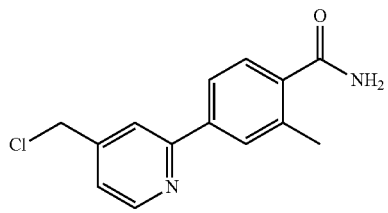

6a

GM 4 was employed using 4-[4-(hydroxymethyl)pyridin-2-yl]-2-methylbenzamide (5a, 8.10 g) as the compound of general Formula 1-5. The mixture was filtered and the collected solids were dried under vacuum to afford 4-[4-(chloromethyl)pyridin-2-yl]-2-methylbenzamide hydrochloride (6a, 7.4 g). ESIMS=261 (M+H$^+$, 100). (DMSO-d$_6$) δ 8.69 (d, 1H), 8.06 (s, 1H), 7.98 (s, 1H), 7.93 (d, 1H), 7.78 (bs, 1H), 7.49 (d, 1H), 7.45 (d, 1H), 7.41 (s, 1H) 4.86 (s, 2H), 2.47 (s, 3H).

4-{4-[4-(trifluoromethyl)phenoxymethyl]pyridin-2-yl}2-methyl-benzamide hydrochloride (1)

GM 5 was followed using 4-(trifluoromethyl)phenol (2A, 0.025 mmol) as HO—Z$^2$, and 4-[4-(chloromethyl)pyridin-2-yl]-2-methylbenzamide hydrochloride (6a, 0.025 mmol) as the compound of general Formula 1-6. ESIMS=387 (M+H$^+$, 100). $^1$H NMR (DMSO-d$_6$) δ 8.75 (d, 1H), 8.19 (s, 1H), 7.99 (s, 1H), 7.94 (d, 1H), 7.62 (bs, 1H), 7.71 (d, 2H), 7.60 (d, 1H), 7.53 (d, 1H), 7.46 (s, 1H), 7.27 (d, 2H), 5.43 (s, 2H), 2.48 (s, 3H).

Other examples of HO—Z$^2$ useful in the preparation of compounds of general Formulae Ia, Ib Ic and Id, include:

TABLE 1

| Intermediate | Chemical Structure | Chemical Name |
| --- | --- | --- |
| 2B | 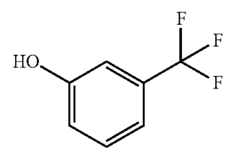 [SMILES: Oc1cccc(C(F)(F)F)c1] | 3-(trifluoromethyl)phenol |
| 2C | 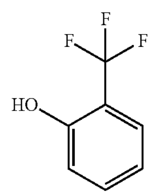 | 2-(trifluoromethyl)phenol |
| 2D | 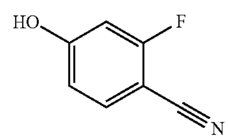 | 4-cyano-3-fluorophenol |
| 2E | 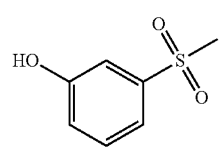 | 3-methanesulfonylphenol |
| 2F | 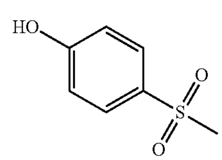 | 4-methanesulfonylphenol |
| 2G | 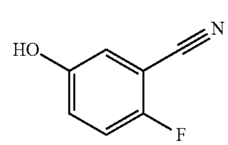 | 3-cyano-4-fluorophenol |
| 2H | 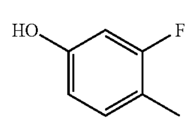 | 3-fluoro-4-methylphenol |

TABLE 1-continued
| Intermediate | Chemical Structure | Chemical Name |
|---|---|---|
| 2I | 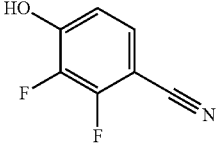 [SMILES: N#Cc1ccc(O)c(F)c1F] | 4-cyano-2,3-difluorophenol |
| 2J | 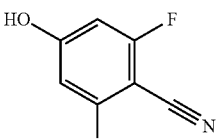 | 4-cyano-3,5-difluorophenol |
| 2K | 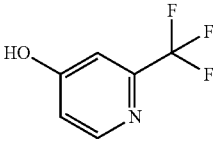 [SMILES: Oc1ccnc(C(F)(F)F)c1] | 2-(trifluoromethyl)pyridin-4-ol |
| 2L | 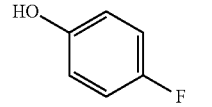 | 4-fluorophenol |
| 2M | 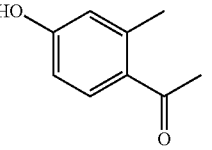 | 4-acetyl-3-methylphenol |
| 2N | 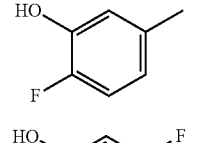 | 2-fluoro-5-methylphenol |
| 2O | 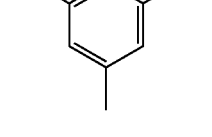 | 3,5-difluorophenol |
| 2P | 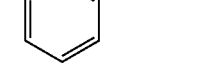 | 3-(2-hydroxyethyl)phenol |
| 2Q | 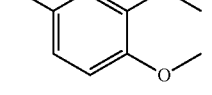 | 3,4-dimethoxyphenol |
| 2R | 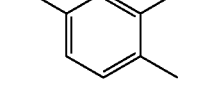 | 3-chloro-4-methylphenol |
| 2S | 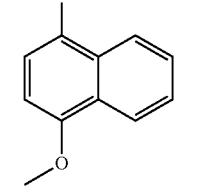 | 4-methoxynaphthalen-1-ol |

TABLE 1-continued

| Intermediate | Chemical Structure | Chemical Name |
| --- | --- | --- |
| 2T | 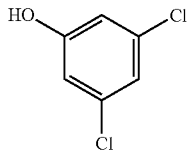 | 3,5-dichlorophenol |
| 2U | 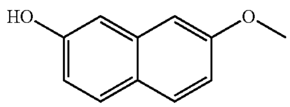 | 7-methoxy-2-hydroxynaphthalene |
| 2V | 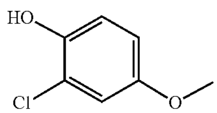 | 2-chloro-4-methoxyphenol |
| 2W | 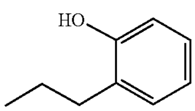 | 2-propylphenol |
| 2X | 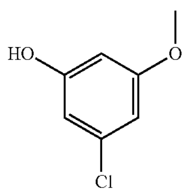 | 3-chloro-5-methoxyphenol |
| 2Y | 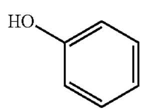 | phenol |
| 2Z | 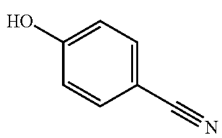 | 4-cyanophenol |
| 2AA | 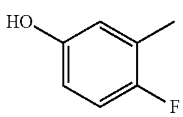 | 4-fluoro-3-methylphenol |
| 2AB | 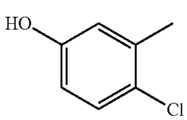 | 4-chloro-3-methylphenol |
| 2AC | 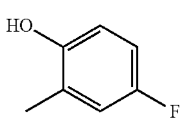 | 4-fluoro-2-methylphenol |
| 2AD | 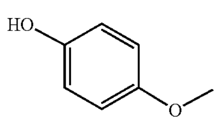 | 4-methoxyphenol |

TABLE 1-continued
| Intermediate | Chemical Structure | Chemical Name |
|---|---|---|
| 2AE | 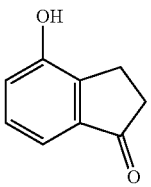 [SMILES: O=C1CCc2c(O)cccc21] | 4-hydroxyindanone |
| 2AF | 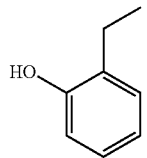 | 2-ethylphenol |
| 2AG | 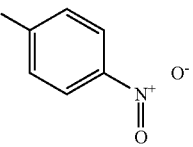 | 4-nitrophenol |
| 2AH | 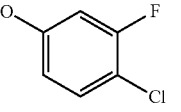 | 4-chloro-3-fluorophenol |
| 2AI | 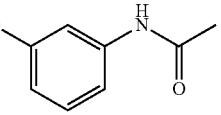 | 3-acetamidophenol |
| 2AJ | 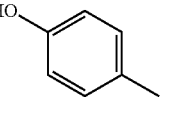 | 4-methylphenol |
| 2AK | 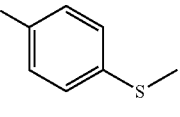 | 4-(methylsulfanyl)phenol |
| 2AL | 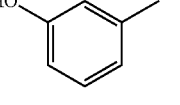 | 3-methylphenol |
| 2AM | 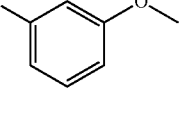 | 3-methoxyphenol |
| 2AN | 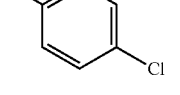 | 4-chlorophenol |
| 2AO | 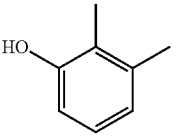 | 2,3-dimethylphenol |

TABLE 1-continued

| Intermediate | Chemical Structure | Chemical Name |
| --- | --- | --- |
| 2AP | 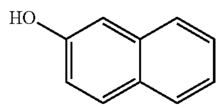 [SMILES: Oc1ccc2ccccc2c1] | 2-naphthol |
| 2AQ | 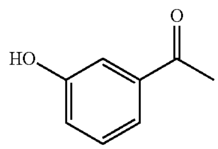 | 3-acetylphenol |
| 2AR | 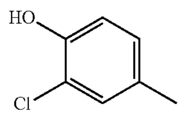 | 2-chloro-4-methylphenol |
| 2AS | 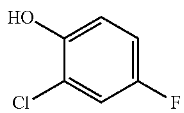 | 2-chloro-4-fluorophenol |
| 2AT | 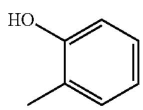 | 2-methylphenol |
| 2AU | 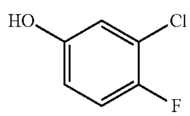 | 3-chloro-4-fluorophenol |
| 2AV | 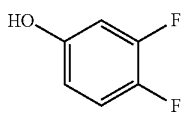 | 3,4-difluorophenol |
| 2AW | 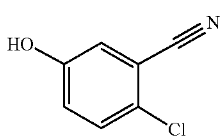 | 4-chloro-3-cyanophenol |
| 2AX | 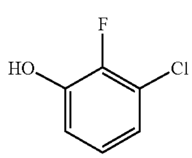 | 3-chloro-2-fluorophenol |
| 2AY | 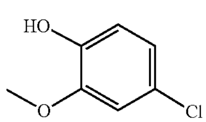 | 4-chloro-2-methoxyphenol |
| 2AZ | 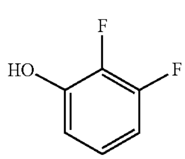 | 2,3-difluorophenol |

TABLE 1-continued
| Intermediate | Chemical Structure | Chemical Name |
|---|---|---|
| 2BA | 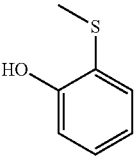 | 2-(methylsulfanyl)phenol |
| 2BB | 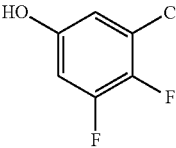 | 3-chloro-4,5-difluorophenol |
| 2BC | 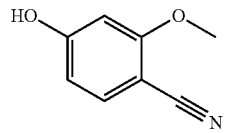 | 4-cyano-3-methoxyphenol |
| 2BD | 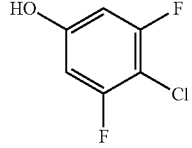 | 4-chloro-3,5-difluorophenol |
| 2BE | 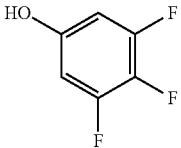 | 3,4,5-trifluorophenol |
| 2BF | 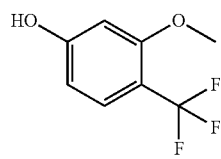 | 3-methoxy-4-(trifluoromethyl)phenol |
| 2BG | 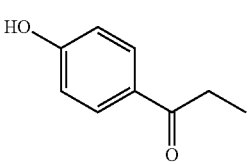 | 4-propanoylphenol |
| 2BH | 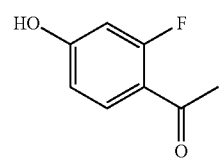 | 4-acetyl-3-fluorophenol |
| 2BI | 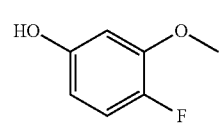 | 4-fluoro-3-methoxyphenol |
| 2BJ | 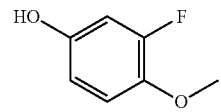 | 3-fluoro-4-methoxyphenol |

TABLE 1-continued

| Intermediate | Chemical Structure | Chemical Name |
|---|---|---|
| 2BK | 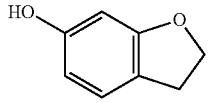 | 2,3-dihydro-1-benzofuran-6-ol |
| 2BL | 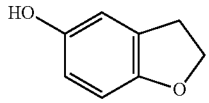 | 2,3-dihydro-1-benzofuran-5-ol |
| 2BM | 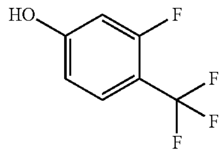 [SMILES: Oc1ccc(C(F)(F)F)c(F)c1] | 3-fluoro-4-(trifluoromethyl)phenol |
| 2BN | 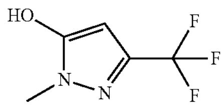 | 2-methyl-5-(trifluoromethyl)pyrazol-3-ol |
| 2BO | 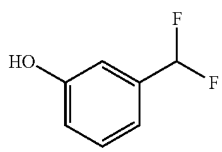 | 3-difluoromethylphenol |
| 2BP | 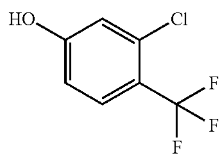 [SMILES: Oc1ccc(C(F)(F)F)c(Cl)c1] | 3-chloro-4-(trifluoromethyl)phenol |
| 2BQ | 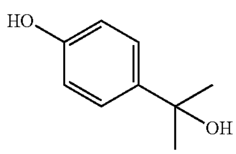 | 4-(2-hydroxypropan-2-yl)phenol |
| 2BR | 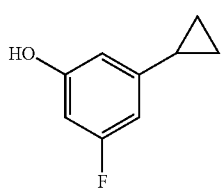 [SMILES: Oc1cc(F)cc(C2CC2)c1] | 3-cyclopropyl-5-fluorophenol |
| 2BS | 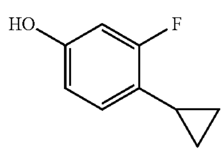 | 4-cyclopropyl-3-fluorophenol |
| 2BT | 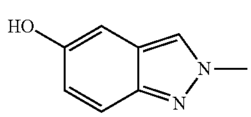 | 2-methyl-2H-indazol-5-ol |
| 2BU | 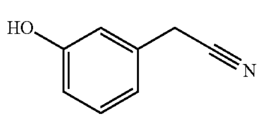 | 3-(cyanomethyl)phenol |

TABLE 1-continued

| Intermediate | Chemical Structure | Chemical Name |
|---|---|---|
| 2BV | HO—⟨pyridine⟩—O— | 5-methoxy-3-hydroxypyridine |
| 2BW | HO—⟨pyridine⟩—CN | 5-cyano-3-hydroxypyridine |
| 2BX | HO—⟨phenyl⟩—C(O)CH₃ | 4-acetylphenol |
| 2BY | HO—⟨indazole⟩-N-CH₃ | 1-methyl-1H-indazol-5-ol |
| 2BZ | HO—⟨indazole⟩-N-CH₃ | 1-methyl-1H-indazol-6-ol |

Example 2: 4-{4-[3-(trifluoromethyl)phenoxymethyl]pyridin-2-yl}-2-methyl benzamide (2)

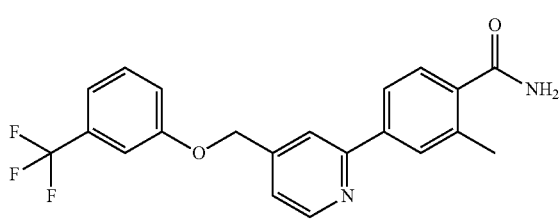 [SMILES: Cc1cc(-c2cc(COc3cccc(C(F)(F)F)c3)ccn2)ccc1C(N)=O]

GM 5 was followed using 3-(trifluoromethyl)phenol (2B, 0.025 mmol) and 4-[4-(chloromethyl)pyridin-2-yl]-2-methylbenzamide (6a, 0.025 mmol). ESIMS=387 (M+H⁺, 100).

Example 3: 4-{4-[2-(trifluoromethyl)phenoxymethyl]pyridin-2-yl}-2-methyl benzamide (3)

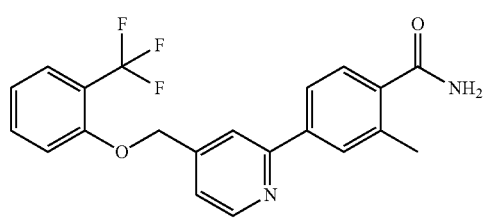 [SMILES: Cc1cc(-c2cc(COc3ccccc3C(F)(F)F)ccn2)ccc1C(N)=O]

GM 5 was followed using 2-(trifluoromethyl)phenol (2C, 0.025 mmol) and 4-[4-(chloromethyl)pyridin-2-yl]-2-methylbenzamide (6a, 0.025 mmol). ESIMS=387 (M+H⁺, 100).

Example 4: 4-[4-(4-cyano-3-fluorophenoxymethyl)pyridin-2-yl]-2-methylbenzamide hydrochloride (4)

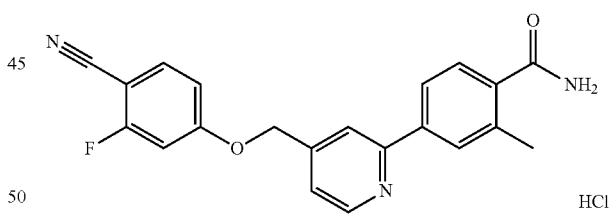

GM 5 was followed using 4-cyano-3-fluorophenol (2D, 0.025 mmol) and 4-[4-(chloromethyl)pyridin-2-yl]-2-methylbenzamide (6a, 0.025 mmol). ESIMS=362 (M+H⁺, 100).
$^1$H NMR (DMSO-$d_6$) δ 8.74 (d, 1H), 8.12 (bs, 1H), 7.98 (s, 1H), 7.93 (d, 1H), 7.90 (s, 1H), 7.80 (bs, 1H), 7.52 (d, 2H), 7.43 (bs, 1H), 7.35 (d, 1H), 7.14 (d, 1H), 5.42 (s, 2H), 2.47 (s, 3H).

Example 5: 4-[4-(3-methanesulfonylphenoxymethyl)pyridin-2-yl]-2-methylbenzamide (5)

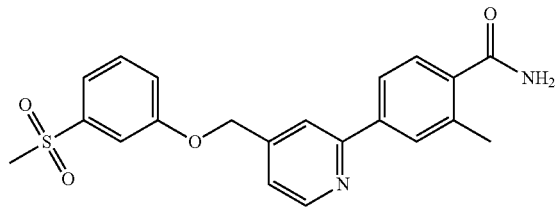 [SMILES: Cc1cc(-c2cc(COc3cccc(S(C)(=O)=O)c3)ccn2)ccc1C(N)=O]

GM 5 was followed using 3-methanesulfonylphenol (2E, 0.025 mmol) and 4-[4-(chloromethyl)pyridin-2-yl]-2-methylbenzamide (6a, 0.025 mmol). ESIMS=397 (M+H$^+$, 100).

Example 6: 4-[4-(4-methanesulfonylphenoxymethyl)pyridin-2-yl]-2-methylbenzamide (6)

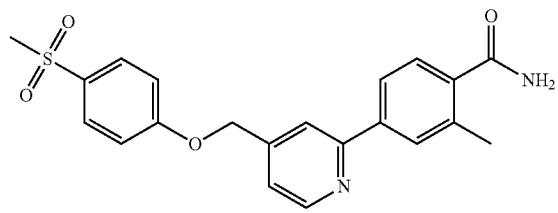 [SMILES: Cc1cc(-c2cc(COc3ccc(S(C)(=O)=O)cc3)ccn2)ccc1C(N)=O]

GM 5 was followed using 4-methanesulfonylphenol (2F, 0.025 mmol) and 4-[4-(chloromethyl)pyridin-2-yl]-2-methylbenzamide (6a, 0.025 mmol). ESIMS=397 (M+H$^+$, 100).

Example 7: 4-[4-(3-cyano-4-fluorophenoxymethyl)pyridin-2-yl]-2-methylbenzamide (7)

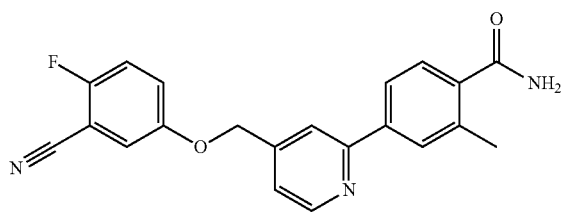 [SMILES: Cc1cc(-c2cc(COc3ccc(F)c(C#N)c3)ccn2)ccc1C(N)=O]

GM 5 was followed using 3-cyano-4-fluorophenol (2G, 0.025 mmol.) and 4-[4-(chloromethyl)pyridin-2-yl]-2-methylbenzamide (6a, 0.025 mmol.). ESIMS=362 (M+H$^+$, 100).

Example 8: 4-[4-(3-fluoro-4-methylphenoxymethyl)pyridin-2-yl]-2-methylbenzamide (8)

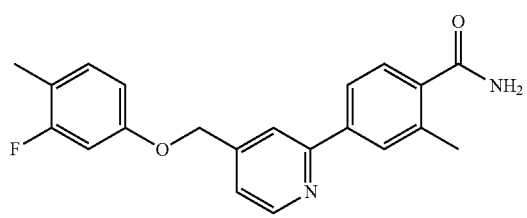 [SMILES: Cc1ccc(OCc2ccnc(-c3ccc(C(N)=O)c(C)c3)c2)cc1F]

GM 5 was followed using 3-fluoro-4-methylphenol (2H, 0.025 mmol) and 4-[4-(chloromethyl)pyridin-2-yl]-2-methylbenzamide (6a, 0.025 mmol). ESIMS=351 (M+H$^+$, 100).

Example 9: 4-[4-(4-cyano-2,3-difluorophenoxymethyl)pyridin-2-yl]-2-methylbenzamide (9)

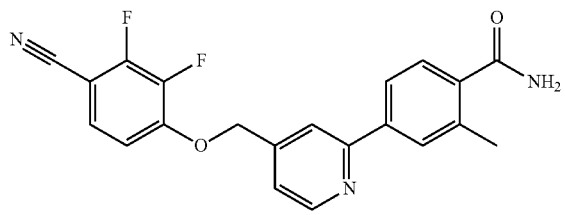 [SMILES: Cc1cc(-c2cc(COc3ccc(C#N)c(F)c3F)ccn2)ccc1C(N)=O]

GM 5 was followed using 4-cyano-2,3-difluorophenol (2I, 0.025 mmol) and 4-[4-(chloromethyl)pyridin-2-yl]-2-methylbenzamide (6a, 0.025 mmol). ESIMS=380 (M+H$^+$, 100).

Example 10: 4-[4-(4-cyano-3,5-difluorophenoxymethyl)pyridin-2-yl]-2-methylbenzamide (10)

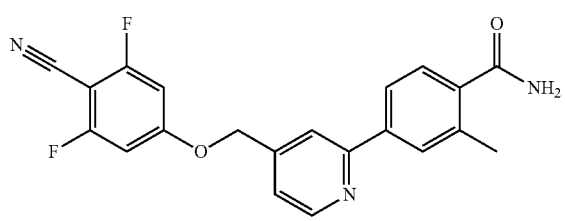 [SMILES: Cc1cc(-c2cc(COc3cc(F)c(C#N)c(F)c3)ccn2)ccc1C(N)=O]

GM 5 was followed using 4-cyano-3,5-difluorophenol (2J, 0.025 mmol) and 4-[4-(chloromethyl)pyridin-2-yl]-2-methylbenzamide (6a, 0.025 mmol). ESIMS=380 (M+H$^+$, 100).

Example 11: 4-[4-({[2-(trifluoromethyl)pyridin-4-yl]oxy}methyl)pyridin-2-yl]-2-methyl benzamide (11)

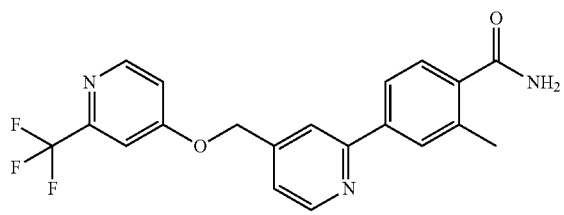 [SMILES: Cc1cc(-c2cc(COc3ccnc(C(F)(F)F)c3)ccn2)ccc1C(N)=O]

GM 5 was followed using 2-(trifluoromethyl)pyridin-4-ol (2K, 0.025 mmol) and 4-[4-(chloromethyl)pyridin-2-yl]-2-methylbenzamide (6a, 0.025 mmol). ESIMS=388 (M+H$^+$, 100).

Example 12: 4-[4-(4-fluorophenoxymethyl)pyridin-2-yl]-2-methylbenzamide (12)

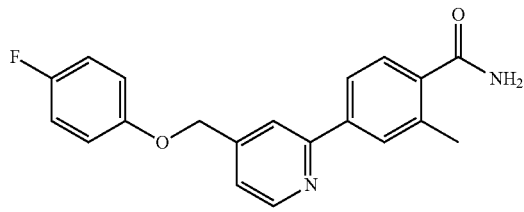 [SMILES: Cc1cc(-c2cc(COc3ccc(F)cc3)ccn2)ccc1C(N)=O]

GM 5 was followed using 4-fluorophenol (2L, 0.025 mmol) and 4-[4-(chloromethyl)pyridin-2-yl]-2-methylbenzamide (6a, 0.025 mmol). ESIMS=339 (M+H$^+$, 100).

Example 13: 4-[4-(4-acetyl-3-methylphenoxymethyl)pyridin-2-yl]-2-methylbenzamide (13)

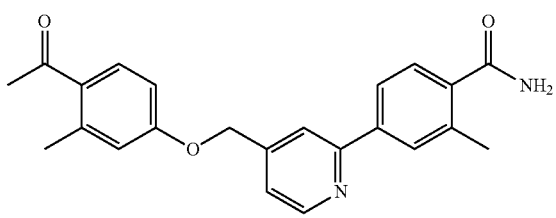 [SMILES: CC(=O)c1ccc(OCc2ccnc(-c3ccc(C(N)=O)c(C)c3)c2)cc1C]

GM 5 was followed using 4-acetyl-3-methylphenol (2M, 0.025 mmol) and 4-[4-(chloromethyl)pyridin-2-yl]-2-methylbenzamide (6a, 0.025 mmol). ESIMS=376 (M+H$^+$, 100).

Example 14: 4-[4-(2-fluoro-5-methylphenoxymethyl)pyridin-2-yl]-2-methylbenzamide (14)

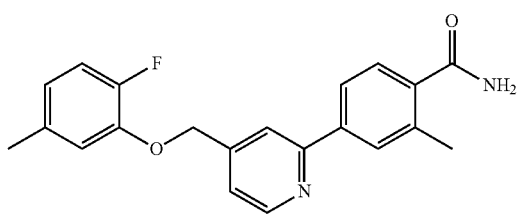 [SMILES: Cc1ccc(F)c(OCc2ccnc(-c3ccc(C(N)=O)c(C)c3)c2)c1]

GM 5 was followed using 2-fluoro-5-methylphenol (2N, 0.025 mmol) and 4-[4-(chloromethyl)pyridin-2-yl]-2-methylbenzamide (6a, 0.025 mmol). ESIMS=352 (M+H$^+$, 100).

Example 15: 4-[4-(3,5-difluorophenoxymethyl)pyridin-2-yl]-2-methylbenzamide (15)

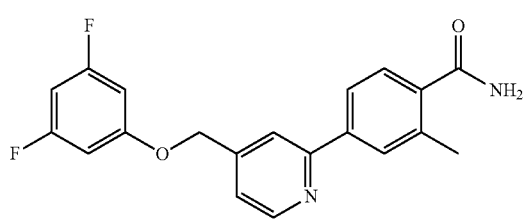 [SMILES: Cc1cc(-c2cc(COc3cc(F)cc(F)c3)ccn2)ccc1C(N)=O]

GM 5 was followed using 3,5-difluorophenol (2O, 0.025 mmol) and 4-[4-(chloromethyl)pyridin-2-yl]-2-methylbenzamide (6a, 0.025 mmol). ESIMS=356 (M+H$^+$, 100).

Example 16: 4-{4-[3-(2-hydroxyethyl)phenoxymethyl]pyridin-2-yl}-2-methylbenzamide (16)

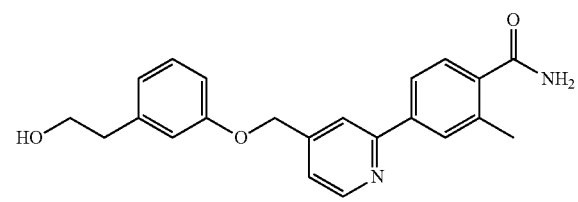 [SMILES: Cc1cc(-c2cc(COc3cccc(CCO)c3)ccn2)ccc1C(N)=O]

GM 5 was followed using 3-(2-hydroxyethyl)phenol (2P, 0.025 mmol) and 4-[4-(chloromethyl)pyridin-2-yl]-2-methylbenzamide (6a, 0.025 mmol). ESIMS=364 (M+H$^+$, 100).

Example 17: 4-[4-(3,4-dimethoxyphenoxymethyl)pyridin-2-yl]-2-methylbenzamide (17)

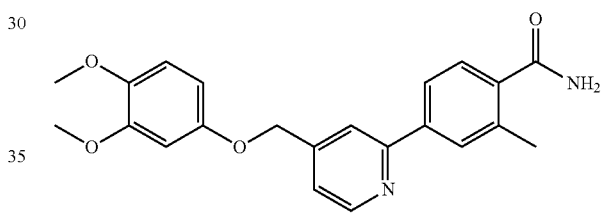

GM 5 was followed using 3,4-dimethoxyphenol (2Q, 0.025 mmol) and 4-[4-(chloromethyl)pyridin-2-yl]-2-methylbenzamide (6a, 0.025 mmol). ESIMS=380 (M+H$^+$, 100).

Example 18: 4-[4-(3-chloro-4-methylphenoxymethyl)pyridin-2-yl]-2-methylbenzamide (18)

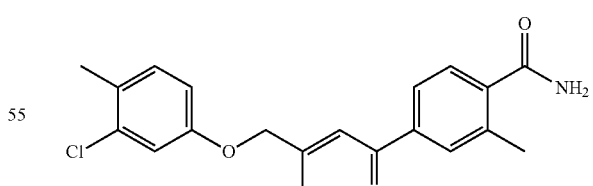

GM 5 was followed using 3-chloro-4-methylphenol (2R, 0.025 mmol) and 4-[4-(chloromethyl)pyridin-2-yl]-2-methylbenzamide (6a, 0.025 mmol). ESIMS=368 (M+H$^+$, 100).

Example 19: 4-(4-{[(4-methoxynaphthalen-1-yl)oxy]methyl}pyridin-2-yl)-2-methylbenzamide (19)

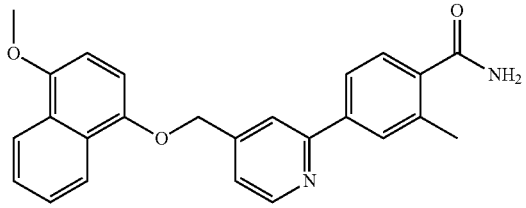

GM 5 was followed using 4-methoxynaphthalen-1-ol (2S, 0.025 mmol) and 4-[4-(chloromethyl)pyridin-2-yl]-2-methylbenzamide (6a, 0.025 mmol). ESIMS=400 (M+H$^+$, 100).

Example 20: 4-[4-(3,5-dichlorophenoxymethyl)pyridin-2-yl]-2-methylbenzamide (20)

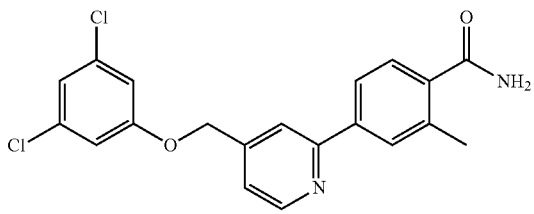 [SMILES: Cc1cc(-c2cc(COc3cc(Cl)cc(Cl)c3)ccn2)ccc1C(N)=O]

GM 5 was followed using 3,5-dichlorophenol (2T, 0.025 mmol) and 4-[4-(chloromethyl)pyridin-2-yl]-2-methylbenzamide (6a, 0.025 mmol). ESIMS=388 (M+H$^+$, 100).

Example 21: 4-(4-{[(7-methoxynaphthalen-2-yl)oxy]methyl}pyridin-2-yl)-2-methylbenzamide (21)

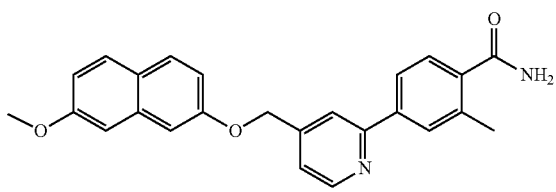 [SMILES: COc1ccc2ccc(OCc3ccnc(-c4ccc(C(N)=O)c(C)c4)c3)cc2c1]

GM 5 was followed using 7-methoxy-2-hydroxynaphthalene (2U, 0.025 mmol) and 4-[4-(chloromethyl)pyridin-2-yl]-2-methylbenzamide (6a, 0.025 mmol). ESIMS=399 (M+H$^+$, 100).

Example 22: 4-[4-(2-chloro-4-methoxyphenoxymethyl)pyridin-2-yl]-2-methylbenzamide (22)

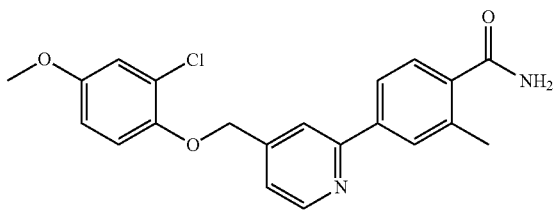 [SMILES: COc1ccc(OCc2ccnc(-c3ccc(C(N)=O)c(C)c3)c2)c(Cl)c1]

GM 5 was followed using 2-chloro-4-methoxyphenol (2V, 0.025 mmol) and 4-[4-(chloromethyl)pyridin-2-yl]-2-methylbenzamide (6a, 0.025 mmol). ESIMS=383 (M+H$^+$, 100).

Example 23: 4-[4-(2-propylphenoxymethyl)pyridin-2-yl]-2-methyl benzamide (23)

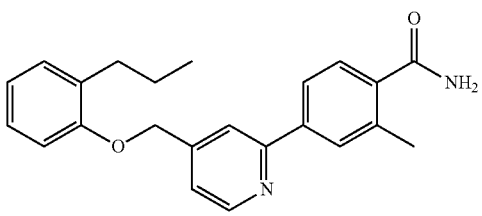 [SMILES: CCCc1ccccc1OCc1ccnc(-c2ccc(C(N)=O)c(C)c2)c1]

GM 5 was followed using 2-propylphenol (2W, 0.025 mmol) and 4-[4-(chloromethyl)pyridin-2-yl]-2-methylbenzamide (6a, 0.025 mmol). ESIMS=361 (M+H$^+$, 100).

Example 24: 4-[4-(3-chloro-5-methoxyphenoxymethyl)pyridin-2-yl]-2-methylbenzamide (24)

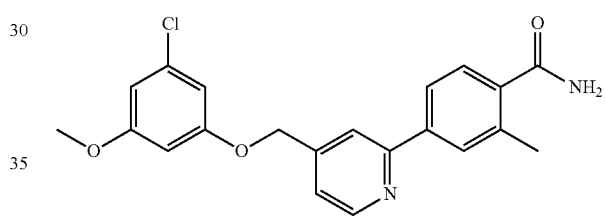

GM 5 was followed using 3-chloro-5-methoxyphenol (2X, 0.025 mmol) and 4-[4-(chloromethyl)pyridin-2-yl]-2-methylbenzamide (6a, 0.025 mmol). ESIMS=383 (M+H$^+$, 100).

Example 25: 4-[4-(phenoxymethyl)pyridin-2-yl]-2-methylbenzamide (25)

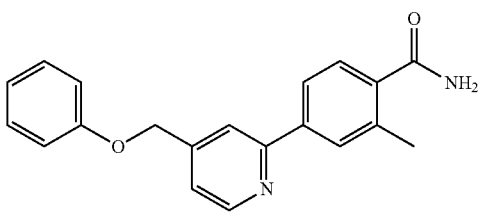 [SMILES: Cc1cc(-c2cc(COc3ccccc3)ccn2)ccc1C(N)=O]

GM 5 was followed using phenol (2Y, 0.025 mmol) and 4-[4-(chloromethyl)pyridin-2-yl]-2-methylbenzamide (6a, 0.025 mmol). ESIMS=319 (M+H$^+$, 100).

Example 26: 4-[4-(4-cyanophenoxymethyl)pyridin-2-yl]-2-methylbenzamide (26)

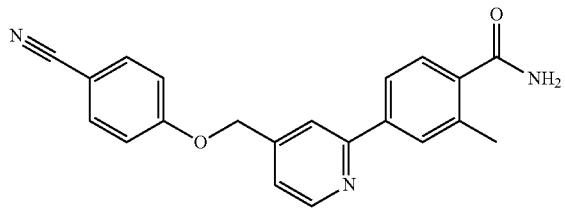 [SMILES: Cc1cc(-c2cc(COc3ccc(C#N)cc3)ccn2)ccc1C(N)=O]

GM 5 was followed using 4-cyanophenol (2Z, 0.025 mmol) and 4-[4-(chloromethyl)pyridin-2-yl]-2-methylbenzamide (6a, 0.025 mmol). ESIMS=344 (M+H⁺, 100).

Example 27: 4-[4-(4-fluoro-3-methylphenoxymethyl)pyridin-2-yl]-2-methylbenzamide (27)

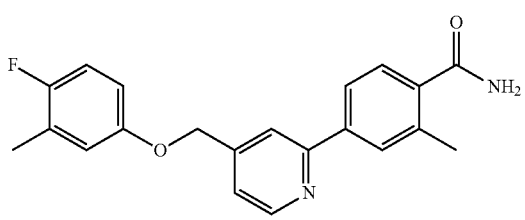 [SMILES: Cc1cc(OCc2ccnc(-c3ccc(C(N)=O)c(C)c3)c2)ccc1F]

GM 5 was followed using 4-fluoro-3-methylphenol (2AA, 0.025 mmol) and 4-[4-(chloromethyl)pyridin-2-yl]-2-methylbenzamide (6a, 0.025 mmol). ESIMS=351 (M+H⁺, 100).

Example 28: 4-[4-(4-chloro-3-methylphenoxymethyl)pyridin-2-yl]-2-methylbenzamide (28)

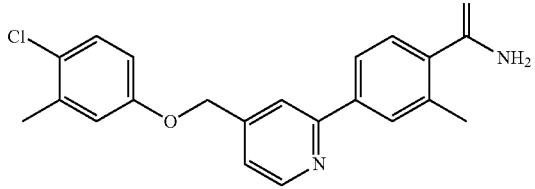

GM 5 was followed using 4-chloro-3-methylphenol (2AB, 0.025 mmol) and 4-[4-(chloromethyl)pyridin-2-yl]-2-methylbenzamide (6a, 0.025 mmol). ESIMS=367 (M+H⁺, 100).

Example 29: 4-[4-(4-fluoro-2-methylphenoxymethyl)pyridin-2-yl]-2-methylbenzamide (29)

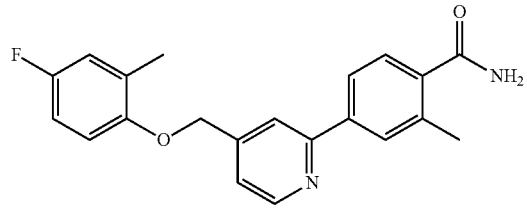 [SMILES: Cc1cc(F)ccc1OCc1ccnc(-c2ccc(C(N)=O)c(C)c2)c1]

GM 5 was followed using 4-fluoro-2-methylphenol (2AC, 0.025 mmol) and 4-[4-(chloromethyl)pyridin-2-yl]-2-methylbenzamide (6a, 0.025 mmol). ESIMS=351 (M+H⁺, 100).

Example 30: 4-[4-(4-methoxyphenoxymethyl)pyridin-2-yl]-2-methylbenzamide (30)

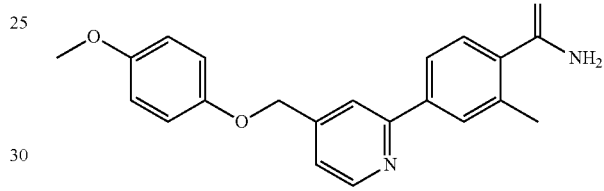

GM 5 was followed using 4-methoxyphenol (2AD, 0.025 mmol) and 4-[4-(chloromethyl)pyridin-2-yl]-2-methylbenzamide (6a, 0.025 mmol). ESIMS=351 (M+H⁺, 100).

Example 31: 4-(4-{[(1-oxo-2,3-dihydro-1H-inden-4-yl)oxy]methyl}pyridin-2-yl)-2-methylbenzamide (31)

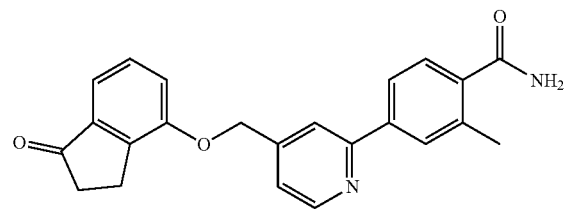 [SMILES: Cc1cc(-c2cc(COc3cccc4c3CCC4=O)ccn2)ccc1C(N)=O]

GM 5 was followed using 4-hydroxyindanone (2AE, 0.025 mmol) and 4-[4-(chloromethyl)pyridin-2-yl]-2-methylbenzamide (6a, 0.025 mmol). ESIMS=373 (M+H⁺, 100).

Example 32: 4-[4-(2-ethylphenoxymethyl)pyridin-2-yl]-2-methylbenzamide (32)

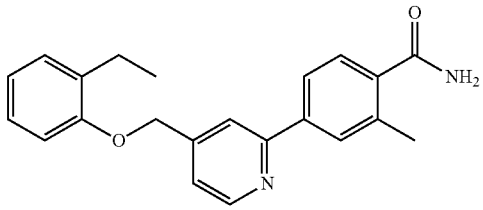 [SMILES: CCc1ccccc1OCc1ccnc(-c2ccc(C(N)=O)c(C)c2)c1]

GM 5 was followed using 2-ethylphenol (2AF, 0.025 mmol) and 4-[4-(chloromethyl)pyridin-2-yl]-2-methylbenzamide (6a, 0.025 mmol). ESIMS=373 (M+H$^+$, 100).

Example 33: 4-[4-(4-nitrophenoxymethyl)pyridin-2-yl]-2-methylbenzamide (33)

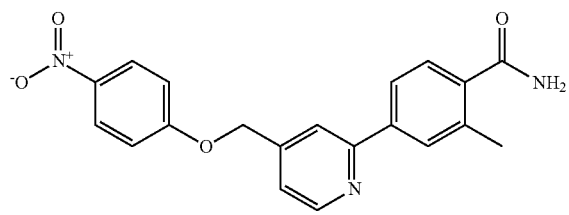

GM 5 was followed using 4-nitrophenol (2AG, 0.025 mmol) and 4-[4-(chloromethyl)pyridin-2-yl]-2-methylbenzamide (6a, 0.025 mmol). ESIMS=364 (M+H$^+$, 100).

Example 34: 4-[4-(4-chloro-3-fluorophenoxymethyl)pyridin-2-yl]-2-methylbenzamide (34)

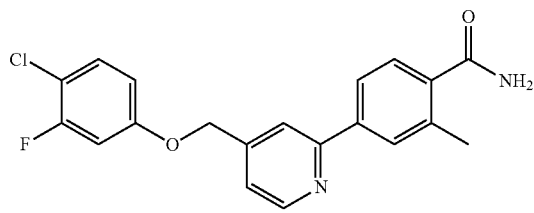 [SMILES: Cc1cc(-c2cc(COc3ccc(Cl)c(F)c3)ccn2)ccc1C(N)=O]

GM 5 was followed using 4-chloro-3-fluorophenol (2AH, 0.025 mmol) and 4-[4-(chloromethyl)pyridin-2-yl]-2-methylbenzamide (6a, 0.025 mmol). ESIMS=371 (M+H$^+$, 100).

Example 35: 4-[4-(3-acetamidophenoxymethyl)pyridin-2-yl]-2-methylbenzamide (35)

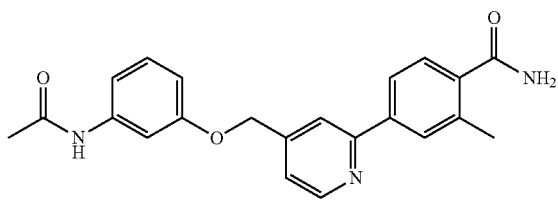 [SMILES: CC(=O)Nc1cccc(OCc2ccnc(-c3ccc(C(N)=O)c(C)c3)c2)c1]

GM 5 was followed using 3-acetamidophenol (2AI, 0.025 mmol) and 4-[4-(chloromethyl)pyridin-2-yl]-2-methylbenzamide (6a, 0.025 mmol). ESIMS=376 (M+H$^+$, 100).

Example 36: 4-[4-(4-methylphenoxymethyl)pyridin-2-yl]-2-methylbenzamide (36)

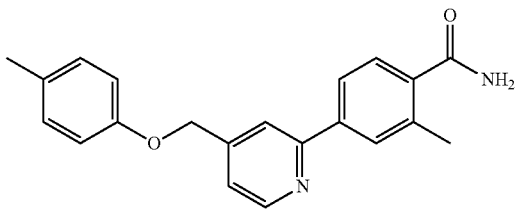 [SMILES: Cc1ccc(OCc2ccnc(-c3ccc(C(N)=O)c(C)c3)c2)cc1]

GM 5 was followed using 4-methylphenol (2AJ, 0.025 mmol) and 4-[4-(chloromethyl)pyridin-2-yl]-2-methylbenzamide (6a, 0.025 mmol). ESIMS=333 (M+H$^+$, 100).

Example 37: 4-{4-[4-(methylsulfanyl)phenoxymethyl]pyridin-2-yl}-2-methyl benzamide (37)

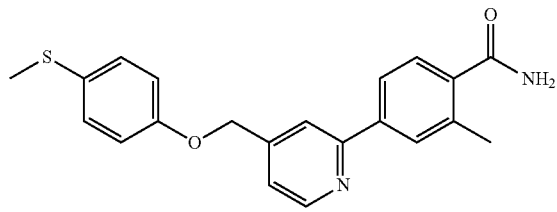

GM 5 was followed using 4-(methylsulfanyl)phenol (2AK, 0.025 mmol) and 4-[4-(chloromethyl)pyridin-2-yl]-2-methylbenzamide (6a, 0.025 mmol). ESIMS=365 (M+H$^+$, 100).

Example 38: 4-[4-(3-methylphenoxymethyl)pyridin-2-yl]-2-methyl benzamide (38)

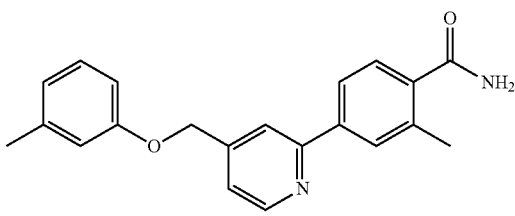 [SMILES: Cc1cccc(OCc2ccnc(-c3ccc(C(N)=O)c(C)c3)c2)c1]

GM 5 was followed using 3-methylphenol (2AL, 0.025 mmol) and 4-[4-(chloromethyl)pyridin-2-yl]-2-methylbenzamide (6a, 0.025 mmol). ESIMS=333 (M+H$^+$, 100).

Example 39: 4-[4-(3-methoxyphenoxymethyl)pyridin-2-yl]-2-methylbenzamide (39)

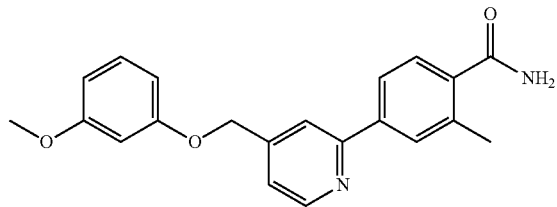 [SMILES: COc1cccc(OCc2ccnc(-c3ccc(C(N)=O)c(C)c3)c2)c1]

GM 5 was followed using 3-methoxyphenol (2AM, 0.025 mmol) and 4-[4-(chloromethyl)pyridin-2-yl]-2-methylbenzamide (6a, 0.025 mmol). ESIMS=348 (M+H$^+$, 100).

Example 40: 4-[4-(4-chlorophenoxymethyl)pyridin-2-yl]-2-methylbenzamide (40)

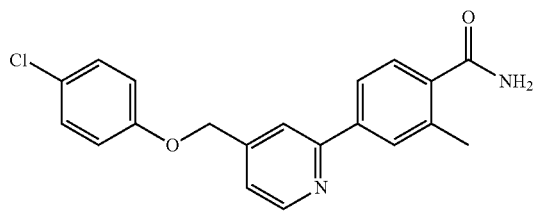 [SMILES: Cc1cc(-c2cc(COc3ccc(Cl)cc3)ccn2)ccc1C(N)=O]

GM 5 was followed using 4-chlorophenol (2AN, 0.025 mmol) and 4-[4-(chloromethyl)pyridin-2-yl]-2-methylbenzamide (6a, 0.025 mmol). ESIMS=353 (M+H$^+$, 100).

Example 41: 4-[4-(2,3-dimethylphenoxymethyl)pyridin-2-yl]-2-methylbenzamide (41)

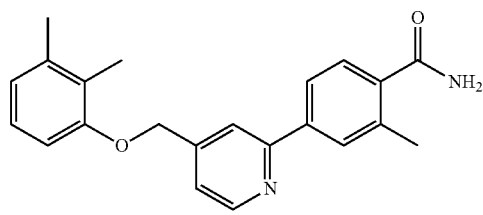 [SMILES: Cc1cc(-c2cc(COc3cccc(C)c3C)ccn2)ccc1C(N)=O]

GM 5 was followed using 2,3-dimethylphenol (2AO, 0.025 mmol) and 4-[4-(chloromethyl)pyridin-2-yl]-2-methylbenzamide (6a, 0.025 mmol). ESIMS=347 (M+H$^+$, 100).

Example 42: 4-{4-[(naphthalen-2-yloxy)methyl]pyridin-2-yl}-2-methylbenzamide (42)

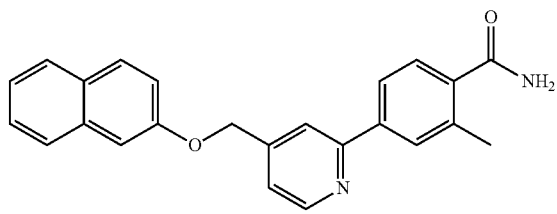 [SMILES: Cc1cc(-c2cc(COc3ccc4ccccc4c3)ccn2)ccc1C(N)=O]

GM 5 was followed using 2-naphthol (2AP, 0.025 mmol) and 4-[4-(chloromethyl)pyridin-2-yl]-2-methylbenzamide (6a, 0.025 mmol). ESIMS=369 (M+H$^+$, 100).

Example 43: 4-[4-(3-acetylphenoxymethyl)pyridin-2-yl]-2-methylbenzamide (43)

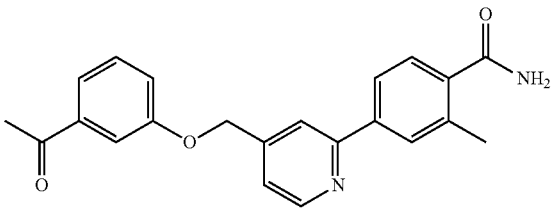 [SMILES: CC(=O)c1cccc(OCc2ccnc(-c3ccc(C(N)=O)c(C)c3)c2)c1]

GM 5 was followed using 3-acetylphenol (2AQ, 0.025 mmol) and 4-[4-(chloromethyl)pyridin-2-yl]-2-methylbenzamide (6a, 0.025 mmol). ESIMS=361 (M+H$^+$, 100).

Example 44: 4-[4-(2-chloro-4-methylphenoxymethyl)pyridin-2-yl]-2-methylbenzamide (44)

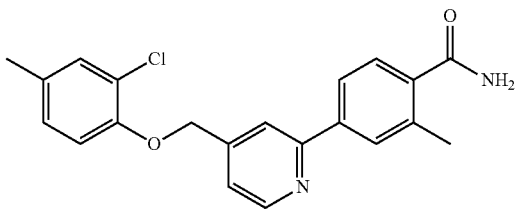 [SMILES: Cc1ccc(OCc2ccnc(-c3ccc(C(N)=O)c(C)c3)c2)c(Cl)c1]

GM 5 was followed using 2-chloro-4-methylphenol (2AR, 0.025 mmol) and 4-[4-(chloromethyl)pyridin-2-yl]-2-methylbenzamide (6a, 0.025 mmol). ESIMS=367 (M+H$^+$, 100).

Example 45: 4-[4-(2-chloro-4-fluorophenoxymethyl)pyridin-2-yl]-2-methylbenzamide (45)

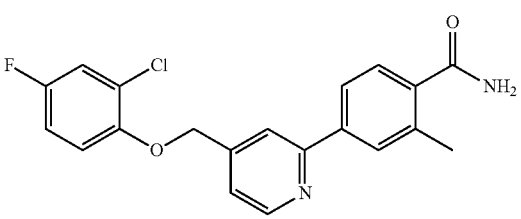 [SMILES: Cc1cc(-c2cc(COc3ccc(F)cc3Cl)ccn2)ccc1C(N)=O]

GM 5 was followed using 2-chloro-4-fluorophenol (2AS, 0.025 mmol) and 4-[4-(chloromethyl)pyridin-2-yl]-2-methylbenzamide (6a, 0.025 mmol). ESIMS=371 (M+H$^+$, 100).

Example 46: 4-[4-(2-methylphenoxymethyl)pyridin-2-yl]-2-methylbenzamide (46)

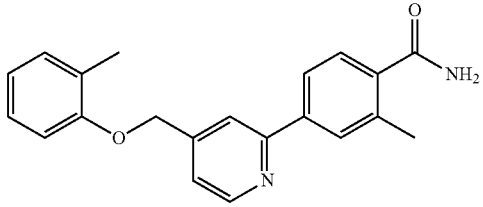 [SMILES: Cc1ccccc1OCc1ccnc(-c2ccc(C(N)=O)c(C)c2)c1]

GM 5 was followed using 2-methylphenol (2AT, 0.025 mmol) and 4-[4-(chloromethyl)pyridin-2-yl]-2-methylbenzamide (6a, 0.025 mmol). ESIMS=333 (M+H$^+$, 100).

Example 47: 4-[4-(3-chloro-4-fluorophenoxymethyl)pyridin-2-yl]-2-methylbenzamide (47)

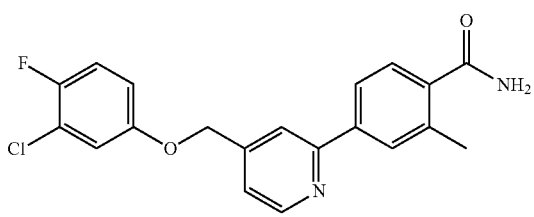 [SMILES: Cc1cc(-c2cc(COc3ccc(F)c(Cl)c3)ccn2)ccc1C(N)=O]

GM 5 was followed using 3-chloro-4-fluorophenol (2AU, 0.025 mmol) and 4-[4-(chloromethyl)pyridin-2-yl]-2-methylbenzamide (6a, 0.025 mmol). ESIMS=371 (M+H$^+$, 100).

Example 48: 4-[4-(3,4-difluorophenoxymethyl)pyridin-2-yl]-2-methylbenzamide (48)

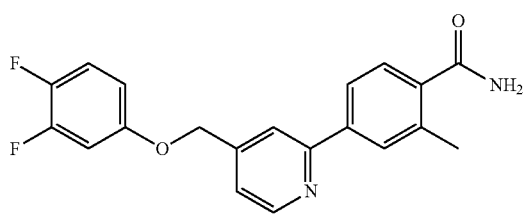 [SMILES: Cc1cc(-c2cc(COc3ccc(F)c(F)c3)ccn2)ccc1C(N)=O]

GM 5 was followed using 3,4-difluorophenol (2AV, 0.025 mmol) and 4-[4-(chloromethyl)pyridin-2-yl]-2-methylbenzamide (6a, 0.025 mmol). ESIMS=355 (M+H$^+$, 100).

Example 49: 4-[4-(4-chloro-3-cyanophenoxymethyl)pyridin-2-yl]-2-methylbenzamide (49)

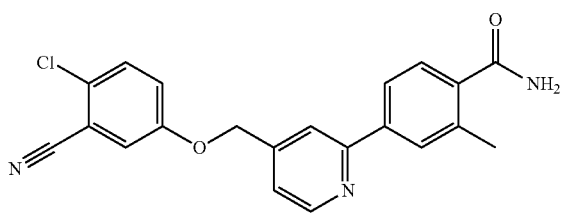 [SMILES: Cc1cc(-c2cc(COc3ccc(Cl)c(C#N)c3)ccn2)ccc1C(N)=O]

GM 5 was followed using 4-chloro-3-cyanophenol (2AW, 0.025 mmol) and 4-[4-(chloromethyl)pyridin-2-yl]-2-methylbenzamide (6a, 0.025 mmol). ESIMS=378 (M+H$^+$, 100).

Example 50: 4-[4-(3-chloro-2-fluorophenoxymethyl)pyridin-2-yl]-2-methylbenzamide (50)

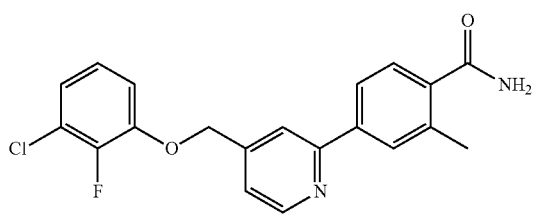 [SMILES: Cc1cc(-c2cc(COc3cccc(Cl)c3F)ccn2)ccc1C(N)=O]

GM 5 was followed using 3-chloro-2-fluorophenol (2AX, 0.025 mmol) and 4-[4-(chloromethyl)pyridin-2-yl]-2-methylbenzamide (6a, 0.025 mmol). ESIMS=371 (M+H$^+$, 100).

Example 51: 4-[4-(4-chloro-2-methoxyphenoxymethyl)pyridin-2-yl]-2-methylbenzamide (51)

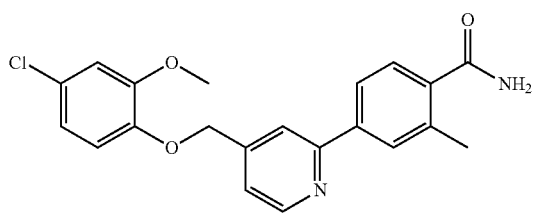 [SMILES: COc1cc(Cl)ccc1OCc1ccnc(-c2ccc(C(N)=O)c(C)c2)c1]

GM 5 was followed using 4-chloro-2-methoxyphenol (2AY, 0.025 mmol) and 4-[4-(chloromethyl)pyridin-2-yl]-2-methylbenzamide (6a, 0.025 mmol). ESIMS=383 (M+H$^+$, 100).

Example 52: 4-[4-(2,3-difluorophenoxymethyl)pyridin-2-yl]-2-methylbenzamide (52)

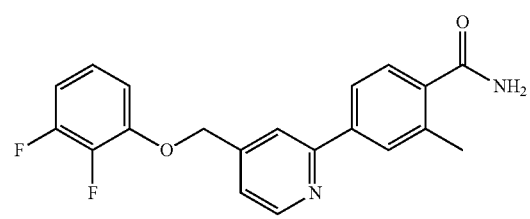 [SMILES: Cc1cc(-c2cc(COc3cccc(F)c3F)ccn2)ccc1C(N)=O]

GM 5 was followed using 2,3-difluorophenol (2AZ, 0.025 mmol) and 4-[4-(chloromethyl)pyridin-2-yl]-2-methylbenzamide (6a, 0.025 mmol). ESIMS=355 (M+H$^+$, 100).

Example 53: 4-{4-[2-(methylsulfanyl)phenoxymethyl]pyridin-2-yl}-2-methyl benzamide (53)

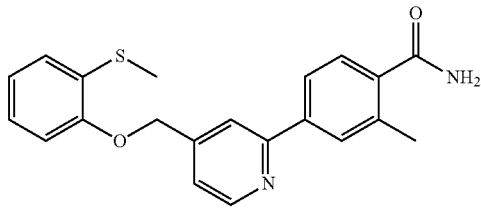 [SMILES: CSc1ccccc1OCc1ccnc(-c2ccc(C(N)=O)c(C)c2)c1]

GM 5 was followed using 2-(methylsulfanyl)phenol (2BA, 0.025 mmol) and 4-[4-(chloromethyl)pyridin-2-yl]-2-methylbenzamide (6a, 0.025 mmol). ESIMS=365 (M+H$^+$, 100).

Example 54: 4-[4-(3-chloro-4,5-difluorophenoxymethyl)pyridin-2-yl]-2-methylbenzamide (54)

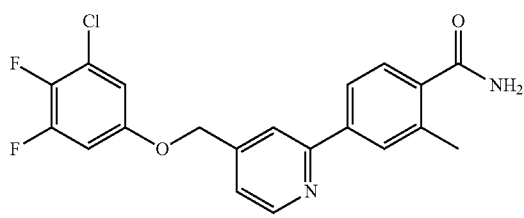

GM 5 was followed using 3-chloro-4,5-difluorophenol (2BB, 0.025 mmol) and 4-[4-(chloromethyl)pyridin-2-yl]-2-methylbenzamide (6a, 0.025 mmol). ESIMS=389 (M+H$^+$, 100).

Example 55: 4-[4-(4-cyano-3-methoxyphenoxymethyl)pyridin-2-yl]-2-methylbenzamide (55)

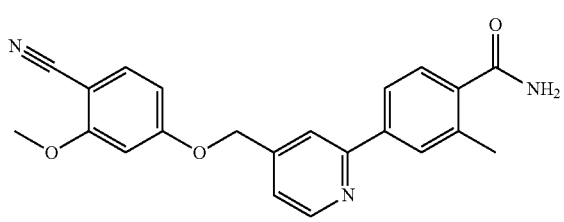 [SMILES: COc1cc(OCc2ccnc(-c3ccc(C(N)=O)c(C)c3)c2)ccc1C#N]

GM 5 was followed using 4-cyano-3-methoxyphenol (2BC, 0.025 mmol) and 4-[4-(chloromethyl)pyridin-2-yl]-2-methylbenzamide (6a, 0.025 mmol). ESIMS=374 (M+H$^+$, 100).

Example 56: 4-[4-(4-chloro-3,5-difluorophenoxymethyl)pyridin-2-yl]-2-methylbenzamide (56)

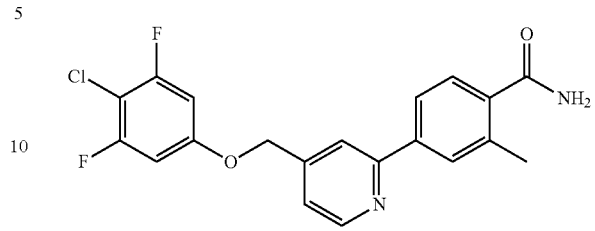

GM 5 was followed using 4-chloro-3,5-difluorophenol (2BD, 0.025 mmol) and 4-[4-(chloromethyl)pyridin-2-yl]-2-methylbenzamide (6a, 0.025 mmol). ESIMS=389 (M+H$^+$, 100).

Example 57: 4-[4-(3,4,5-trifluorophenoxymethyl)pyridin-2-yl]-2-methyl benzamide (57)

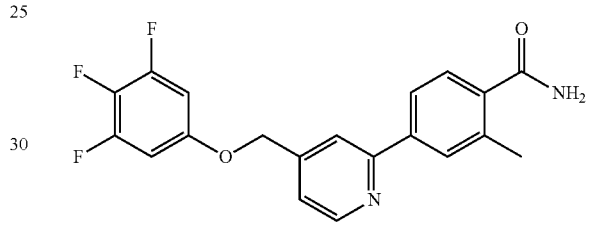

GM 5 was followed using 3,4,5-trifluorophenol (2BE, 0.025 mmol) and 4-[4-(chloromethyl)pyridin-2-yl]-2-methylbenzamide (6a, 0.025 mmol). ESIMS=373 (M+H$^+$, 100).

Example 58: 4-{4-[3-methoxy-4-(trifluoromethyl)phenoxymethyl]pyridin-2-yl}-2-methylbenzamide (58)

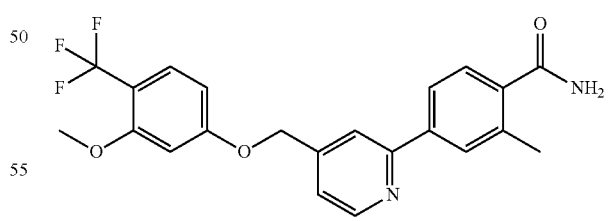

GM 5 was followed using 3-methoxy-4-(trifluoromethyl)phenol (2BF, 0.025 mmol) and 4-[4-(chloromethyl)pyridin-2-yl]-2-methylbenzamide (6a, 0.025 mmol). ESIMS=417 (M+H$^+$, 100).

Example 59: 4-[4-(4-propanoylphenoxymethyl)pyridin-2-yl]2-methylbenzamide (59)

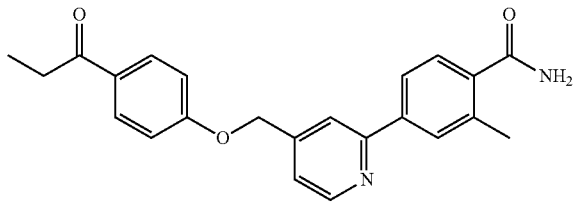 [SMILES: CCC(=O)c1ccc(OCc2ccnc(-c3ccc(C(N)=O)c(C)c3)c2)cc1]

GM 5 was followed using 4-propanoylphenol (2BG, 0.025 mmol) and 4-[4-(chloromethyl)pyridin-2-yl]-2-methylbenzamide (6a, 0.025 mmol). ESIMS=375 (M+H$^+$, 100).

Example 60: 4-[4-(4-acetyl-3-fluorophenoxymethyl)pyridin-2-yl]-2-methylbenzamide (60)

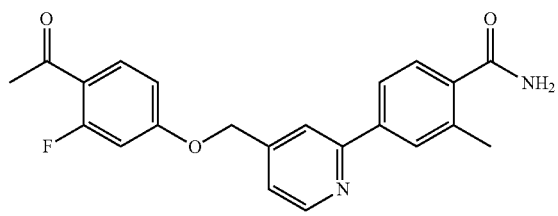

GM 5 was followed using 4-acetyl-3-fluorophenol (2BH, 0.025 mmol) and 4-[4-(chloromethyl)pyridin-2-yl]-2-methylbenzamide (6a, 0.025 mmol). ESIMS=379 (M+H$^+$, 100).

Example 61: 4-[4-(4-fluoro-3-methoxyphenoxymethyl)pyridin-2-yl]-2-methylbenzamide (61)

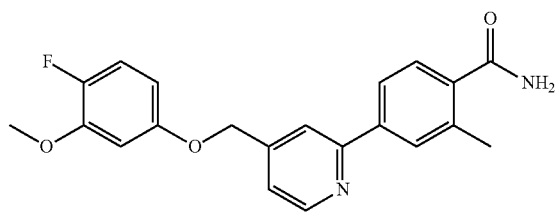

GM 5 was followed using 4-fluoro-3-methoxyphenol (2BI, 0.025 mmol) and 4-[4-(chloromethyl)pyridin-2-yl]-2-methylbenzamide (6a, 0.025 mmol). ESIMS=367 (M+H$^+$, 100).

Example 62: 4-[4-(3-fluoro-4-methoxyphenoxymethyl)pyridin-2-yl]-2-methylbenzamide (62)

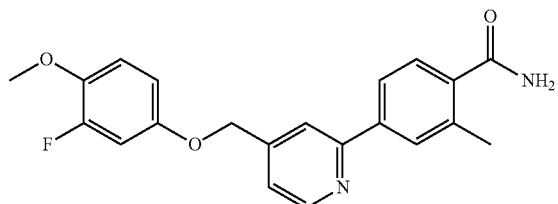

GM 5 was followed using 3-fluoro-4-methoxyphenol (2BJ, 0.025 mmol) and 4-[4-(chloromethyl)pyridin-2-yl]-2-methylbenzamide (6a, 0.025 mmol). ESIMS=367 (M+H$^+$, 100).

Example 63: 4-{4-[(2,3-dihydro-1-benzofuran-6-yloxy)methyl]pyridin-2-yl}-2-methylbenzamide (63)

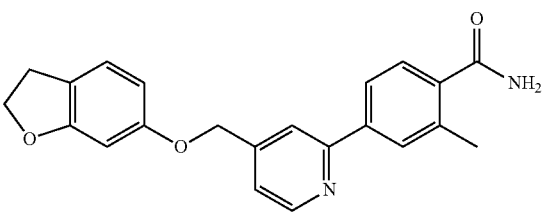 [SMILES: Cc1cc(-c2cc(COc3ccc4c(c3)OCC4)ccn2)ccc1C(N)=O]

GM 5 was followed using 2,3-dihydro-1-benzofuran-6-ol (2BK, 0.025 mmol) and 4-[4-(chloromethyl)pyridin-2-yl]-2-methylbenzamide (6a, 0.025 mmol). ESIMS=361 (M+H$^+$, 100).

Example 64: 4-{4-[(2,3-dihydro-1-benzofuran-5-yloxy)methyl]pyridin-2-yl}-2-methylbenzamide (64)

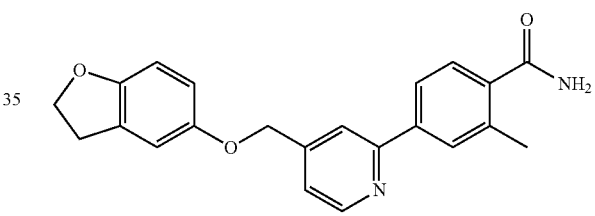

GM 5 was followed using 2,3-dihydro-1-benzofuran-5-ol (2BL, 0.025 mmol) and 4-[4-(chloromethyl)pyridin-2-yl]-2-methylbenzamide (6a, 0.025 mmol). ESIMS=361 (M+H$^+$, 100).

Example 65: 4-{4-[3-fluoro-4-(trifluoromethyl)phenoxymethyl]pyridin-2-yl}-2-methylbenzamide (65)

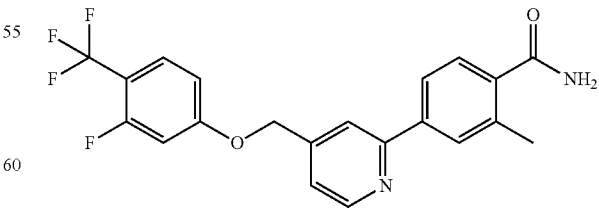

GM 5 was followed using 3-fluoro-4-(trifluoromethyl)phenol (2BM, 0.025 mmol) and 4-[4-(chloromethyl)pyridin-2-yl]-2-methylbenzamide (6a, 0.025 mmol). ESIMS=405 (M+H$^+$, 100).

Example 66: 4-[4-({[1-methyl-3-(trifluoromethyl)-1H-pyrazol-5-yl]oxy}methyl)pyridin-2-yl]2-methylbenzamide (66)

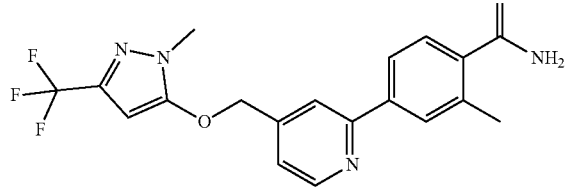

GM 5 was followed using 2-methyl-5-(trifluoromethyl)pyrazol-3-ol (2BN, 0.025 mmol) and 4-[4-(chloromethyl)pyridin-2-yl]-2-methylbenzamide (6a, 0.025 mmol). ESIMS=391 (M+H$^+$, 100).

Example 67: 4-{4-[3-(difluoromethyl)phenoxymethyl]pyridin-2-yl}-2-methylbenzamide (67)

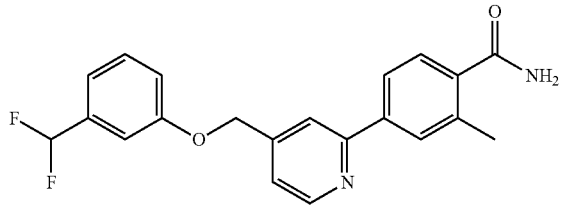

GM 5 was followed using 3-difluoromethylphenol (2BO, 0.025 mmol) and 4-[4-(chloromethyl)pyridin-2-yl]-2-methylbenzamide (6a, 0.025 mmol). ESIMS=369 (M+H$^+$, 100).

Example 68: 4-{4-[3-chloro-4-(trifluoromethyl)phenoxymethyl]pyridin-2-yl}-2-methylbenzamide (68)

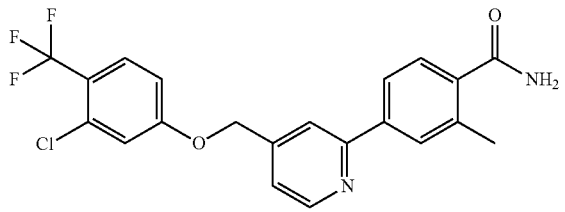 [SMILES: Cc1cc(-c2cc(COc3ccc(C(F)(F)F)c(F)c3)ccn2)ccc1C(N)=O]

GM 5 was followed using 3-chloro-4-(trifluoromethyl)phenol (2BP, 0.025 mmol) and 4-[4-(chloromethyl)pyridin-2-yl]-2-methylbenzamide (6a, 0.025 mmol). ESIMS=421 (M+H$^+$, 100).

Example 69: 4-{4-[4-(2-hydroxypropan-2-yl)phenoxymethyl]pyridin-2-yl}-2-methylbenzamide (69)

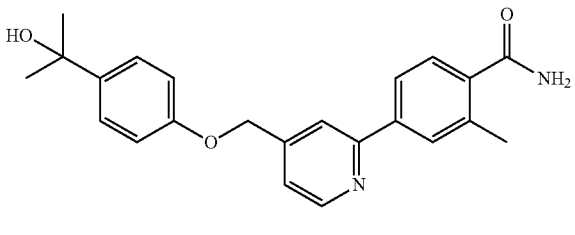 [SMILES: Cc1cc(-c2cc(COc3ccc(C(C)(C)O)cc3)ccn2)ccc1C(N)=O]

GM 5 was followed using 4-(2-hydroxypropan-2-yl)phenol (2BQ, 0.025 mmol) and 4-[4-(chloromethyl)pyridin-2-yl]-2-methylbenzamide (6a, 0.025 mmol). ESIMS=377 (M+H$^+$, 100).

Example 70: 4-[4-(3-cyclopropyl-5-fluorophenoxymethyl)pyridin-2-yl]-2-methylbenzamide (70)

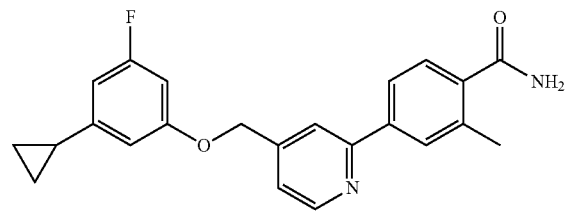 [SMILES: Cc1cc(-c2cc(COc3cc(F)cc(C4CC4)c3)ccn2)ccc1C(N)=O]

GM 5 was followed using 3-cyclopropyl-5-fluorophenol (2BR, 0.025 mmol) and 4-[4-(chloromethyl)pyridin-2-yl]-2-methylbenzamide (6a, 0.025 mmol). ESIMS=377 (M+H$^+$, 100).

Example 71: 4-[4-(4-cyclopropyl-3-fluorophenoxymethyl)pyridin-2-yl]-2-methylbenzamide (71)

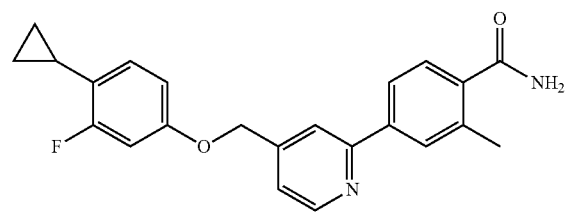 [SMILES: Cc1cc(-c2cc(COc3ccc(C4CC4)c(F)c3)ccn2)ccc1C(N)=O]

GM 5 was followed using 4-cyclopropyl-3-fluorophenol (2BS, 0.025 mmol) and 4-[4-(chloromethyl)pyridin-2-yl]-2-methylbenzamide (6a, 0.025 mmol). ESIMS=377 (M+H$^+$, 100).

Example 72: 4-(4-{[(2-methyl-2H-indazol-5-yl)oxy]methyl}pyridin-2-yl)-2-methyl benzamide (72)

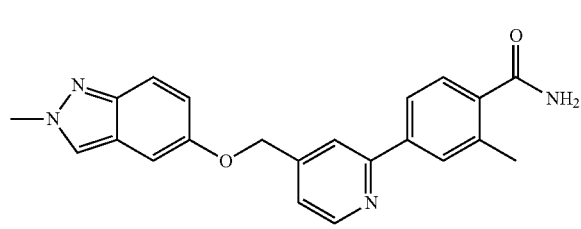 [SMILES: Cc1cc(-c2cc(COc3ccc4nn(C)cc4c3)ccn2)ccc1C(N)=O]

GM 5 was followed using 2-methyl-2H-indazol-5-ol (2BT, 0.025 mmol) and 4-[4-(chloromethyl)pyridin-2-yl]-2-methylbenzamide (6a, 0.025 mmol). ESIMS=373 (M+H$^+$, 100).

Example 73: 4-{4-[3-(cyanomethyl)phenoxymethyl]pyridin-2-yl}-2-methylbenzamide (73)

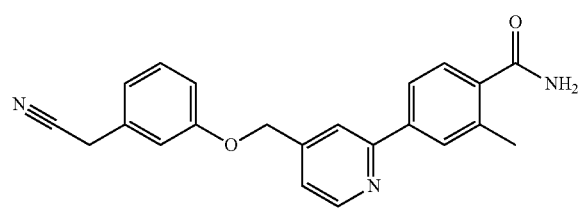 [SMILES: Cc1cc(-c2cc(COc3cccc(CC#N)c3)ccn2)ccc1C(N)=O]

GM 5 was followed using 3-(cyanomethyl)phenol (2BU, 0.025 mmol) and 4-[4-(chloromethyl)pyridin-2-yl]-2-methylbenzamide (6a, 0.025 mmol). ESIMS=358 (M+H$^+$, 100).

Example 74: 4-(4-{[(5-methoxypyridin-3-yl)oxy]methyl}pyridin-2-yl)-2-methylbenzamide (74)

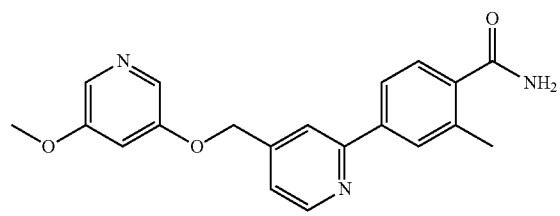 [SMILES: COc1cncc(OCc2ccnc(-c3ccc(C(N)=O)c(C)c3)c2)c1]

GM 5 was followed using 5-methoxy-3-hydroxypyridine (2BV, 0.025 mmol) and 4-[4-(chloromethyl)pyridin-2-yl]-2-methylbenzamide (6a, 0.025 mmol). ESIMS=350 (M+H$^+$, 100).

Example 75: 4-(4-{[(5-cyanopyridin-3-yl)oxy]methyl}pyridin-2-yl)-2-methylbenzamide (75)

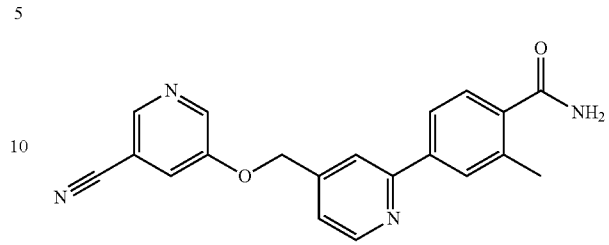

GM 5 was followed using 5-cyano-3-hydroxypyridine (2BW, 0.025 mmol) and 4-[4-(chloromethyl)pyridin-2-yl]-2-methylbenzamide (6a, 0.025 mmol). ESIMS=345 (M+H$^+$, 100).

IV. Preparation of Compounds of Formula (Ia): R$^8$ is Cl, X is N, Y is CH

Example 76: 4-{4-[4-(trifluoromethyl)phenoxymethyl]pyridin-2-yl}2-chlorobenzamide (76)

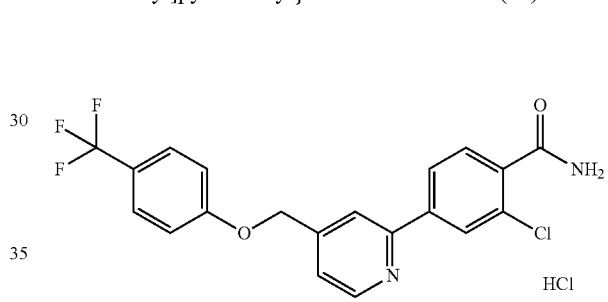

The title compound was prepared as shown in Scheme 3.

Scheme 3

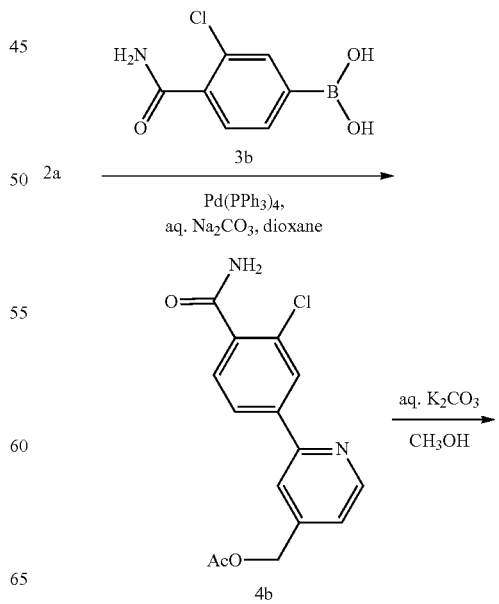

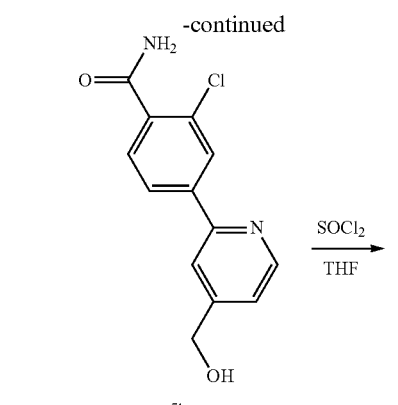

5b

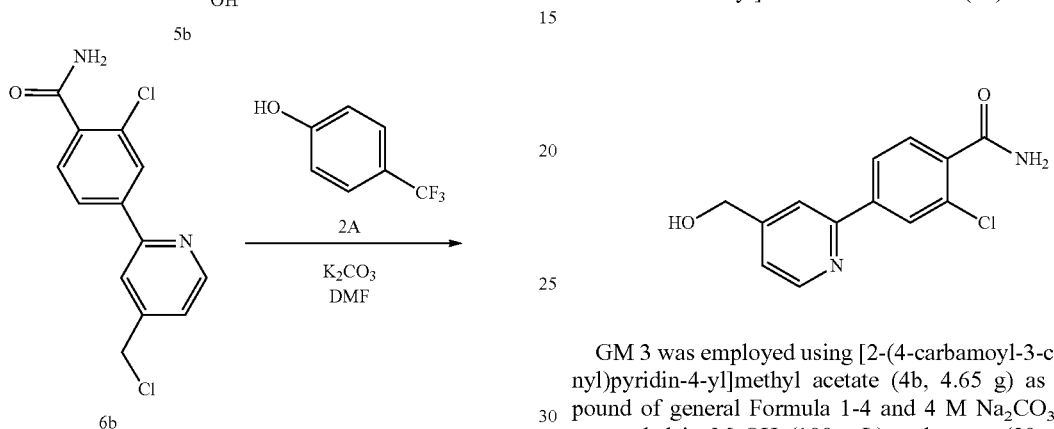

6b

Step 1: Preparation of [2-(4-carbamoyl-3-chlorophenyl)pyridin-4-yl]methyl acetate (4b)

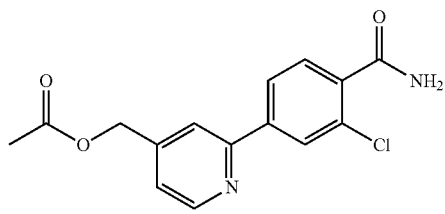 [SMILES: CC(=O)OCc1ccnc(-c2ccc(C(N)=O)c(Cl)c2)c1]

GM 2 was employed using (2-chloropyridin-4-yl)methyl acetate (2a, 5.13 g, 27.01 mmol.) as the compound of general Formula 1-2 and (4-carbamoyl-3-chlorophenyl)boronic acid (3b, 5.36 g, 27.01 mmol.) as the compound of general Formula 1-3 in 1,4-dioxane (100 mL) and a 4 M aqueous solution of Na$_2$CO$_3$ (25 mL). The resulting mixture was heated to 95° C. overnight. The product was purified by silica gel column chromatography eluting with CH$_2$Cl$_2$/MeOH up to 7% MeOH to give 4.65 g of the title compound as a beige solid. ESIMS=305 (M+H$^+$, 100).

Step 2: Preparation of 4-[4-(hydroxymethyl)pyridin-2-yl]-2-chlorobenzamide (5b)

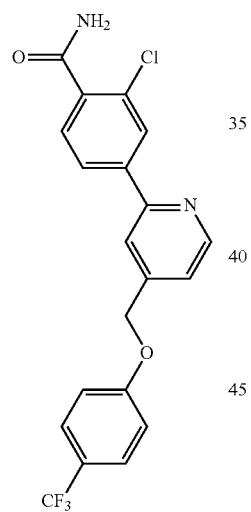

GM 3 was employed using [2-(4-carbamoyl-3-chlorophenyl)pyridin-4-yl]methyl acetate (4b, 4.65 g) as the compound of general Formula 1-4 and 4 M Na$_2$CO$_3$ (20 mL) suspended in MeOH (100 mL) and water (20 mL). This mixture was heated overnight at 65° C. Recovered the title compound as a white solid.

Step 3: Preparation of 4-[4-(chloromethyl)pyridin-2-yl]-2-chlorobenzamide hydrochloride (6b)

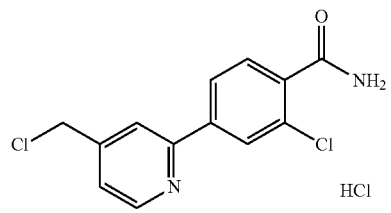 [SMILES: NC(=O)c1ccc(-c2cc(CCl)ccn2)cc1Cl ; Cl]

GM 4 was employed using 4-[4-(hydroxymethyl)pyridin-2-yl]-2-chlorobenzamide (5b, 130 mg) as the compound of general Formula 1-5. The mixture was filtered and the collected solids were dried under vacuum to afford 4-[4-(chloromethyl)pyridin-2-yl]-2-chlorobenzamide hydrochloride (6b, 150 mg) as a white powder. ESIMS=282 (M+H$^+$, 100).

Step 4: Preparation of 4-{4-[4-(trifluoromethyl)phenoxymethyl]pyridin-2-yl}2-chlorobenzamide (76)

GM 5 was followed using 4-trifluoromethylphenol (2A, 0.025 mmol) as HO—Z$^2$, and 4-[4-(chloromethyl)pyridin-2-yl]-2-chlorobenzamide hydrochloride (6b, 0.025 mmol) as the compound of general Formula 1-6. ESIMS=407 (M+H$^+$, 100).

Example 77: 4-[4-(4-cyano-3-fluorophenoxymethyl)pyridin-2-yl]-2-chlorobenzamide (77)

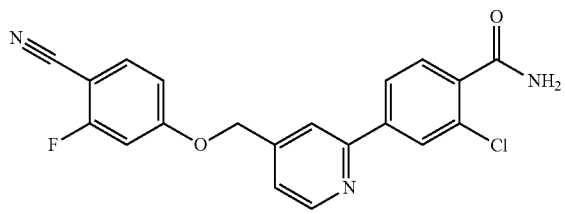 [SMILES: N#Cc1ccc(OCc2ccnc(-c3ccc(C(N)=O)c(Cl)c3)c2)cc1F]

GM 5 was followed using 4-cyano-3-fluorophenol (2D, 0.025 mmol) and 4-[4-(chloromethyl)pyridin-2-yl]-2-chlorobenzamide hydrochloride (6b, 0.025 mmol). ESIMS=482 (M+H+, 100).

V. Alternative General Synthetic Scheme for the Preparation of Compounds of Formula (Ia)

Scheme 4

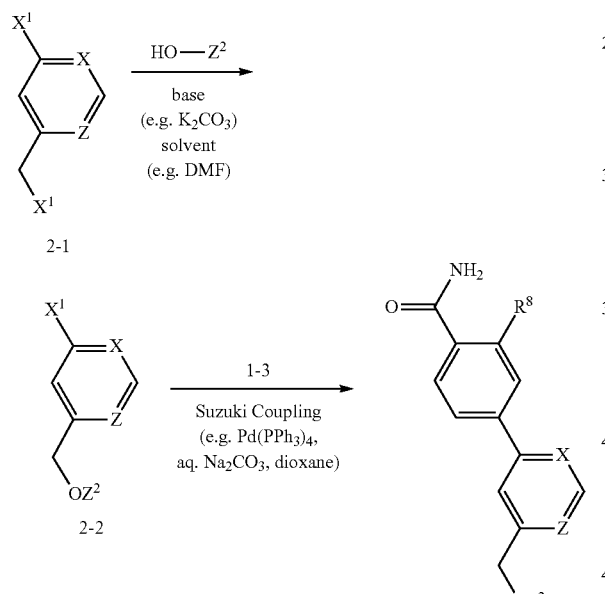

$X^1$ is halo (e.g. Cl or Br). The remaining variables are defined according to any of the embodiments described herein.

According to Scheme 4, compounds of general Formula (I)a can be synthesized in two steps from compounds of general Formula 2-1. In one instance, Williamson ether synthesis of compounds of general Formula 2-2 involves coupling of alkyl halide compounds, such as compounds of general Formula 2-1, with HO—$Z^1$ in the presence of a base, such as $K_2CO_3$, $Na_2CO_3$, or $Cs_2CO_3$ in a solvent, such as DMF and the like provides compounds of general Formula 2-2. Suzuki coupling of compounds of general Formula 2-2, compounds of general Formula 1-3, in the presence of a palladium catalyst, such as Pd(dppf)$Cl_2$ $CH_2Cl_2$ or Pd(PPh$_3$)$_4$, and a base, such as $K_2CO_3$, $Na_2CO_3$, or $Cs_2CO_3$, in a solvent or solvent mixture, such as dioxane, THF and $CH_2Cl_2$ or toluene, water and ethyl alcohol and the like provides compounds of general Formula (I)a.

VI. Preparation of Compounds of Formula (Ia): $R^8$ is $CF_3$, X is N, Y is CH

Example 78: 4-{4-[4-(trifluoromethyl)phenoxymethyl]pyridin-2-yl}-2-(trifluoromethyl)benzamide (78)

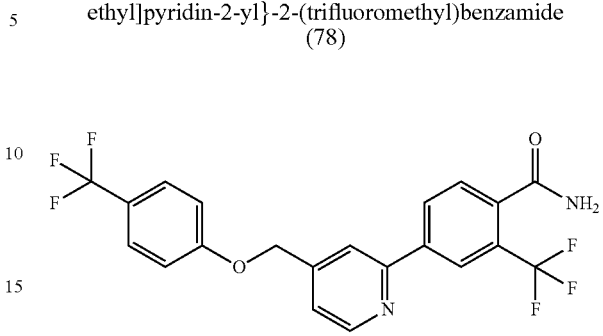

The title compound was prepared as shown in Scheme 5.

Scheme 5

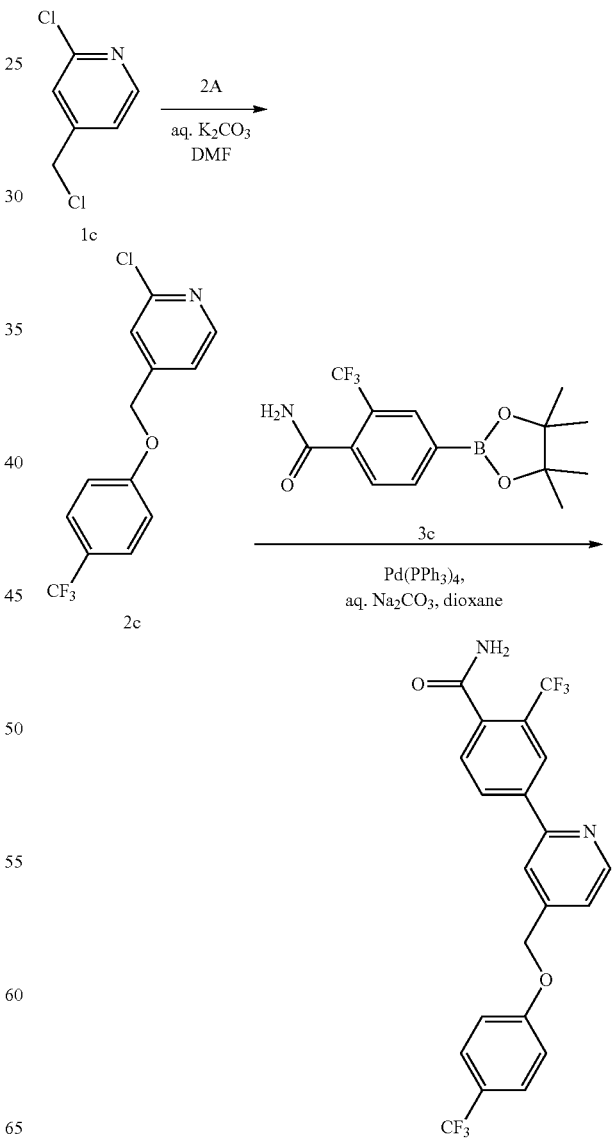

Step 1: Preparation of 2-chloro-4-[4-(trifluoromethyl)phenoxymethyl]pyridine (2c)

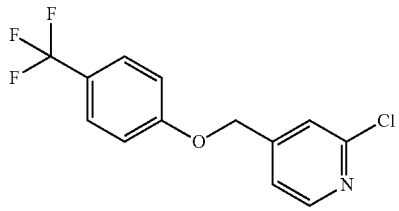

GM 5 was followed using 4-(trifluoromethyl)phenol (1A, 1.34 g, 8.271 mmol) as HO—$Z^2$, and 2-chloro-4-(chloromethyl)pyridine (1c, 1.34 g, 8.271 mmol) as the compound of general Formula 2-1 at 80° C. The product was purified by silica gel column chromatography eluting with a gradient of EtOAc/hexanes up to 40% EtOAc to afford 2.04 g of the title compound as a white solid. ESIMS=288 (M+H$^+$, 100).

Step 2: Preparation of 4-{4-[4-(trifluoromethyl)phenoxymethyl]pyridin-2-yl}-2-(trifluoromethyl)benzamide (78)

GM 2 was followed using 2-chloro-4-[4-(trifluoromethyl)phenoxymethyl]pyridine (2c, 0.025 mmol) as the compound of general Formula 2-2 and 2-trifluoromethyl-4-(tetramethyl-1,3,2-dioxaborolan-2-yl)benzamide (3c, 0.025 mmol) as the compound of general Formula 1-3 in dioxane (0.5 mL), and 4 M Na$_2$CO$_3$ (0.2 mL). Purified by HPLC. ESIMS=441 (M+H$^+$, 100).

VI. General Synthetic Scheme for the Preparation of Compounds of Formula (Ib)

Scheme 6

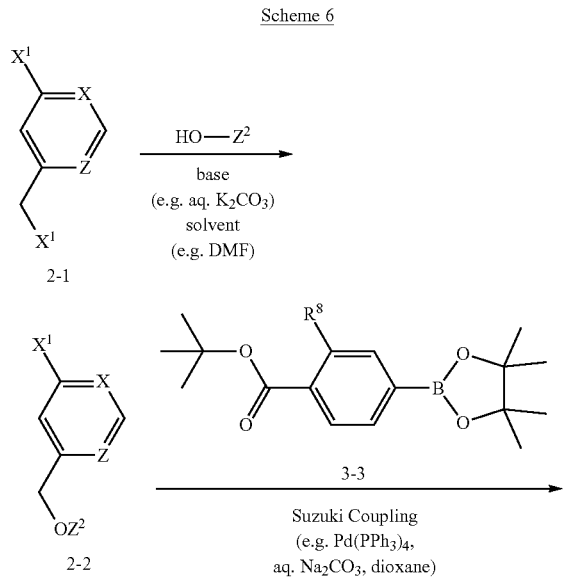

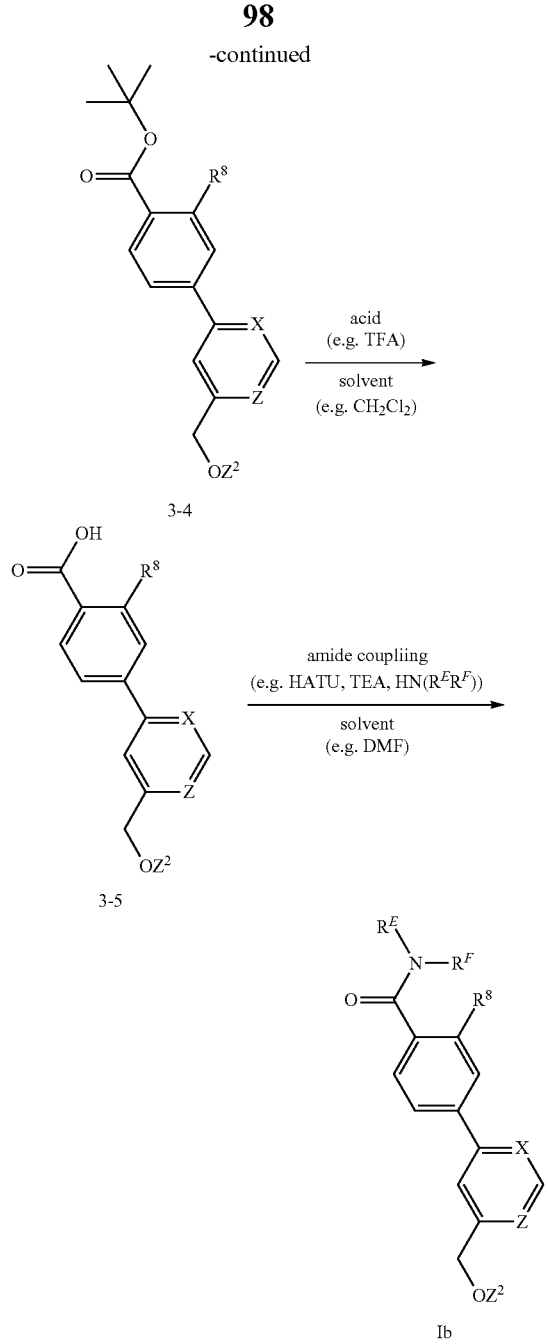

$X^1$ is halo (e.g. Cl or Br). The remaining variables are defined according to any of the embodiments described herein.

According to Scheme 6, compounds of general Formula (I)b can be synthesized in several steps from compounds of general Formula 2-1. In one instance, Williamson ether synthesis of compounds of general Formula 2-2 involves coupling of alkyl halide compounds, such as compounds of general Formula 2-1, with HO—$Z^1$ in the presence of a base, such as K$_2$CO$_3$, Na$_2$CO$_3$, or Cs$_2$CO$_3$ in a solvent, such as DMF and the like provides compounds of general Formula 2-2. Suzuki coupling of compounds of general Formula 2-2, compounds of general Formula 3-3, in the presence of a palladium catalyst, such as Pd(dppf)Cl$_2$ CH$_2$Cl$_2$ or Pd(PPh$_3$)$_4$, and a base, such as K$_2$CO$_3$, Na$_2$CO$_3$, or Cs$_2$CO$_3$, in a solvent or solvent mixture, such as dioxane, THF and CH₂Cl₂ or toluene, water and ethyl alcohol and the like provides compounds of general Formula 3-4. Preparation of compounds of general Formula 2-5 can be accomplished by treating compounds of general Formula 2-4 with an acid, such as HCl or TFA in a solvent or a solvent or solvent mixture, such as CH₂Cl₂, dioxane, THF and CH₂Cl₂ or toluene and water and the like. Preparation of compounds of general Formula (I)b can be accomplished by coupling compounds of general Formula 3-5 with HN(R^E R^F), in the presence of an amide coupling agent, such as N,N,N',N'-tetramethyl-O—(N-succinimidyl)uronium hexafluorophosphate (HSTU) 2-(1H-benzotriazole-1-yl)-1,1,3,3-tetramethyluronium hexafluorophosphate (HBTU), 2-(6-Chloro-1-H-benzotriazole-1-yl)-1,1,3,3-tetramethylaminium hexafluorophosphate (HCTU), or 1-[bis(dimethylamino)methylene]-1H-1,2,3-triazolo[4,5-b]pyridinium 3-oxide hexafluorophosphate (HATU), and a base, such as TEA, in a solvent, such as CH₂Cl₂, dioxane, or THE and the like.

VIII. Preparation of Compounds of Formula (Ib): X is N, Y is CH

Example 79: 4-[4-(4-cyano-3-fluorophenoxymethyl)pyridin-2-yl]-N-(2-hydroxyethyl)-2-methylbenzamide (79)

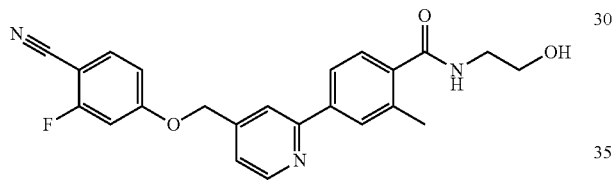

The title compound was prepared as shown in Scheme 7.

Scheme 7

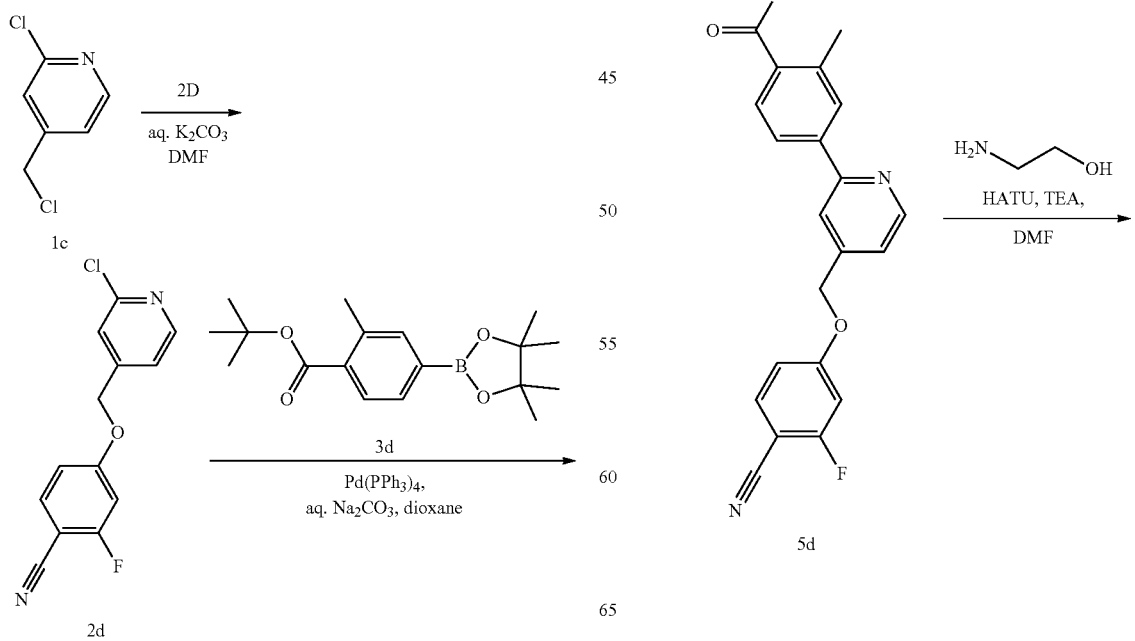

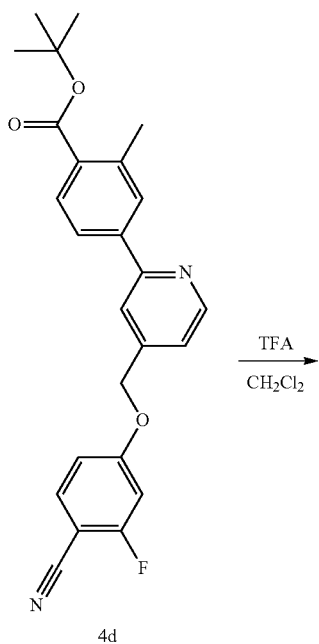

-continued

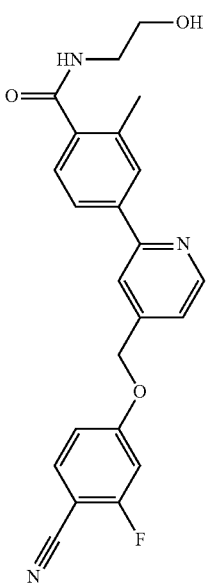

Step 1: Preparation of 4-[(2-chloropyridin-4-yl)methoxy]-2-fluorobenzonitrile (2d)

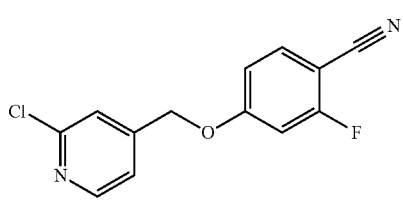 [SMILES: N#Cc1ccc(OCc2ccnc(Cl)c2)cc1F]

GM 5 was followed using 4-cyano-3-fluorophenol (2D, 1.36 g, 9.925 mmol) as HO—$Z^2$, and 2-chloro-4-(chloromethyl)pyridine (1c, 1.34 g, 8.27 mmol) as the compound of general Formula 2-1 in DMF (6 mL) at 80° C. overnight. The product was purified by recrystallization from EtOAc. ESIMS=263 (M+H$^+$, 100).

Step 2: Preparation of tert-butyl 4-(4-((4-cyano-3-fluorophenoxy)methyl)pyridin-2-yl)-2-methylbenzoate (4d)

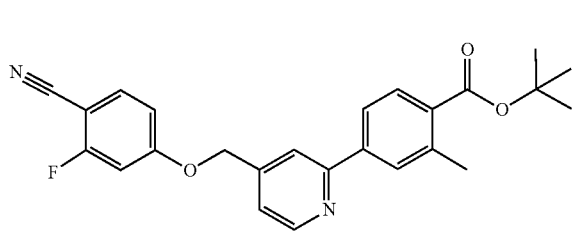 [SMILES: Cc1cc(-c2cc(COc3ccc(C#N)c(F)c3)ccn2)ccc1C(=O)OC(C)(C)C]

GM 2 was followed 4-[(2-chloropyridin-4-yl)methoxy]-2-fluorobenzonitrile (2d, 95 mg, 0.30 mmol) as the compound of general Formula 2-2 and tert-butyl 2-methyl-4-(tetramethyl-1,3,2-dioxaborolan-2-yl)benzoate (3d, 86 mg, 0.33 mmol)) as the compound of general Formula 3-3 in dioxane (2 mL), and 4 M Na$_2$CO$_3$ (1 mL). Purified by silica gel column chromatography eluting with EtOAc/hexanes to afford tert-butyl 4-(4-((4-cyano-3-fluorophenoxy)methyl)pyridin-2-yl)-2-methylbenzoate (4d). ESIMS=419 (M+H$^+$, 100).

Step 3: Preparation of 4-[4-(4-cyano-3-fluorophenoxymethyl)pyridin-2-yl]-2-methylbenzoic acid (5d)

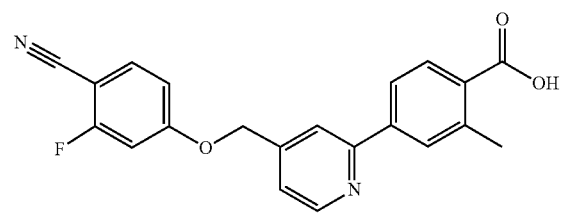 [SMILES: Cc1cc(-c2cc(COc3ccc(C#N)c(F)c3)ccn2)ccc1C(=O)O]

tert-Butyl 4-(4-((4-cyano-3-fluorophenoxy)methyl)pyridin-2-yl)-2-methylbenzoate (4d) was then dissolved in 30% CF$_3$COOH (5 mL) in CH$_2$Cl$_2$ for 5 hours. The solvents were removed, and the remaining solids were suspended in water/CH$_2$Cl$_2$ and then collected by filtration to afford 4-[4-(4-cyano-3-fluorophenoxymethyl)pyridin-2-yl]-2-methylbenzoic acid (5d). ESIMS=363 (M+H$^+$, 100).

Step 4: Preparation of 4-[4-(4-cyano-3-fluorophenoxymethyl)pyridin-2-yl]-N-(2-hydroxyethyl)-2-methylbenzamide (79)

4-[4-(4-Cyano-3-fluorophenoxymethyl)pyridin-2-yl]-2-methylbenzoic acid (5d, 0.025 mml) in DMF (0.5 mL) was treated with Et$_3$N (0.050 mmol) and HATU (0.050 mmol). The mixture stirred for 20 min and then 2-ethanolamine (0.050 mmol) was added. The resulting mixture was stirred overnight, and then purified by HPLC to afford the title compound. ESIMS=406 (M+H$^+$, 100)

Example 80: 4-[4-(4-cyano-3-fluorophenoxymethyl)pyridin-2-yl]-N-[2-(dimethylamino)ethyl]-2-methylbenzamide (80)

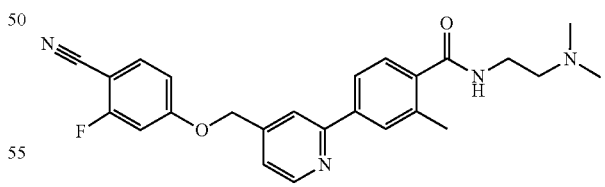

4-[4-(4-Cyano-3-fluorophenoxymethyl)pyridin-2-yl]-2-methylbenzoic acid (5d, 0.025 mml) in DMF (0.5 mL) was treated with Et$_3$N (0.050 mmol) and HATU (0.050 mmol). The mixture stirred for 20 min and then N,N-dimethylethylenediamine (0.050 mmol) was added. The resulting mixture was stirred overnight, and then purified by HPLC to afford the title compound. ESIMS=433 (M+H$^+$, 100).

IX. Preparation of Compounds of Formula (Ia): R⁸ is CH₃, X is CH, Y is N
Example 81: 4-{2-[4-(trifluoromethyl)phenoxymethyl]pyridin-4-yl}-2-methylbenzamide hydrochloride (81)
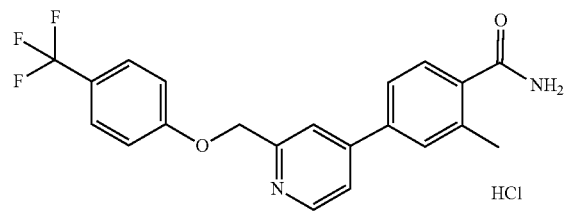 [SMILES: Cc1cc(-c2ccnc(COc3ccc(C(F)(F)F)cc3)c2)ccc1C(N)=O ; Cl]
The title compound was prepared as shown in Scheme 8.
Scheme 8
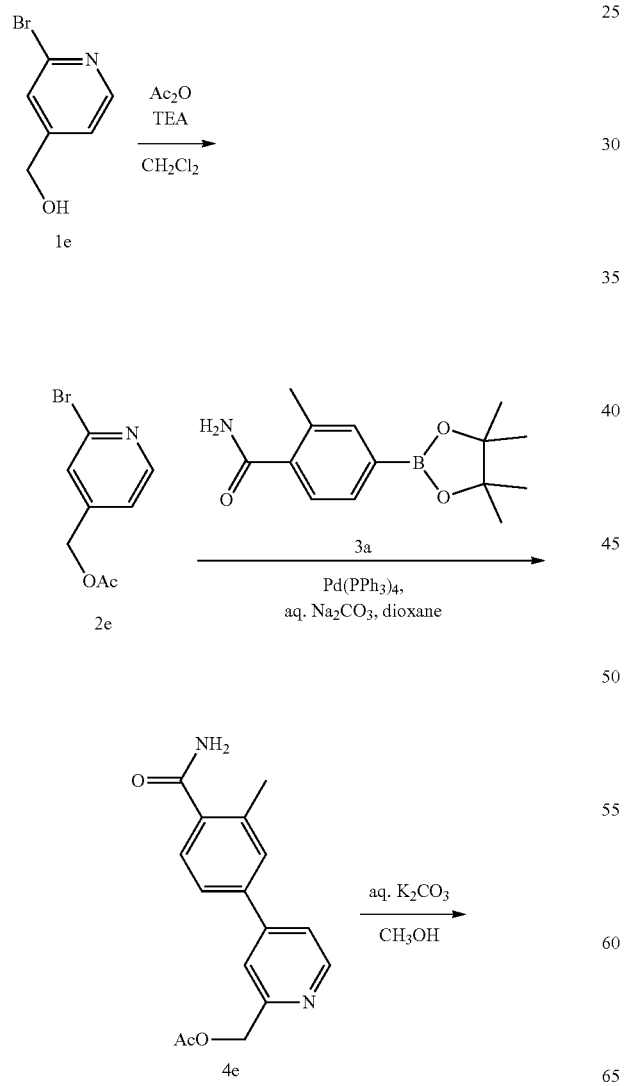
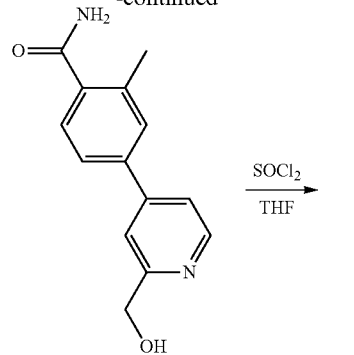
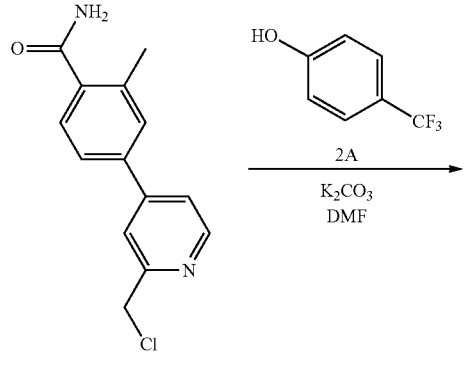
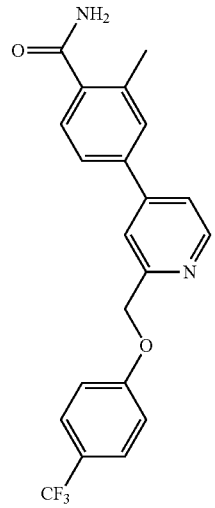
Step 1: Preparation of (4-bromopyridin-2-yl)methyl acetate (2e)
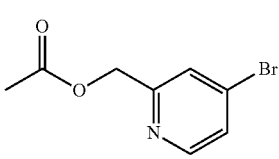
GM 1 was employed using 2-hydroxymethyl-4-bromopyridine (1e, 4.21 g, 22.38 mmol.) as the compound of general Formula 1-1, and affording the title compound (2e, 4.75 g) as the compound of general Formula 1-2 as a yellow oil. ESIMS=232 (M+H+, 100).

Step 2: Preparation of [4-(4-carbamoyl-3-methylphenyl)pyridin-2-yl]methyl acetate (4e)

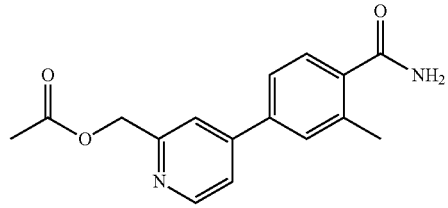 [SMILES: CC(=O)OCc1cc(-c2ccc(C(N)=O)c(C)c2)ccn1]

GM 2 was employed using (4-bromopyridin-2-yl)methyl acetate (2e, 4.17 g, 18.1 mmol.) as the compound of general Formula 1-2, and 2-methyl-4-(tetramethyl-1,3,2-dioxaborolan-2-yl)benzamide (3a, 5.20 g, 19.9 mmol.) as the compound of general Formula 1-3 in 1,4-dioxane (30 mL) and a 4 M aqueous solution of $Na_2CO_3$ (7 mL). The resulting mixture was heated to 95° C. overnight. The crude material was purified by silica gel column chromatography eluting with acetone/hexane up to 100% acetone to afford, after drying under vacuum, the title compound (4e, 2.04 g) as the compound of general Formula 1-4 as a tan solid. ESIMS=285 (M+H+, 100).

Step 3: Preparation of 4-[2-(hydroxymethyl)pyridin-4-yl]-2-methylbenzamide (5e)

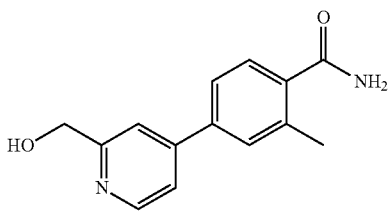 [SMILES: Cc1cc(-c2ccnc(CO)c2)ccc1C(N)=O]

GM 3 was employed using [4-(4-carbamoyl-3-methylphenyl)pyridin-2-yl]methyl acetate (4e, 2.04 g, 7.18 mmol.) as the compound of general Formula 1-4 and 4 M $Na_2CO_3$ (7 mL) in MeOH (150 mL) and water (50 mL). This mixture was stirred for 30 min at 75° C. and purified as described in GM 3 affording the title compound (5e, 1.57 g) as a white powder. ESIMS=243 (M+H+, 100). $^1$H NMR (DMSO-$d_6$) δ 8.61 (d, 1H), 7.95 (m, 1H), 7.91 (m, 2H), 7.77 (bs, 1H), 7.48 (d, 1H), 7.39 (bs, 1H), 7.33 (d, 1H), 4.63 (d, 2H), 2.46 (s, 1H).

Step 4: Preparation of 4-[2-(chloromethyl)pyridin-4-yl]-2-methylbenzamide hydrochloride (6e)

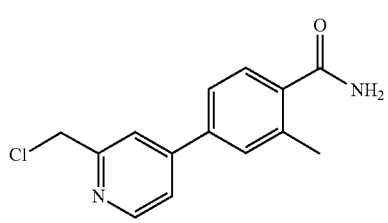

GM 4 was employed using 4-[2-(hydroxymethyl)pyridin-4-yl]-2-methylbenzamide (5e, 1.57 g) as the compound of general Formula 1-5. The mixture was treated with $Et_2O$ and the resulting solid collected by filtration and dried under vacuum to afford 4-[2-(chloromethyl)pyridin-4-yl]-2-methylbenzamide hydrochloride (6e, 1.96 g) as a white powder. ESIMS=261 (M+H+, 100). $^1$H NMR (DMSO-$d_6$) δ 8.70 (m, 1H), 8.02 (m, 1H), 7.82 (m, 2H), 7.71 (bs, 1H), 7.70 (m, 2H), 7.65 (d, 1H), 7.50 (d, 1H), 7.43 (bs, 1H), 7.19 (d, 2H), 5.35 (d, 2H), 3.32 (s, 3H), 2.46 (s, 3H).

Step 5: Preparation of 4-{2-[4-(trifluoromethyl)phenoxymethyl]pyridin-4-yl}-2-methylbenzamide hydrochloride (81)

GM 5 was followed using of 4-(trifluoromethyl)phenol (2A, 254 mg, 0.97 mmol)) as HO—$Z^2$, and 4-[2-(chloromethyl)pyridin-4-yl]-2-methylbenzamide hydrochloride (6e, 158 mg, 0.97 mmol) as the compound of general Formula 1-6 in DMF (10 mL). The product was purified by silica-gel column chromatography eluting with a $CH_2Cl_2$/MeOH gradient (up to 10% MeOH). The HCl salt was formed upon addition of 4 eq of HCl as a 1 M solution in $Et_2O$ into a solution of the product in MeOH (1 mL/mg) and evaporation under vacuum. The HCl salt was recrystallized from MeOH/EtOAc and dried under vacuum to afford 4-{2-[4-(trifluoromethyl)phenoxymethyl]pyridin-4-yl}-2-methylbenzamide hydrochloride (118 mg) as on off white powder. ESIMS=387 (M+H+, 100). $^1$H NMR (DMSO-$d_6$) δ 8.66 (d, 1H), 7.88 (s, 1H), 7.78 (bs, 1H), 7.73-7.65 (m, 5H), 7.50 (d, 1H), 7.44 (bs, 1H), 7.29 (d, 2H), 5.34 (d, 2H), 2.46 (s, 3H).

Example 82: 4-[2-(4-cyano-3-fluorophenoxymethyl)pyridin-4-yl]-2-methylbenzamide (82)

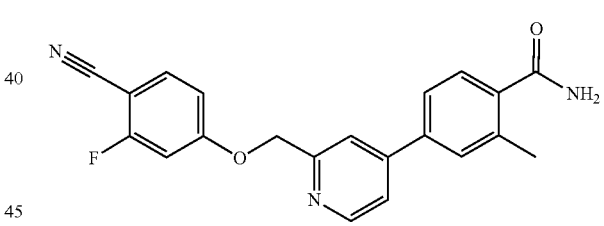

GM 5 was followed using 4-cyano-3-fluorophenol (2D, 92 mg, 0.673 mmol) and 4-[2-(chloromethyl)pyridin-4-yl]-2-methylbenzamide hydrochloride (6e, 200 mg, 0.673 mmol) in DMF (4 mL). The product was purified by HPLC. ESIMS=362 (M+H+, 100).

Example 83: 4-[2-(3,4,5-trifluorophenoxymethyl)pyridin-4-yl]-2-methylbenzamide (83)

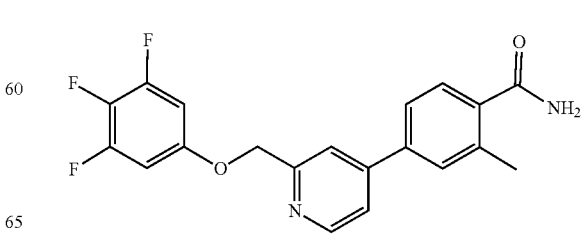

GM 5 was followed using 85 µL of a 0.5 M solution of 3,4,5-trifluorophenol (2BE, 0.043 mmol) in DMF and 4-[2-(chloromethyl)pyridin-4-yl]-2-methylbenzamide hydrochloride (6e, 8 mg, 0.027 mmol) in DMF (200 µL). The product was purified by HPLC. ESIMS=373 (M+H⁺, 100).

Example 84: 4-[2-(4-cyano-2,3-difluorophenoxymethyl)pyridin-4-yl]-2-methylbenzamide (84)

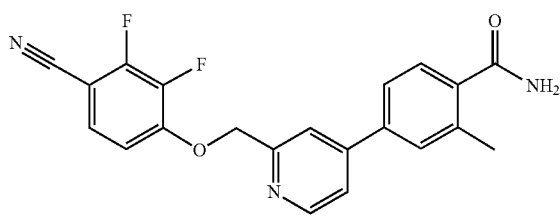 [SMILES: Cc1cc(-c2ccnc(COc3ccc(C#N)c(F)c3F)c2)ccc1C(N)=O]

GM 5 was followed using 4-cyano-2,3-difluorophenol (2I, 0.025 mmol) and 4-[2-(chloromethyl)pyridin-4-yl]-2-methylbenzamide hydrochloride (6e, 0.025 mmol). ESIMS=380 (M+H⁺, 100).

Example 85: 4-[2-(3,5-difluorophenoxymethyl)pyridin-4-yl]-2-methylbenzamide (85)

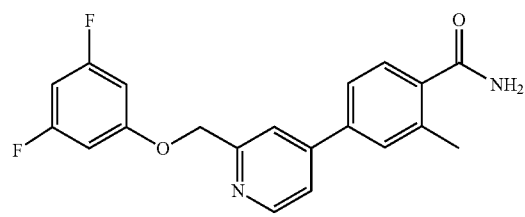 [SMILES: Cc1cc(-c2ccnc(COc3cc(F)cc(F)c3)c2)ccc1C(N)=O]

GM 5 was followed using 3,5-difluorophenol (20, 0.025 mmol) and 4-[2-(chloromethyl)pyridin-4-yl]-2-methylbenzamide hydrochloride (6e, 0.025 mmol). ESIMS=355 (M+H⁺, 100).

Example 86: 4-[2-(4-acetylphenoxymethyl)pyridin-4-yl]-2-methylbenzamide hydrochloride (86)

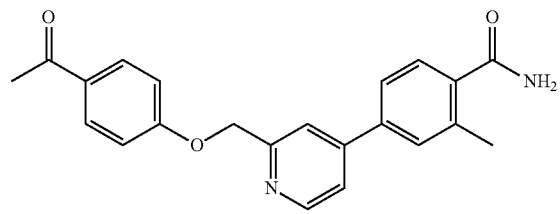 [SMILES: CC(=O)c1ccc(OCc2cc(-c3ccc(C(N)=O)c(C)c3)ccn2)cc1]

GM 5 was followed using 4-acetylphenol (2BX, 161 mg, 1.18 mmol) and 350 mg (1.18 mmol) of 4-[2-(chloromethyl)pyridin-4-yl]-2-methylbenzamide hydrochloride (6e, 350 mg, 1.18 mmol) in DMF (6 mL). Purified by silica-gel column chromatography eluting with a hexane/acetone gradient (10% to 100% acetone). The isolate was dissolved in hot MeOH (150 mL) and allowed to cool. Into this solution was added 1 M HCl in diethyl ether (2 mL). The solution was rotary evaporated, and the resulting solids were recrystallized from MeOH/water. Dried under vacuum to afford 4-[4-(4-acetylphenoxymethyl)pyridin-2-yl]-2-methylbenzamide hydrochloride (120 mg) as on off white powder. ESIMS=361 (M+H⁺, 100). ¹H NMR (DMSO-d₆) δ 8.66 (d, 1H), 7.95 (d, 1H), 7.87 (s, 1H), 7.78 (bs, 1H), 7.70 (m, 2H), 7.65 (d, 1H), 7.50 (d, 1H), 7.43 (bs, 1H), 7.19 (d, 2H), 5.35 (d, 2H), 3.32 (s, 3H), 2.46 (s, 3H).

Example 87: 4-(2-{[(1-methyl-1H-indazol-5-yl)oxy]methyl}pyridin-4-yl)-2-methyl-benzamide (87)

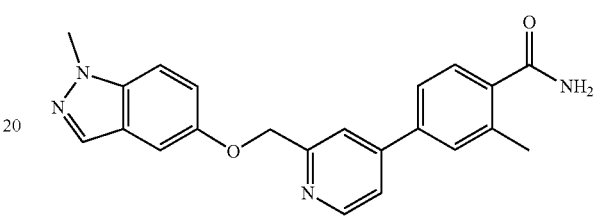

GM 5 was followed using 1-methyl-1H-indazol-5-ol (2BY, 0.025 mmol) and of 4-[2-(chloromethyl)pyridin-4-yl]-2-methylbenzamide hydrochloride (6e, 0.031 mmol). ESIMS=373 (M+H⁺, 100).

Example 88: 4-{2-[(2,3-dihydro-1-benzofuran-6-yloxy)methyl]pyridin-4-yl}-2-methylbenzamide (88)

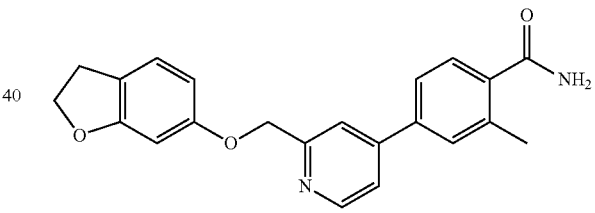

GM 5 was followed using 2,3-dihydro-1-benzofuran-6-ol (2BK, 0.025 mmol) and of 4-[2-(chloromethyl)pyridin-4-yl]-2-methylbenzamide hydrochloride (6e, 0.025 mmol). ESIMS=361 (M+H⁺, 100).

X. General Synthetic Scheme for the Preparation of Compounds of Formula (Ic)

Scheme 9

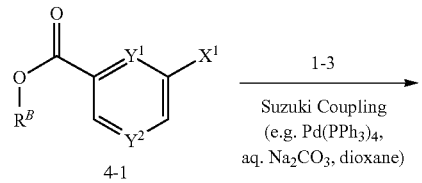

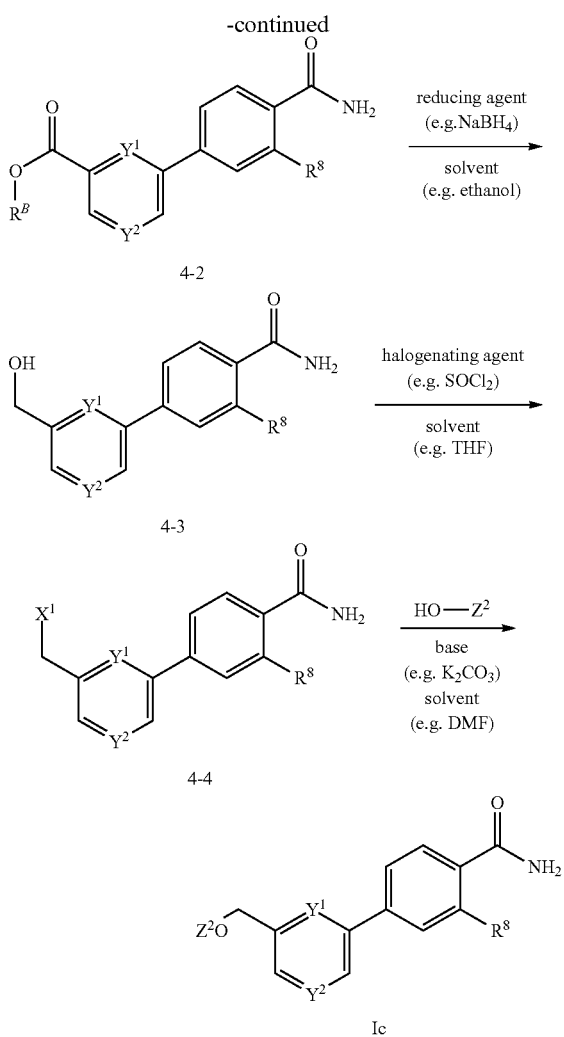

ride and NaI, p-toluenesulfonyl chloride and NaI, phosphorus tribromide, triphenylphosphine dibromide, phosphorus pentabromide or thionyl bromide, in a solvent, such as $CH_2Cl_2$, THF, dioxane or acetone and the like. Finally, compounds of general Formula 4-4 can be treated with HO—$Z^2$ in the presence of a base, such as $K_2CO_3$, $Na_2CO_3$, or $Cs_2CO_3$ in a solvent, such as DMF and the like to afford compounds of general Formula (I)c.

XI. General Synthetic Method for the Preparation of Compounds of Formula (Ic)

General Method (GM) 6: Preparation of Compound of General Formula 4-3

A compound of general Formula 4-2 in ethanol or methanol (50 mg/mL) is treated with $NaBH_4$ (10 eq.) in a flask with a reflux condenser. The resulting mixture is stirred for 2 hours to 24 hours (or until effervescence ceases) and then optionally carefully treated with water for larger scale reactions. The solvent is removed under reduced pressure and partitioned between EtOAc and water (when water is not used to quench the excess $NaBH_4$). The organic layer is washed with brine, dried over $MgSO_4$ and filtered to remove solid. The solvent is removed under reduced pressure and the isolate purified by silica gel column chromatography eluting with 5% MeOH in $CH_2Cl_2$. Alternatively, the solvents are removed under reduced pressure and water is added to the remainder and the aqueous mixture is extracted with EtOAc when water is used to quench the excess $NaBH_4$. The organic solvent is then evaporated under reduced pressure, and the remainder purified by silica gel column chromatography eluting with 5% MeOH in $CH_2Cl_2$.

XI. Preparation of Compounds of Formula (Ic): $R^8$ is $CH_3$, $Y^1$ is CH, $Y^2$ is N Example 89: 4-[5-(3-fluoro-4-methylphenoxymethyl)pyridin-3-yl]-2-methylbenzamide (89)

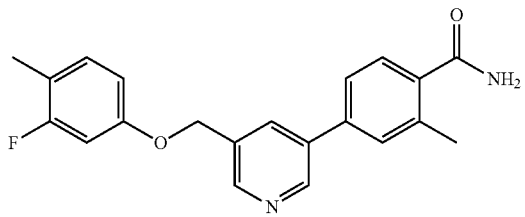 [SMILES: Cc1ccc(OCc2cncc(-c3ccc(C(N)=O)c(C)c3)c2)cc1F]

The title compound was prepared as shown in Scheme 10.

Scheme 10

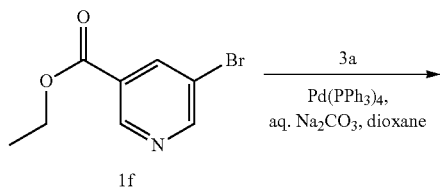

$X^1$ is halo (e.g. Cl or Br). The remaining variables are defined according to any of the embodiments described herein.

According to Scheme 9, compounds of general Formula (I)c can be synthesized in several steps from compounds of general Formula 4-1. In one instance, Suzuki coupling of compounds of general Formula 4-1, compounds of general Formula 1-3, in the presence of a palladium catalyst, such as $Pd(dppf)Cl_2 \cdot CH_2Cl_2$ or $Pd(PPh_3)_4$, and a base, such as $K_2CO_3$, $Na_2CO_3$, or $Cs_2CO_3$, in a solvent or solvent mixture, such as dioxane, THF and $CH_2Cl_2$ or toluene, water and dioxane, water and ethyl alcohol and the like provides compounds of general Formula 4-2. Preparation of compounds of general Formula 4-3 can be accomplished by treating compounds of general Formula 4-2 with a reducing agent, such as sodium borohydride, calcium borohydride, lithium borohydride, magnesium borohydride, potassium borohydride, tetrabutylammonium borohydride, tetraethylammonium borohydride, tetramethylammonium borohydride and the like, in a solvent or a solvent or solvent mixture, such as methanol, or ethanol and the like.

Preparation of compounds of general Formula 4-4 can be accomplished by treating compounds of general Formula 4-3 with a halogenating agent, such as thionyl chloride, oxalyl chloride, phosphorus oxychloride, phosphorus pentachloride, phosphorus trichloride, methanesulfonyl chlo- Step 2: Preparation of 4-[5-(hydroxymethyl)pyridin-3-yl]-2-methylbenzamide (3f)

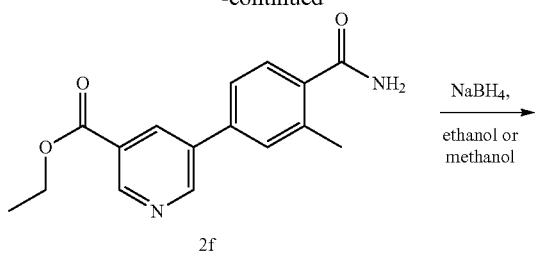

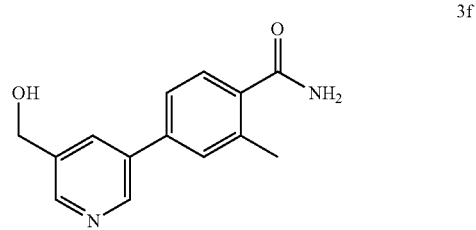

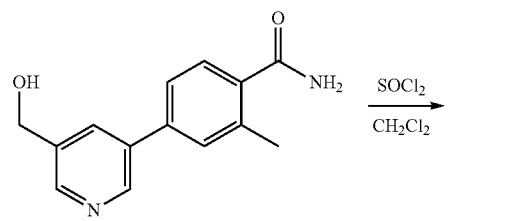

GM 6 was followed using ethyl 5-(4-carbamoyl-3-methylphenyl)pyridine-3-carboxylate (2f, 1.0 g, 3.52 mmol) and NaBH$_4$ (1.33 g, 35.17 mmol.) in MeOH (10 mL). After addition, an additional portion of MeOH (10 mL) was added, and the mixture was stirred under a condenser overnight. The mixture was carefully treated with water (10 mL) and stirred until effervescence stopped (24 h). The solvents were then removed under reduced pressure and water (400 mL) was added. The aqueous mixture was extracted with EtOAc (4×100 mL). The organic solvent was then removed under reduced pressure, and the remainder purified by silica gel column chromatography eluting with 5% MeOH in CH$_2$Cl$_2$. ESIMS 243 (M+H$^+$, 100).

Step 3: Preparation of 4-[5-(chloromethyl)pyridin-3-yl]-2-methylbenzamide hydrochloride (4f)

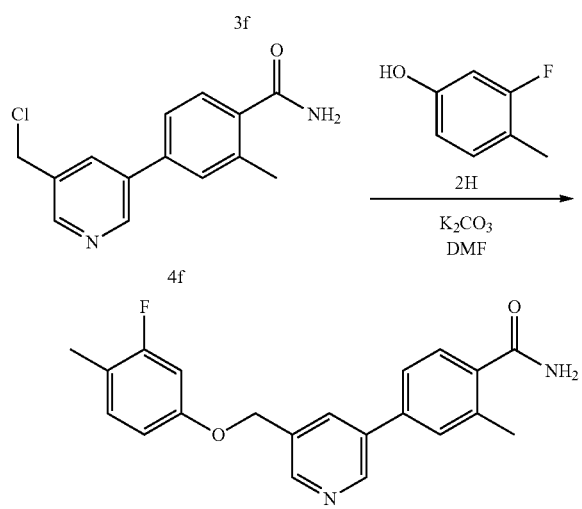

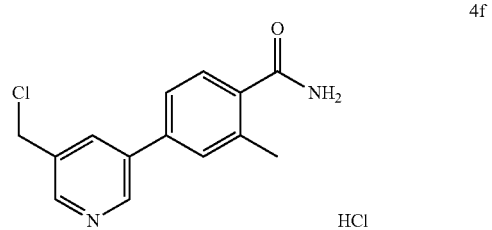 [SMILES: Cc1cc(-c2cncc(CCl)c2)ccc1C(N)=O ; Cl]

Step 1: Preparation of ethyl 5-(4-carbamoyl-3-methylphenyl)pyridine-3-carboxylate (2f)

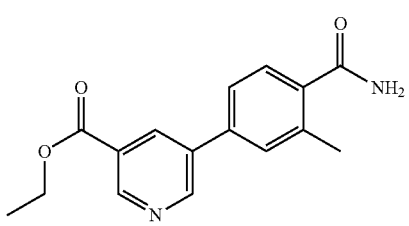

GM 2 was employed using ethyl 5-bromopyridine-3-carboxylate (1f, 2.53 g, 11.0 mmol.) and 2-methyl-4-(tetramethyl-1,3,2-dioxaborolan-2-yl)benzamide (3a, 3.11 g, 11.9 mmol.) in 1,4-dioxane (12 mL) and a 4 M aqueous solution of Na$_2$CO$_3$ (2 mL). The product was isolated by silica gel column chromatography eluting with EtOAc/hexane up to 100% EtOAc. ESIMS=285 (M+H$^+$, 100). $^1$H NMR (DMSO-d$_6$) δ 9.16 (s, 1H), 9.10 (s, 1H), 8.49 (m, 1H), 7.79 (bs, 1H), 7.70 (s, 1H), 7.66 (d, 1H), 7.52 (m, 1H), 7.43 (bs, 1H), 4.40 (q, 2H), 2.32 (s, 3H), 1.37 (t, 3H).

GM 4 was employed using 4-[5-(hydroxymethyl)pyridin-3-yl]-2-methylbenzamide (2f, 200 mg). The mixture was filtered and the collected solids were dried under vacuum to afford 4-[5-(chloromethyl)pyridin-3-yl]-2-methylbenzamide hydrochloride (4f, 212 mg). ESIMS=261 (M+H$^+$, 100).

Step 4: Preparation of 4-[5-(3-fluoro-4-methylphenoxymethyl)pyridin-3-yl]-2-methylbenzamide (89)

GM 5 was followed using 3-fluoro-4-methylphenol (2H, 0.025 mmol.) and 4-[5-(chloromethyl)pyridin-3-yl]-2-methylbenzamide (4f, 0.025 mmol.). ESIMS=351 (M+H$^+$, 100).

Example 90: 4-{5-[4-(trifluoromethyl)phenoxymethyl]pyridin-3-yl}-2-methylbenzamide (90)

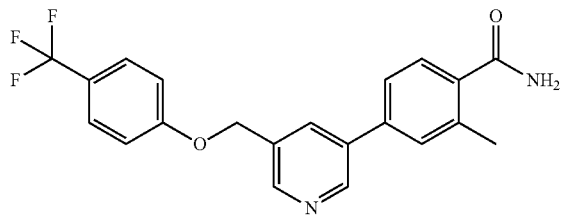 [SMILES: Cc1cc(-c2cncc(COc3ccc(C(F)(F)F)cc3)c2)ccc1C(N)=O]

GM 5 was followed using 4-(trifluoromethyl)phenol (2A, 0.025 mmol) and 4-[5-(chloromethyl)pyridin-3-yl]-2-methylbenzamide (4f, 0.025 mmol.). ESIMS=387 (M+H⁺, 100).

Example 91: 4-[5-(4-cyano-3-fluorophenoxymethyl) pyridin-3-yl]-2-methylbenzamide (91)

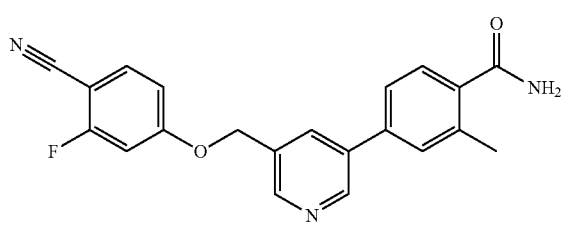 [SMILES: Cc1cc(-c2cncc(COc3ccc(C#N)c(F)c3)c2)ccc1C(N)=O]

GM 5 was followed using 4-cyano-3-fluorophenol (2D, 0.025 mmol) and 4-[5-(chloromethyl)pyridin-3-yl]-2-methylbenzamide (4f, 0.025 mmol.). ESIMS=362 (M+H⁺, 100).

Example 92: 4-[5-(3-cyano-5-fluorophenoxymethyl) pyridin-3-yl]-2-methylbenzamide (92)

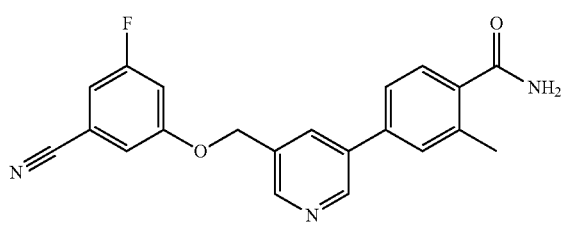 [SMILES: Cc1cc(-c2cncc(COc3cc(F)cc(C#N)c3)c2)ccc1C(N)=O]

GM 5 was followed using 3-cyano-4-fluorophenol (2G, 0.025 mmol) and 4-[5-(chloromethyl)pyridin-3-yl]-2-methylbenzamide (4f, 0.025 mmol.). ESIMS=362 (M+H⁺, 100).

Example 93: 4-[5-(3,5-difluorophenoxymethyl)pyridin-3-yl]-2-methylbenzamide (93)

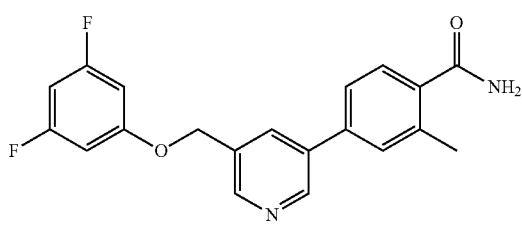 [SMILES: Cc1cc(-c2cncc(COc3cc(F)cc(F)c3)c2)ccc1C(N)=O]

GM 5 was followed using 3,5-difluorophenol (20, 0.025 mmol) and 4-[5-(chloromethyl)pyridin-3-yl]-2-methylbenzamide (4f, 0.025 mmol.). ESIMS=355 (M+H⁺, 100).

Example 94: 4-[5-(4-cyano-3-methoxyphenoxymethyl)pyridin-3-yl]-2-methylbenzamide (94)

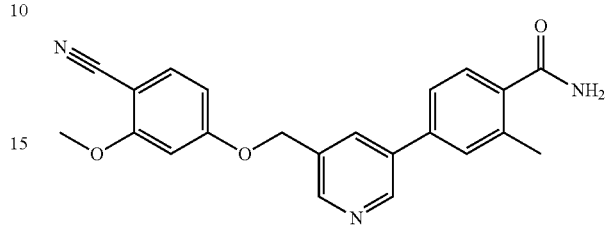

GM 5 was followed using 4-cyano-3-methoxyphenol (2BC, 0.025 mmol) and 4-[5-(chloromethyl)pyridin-3-yl]-2-methylbenzamide (4f, 0.025 mmol.). ESIMS=374 (M+H⁺, 100).

Example 95: 4-(5-{[(1-methyl-1H-indazol-6-yl)oxy]methyl}pyridin-3-yl)-2-methylbenzamide (95)

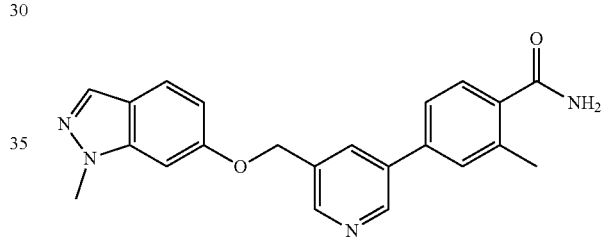

GM 5 was followed using 1-methyl-1H-indazol-6-ol (2BZ, 0.025 mmol) and 4-[5-(chloromethyl)pyridin-3-yl]-2-methylbenzamide (4f, 0.025 mmol.). ESIMS=374 (M+H⁺, 100).

Example 96: 4-[5-(3,4-dimethoxyphenoxymethyl) pyridin-3-yl]-2-methylbenzamide (96)

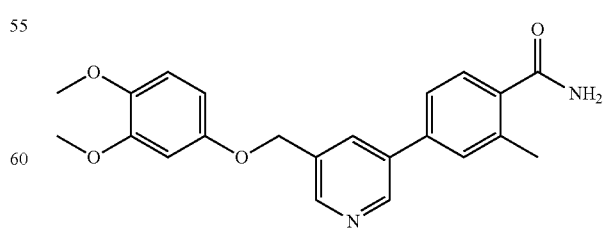

GM 5 was followed using 3,4-dimethoxyphenol (2Q, 0.025 mmol) and 4-[5-(chloromethyl)pyridin-3-yl]-2-methylbenzamide (4f, 0.025 mmol.). ESIMS=379 (M+H⁺, 100).

Example 97: 4-[5-(4-fluorophenoxymethyl)pyridin-3-yl]-2-methylbenzamide (97)

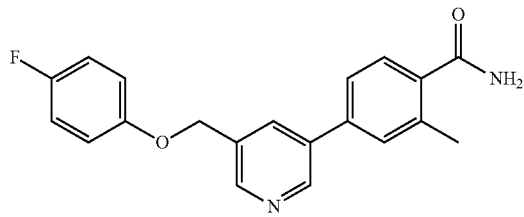 [SMILES: Cc1cc(-c2cncc(COc3ccc(F)cc3)c2)ccc1C(N)=O]

GM 5 was followed using 4-fluorophenol (2L, 0.025 mmol) and 4-[5-(chloromethyl)pyridin-3-yl]-2-methylbenzamide (4f, 0.025 mmol.). ESIMS=337 (M+H⁺, 100).

Example 98: 4-[5-(4-methoxyphenoxymethyl)pyridin-3-yl]-2-methylbenzamide (98)

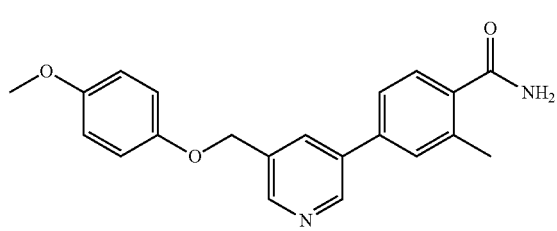 [SMILES: COc1ccc(OCc2cncc(-c3ccc(C(N)=O)c(C)c3)c2)cc1]

GM 5 was followed using 4-methoxyphenol (2AD, 0.025 mmol) and 4-[5-(chloromethyl)pyridin-3-yl]-2-methylbenzamide (4f, 0.025 mmol.). ESIMS=349 (M+H⁺, 100).

Example 99: 4-[5-(2-chloro-4-methoxyphenoxymethyl)pyridin-3-yl]-2-methylbenzamide (99)

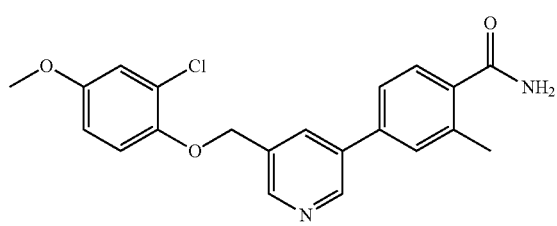 [SMILES: COc1ccc(OCc2cncc(-c3ccc(C(N)=O)c(C)c3)c2)c(Cl)c1]

GM 5 was followed using 2-chloro-4-methoxyphenol (2V, 0.025 mmol) and 4-[5-(chloromethyl)pyridin-3-yl]-2-methylbenzamide (4f, 0.025 mmol.). ESIMS=383 (M+H⁺, 100).

Example 100: 4-[5-(3,4,5-trifluorophenoxymethyl)pyridin-3-yl]2-methylbenzamide (100)

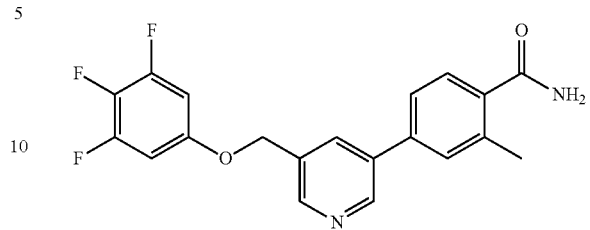

GM 5 was followed using 3,4,5-trifluorophenol (2BE, 0.025 mmol) and 4-[5-(chloromethyl)pyridin-3-yl]-2-methylbenzamide (4f, 0.025 mmol.). ESIMS=373 (M+H⁺, 100).

Example 101: 4-{5-[3-methoxy-4-(trifluoromethyl)phenoxymethyl]pyridin-3-yl}-2-methylbenzamide (101)

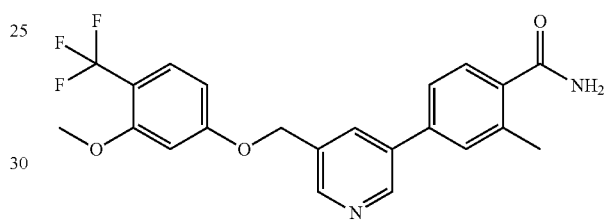

GM 5 was followed using 3-methoxy-4-(trifluoromethyl)phenol (2BF, 0.025 mmol) and 4-[5-(chloromethyl)pyridin-3-yl]-2-methylbenzamide (4f, 0.025 mmol.). ESIMS=417 (M+H⁺, 100).

XIII. Preparation of Compounds of Formula (Ic): R⁸ is CH₃, Y¹ is N, Y² is CH

Example 102: 4-{6-[3-(trifluoromethyl)phenoxymethyl]pyridin-2-yl}-2-methylbenzamide (102)

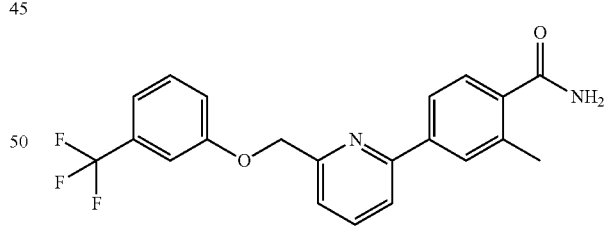

The title compound was prepared as shown in Scheme 11.

Scheme 11

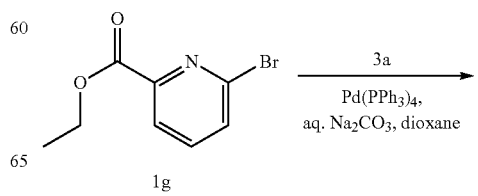

Step 2: Preparation of 4-[6-(hydroxymethyl)pyridin-2-yl]-2-methylbenzamide (3g)

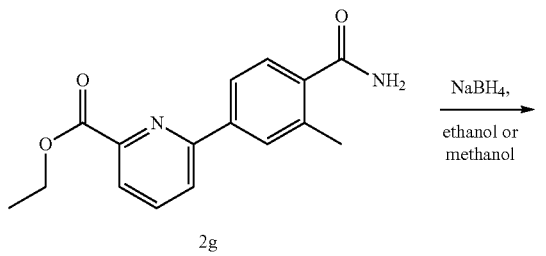

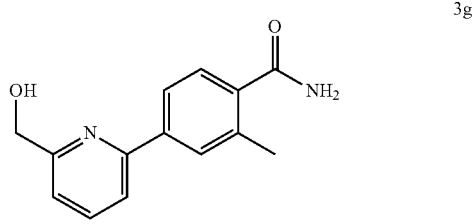 [SMILES: Cc1cc(-c2cccc(CO)n2)ccc1C(N)=O]

GM 6 was employed using ethyl 6-(4-carbamoyl-3-methylphenyl)pyridine-2-carboxylate (2 g, 359 mg, 1.26 mmol.) in MeOH (3 mL). ESIMS 243 (M+H+, 100).

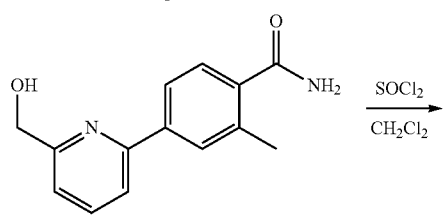

Step 3: Preparation of 4-[6-(chloromethyl)pyridin-2-yl]-2-methylbenzamide hydrochloride (4g)

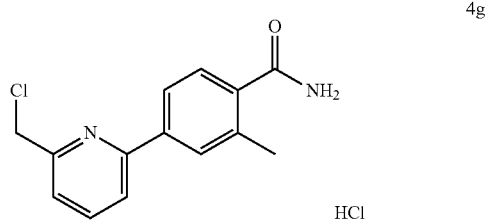 [SMILES: Cc1cc(-c2cccc(CCl)n2)ccc1C(N)=O ; Cl]

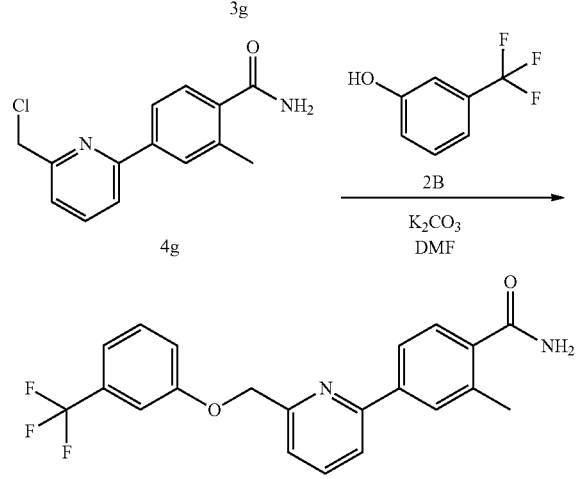

GM 4 was employed using 4-[6-(hydroxymethyl)pyridin-2-yl]-2-methylbenzamide (3 g, 200 mg). The mixture was filtered and the collected solids were dried under vacuum to afford 4-[6-(chloromethyl)pyridin-2-yl]-2-methylbenzamide hydrochloride (4 g, 215 mg). ESIMS=261 (M+H+, 100).

Step 1: Preparation of ethyl 6-(4-carbamoyl-3-methylphenyl)pyridine-2-carboxylate (2g)

Step 3: Preparation of 4-{6-[3-(trifluoromethyl)phenoxymethyl]pyridin-2-yl}-2-methylbenzamide (102)

GM 5 was followed using 3-(trifluoromethyl)phenol (2B, 0.025 mmol) and 4-[6-(chloromethyl)pyridin-2-yl]-2-methylbenzamide hydrochloride (4 g, 0.025 mmol). ESIMS=387 (M+H+, 100).

XIV. General Synthetic Scheme for the Preparation of Compounds of Formula (Id)

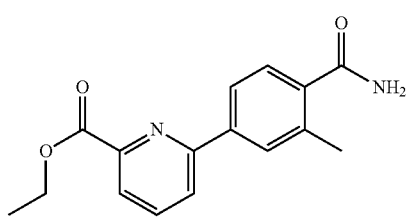

Scheme 12

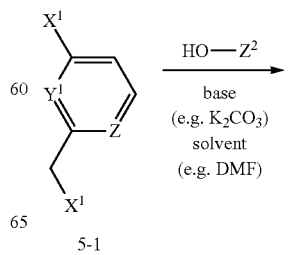

GM 2 was employed using ethyl 6-bromopyridine-2-carboxylate (1 g, 2.60 g, 11.30 mmol.) and 2-methyl-4-(tetramethyl-1,3,2-dioxaborolan-2-yl)benzamide (3a, 2.95 g, 11.30 mmol.) in 1,4-dioxane (12 mL) and a 4 M aqueous solution of Na2CO3 (2 mL). The resulting mixture was heated to 95° C., and cooled to rt. The title compound was isolated by silica gel column chromatography eluting with EtOAc/hexane up to 100% EtOAc. ESIMS=285 (M+H+, 100).

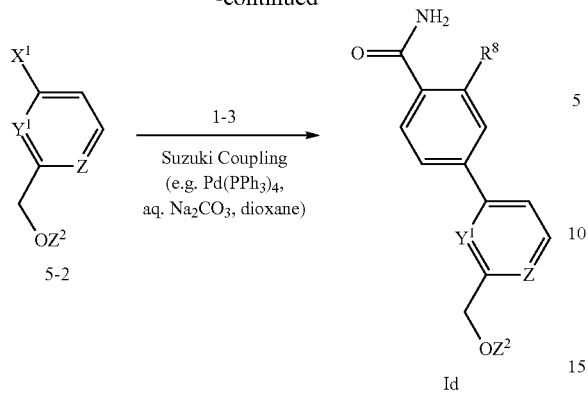

X¹ is halo (e.g. Cl or Br). The remaining variables are defined according to any of the embodiments described herein.

According to Scheme 12, compounds of general Formula (I)d can be synthesized in two steps from compounds of general Formula 5-1. In one instance, compounds of general Formula 5-1 can be treated with HO—$Z^2$ in the presence of a base, such as $K_2CO_3$, $Na_2CO_3$, or $Cs_2CO_3$ in a solvent, such as DMF and the like to afford compounds of general Formula 5-2. Finally, Suzuki coupling of compounds of general Formula 5-2, compounds of general Formula 1-3, in the presence of a palladium catalyst, such as Pd(dppf)Cl₂ CH₂Cl₂ or Pd(PPh₃)₄, and a base, such as $K_2CO_3$, $Na_2CO_3$, or $Cs_2CO_3$, in a solvent or solvent mixture, such as dioxane, THF and CH₂Cl₂ or toluene, water and dioxane, water and ethyl alcohol and the like provides compounds of general Formula (I)d.

XV. Preparation of Compounds of Formula (Id): $R^1$ is $CH_3$, $Y^1$ is N, Z is N Example 103: 4-[2-(4-cyano-3-fluorophenoxymethyl)pyrimidin-4-yl]-2-methylbenzamide (103)

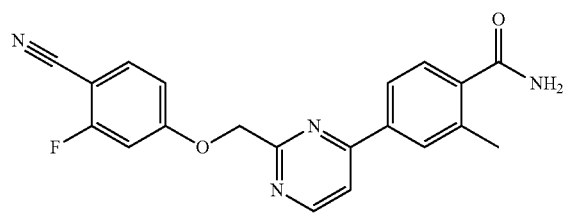 [SMILES: Cc1cc(-c2ccnc(COc3ccc(C#N)c(F)c3)n2)ccc1C(N)=O]

The title compound was prepared as shown in Scheme 13.

Scheme 13

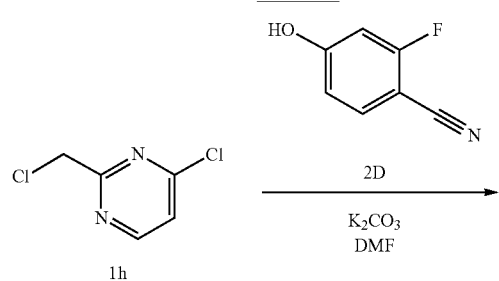

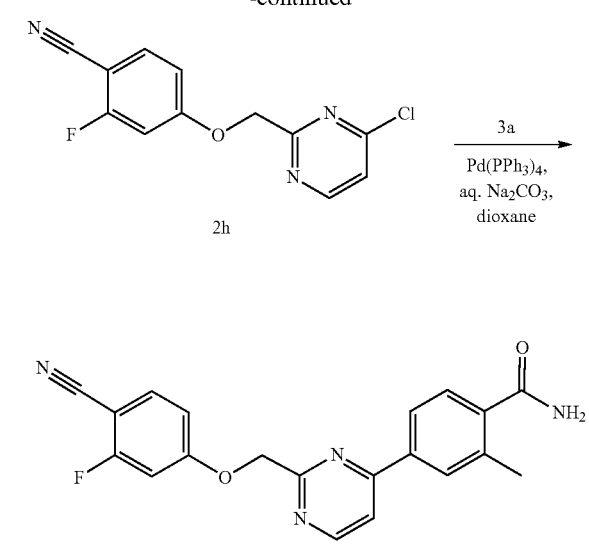

Step 1: Preparation of 4-[(4-chloropyrimidin-2-yl)methoxy]-2-fluorobenzonitrile (2h)

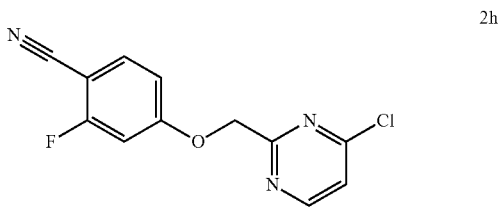 [SMILES: N#Cc1ccc(OCc2nccc(Cl)n2)cc1F]

GM 5 was followed using 4-chloro-2-(chloromethyl)pyrimidine (1h, 163 mg, 1.0 mmol) and 4-cyano-3-fluorophenol (2D, 131 mg, 0.95 mmol) at room temperature for 18 h. The product was purified by silica gel column chromatography eluting with a gradient of EtOAc/hexanes up to 60% EtOAc to afford 4-[(4-chloropyrimidin-2-yl)methoxy]-2-fluorobenzonitrile (2h, 156 mg, 61%) as a white solid. ESIMS=264 (M+H⁺, 100). ¹H NMR (CDCl₃) δ 8.65 (d, 1H), 7.52 (t, 1H), 7.35 (d, 1H), 6.87-6.80 (m, 1H), 5.31 (s, 2H).

Step 2: Preparation of 4-[2-(4-cyano-3-fluorophenoxymethyl)pyrimidin-4-yl]-2-methylbenzamide (103)

GM 2 was employed using 4-[(4-chloropyrimidin-2-yl)methoxy]-2-fluorobenzonitrile (2h, 21 mg, 0.08 mmol) and 2-methyl-4-(tetramethyl-1,3,2-dioxaborolan-2-yl)benzamide (3a, 0.096 mmol, 1.2 eq) in toluene (0.2 mL), EtOH (0.2 mL) and 4 M Na₂CO₃ (0.1 mL) in a sealed vial. The resulting mixture was heated to 95° C. overnight. The title compound was purified by HPLC. ESIMS=363 (M+H⁺, 100).

XVI. Preparation of Compound of Formula (Ia): HO—Z[1] is cyclohexanol, R[1] is CH$_3$, X is N, Y is CH Example 104: 4-{4-[(cyclohexyloxy)methyl]pyridin-2-yl}-2-methylbenzamide (104)

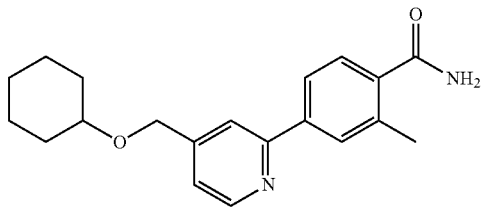 [SMILES: Cc1cc(-c2cc(COC3CCCCC3)ccn2)ccc1C(N)=O]

The title compound was prepared as shown in Scheme 14.

Scheme 14

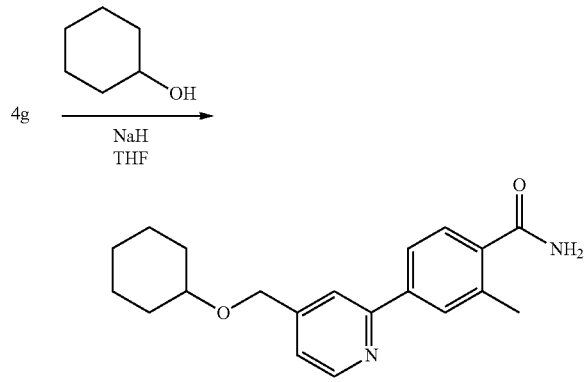

Preparation of 4-{4-[(cyclohexyloxy)methyl]pyridin-2-yl}-2-methylbenzamide (104)

In a round-bottom flask, anhydrous THF (200 μL, 0.5 M) was added to NaH (10 mg, 0.25 mmol, 2.5 eq, 60% dispersion in oil) and cooled to 0° C. The resulting mixture was treated with cyclohexanol (0.4 mmol, 4 eq) by dropwise addition. Once H$_2$ evolution ceased, the mixture was treated with 4-[4-(chloromethyl)pyridin-2-yl]-2-methylbenzamide hydrochloride (29 mg, 0.1 mmol) in one portion and the resulting mixture was heated to 75° C. After 18 h, the mixture was cooled to rt, diluted with dichloromethane (3 mL) and filtered. The filtrate was purified by silica gel column chromatography eluting with a gradient of EtOAc in hexane (up to 100% EtOAc) to afford an isolate that was then purified by HPLC. ESIMS=325 (M+H$^+$, 100).

Example 105: GPR52 Activity

TR-FRET cAMP assays were performed using commercially available assay kits (LANCE™ Ultra cAMP Kit). Controls and compounds were solubilized in DMSO using ½ log dilution to generate duplicate 10-point dose response curves in 384-well polypropylene compound plates. Sixty nanoliters of the diluted compounds were transferred into 384-well NBS assay plates and further diluted to 1× with the addition of 2000 cells per well. Flp-In™—CHO cells that stably express recombinant human GPR52.

Cells were harvested with cell stripper and resuspended in Stimulation Buffer (5 mM HEPES, 0.1% bovine serum albumin (BSA), 0.5 mM IBMX, pH 7.4). After thirty minutes incubation at room temperature, detection reagents were added to each well. Plates were then incubated for 30 minutes at room temperature. The LANCE™ Ultra cAMP assay uses time-resolved fluorescence resonance energy transfer (TR-FRET) to detect cAMVP production; this signal was quantified using a Pherastar multi-mode plate reader.

Dose-response curves were generated from the fluorescence counts normalized to the positive control. E EC$_{50}$ values were obtained using a nonlinear regression curve-fitting program. Table 2 provides EC$_{50}$ values where A is <25 nM; B is 25-100 nM; C is 101-1000 nM; and D is >1000 nM.

TABLE 2

| No. | Chemical Structure | Chemical Name | EC$_{50}$ |
|---|---|---|---|
| 1 | 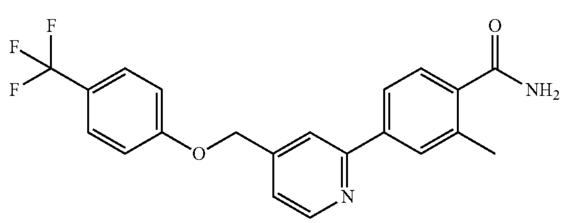 [SMILES: Cc1cc(-c2cc(COc3ccc(C(F)(F)F)cc3)ccn2)ccc1C(N)=O] | 4-{4-[4-(trifluoromethyl)phenoxymethyl]pyridin-2-yl}2-methyl-benzamide | B |
| 2 | 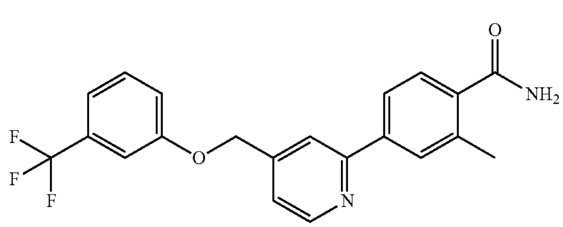 [SMILES: Cc1cc(-c2cc(COc3cccc(C(F)(F)F)c3)ccn2)ccc1C(N)=O] | 4-{4-[3-(trifluoromethyl)phenoxymethyl]pyridin-2-yl}-2-methyl benzamide | A |

TABLE 2-continued

| No. | Chemical Structure | Chemical Name | EC$_{50}$ |
|---|---|---|---|
| 3 | 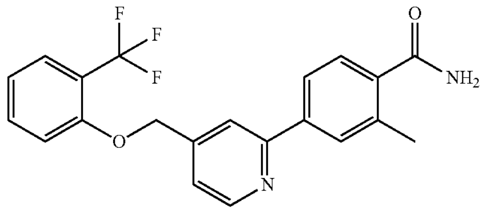 [SMILES: Cc1cc(-c2cc(COc3ccccc3C(F)(F)F)ccn2)ccc1C(N)=O] | 4-{4-[2-(trifluoromethyl)phenoxymethyl]pyridin-2-yl}-2-methyl benzamide | C |
| 4 | 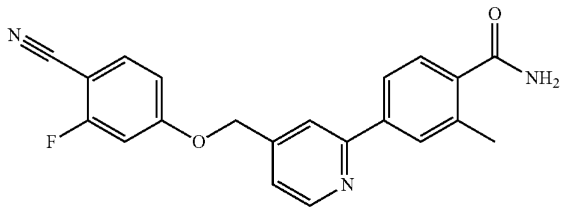 [SMILES: Cc1cc(-c2cc(COc3ccc(C#N)c(F)c3)ccn2)ccc1C(N)=O] | 4-[4-(4-cyano-3-fluorophenoxymethyl)pyridin-2-yl]-2-methylbenzamide | B |
| 5 | 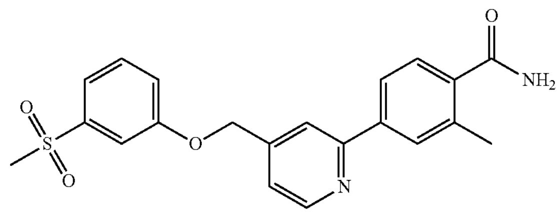 [SMILES: Cc1cc(-c2cc(COc3cccc(S(C)(=O)=O)c3)ccn2)ccc1C(N)=O] | 4-[4-(3-methanesulfonylphenoxymethyl)pyridin-2-yl]-2-methylbenzamide | C |
| 6 | 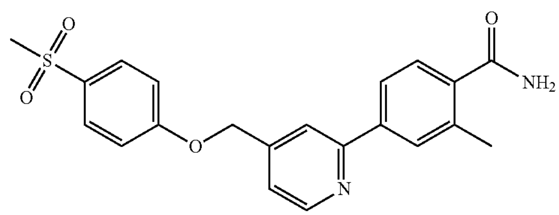 [SMILES: Cc1cc(-c2cc(COc3ccc(S(C)(=O)=O)cc3)ccn2)ccc1C(N)=O] | 4-[4-(4-methanesulfonylphenoxymethyl)pyridin-2-yl]-2-methylbenzamide | C |
| 7 | 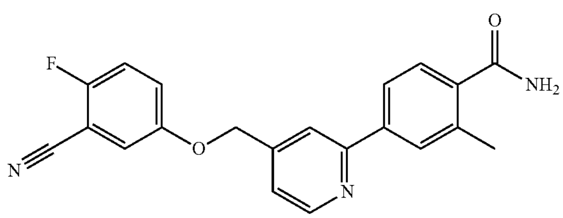 | 4-[4-(3-cyano-4-fluorophenoxymethyl)pyridin-2-yl]-2-methylbenzamide | C |
| 8 | 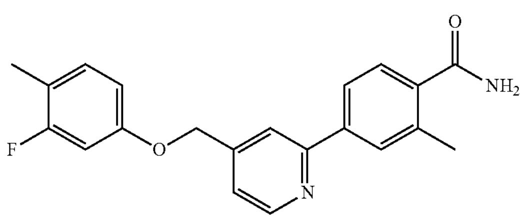 | 4-[4-(3-fluoro-4-methylphenoxymethyl)pyridin-2-yl]-2-methylbenzamide | C |
| 9 | 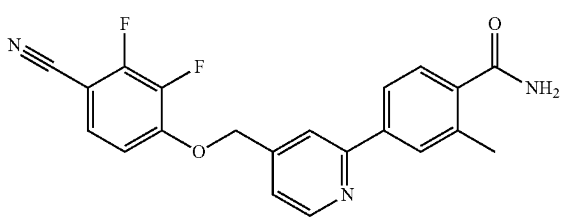 [SMILES: Cc1cc(-c2cc(COc3ccc(C#N)c(F)c3F)ccn2)ccc1C(N)=O] | 4-[4-(4-cyano-2,3-difluorophenoxymethyl)pyridin-2-yl]-2-methylbenzamide | C |

TABLE 2-continued

| No. | Chemical Structure | Chemical Name | EC$_{50}$ |
|---|---|---|---|
| 10 | 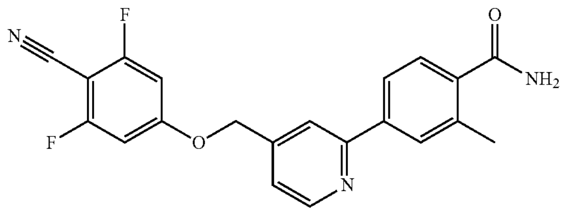 [SMILES: Cc1cc(-c2cc(COc3cc(F)c(C#N)c(F)c3)ccn2)ccc1C(N)=O] | 4-[4-(4-cyano-3,5-difluorophenoxymethyl)pyridin-2-yl]-2-methylbenzamide | B |
| 11 | 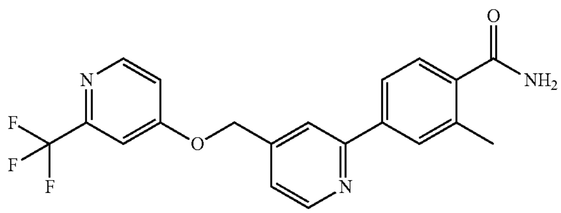 [SMILES: Cc1cc(-c2cc(COc3ccnc(C(F)(F)F)c3)ccn2)ccc1C(N)=O] | 4-[4-({[2-(trifluoromethyl)pyridin-4-yl]oxy}methyl)pyridin-2-yl]-2-methyl | C |
| 12 | 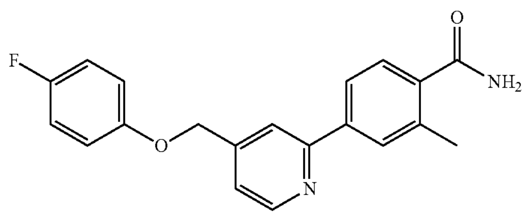 [SMILES: Cc1cc(-c2cc(COc3ccc(F)cc3)ccn2)ccc1C(N)=O] | 4-[4-(4-fluorophenoxymethyl)pyridin-2-yl]-2-methylbenzamide | B |
| 13 | 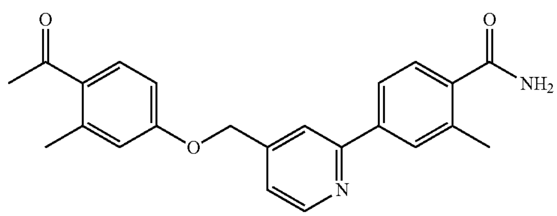 [SMILES: CC(=O)c1ccc(OCc2ccnc(-c3ccc(C(N)=O)c(C)c3)c2)cc1C] | 4-[4-(4-acetyl-3-methylphenoxymethyl)pyridin-2-yl]-2-methylbenzamide | A |
| 14 | 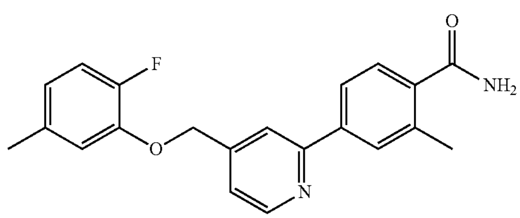 [SMILES: Cc1ccc(F)c(OCc2ccnc(-c3ccc(C(N)=O)c(C)c3)c2)c1] | 4-[4-(2-fluoro-5-methylphenoxymethyl)pyridin-2-yl]-2-methylbenzamide | C |
| 15 | 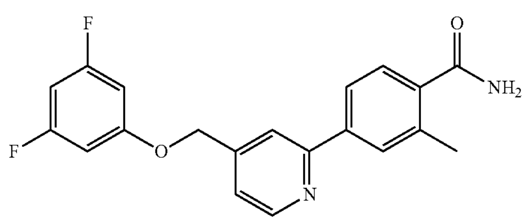 [SMILES: Cc1cc(-c2cc(COc3cc(F)cc(F)c3)ccn2)ccc1C(N)=O] | 4-[4-(3,5-difluorophenoxymethyl)pyridin-2-yl]-2-methylbenzamide | B |
| 16 | 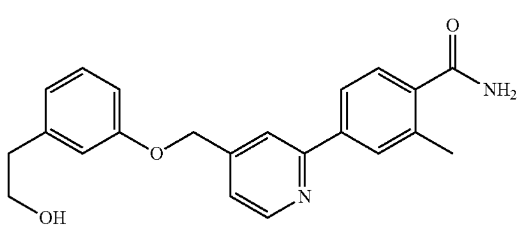 [SMILES: Cc1cc(-c2cc(COc3cccc(CCO)c3)ccn2)ccc1C(N)=O] | 4-{4-[3-(2-hydroxyethyl)phenoxymethyl]pyridin-2-yl}-2-methylbenzamide | C |

TABLE 2-continued

| No. | Chemical Structure | Chemical Name | EC$_{50}$ |
|---|---|---|---|
| 17 | 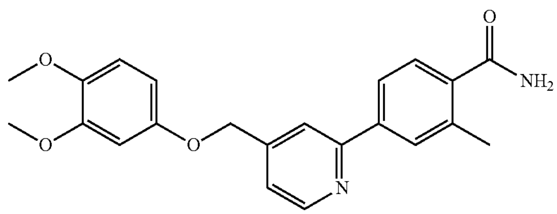 [SMILES: COc1ccc(OCc2ccnc(-c3ccc(C(N)=O)c(C)c3)c2)cc1OC] | 4-[4-(3,4-dimethoxyphenoxymethyl)pyridin-2-yl]-2-methylbenzamide | C |
| 18 | 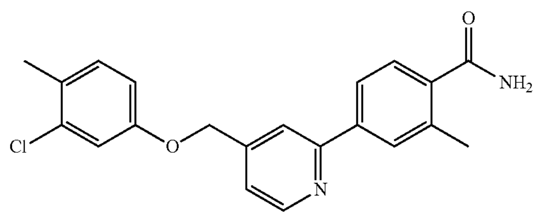 [SMILES: Cc1ccc(OCc2ccnc(-c3ccc(C(N)=O)c(C)c3)c2)cc1Cl] | 4-[4-(3-chloro-4-methylphenoxymethyl)pyridin-2-yl]-2-methylbenzamide | A |
| 19 | 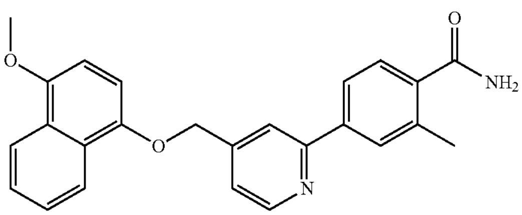 [SMILES: COc1ccc(OCc2ccnc(-c3ccc(C(N)=O)c(C)c3)c2)c2ccccc12] | 4-(4-{[(4-methoxynaphthalen-1-yl)oxy]methyl}pyridin-2-yl)-2-methylbenzamide | C |
| 20 | 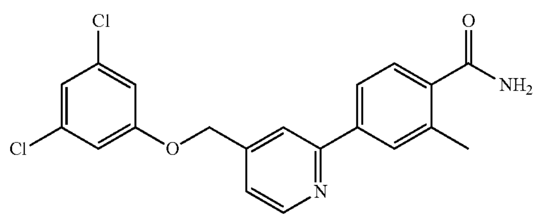 [SMILES: Cc1cc(-c2cc(COc3cc(Cl)cc(Cl)c3)ccn2)ccc1C(N)=O] | 4-[4-(3,5-dichlorophenoxymethyl)pyridin-2-yl]-2-methylbenzamide | A |
| 21 | 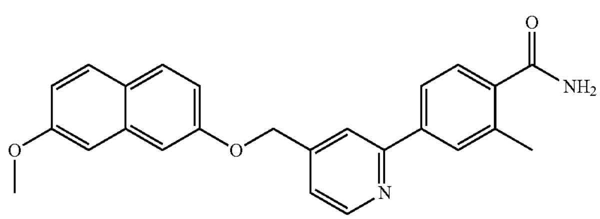 [SMILES: COc1ccc2ccc(OCc3ccnc(-c4ccc(C(N)=O)c(C)c4)c3)cc2c1] | 4-(4-{[(7-methoxynaphthalen-2-yl)oxy]methyl}pyridin-2-yl)-2-methylbenzamide | B |
| 22 | 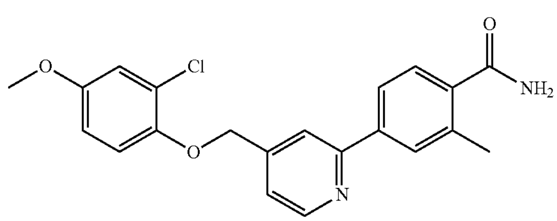 [SMILES: COc1ccc(OCc2ccnc(-c3ccc(C(N)=O)c(C)c3)c2)c(Cl)c1] | 4-[4-(2-chloro-4-methoxyphenoxymethyl)pyridin-2-yl]-2-methylbenzamide | A |
| 23 | 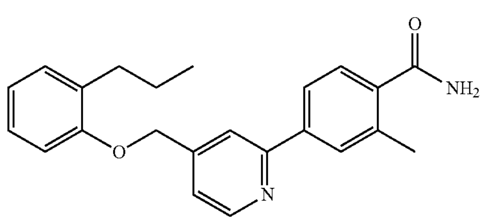 [SMILES: CCCc1ccccc1OCc1ccnc(-c2ccc(C(N)=O)c(C)c2)c1] | 4-[4-(2-propylphenoxymethyl)pyridin-2-yl]-2-methyl benzamide | A |

TABLE 2-continued

| No. | Chemical Structure | Chemical Name | EC$_{50}$ |
|-----|---|---|---|
| 24 | 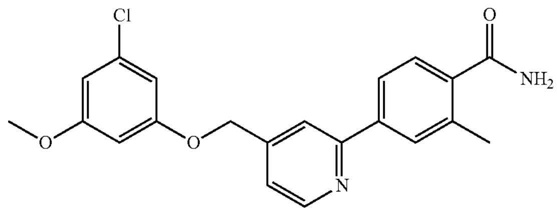 [SMILES: COc1cc(Cl)cc(OCc2ccnc(-c3ccc(C(N)=O)c(C)c3)c2)c1] | 4-[4-(3-chloro-5-methoxyphenoxymethyl)pyridin-2-yl]-2-methylbenzamide | B |
| 25 | 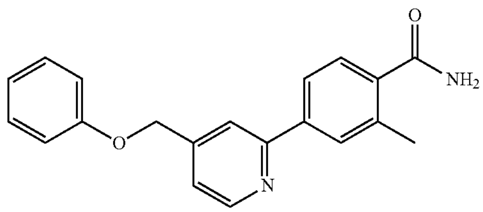 [SMILES: Cc1cc(-c2cc(COc3ccccc3)ccn2)ccc1C(N)=O] | 4-[4-(phenoxymethyl)pyridin-2-yl]-2-methylbenzamide | C |
| 26 | 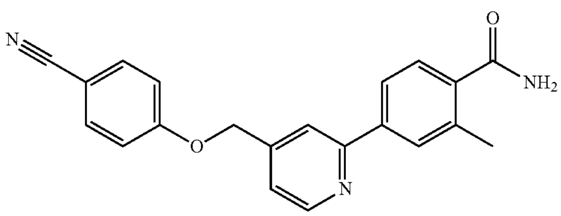 [SMILES: Cc1cc(-c2cc(COc3ccc(C#N)cc3)ccn2)ccc1C(N)=O] | 4-[4-(4-cyanophenoxymethyl)pyridin-2-yl]-2-methylbenzamide | B |
| 27 | 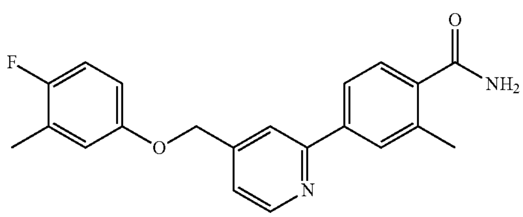 | 4-[4-(4-fluoro-3-methylphenoxymethyl)pyridin-2-yl]-2-methylbenzamide | C |
| 28 | 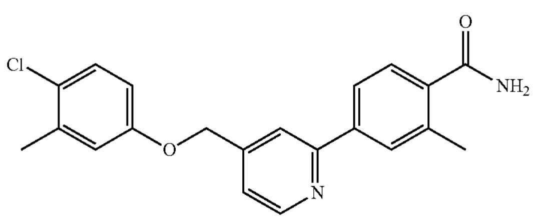 [SMILES: Cc1cc(OCc2ccnc(-c3ccc(C(N)=O)c(C)c3)c2)ccc1Cl] | 4-[4-(4-chloro-3-methylphenoxymethyl)pyridin-2-yl]-2-methylbenzamide | C |
| 29 | 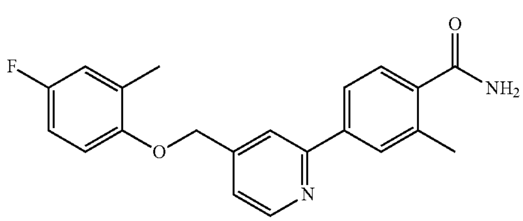 | 4-[4-(4-fluoro-2-methylphenoxymethyl)pyridin-2-yl]-2-methylbenzamide | C |
| 30 | 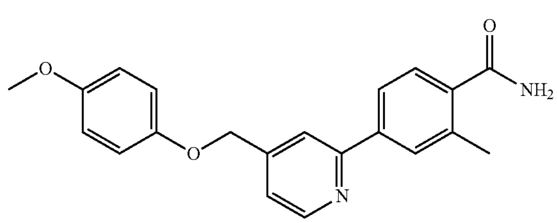 [SMILES: COc1ccc(OCc2ccnc(-c3ccc(C(N)=O)c(C)c3)c2)cc1] | 4-[4-(4-methoxyphenoxymethyl)pyridin-2-yl]-2-methylbenzamide | C |

TABLE 2-continued

| No. | Chemical Name | EC$_{50}$ |
|---|---|---|
| 31 | 4-(4-{[(1-oxo-2,3-dihydro-1H-inden-4-yl)oxy]methyl}pyridin-2-yl)-2-methylbenzamide | C |
| 32 | 4-[4-(2-ethylphenoxymethyl)pyridin-2-yl]-2-methylbenzamide | C |
| 33 | 4-[4-(4-nitrophenoxymethyl)pyridin-2-yl]-2-methylbenzamide | A |
| 34 | 4-[4-(4-chloro-3-fluorophenoxymethyl)pyridin-2-yl]-2-methylbenzamide | C |
| 35 | 4-[4-(3-acetamidophenoxymethyl)pyridin-2-yl]-2-methylbenzamide | C |
| 36 | 4-[4-(4-methylphenoxymethyl)pyridin-2-yl]-2-methylbenzamide | C |
| 37 | 4-{4-[4-(methylsulfanyl)phenoxymethyl]pyridin-2-yl}-2-methyl benzamide | B |

TABLE 2-continued

| No. | Chemical Structure | Chemical Name | EC$_{50}$ |
|---|---|---|---|
| 38 | 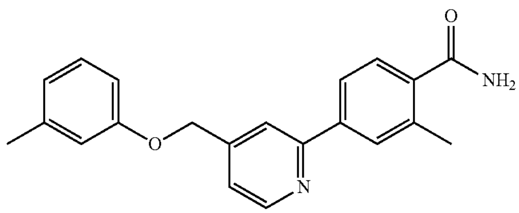 [SMILES: Cc1cccc(OCc2ccnc(-c3ccc(C(N)=O)c(C)c3)c2)c1] | 4-[4-(3-methylphenoxymethyl)pyridin-2-yl]-2-methyl benzamide | B |
| 39 | 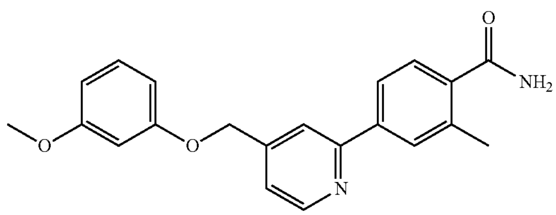 [SMILES: COc1cccc(OCc2ccnc(-c3ccc(C(N)=O)c(C)c3)c2)c1] | 4-[4-(3-methoxyphenoxymethyl)pyridin-2-yl]-2-methylbenzamide | C |
| 40 | 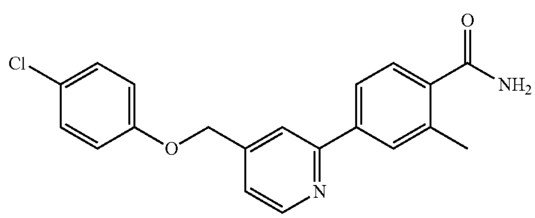 [SMILES: Cc1cc(-c2cc(COc3ccc(Cl)cc3)ccn2)ccc1C(N)=O] | 4-[4-(4-chlorophenoxymethyl)pyridin-2-yl]-2-methylbenzamide | D |
| 41 | 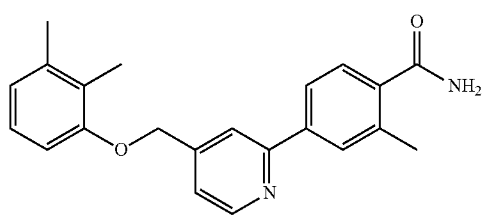 | 4-[4-(2,3-dimethylphenoxymethyl)pyridin-2-yl]-2-methylbenzamide | C |
| 42 | 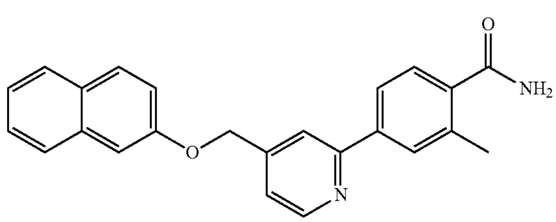 [SMILES: Cc1cc(-c2cc(COc3ccc4ccccc4c3)ccn2)ccc1C(N)=O] | 4-{4-[(naphthalen-2-yloxy)methyl]pyridin-2-yl}-2-methylbenzamide | B |
| 43 | 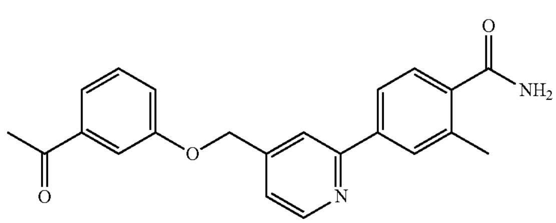 [SMILES: CC(=O)c1cccc(OCc2ccnc(-c3ccc(C(N)=O)c(C)c3)c2)c1] | 4-[4-(3-acetylphenoxymethyl)pyridin-2-yl]-2-methylbenzamide | C |
| 44 | 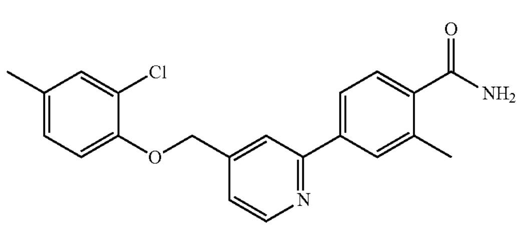 [SMILES: Cc1ccc(OCc2ccnc(-c3ccc(C(N)=O)c(C)c3)c2)c(Cl)c1] | 4-[4-(2-chloro-4-methylphenoxymethyl)pyridin-2-yl]-2-methylbenzamide | A |

TABLE 2-continued

| No. | Chemical Name | EC$_{50}$ |
|---|---|---|
| 45 | 4-[4-(2-chloro-4-fluorophenoxymethyl)pyridin-2-yl]-2-methylbenzamide | C |
| 46 | 4-[4-(2-methylphenoxymethyl)pyridin-2-yl]-2-methylbenzamide | C |
| 47 | 4-[4-(3-chloro-4-fluorophenoxymethyl)pyridin-2-yl]-2-methylbenzamide | A |
| 48 | 4-[4-(3,4-difluorophenoxymethyl)pyridin-2-yl]-2-methylbenzamide | A |
| 49 | 4-[4-(4-chloro-3-cyanophenoxymethyl)pyridin-2-yl]-2-methylbenzamide | B |
| 50 | 4-[4-(3-chloro-2-fluorophenoxymethyl)pyridin-2-yl]-2-methylbenzamide | B |
| 51 | 4-[4-(4-chloro-2-methoxyphenoxymethyl)pyridin-2-yl]-2-methylbenzamide | B |

TABLE 2-continued

| No. | Chemical Structure | Chemical Name | EC$_{50}$ |
|---|---|---|---|
| 52 | 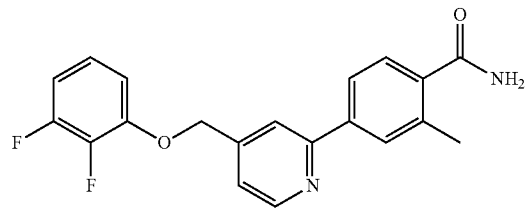 [SMILES: Cc1cc(-c2cc(COc3cccc(F)c3F)ccn2)ccc1C(N)=O] | 4-[4-(2,3-difluorophenoxymethyl)pyridin-2-yl]-2-methylbenzamide | B |
| 53 | 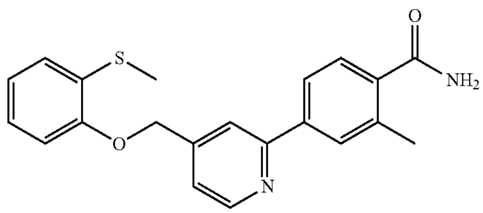 | 4-{4-[2-(methylsulfanyl)phenoxymethyl]pyridin-2-yl}-2-methyl benzamide | B |
| 54 | 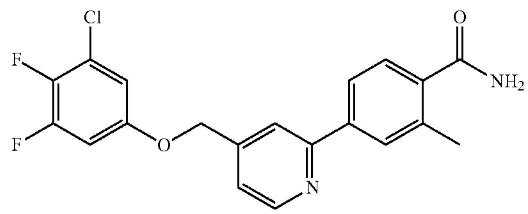 | 4-[4-(3-chloro-4,5-difluorophenoxymethyl)pyridin-2-yl]-2-methylbenzamide | A |
| 55 | 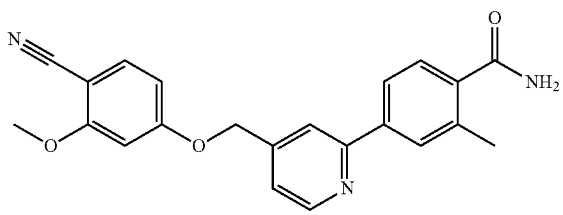 [SMILES: COc1cc(OCc2ccnc(-c3ccc(C(N)=O)c(C)c3)c2)ccc1C#N] | 4-[4-(4-cyano-3-methoxyphenoxymethyl)pyridin-2-yl]-2-methylbenzamide | A |
| 56 | 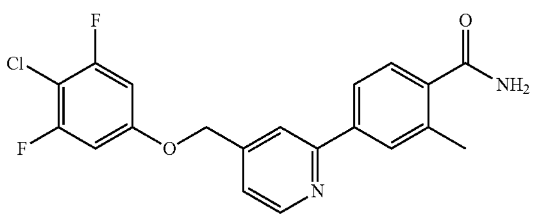 [SMILES: Cc1cc(-c2cc(COc3cc(F)c(Cl)c(F)c3)ccn2)ccc1C(N)=O] | 4-[4-(4-chloro-3,5-difluorophenoxymethyl)pyridin-2-yl]-2-methylbenzamide | A |
| 57 | 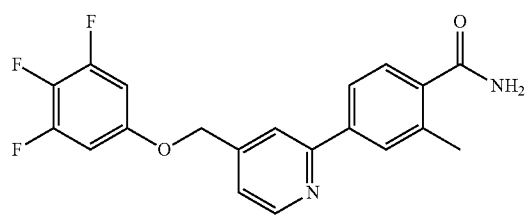 | 4-[4-(3,4,5-trifluorophenoxymethyl)pyridin-2-yl]-2-methyl benzamide | A |
| 58 | 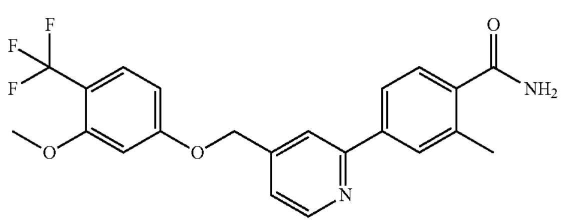 [SMILES: COc1cc(OCc2ccnc(-c3ccc(C(N)=O)c(C)c3)c2)ccc1C(F)(F)F] | 4-{4-[3-methoxy-4-(trifluoromethyl)phenoxymethyl]pyridin-2-yl}-2-methylbenzamide | B |

TABLE 2-continued

| No. | Chemical Structure | Chemical Name | EC$_{50}$ |
|---|---|---|---|
| 59 | 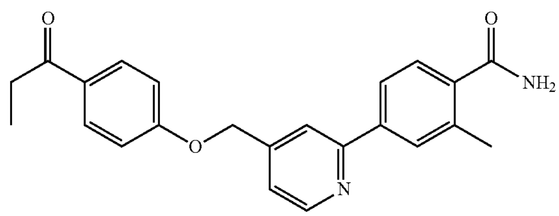 [SMILES: CCC(=O)c1ccc(OCc2ccnc(-c3ccc(C(N)=O)c(C)c3)c2)cc1] | 4-[4-(4-propanoylphenoxymethyl)pyridin-2-yl]-2-methylbenzamide | C |
| 60 | 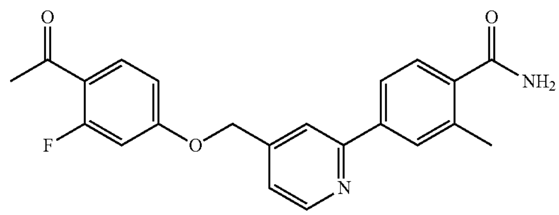 | 4-[4-(4-acetyl-3-fluorophenoxymethyl)pyridin-2-yl]-2-methylbenzamide | A |
| 61 | 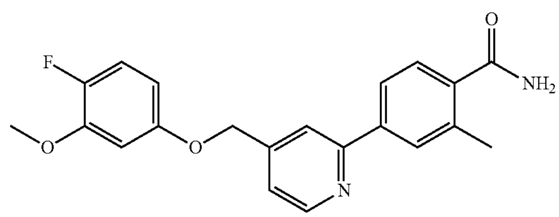 [SMILES: COc1cc(OCc2ccnc(-c3ccc(C(N)=O)c(C)c3)c2)ccc1F] | 4-[4-(4-fluoro-3-methoxyphenoxymethyl)pyridin-2-yl]-2-methylbenzamide | A |
| 62 | 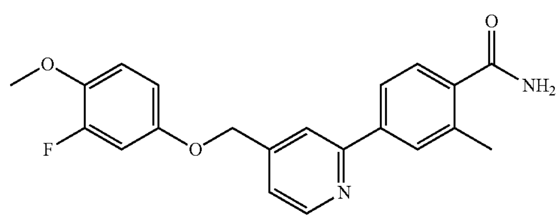 [SMILES: COc1ccc(OCc2ccnc(-c3ccc(C(N)=O)c(C)c3)c2)cc1F] | 4-[4-(3-fluoro-4-methoxyphenoxymethyl)pyridin-2-yl]-2-methylbenzamide | A |
| 63 | 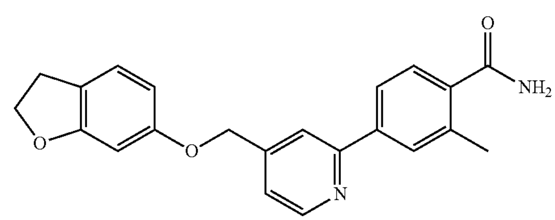 [SMILES: Cc1cc(-c2cc(COc3ccc4c(c3)OCC4)ccn2)ccc1C(N)=O] | 4-{4-[(2,3-dihydro-1-benzofuran-6-yloxy)methyl]pyridin-2-yl}-2-methylbenzamide | C |
| 64 | 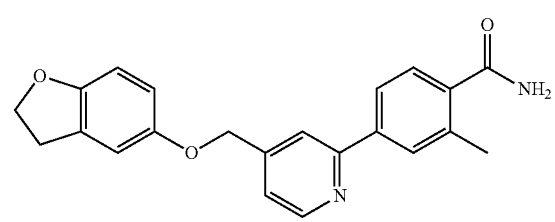 [SMILES: Cc1cc(-c2cc(COc3ccc4c(c3)CCO4)ccn2)ccc1C(N)=O] | 4-{4-[(2,3-dihydro-1-benzofuran-5-yloxy)methyl]pyridin-2-yl}-2-methylbenzamide | A |
| 65 | 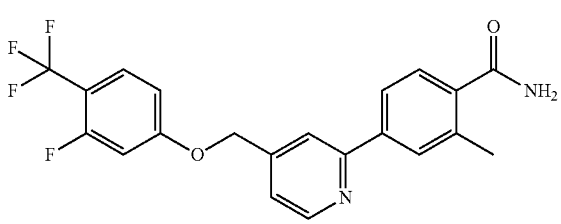 [SMILES: Cc1cc(-c2cc(COc3ccc(C(F)(F)F)c(F)c3)ccn2)ccc1C(N)=O] | 4-{4-[3-fluoro-4-(trifluoromethyl)phenoxymethyl]pyridin-2-yl}-2-methylbenzamide | A |

TABLE 2-continued

| No. | Chemical Structure | Chemical Name | $EC_{50}$ |
|---|---|---|---|
| 66 | 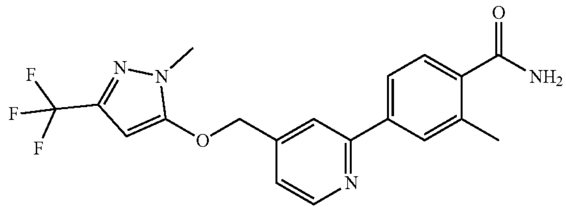 [SMILES: Cc1cc(-c2cc(COc3cc(C(F)(F)F)nn3C)ccn2)ccc1C(N)=O] | 4-[4-({[1-methyl-3-(trifluoromethyl)-1H-pyrazol-5-yl]oxy}methyl)pyridin-2-yl]2-methylbenzamide | B |
| 67 | 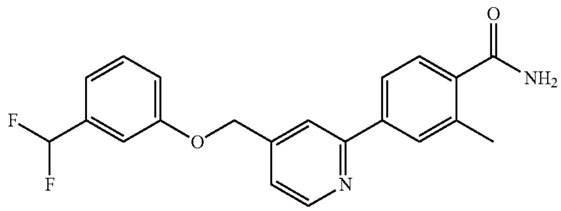 [SMILES: Cc1cc(-c2cc(COc3cccc(C(F)F)c3)ccn2)ccc1C(N)=O] | 4-{4-[3-(difluoromethyl)phenoxymethyl]pyridin-2-yl}-2-methylbenzamide | A |
| 68 | 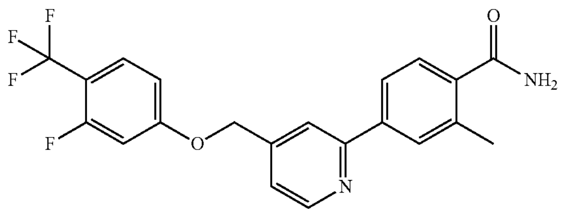 [SMILES: Cc1cc(-c2cc(COc3ccc(C(F)(F)F)c(F)c3)ccn2)ccc1C(N)=O] | 4-{4-[3-chloro-4-(trifluoromethyl)phenoxymethyl]pyridin-2-yl}-2-methylbenzamide | A |
| 69 | 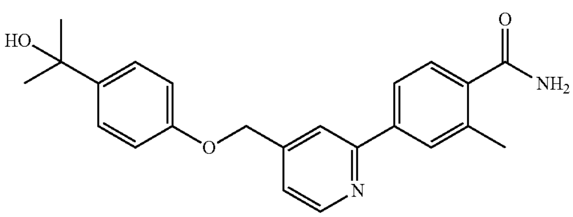 [SMILES: Cc1cc(-c2cc(COc3ccc(C(C)(C)O)cc3)ccn2)ccc1C(N)=O] | 4-{4-[4-(2-hydroxypropan-2-yl)phenoxymethyl]pyridin-2-yl}-2-methylbenzamide | B |
| 70 | 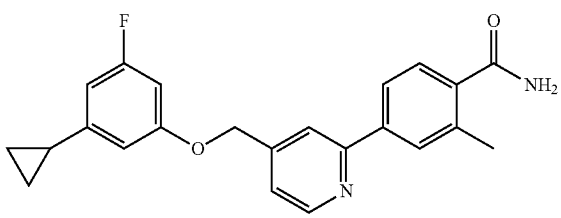 [SMILES: Cc1cc(-c2cc(COc3cc(F)cc(C4CC4)c3)ccn2)ccc1C(N)=O] | 4-[4-(3-cyclopropyl-5-fluorophenoxymethyl)pyridin-2-yl]-2-methylbenzamide | A |
| 71 | 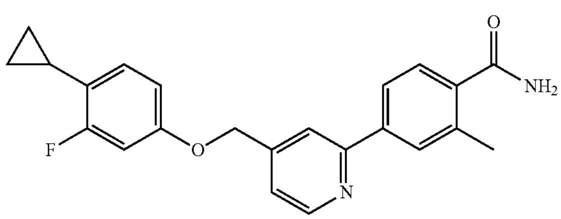 [SMILES: Cc1cc(-c2cc(COc3ccc(C4CC4)c(F)c3)ccn2)ccc1C(N)=O] | 4-[4-(4-cyclopropyl-3-fluorophenoxymethyl)pyridin-2-yl]-2-methylbenzamide | A |
| 72 | 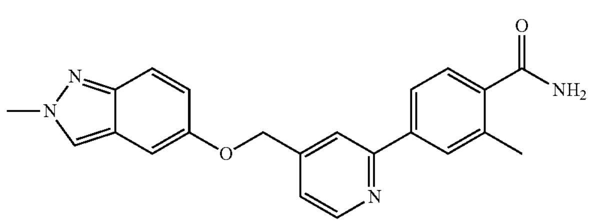 [SMILES: Cc1cc(-c2cc(COc3ccc4nn(C)cc4c3)ccn2)ccc1C(N)=O] | 4-(4-{[(2-methyl-2H-indazol-5-yl)oxy]methyl}pyridin-2-yl)-2-methyl benzamide | C |

TABLE 2-continued

| No. | Chemical Name | EC$_{50}$ |
|---|---|---|
| 73 | 4-{4-[3-(cyanomethyl)phenoxymethyl]pyridin-2-yl}-2-methylbenzamide | C |
| 74 | 4-(4-{[(5-methoxypyridin-3-yl)oxy]methyl}pyridin-2-yl)-2-methylbenzamide | C |
| 75 | 4-(4-{[(5-cyanopyridin-3-yl)oxy]methyl} pyridin-2-yl)-2-methylbenzamide | C |
| 76 | 4-{4-[4-(trifluoromethyl)phenoxymethyl]pyridin-2-yl}2-chlorobenzamide | A |
| 77 | 4-[4-(4-cyano-3-fluorophenoxymethyl)pyridin-2-yl]-2-chlorobenzamide | B |
| 78 | 4-{4-[4-(trifluoromethyl)phenoxymethyl]pyridin-2-yl}-2-(trifluoromethyl)benzamide | B |
| 79 | 4-[4-(4-cyano-3-fluorophenoxymethyl)pyridin-2-yl]-N-(2-hydroxyethyl)-2-methylbenzamide | C |

TABLE 2-continued

| No. | Chemical Name | EC$_{50}$ |
|---|---|---|
| 80 | 4-[4-(4-cyano-3-fluorophenoxymethyl)pyridin-2-yl]-N-[2-(dimethylamino)ethyl]-2-methylbenzamide | A |
| 81 | 4-{2-[4-(trifluoromethyl)phenoxymethyl]pyridin-4-yl}-2-methylbenzamide | A |
| 82 | 4-[2-(4-cyano-3-fluorophenoxymethyl)pyridin-4-yl]-2-methylbenzamide | B |
| 83 | 4-[2-(3,4,5-trifluorophenoxymethyl)pyridin-4-yl]-2-methylbenzamide | C |
| 84 | 4-[2-(4-cyano-2,3-difluorophenoxymethyl)pyridin-4-yl]-2-methylbenzamide | C |
| 85 | 4-[2-(3,5-difluorophenoxymethyl)pyridin-4-yl]-2-methylbenzamide | C |
| 86 | 4-[2-(4-acetylphenoxymethyl)pyridin-4-yl]-2-methylbenzamide | A |

TABLE 2-continued

| No. | Chemical Structure | Chemical Name | EC$_{50}$ |
|---|---|---|---|
| 87 | 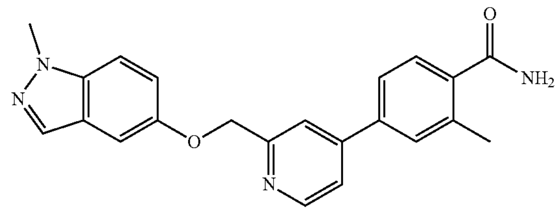 [SMILES: Cc1cc(-c2ccnc(COc3ccc4c(cnn4C)c3)c2)ccc1C(N)=O] | 4-(2-{[(1-methyl-1H-indazol-5-yl)oxy]methyl}pyridin-4-yl)-2-methyl-benzamide | C |
| 88 | 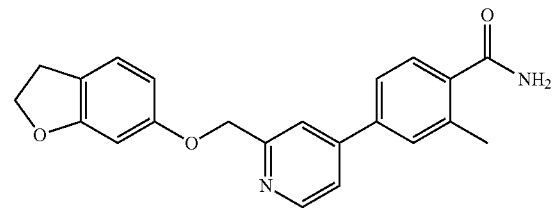 [SMILES: Cc1cc(-c2ccnc(COc3ccc4c(c3)OCC4)c2)ccc1C(N)=O] | 4-{2-[(2,3-dihydro-1-benzofuran-6-yloxy)methyl]pyridin-4-yl}-2-methylbenzamide | A |
| 89 | 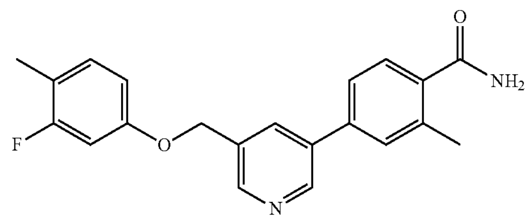 [SMILES: Cc1ccc(OCc2cncc(-c3ccc(C(N)=O)c(C)c3)c2)cc1F] | 4-[5-(3-fluoro-4-methylphenoxymethyl)pyridin-3-yl]-2-methylbenzamide | B |
| 90 | 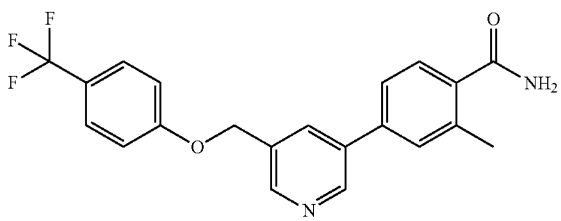 [SMILES: Cc1cc(-c2cncc(COc3ccc(C(F)(F)F)cc3)c2)ccc1C(N)=O] | 4-{5-[4-(trifluoromethyl)phenoxymethyl]pyridin-3-yl}-2-methylbenzamide | B |
| 91 | 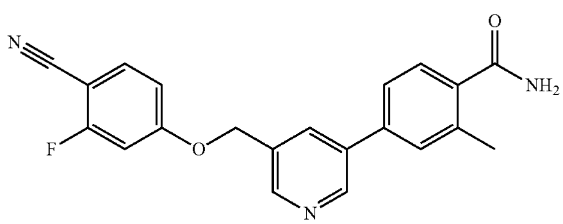 [SMILES: Cc1cc(-c2cncc(COc3ccc(C#N)c(F)c3)c2)ccc1C(N)=O] | 4-[5-(4-cyano-3-fluorophenoxymethyl)pyridin-3-yl]-2-methylbenzamide | D |
| 92 | 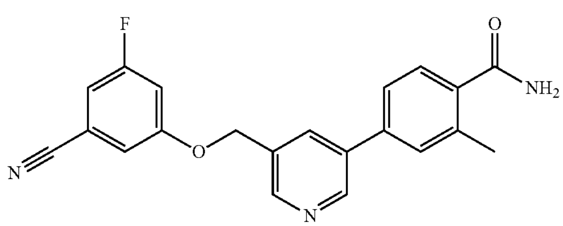 [SMILES: Cc1cc(-c2cncc(COc3cc(F)cc(C#N)c3)c2)ccc1C(N)=O] | 4-[5-(3-cyano-5-fluorophenoxymethyl)pyridin-3-yl]-2-methylbenzamide | D |
| 93 | 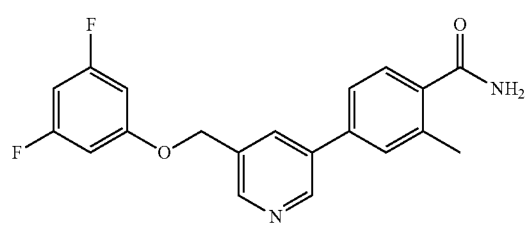 [SMILES: Cc1cc(-c2cncc(COc3cc(F)cc(F)c3)c2)ccc1C(N)=O] | 4-[5-(3,5-difluorophenoxymethyl)pyridin-3-yl]-2-methylbenzamide | C |

TABLE 2-continued

| No. | Chemical Structure | Chemical Name | EC₅₀ |
|---|---|---|---|
| 94 | 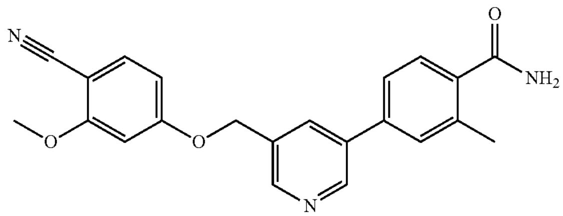 [SMILES: COc1cc(OCc2cncc(-c3ccc(C(N)=O)c(C)c3)c2)ccc1C#N] | 4-[5-(4-cyano-3-methoxyphenoxymethyl)pyridin-3-yl]-2-methylbenzamide | C |
| 95 | 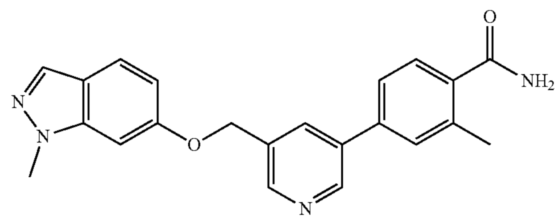 [SMILES: Cc1cc(-c2cncc(COc3ccc4cnn(C)c4c3)c2)ccc1C(N)=O] | 4-(5-{[(1-methyl-1H-indazol-6-yl)oxy]methyl}pyridin-3-yl)-2-methylbenzamide | D |
| 96 | 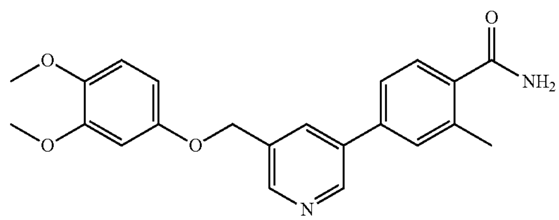 [SMILES: COc1ccc(OCc2cncc(-c3ccc(C(N)=O)c(C)c3)c2)cc1OC] | 4-[5-(3,4-dimethoxyphenoxymethyl)pyridin-3-yl]-2-methylbenzamide | D |
| 97 | 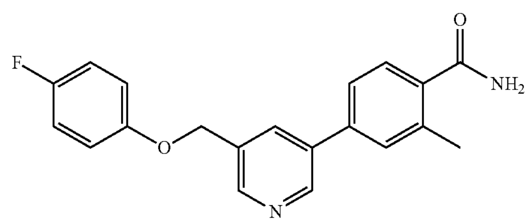 [SMILES: Cc1cc(-c2cncc(COc3ccc(F)cc3)c2)ccc1C(N)=O] | 4-[5-(4-fluorophenoxymethyl)pyridin-3-yl]-2-methylbenzamide | D |
| 98 | 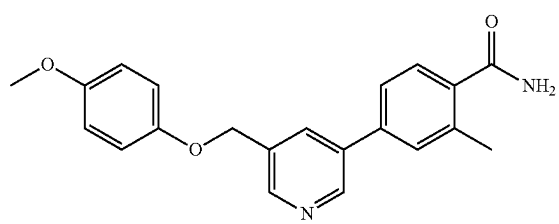 [SMILES: COc1ccc(OCc2cncc(-c3ccc(C(N)=O)c(C)c3)c2)cc1] | 4-[5-(4-methoxyphenoxymethyl)pyridin-3-yl]-2-methylbenzamide | B |
| 99 | 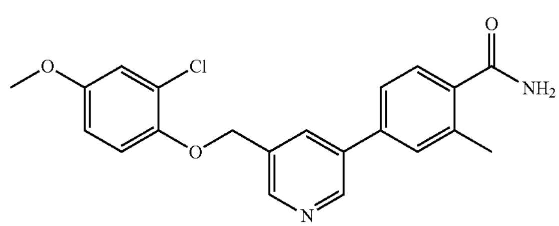 [SMILES: COc1ccc(OCc2cncc(-c3ccc(C(N)=O)c(C)c3)c2)c(Cl)c1] | 4-[5-(2-chloro-4-methoxyphenoxymethyl)pyridin-3-yl]-2-methylbenzamide | D |
| 100 | 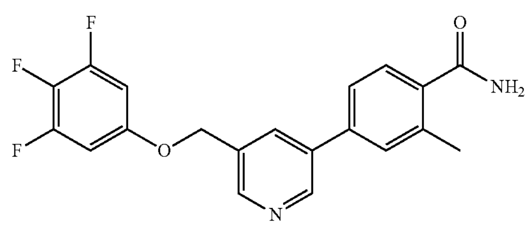 [SMILES: Cc1cc(-c2cncc(COc3cc(F)c(F)c(F)c3)c2)ccc1C(N)=O] | 4-[5-(3,4,5-trifluorophenoxymethyl)pyridin-3-yl] 2-methylbenzamide | C |

TABLE 2-continued

| No. | Chemical Structure | Chemical Name | $EC_{50}$ |
|---|---|---|---|
| 101 | 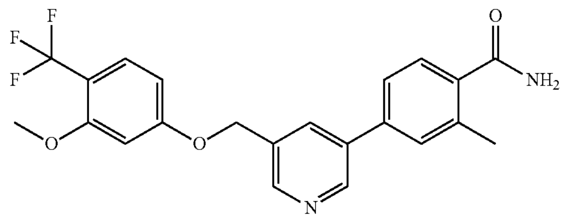 [SMILES: COc1cc(OCc2cncc(-c3ccc(C(N)=O)c(C)c3)c2)ccc1C(F)(F)F] | 4-{5-[3-methoxy-4-(trifluoromethyl)phenoxymethyl]pyridin-3-yl}-2-methylbenzamide | C |
| 102 | 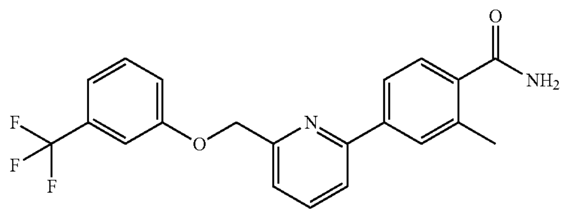 [SMILES: Cc1cc(-c2cccc(COc3cccc(C(F)(F)F)c3)n2)ccc1C(N)=O] | 4-{6-[3-(trifluoromethyl)phenoxymethyl]pyridin-2-yl}-2-methylbenzamide | D |
| 103 | 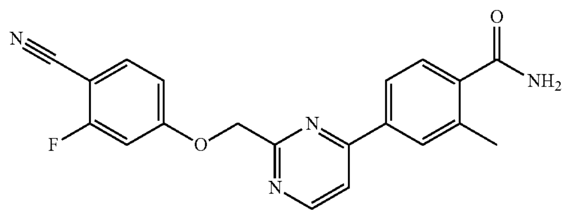 [SMILES: Cc1cc(-c2ccnc(COc3ccc(C#N)c(F)c3)n2)ccc1C(N)=O] | 4-[2-(4-cyano-3-fluorophenoxymethyl)pyrimidin-4-yl]-2-methylbenzamide | C |
| 104 | 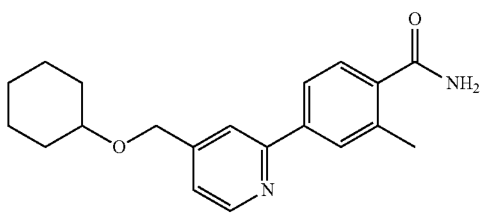 [SMILES: Cc1cc(-c2cc(COC3CCCCC3)ccn2)ccc1C(N)=O] | 4-{4-[(cyclohexyloxy)methyl]pyridin-2-yl}-2-methylbenzamide | C |

Example 106: Novel Object Recognition (NOR) Training and Testing

Male Lister-Hooded rats are habituated to the testing arena NOR box twice a day, on two consecutive days, prior to testing. Each habituation session, consists of a 3 min exposure to the empty test box (46×30×45 cm), followed by 1 min in the side annex (13×30×45 cm), and then a further 3 min in the test area. Animals are sham dosed with vehicle (30% PG, 20% PEG 400, 50% (0.25%) methylcellulose) prior to the second habituation session on each day.

The NOR test comprises of two sessions, T1 and T2, each lasting 3 minutes. On training day, the test compound is administered (1, 3, 10 and 30 mg/kg p.o.) in vehicle to rats, 3 mL/kg 120 min prior to T1 and T2 testing, vehicle is administered to rats as a control group prior to T1 and T2 testing, and SB399885 (Concept Life Sciences Ltd, Manchester, United Kingdom) dosed p.o. at 10 mg/kg (in 2 mL/kg 1% methylcellulose) is administered to rats 4 hrs before T1 and T2 trials as a reference group.

On the first test day (T1), rats are again habituated for 3 min in the empty test box prior to testing. Following 3 min habituation to the empty test box, the rat is placed into the side annex and 2 identical objects are placed into the test arena, equally spaced to each other and the 2 side walls. The rat is then returned to the test area and allowed to freely explore the objects for 3 min. Following the 3 min test session, the rat is returned to its home cage.

Following a 24 hr delay, the test is repeated (T2) except that one of the familiar objects is substituted for a novel one of the same color, material and similar size but different shape. The objects are black pyramid and tower shapes that are previously validated in this test and shown to be of equal saliency. The protocol is similar to T1 with a 3 min habituation, followed by approx. 1 min in the annex while the objects are positioned in the box, followed by 3 min exposure to the objects. Animals are dosed prior to T1 and T2 test sessions.

An overall index (d1) is determined as time spent exploring novel object—time spent exploring familiar object (overall difference). To evaluate mnemonic processing in the 24h temporal deficit novel object recognition, an object-discrimination index (d2) is determined as d1/[total exploration time in T2]. T1 score=total exploration of both objects in T1, and T2 score=total exploration of both objects in T2.

The T1 score and T2 score, d1 and d2 index are analyzed using 2-way ANOVA (treatment×object) followed by planned comparisons post-hoc LSD using single measure parametric analysis, based on least square (predicted) means in InVivoStat, UK. Planned comparisons are made versus the Vehicle group.

The specification, including the examples, is intended to be exemplary only, and it will be apparent to those skilled in the art that various modifications and variations can be made in the present application without departing from the scope or spirit of the disclosure as defined by the appended claims. Each reference, including all patent, patent applications, and publications, cited in the present application is incorporated herein by reference in its entirety.

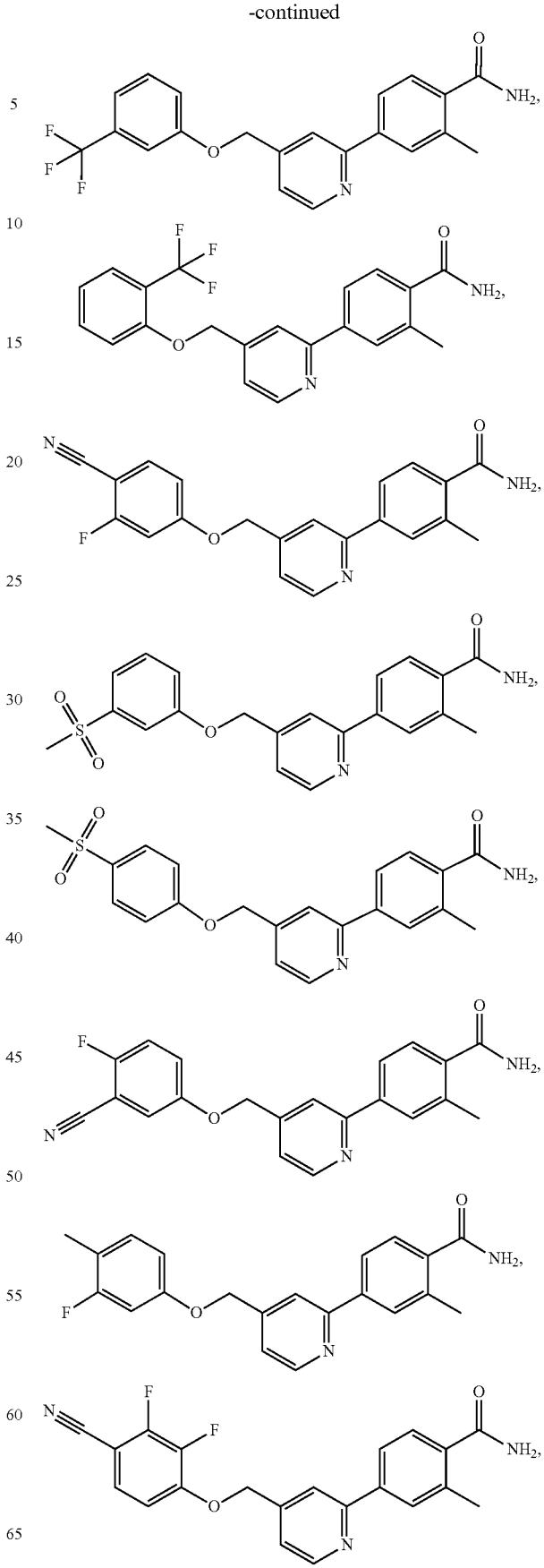

-continued
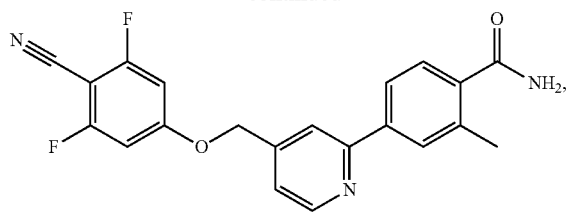
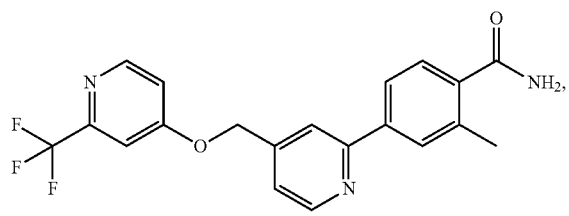
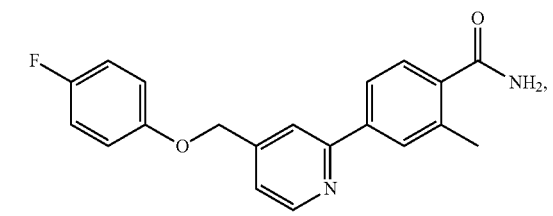
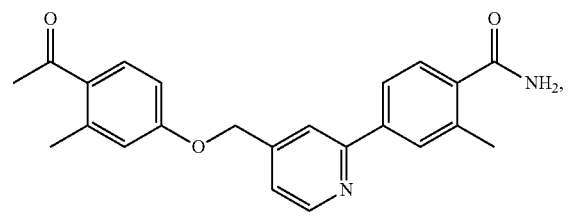
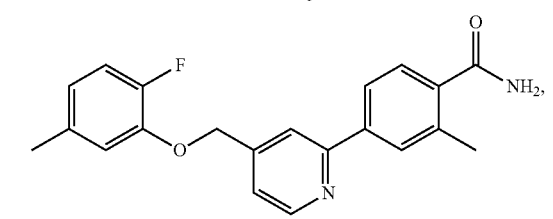
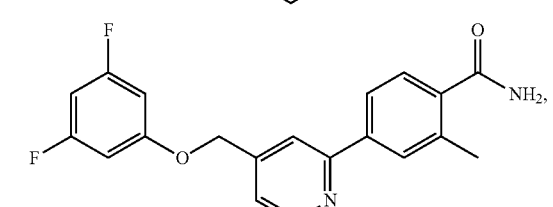
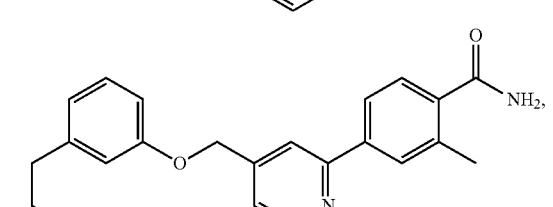
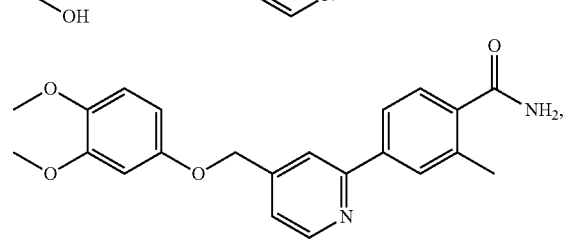
-continued
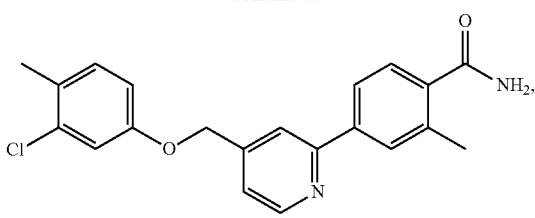
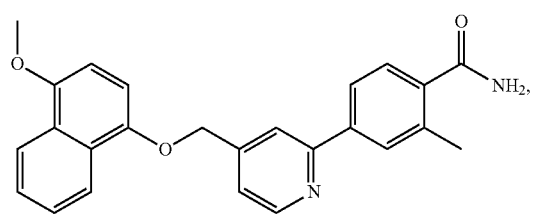
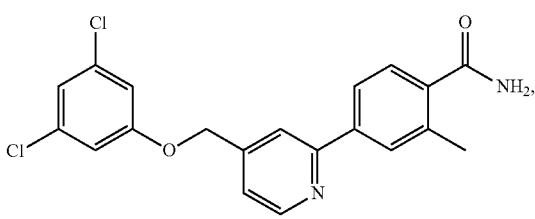
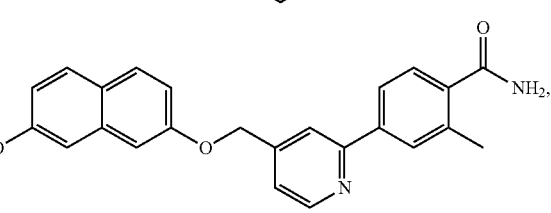
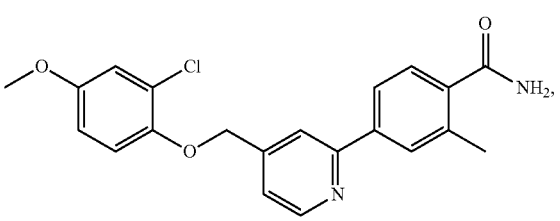
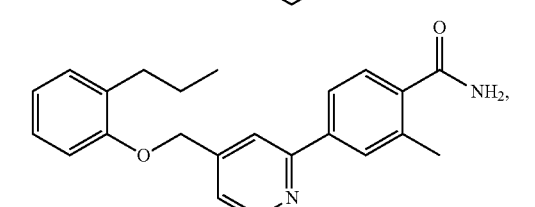
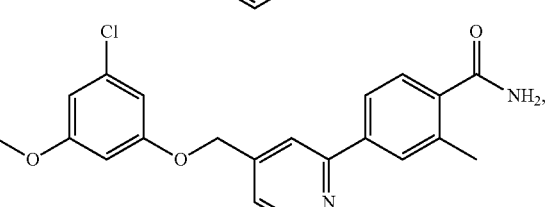
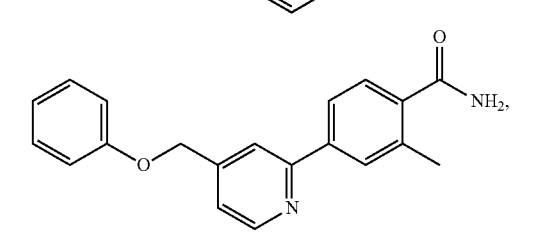

161
-continued
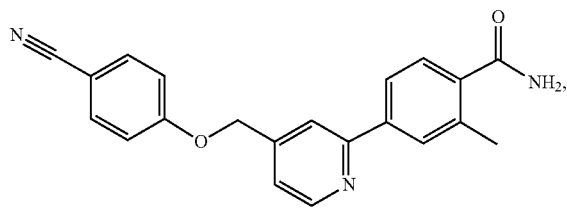
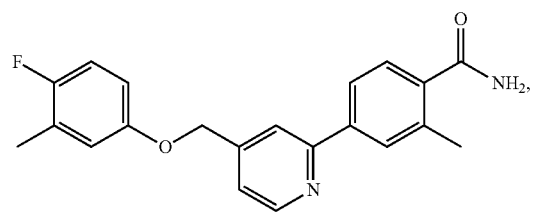
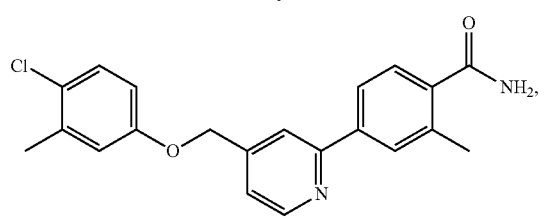
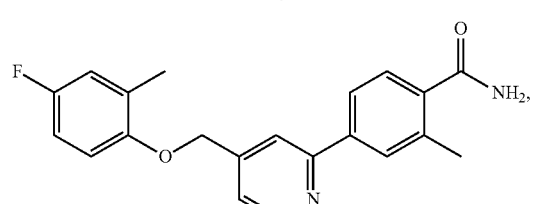
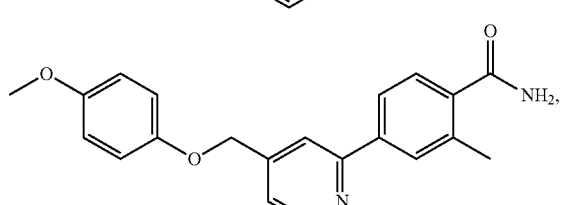
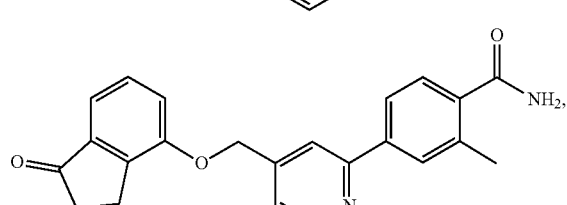
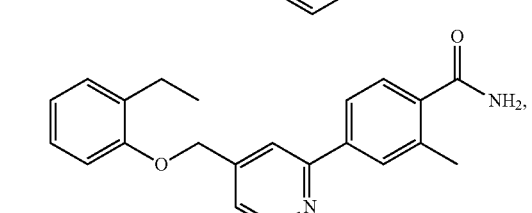
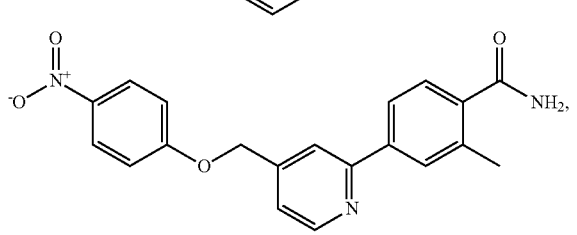
162
-continued
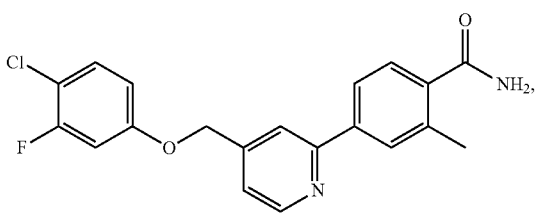
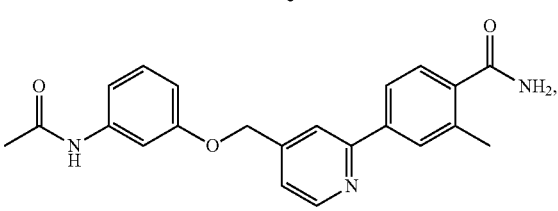
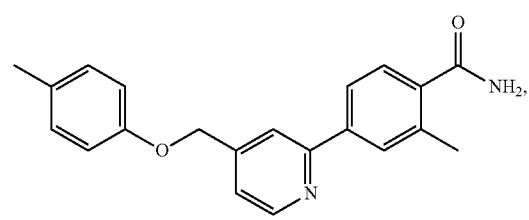
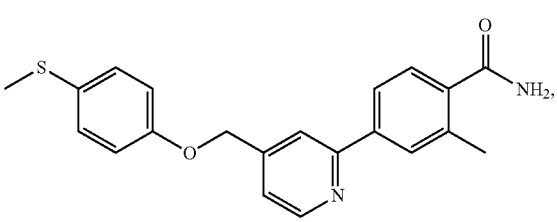
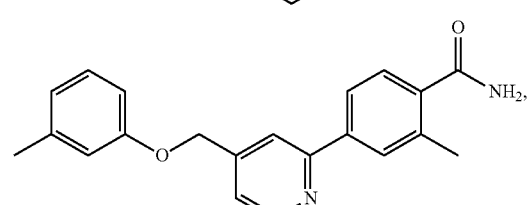
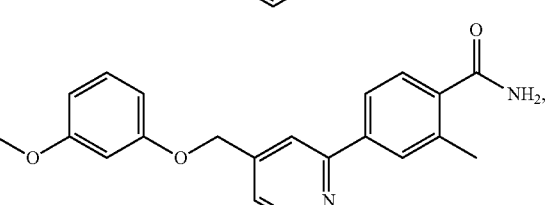
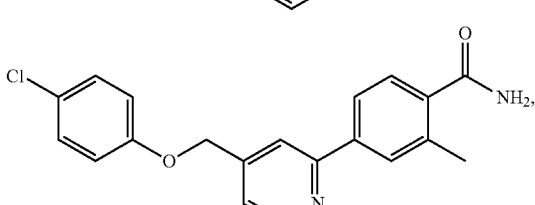
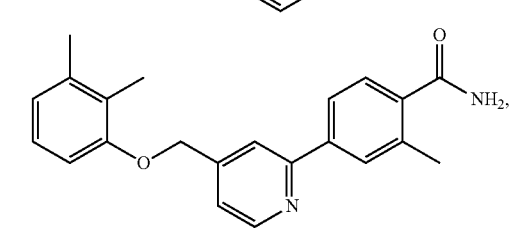

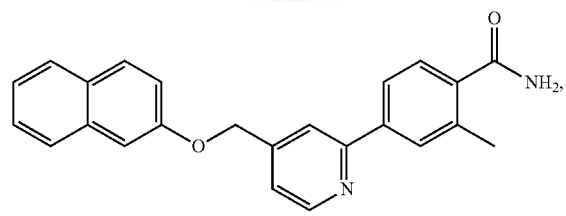
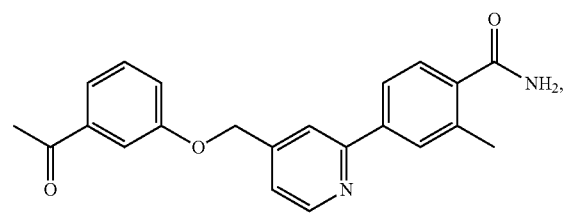
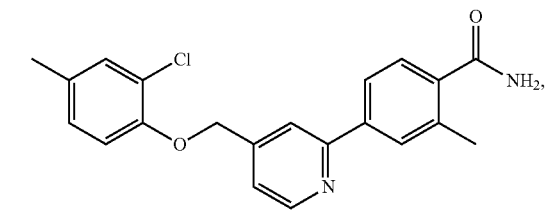
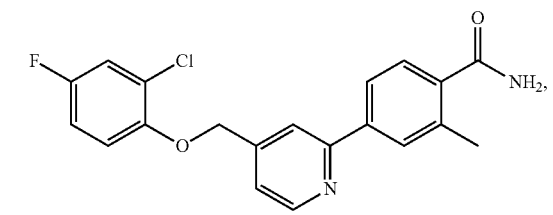
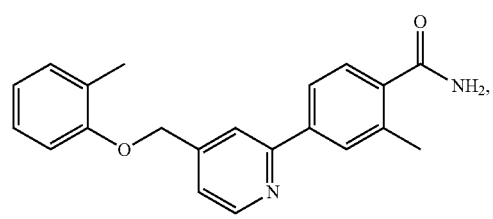
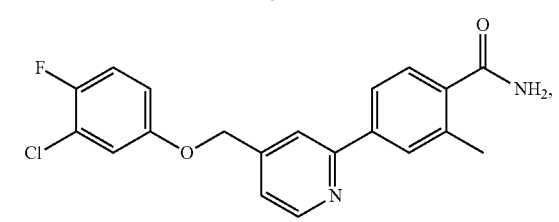
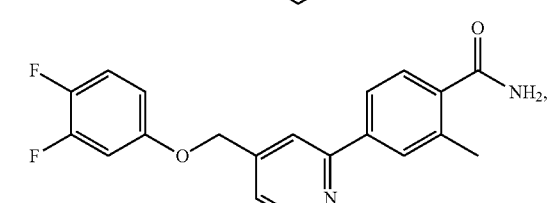
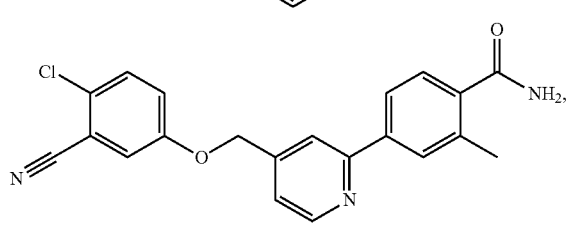
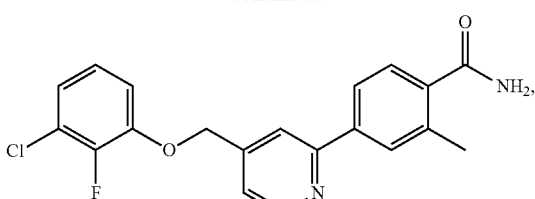
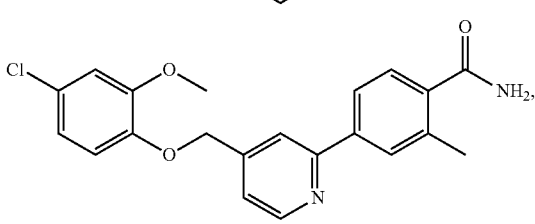
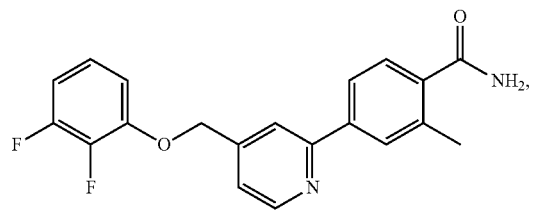
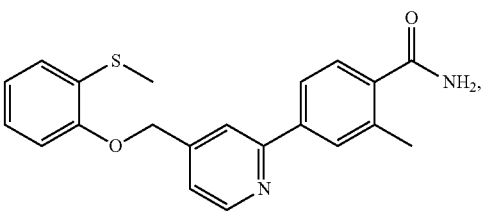
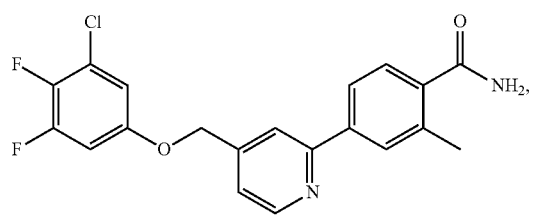
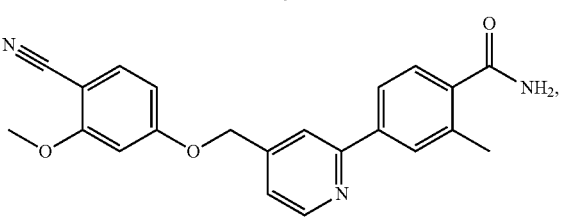
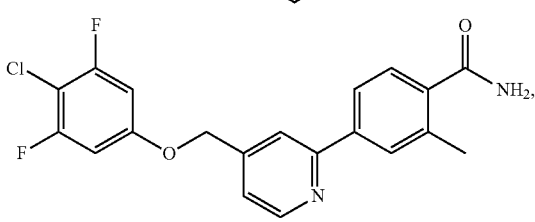
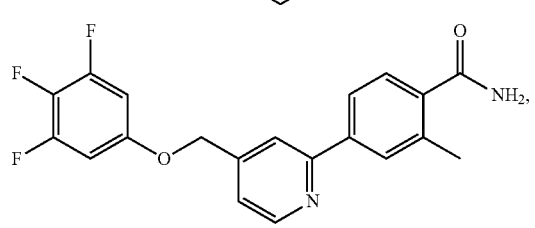

-continued
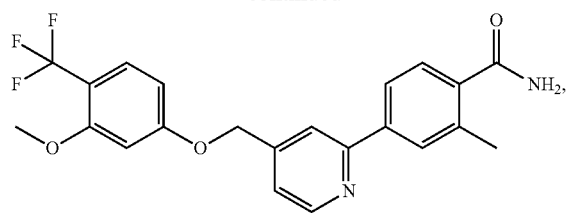
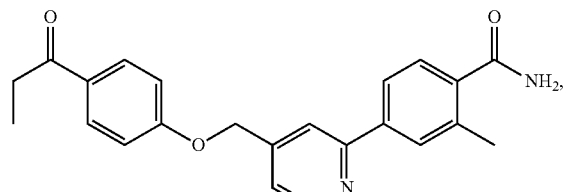
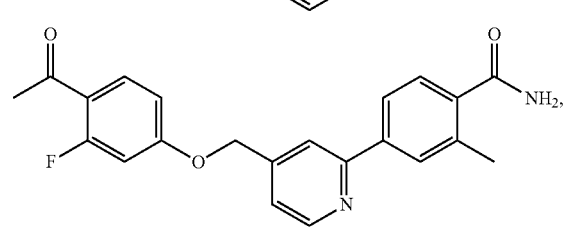
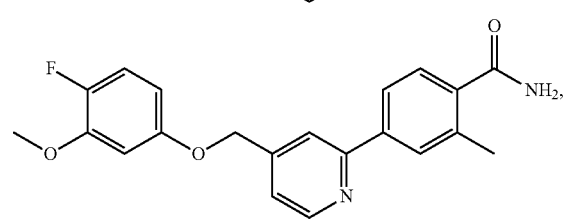
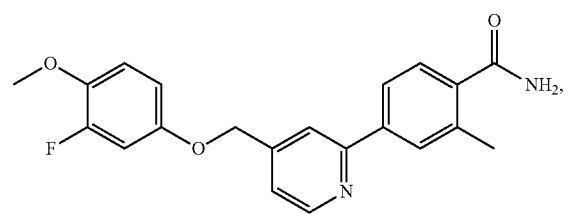
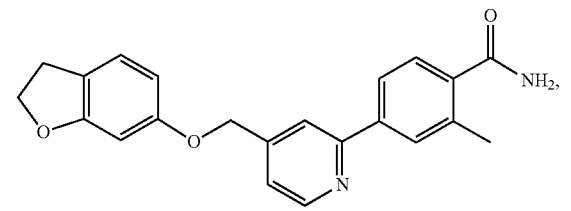
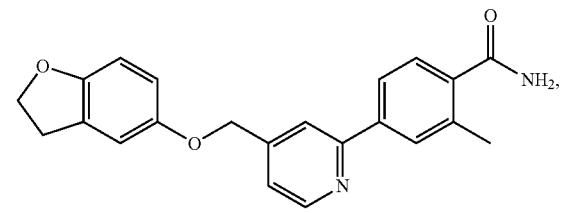
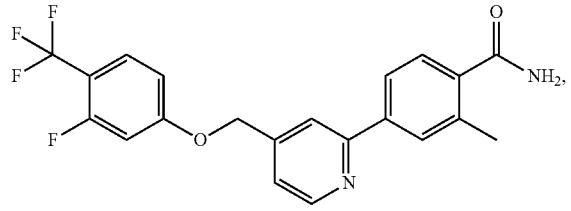
-continued
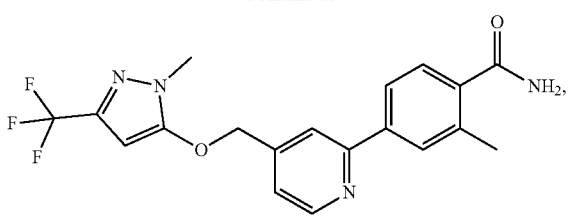
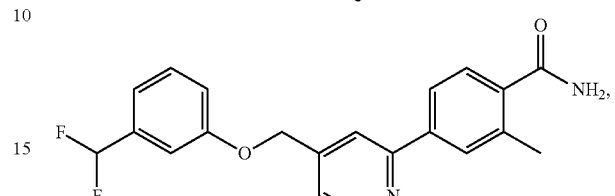
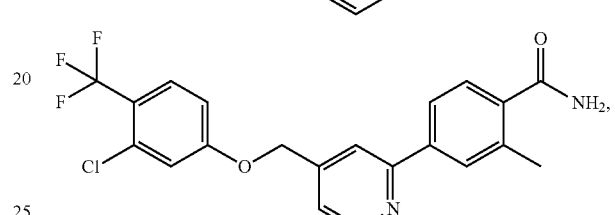
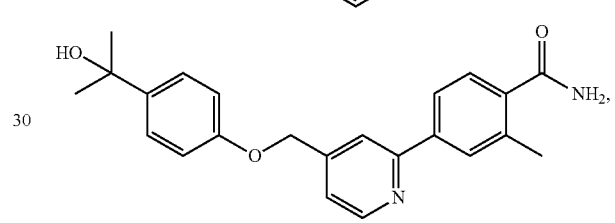
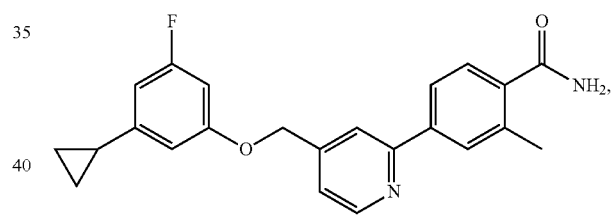
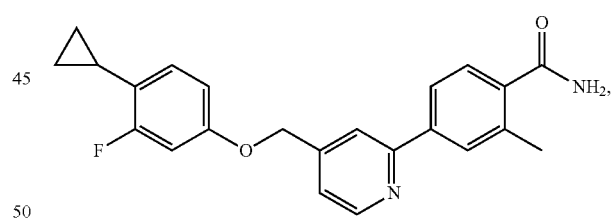
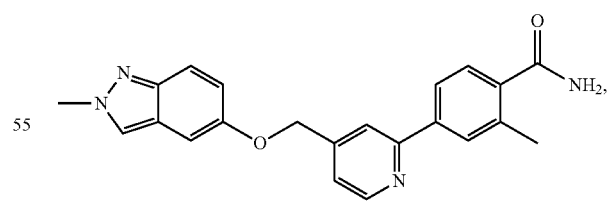
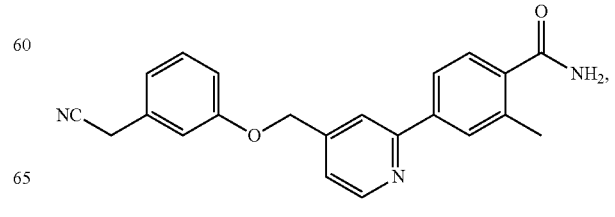

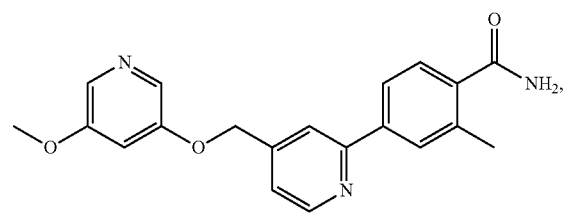
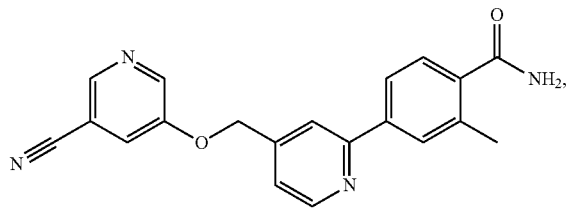
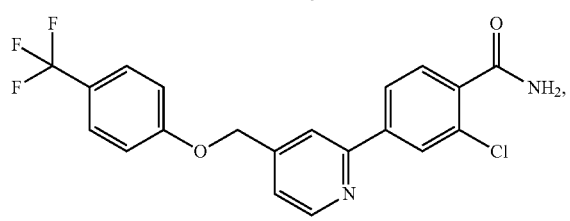
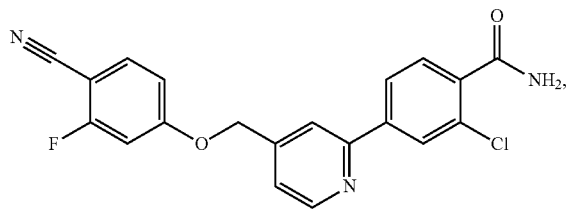
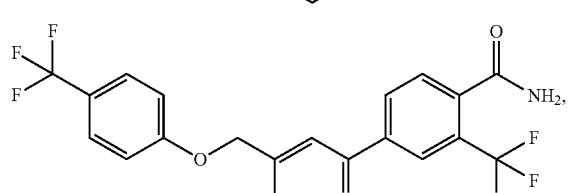
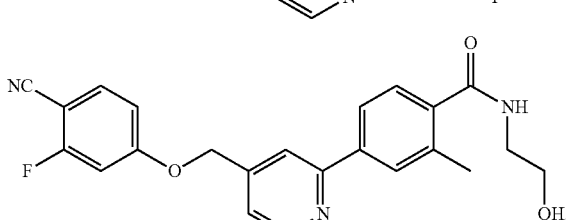
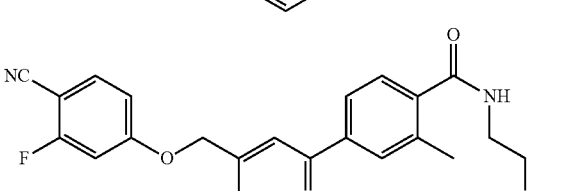
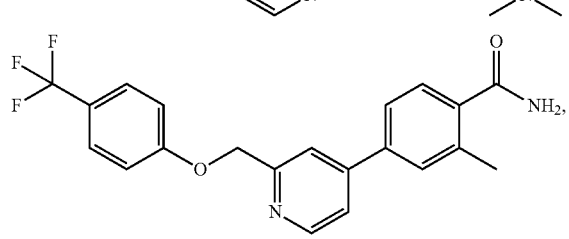
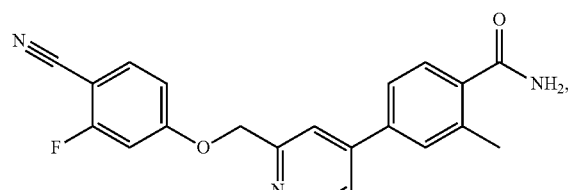
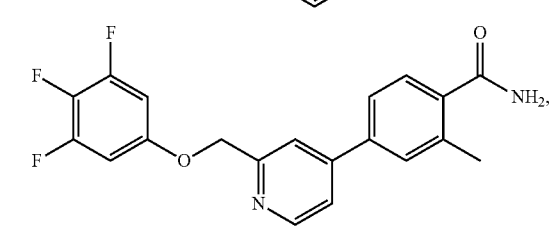
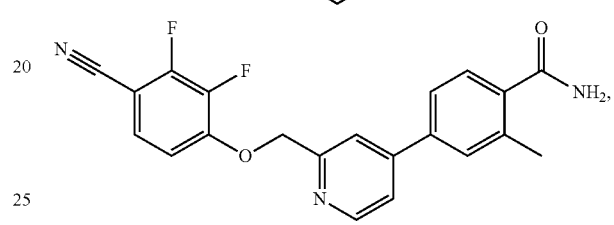
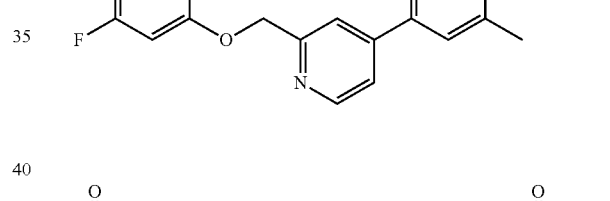
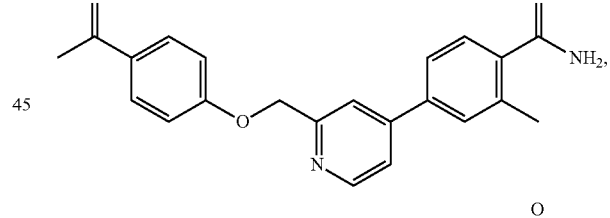
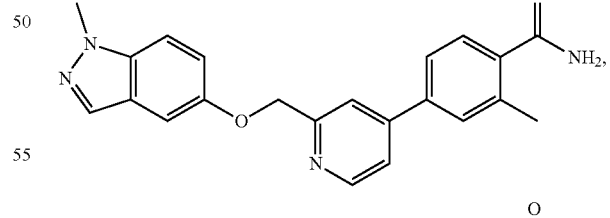
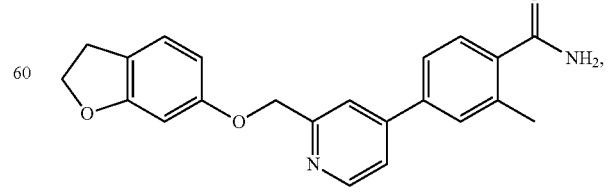

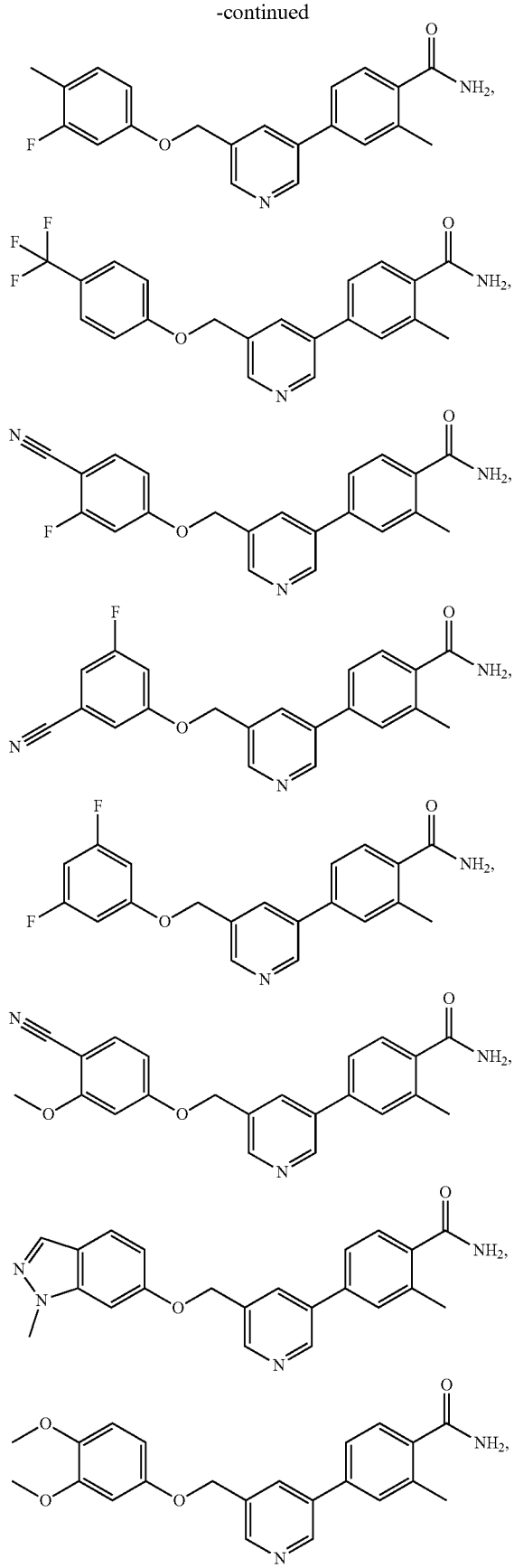
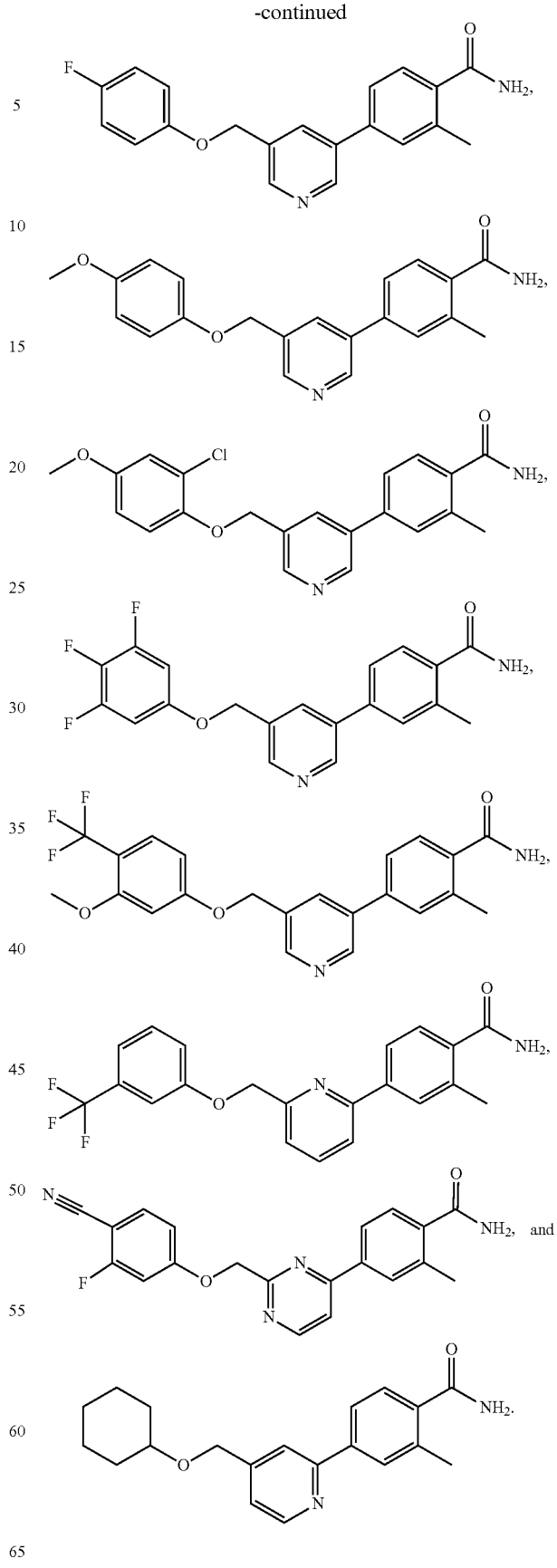

What is claimed is:

1. A compound of Formula (I):

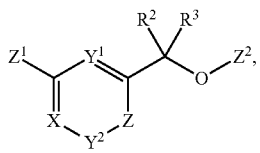

or a pharmaceutically acceptable salt thereof, wherein:
X, $Y^1$ and $Y^2$ are independently N (nitrogen) or CH;
Z is N or $CR^1$, where at least one of Z, X, $Y^1$ and $Y^2$ is N (nitrogen);
$Z^1$ is

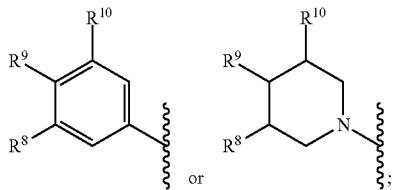

$Z^2$ is

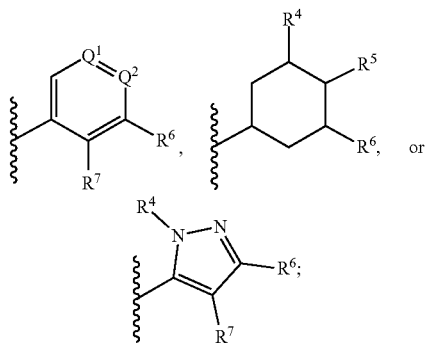

$Q^1$ is N (nitrogen) or $CR^4$;
$Q^2$ is N (nitrogen) or $CR^5$;
$R^1$ is hydrogen, halogen, $C_1$-$C_6$alkyl or halo$C_1$-$C_6$alkyl;
$R^2$ is hydrogen, halogen, $C_1$-$C_6$alkyl, halo$C_1$-$C_6$alkyl, or —$OR^A$;
$R^3$ is hydrogen, halogen, $C_1$-$C_6$alkyl, or halo$C_1$-$C_6$alkyl;
i) $R^4$, $R^5$, $R^6$, and $R^7$, are independently hydrogen, halogen, —$(CH_2)_n$—CN, nitro, halo$C_1$-$C_6$alkyl, $C_3$-$C_8$cycloalkyl, —NHC(=O)$R^B$, —$OR^B$, —S(O)$_m R^B$, —$(CH_2)_m C(=O)R^B$, —S(O)$_p$N($R^B R^C$), or $C_1$-$C_6$alkyl optionally substituted with hydroxyl; or
ii) $R^4$ and $R^5$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^6$ and $R^7$ are independently hydrogen, halogen, —$(CH_2)_n$—CN, nitro, $C_1$-$C_6$alkyl optionally substituted with hydroxyl, halo$C_1$-$C_6$alkyl, $C_3$-$C_8$cycloalkyl, —NHC(=O)$R^B$, —$OR^B$, —S(O)$_m R^B$, —$(CH_2)_m C(=O)R^B$ or —S(O)$_p$N($R^B R^C$); or
iii) $R^5$ and $R^6$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^4$ and $R^7$, are independently hydrogen, halogen, —$(CH_2)_n$—CN, nitro, $C_1$-$C_6$alkyl optionally substituted with hydroxyl, halo$C_1$-$C_6$alkyl, $C_3$-$C_8$cycloalkyl, —NHC(=O)$R^B$, —$OR^B$, —S(O)$_m R^B$, —$(CH_2)_m C(=O)R^B$ or —S(O)$_p$N($R^B R^C$); or
iv) $R^6$ and $R^7$, together with the carbon atoms to which they are attached, form a 6 membered aryl group, a 5-6 membered heteroaryl group optionally substituted with $C_1$-$C_6$alkyl, a 5-6 membered cycloalkyl group optionally substituted with =O, or a 5-6 membered heterocyclyl group, and $R^4$ and $R^5$, are independently hydrogen, halogen, —$(CH_2)_n$—CN, nitro, $C_1$-$C_6$alkyl optionally substituted with hydroxyl, halo$C_1$-$C_6$alkyl, $C_3$-$C_8$cycloalkyl, —NHC(=O)$R^B$, —$OR^B$, —S(O)$_m R^B$, —$(CH_2)_m C(=O)R^B$ or —S(O)$_p$N($R^B R^C$);
one of $R^8$ and $R^9$ is —$(CH_2)_n C(=O)N(R^E R^F)$ and the other of $R^8$ and $R^9$ is hydrogen, halogen, $C_1$-$C_6$alkyl, halo$C_1$-$C_6$alkyl, —C(=O)$R^D$, or —$OR^E$; or
$R^8$ and $R^9$ together with the carbon atom to which they are attached, form a 5-6 membered heterocyclyl group, said 5-6 membered heterocyclyl group optionally substituted with =O, with the proviso that the heterocyclic group formed is not a 1,3-dioxolanyl ring when $Y^1$ and Z are each N and X and $Y^2$ are each CH;
$R^{10}$ is hydrogen, halogen, $C_1$-$C_6$alkyl, halo$C_1$-$C_6$alkyl, —C(=O)$R^D$, or —$OR^E$;
each $R^A$, $R^B$, $R^C$, is independently hydrogen, $C_1$-$C_6$alkyl, or halo$C_1$-$C_6$alkyl;
each $R^D$ is independently hydrogen, $C_1$-$C_6$alkyl, halo$C_1$-$C_6$alkyl, —$NH_2$, or —NH($CH_2$)$_q$OH;
each $R^E$, and $R^F$, is independently hydrogen, $C_1$-$C_6$alkyl, or halo$C_1$-$C_6$alkyl; or
$R^E$ and $R^F$, together with the nitrogen atom to which they are attached, form a 5-6 membered heterocyclyl group;
each m is independently 0, 1, 2 or 3;
each n is independently 0, 1, 2 or 3;
each p is independently 1 or 2; and
each q is independently 2, 3 or 4.

2. The compound of claim 1, wherein X, $Y^1$ and $Y^2$ are CH and Z is N (nitrogen), or Z, $Y^1$ and $Y^2$ are CH and X is N (nitrogen), or X, $Y^1$ and Z are CH and $Y^2$ is N (nitrogen).

3. The compound of claim 1, wherein X and $Y^1$ are each N or wherein X and $Y^1$ are each CH.

4. The compound of claim 1, wherein $R^2$ and $R^3$ are each hydrogen.

5. The compound of claim 1, wherein $Z^2$ is

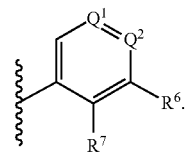

6. The compound of claim 1, wherein $Z^2$ is

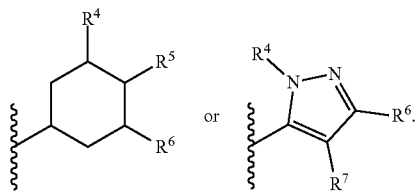

7. The compound of claim 1, wherein $Q^1$ is $CR^4$ and $R^4$ is hydrogen; and $R^7$ is hydrogen.

8. The compound of claim 1, wherein $Q^2$ is $CR^5$ and $R^5$ is halogen, —$(CH_2)_p$—CN, $C_1$-$C_3$alkyl, halo$C_1$-$C_3$alkyl, —$OR^B$ or —$S(O)_mR^B$.

9. The compound of claim 1, wherein $Q^2$ is $CR^5$ and $R^5$ is unsubstituted $C_1$-$C_6$alkyl or $C_1$-$C_6$alkyl substituted by hydroxyl.

10. The compound of claim 1, wherein $R^6$ is halogen, halo$C_1$-$C_6$alkyl, —$(CH_2)_n$—CN, unsubstituted $C_1$-$C_6$alkyl, $C_1$-$C_6$alkyl substituted by hydroxyl or nitro.

11. The compound of claim 1, wherein $R^6$ is hydrogen.

12. The compound of claim 1, wherein $R^5$ is —NHC(=O)$R^B$, —$OR^B$, —$S(O)_mR^B$, or —$S(O)_pN(R^BR^C)$.

13. The compound of claim 1, wherein $R^6$ is —NHC(=O)$R^B$, —$OR^B$, —$S(O)_mR^B$, or —$S(O)_pN(R^BR^C)$.

14. The compound of claim 1, wherein $Z^1$ is

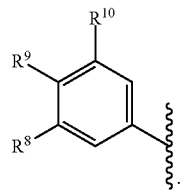

15. The compound of claim 1, wherein $Z^1$ is

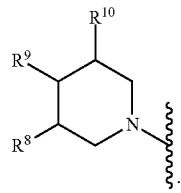

16. The compound of claim 1, wherein $R^8$ is hydrogen, halogen, $C_1$-$C_6$alkyl or halo$C_1$-$C_6$alkyl; or wherein $R^8$ is —$OR^E$, —$C(=O)R^D$, or —$(CH_2)_nC(=O)N(R^ER^F)$.

17. The compound of claim 1, wherein $R^9$ is hydrogen, halogen, $C_1$-$C_6$alkyl or halo$C_1$-$C_6$alkyl; or wherein $R^9$ is —$OR^E$, —$C(=O)R^D$, or —$(CH_2)_nC(=O)N(R^ER^F)$.

18. The compound of claim 1, wherein $Z^2$ is

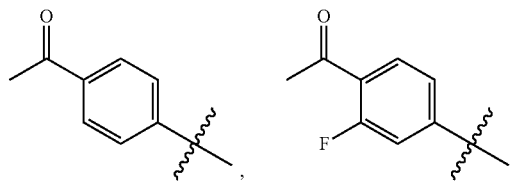

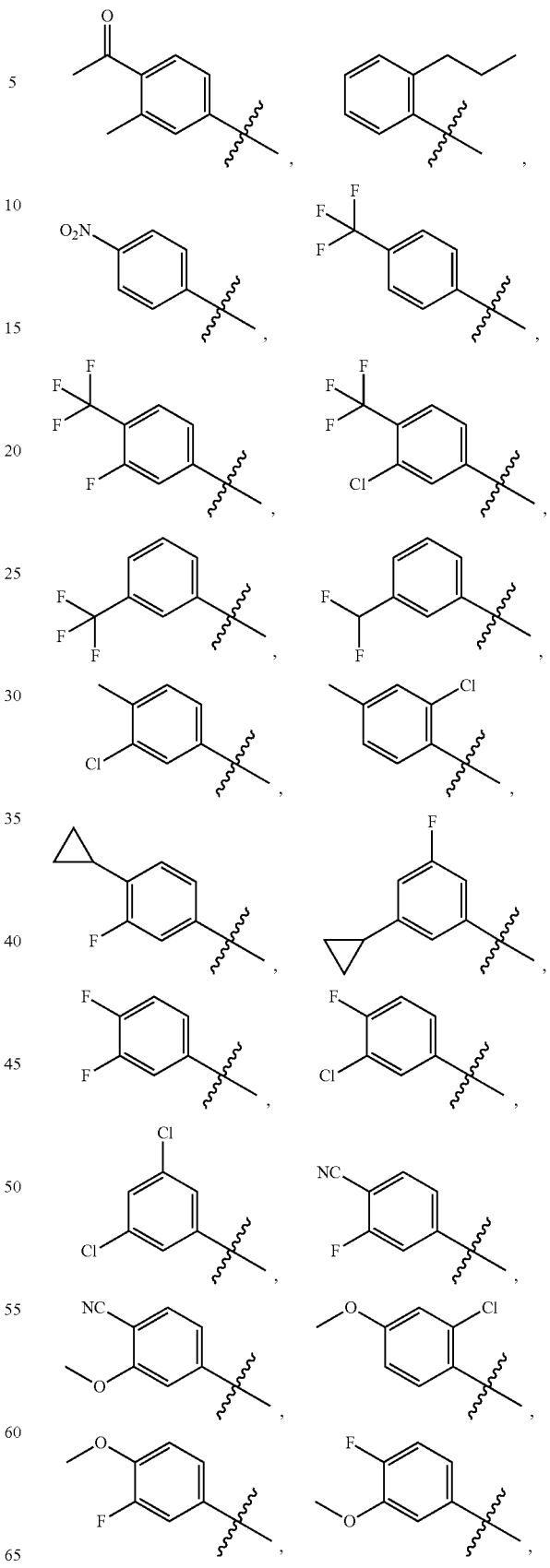

-continued

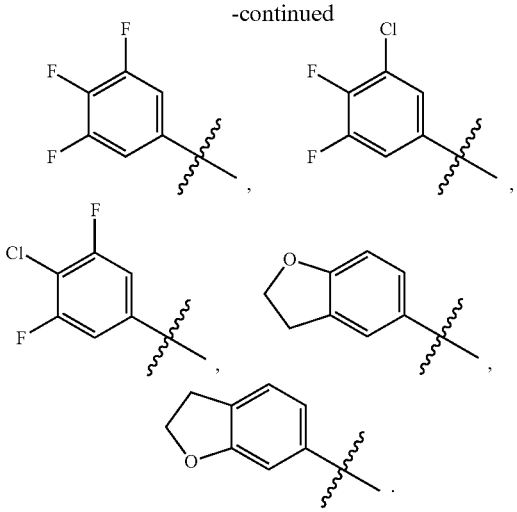

19. A pharmaceutical composition comprising a compound of claim 1, or a pharmaceutically acceptable salt thereof, and one or more excipients.

20. A method of treating a neurological disorder, comprising administering to a subject in need thereof an effective amount of a compound of claim 1, or a pharmaceutically acceptable salt thereof; wherein the neurological disorder is selected from the group consisting of:

schizophrenia, cognitive impairment, a panic disorder, a phobic disorder, drug-induced psychotic disorder, delusional psychosis, neuroleptic-induced dyskinesia, Parkinson's disease, drug-induced Parkinson's syndrome, extrapyramidal syndrome, Alzheimer's Disease, Lewy Body Dementia, bipolar disorder, ADHD, Tourette's syndrome, an extrapyramidal or movement disorder, a motor disorder, a hyperkinetic movement disorder, a psychotic disorder, catatonia, a mood disorder, a depressive disorder, an anxiety disorder, obsessive-compulsive disorder (OCD), an autism spectrum disorder, a prolactin-related disorder, a neurocognitive disorder, a trauma- or stressor-related disorder; a disruptive, impulse-control, or conduct disorder, a sleep-wake disorder, a substance-related disorder, an addictive disorder, a behavioral disorder, hypofrontality, an abnormality in the tuberoinfundibular, mesolimbic, mesocortical, or nigrostriatal pathway, decreased activity in the striatum, cortical dysfunction, neurocognitive dysfunction and the cognitive deficits associated with schizophrenia; dyskinesias, dystonia, chorea, levodopa induced dyskinesia, cerebral palsy and progressive supranuclear palsy, and Huntington's disease.

21. The compound of claim 1, wherein the compound is selected from the group consisting of: